(12) United States Patent
Nishimune et al.

(10) Patent No.: US 7,842,783 B2
(45) Date of Patent: Nov. 30, 2010

(54) MOUSE SPERMATOGENESIS GENES RELATED TO HUMAN MALE STERILITY

(75) Inventors: Yoshitake Nishimune, Hyogo (JP); Hiromitsu Tanaka, Osaka (JP); Masami Nozaki, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 1573 days.

(21) Appl. No.: 10/504,582

(22) PCT Filed: Feb. 14, 2003

(86) PCT No.: PCT/JP03/01572

§ 371 (c)(1),
(2), (4) Date: Oct. 6, 2004

(87) PCT Pub. No.: WO03/068969

PCT Pub. Date: Aug. 21, 2003

(65) Prior Publication Data

US 2005/0176943 A1    Aug. 11, 2005

(30) Foreign Application Priority Data

Feb. 14, 2002  (JP) .............................. 2002-036649
Dec. 27, 2002  (JP) .............................. 2002-381241

(51) Int. Cl.
*C07K 17/00* (2006.01)
(52) U.S. Cl. ........................ 530/350; 506/7; 530/387.3
(58) Field of Classification Search ........................ None
See application file for complete search history.

(56) References Cited

U.S. PATENT DOCUMENTS 6,090,555 A * 7/2000 Fiekowsky et al. ............. 435/6

OTHER PUBLICATIONS

Tschanter et al., Human Reproduction 19(12):2771-2776 (2004).*
Burton et al., Mol. Endocrinol., 20(10): 2504-2513 (2006).*
Bannister et al., PLOS Biology, 5(5):e105 1016-1025 (2007).*
Magyari et al., World J. Gastroenterol. 13(15):2205-2208 (2007).*
Bagieyeva et al., Molecular Vision, 13:1458-1468 (2007).*
Goodman, Seminars in Hematology, 45(3):135-140 (2008).*
Tanaka et al., Journal Human Reproduction, 8(1):16-23 (2001).*
S. Vijayaraghavan et al., "Isolation and Molecular Characterization of AKAP110, A Novel, Sperm-Specific Protein Kinase A-Anchoring Protein", Mol. Endocrinol., 1999, vol. 13, No. 5, pp. 705-717.

* cited by examiner

*Primary Examiner*—Jeffrey S. Lundgren
(74) *Attorney, Agent, or Firm*—Wenderoth, Lind & Ponack, L.L.P.

(57) ABSTRACT

The present invention provides a polynucleotide or a complementary sequence thereof, which polynucleotide is complementary to mRNA transcribed from a human male infertility-associated gene Scot-t, and has one or more mutations selected from the following group: "t" at 870th position is replaced by "g"; and "t" at 1667th position is replaced by "c", in the DNA sequence of SEQ ID NO:168; various molecular biological materials relating thereto; various molecular biological materials relating to male infertility-associated gene mutations; and various test methods and diagnostic methods using the same.

1 Claim, 3 Drawing Sheets

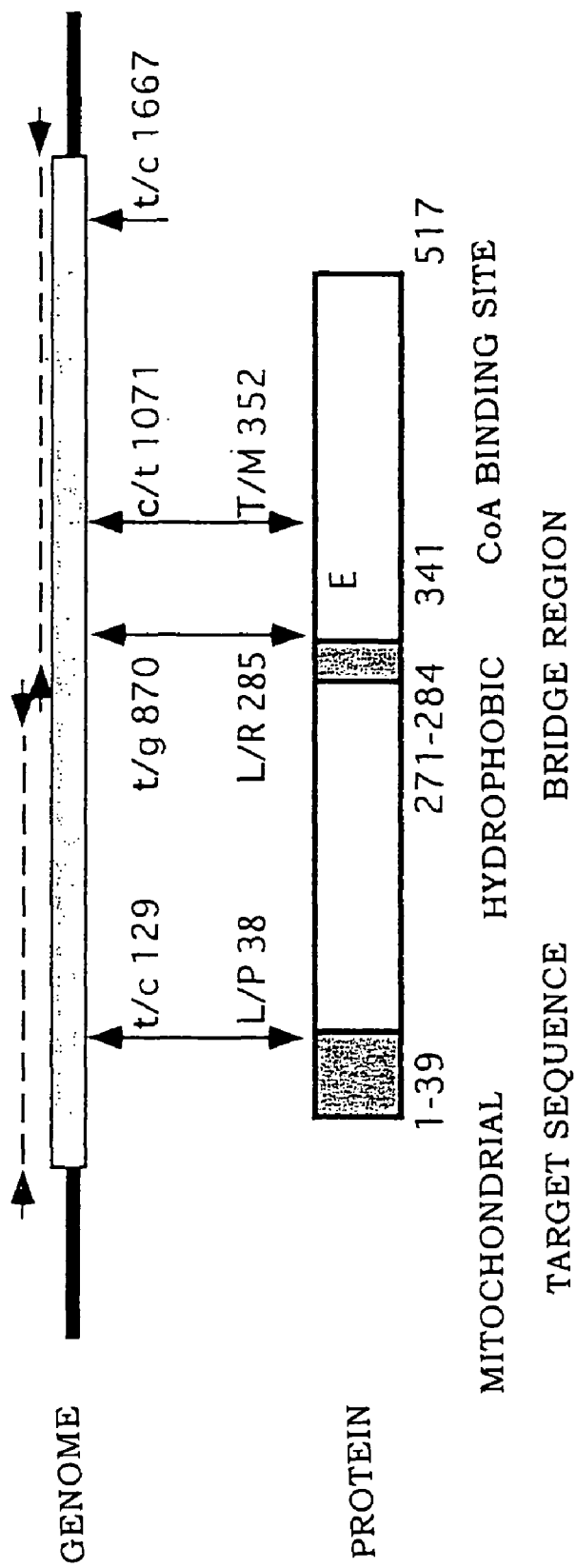

Fig. 2

```
primer P1A
ccctggcatctataacaggccgcagagctgctggcccctgactcacagcccacagagttcca       18
         *
cctgctcacaggttgctggctcagcaggtgtcaagcattcagg**gccaag              78
          M  A  R  Y  R  C  C  R  S  Q  S  R  S  R/RY  Y       16
cccatcctgcaccatggccaccatgtgctgtcgcagccagagccgcagacacggaggagagc       138
                                                          g
        R  Q  R  Q  R  S  R/RR  R  R  R  R  R  S  C  Q  T  R  R  R  A  36
ccgccagagacaaagagtcgcagagaggcggagctgccagacacggaggagagc
    a
catgagtgggcccagctgaggctgggctgggagctctcaggcc                        258
                                                              g
         M  R                                                     38
cagccttcctccaccttttcttggtctcaccaggg tgctgccgcccagtacagac          318
         C  C  R  P  R  Y  R  P/P   46
cgcgatgtgtagaagacactaattgcacaaaatagcacatccaaactcctgctgagaa       378
         R/RC  R  R  H  Ter                                    51
tgttaccagacttcaggatctcttgccacatccttgaaaatgccaccatccaataaaaat       438
caggagcctgctaaggaacaatgccgcctgtgccgcctgtgc tgttgaaaagtcatcccactct   498
                                         aa
tctctccttgttcttga
         primer P1B
```

Fig. 3

```
    +1
     1 aacagtaacaccaagggcaggtggcaggcctccgccctcctcccctactccagggcca    60
                                                 primer P2A
    61 ctgcagcctcagcccaggagcccaccagatctcccaacaccatgtccgataccgcgtgag   120
                                          M  V  R  Y  R  V  R     7
   121 gagcctgagcgaacgctcgcacgagtgtacaggcagcagttgcatgggcaagagcaagg   180
         S  L  S  E  R  S  H  E  V  Y  R  Q  Q  L  H  G  Q  E  Q  G    27
   181 acaccacggccaagaggagcaaggctgagccgagcacgtcgaggtctacgagaggac    240
         H  H  G  Q  E  E  Q  G  L  S  P  E  H  V  E  V  Y  E  R  T    47
   241 ccatggccagtctcactataggcagacactgctctcgaaggaggctgcaccggatcca    300
         H  H  G  Q  * (TER) S  H  Y  R  R  H  C  S  R  R  L  H  R  I  H    67
         H  G  Q  t(TER)
   301 caggcggcagcatcgctcctgcagaaggcgcaaaagacgctcctgcaggcaccggaggag   360
         R  R  Q  H  R  S  C  R  R  R  K  R  R  S  C  R  H  R  R  R    87
   361 gcatcgcgagagtctgctgcgcccccgcttgcgcccctgcatgtcctgaccaccccaggc    420
         A  S  R  E  S  A  A  P  L  A  P  L  H  V  L  D  H  P  R    91
         H  R  G
   421 acaggaggaggcggggaccctagtgacccctcaacagctccagccccctaaacccgtc    480
                                                                    c
   481 ccacccagagtccctagtgaccccctcaacagaacttctttcccaaaaggtgcag    540
                                                            C  R    93
   541 aaccaggaagagaacatgcagaaggcactaagcttcctggcccctcagccccagctgga    600
         T  R  K  R  T  C  R  R  H  Ter                            102
   601 aattaagaaaaagtcgcccgaaacaccaagtgaggcatagcaattcccctacatcaaat   660
                                                    primer P2B
   661 gctcaagcccccagctggaagctggaagttaagagaaagtcacctgcccaagaaacaccgagtgagg   720
   721 ccatagcaactcccctactacatcaaatgctcaagccctgagttgccgccgagaagcccacaa   780
   781 gatctggagtgaaattgagcaaagtcacctgcccgccgcttga
```

MOUSE SPERMATOGENESIS GENES RELATED TO HUMAN MALE STERILITY

TECHNICAL FIELD

The invention of this application relates to an assembly (a group of genes: MSGs) of genes involved in mouse spermatogenesis (mouse spermatogenesis genes: hereinafter sometimes referred to as "MSG") and a diagnostic system using the MSGs. More specifically, the invention relates to respective methods, e.g., toxicity test, mutagenicity test, and genetic diagnosis, which comprise detecting expression modulation, mutation, replacement of amino acid(s), and the like of MSG using respective genes and gene materials (purified polynucleotides, polypeptides as gene expression products, antibodies, etc.). The methods of the invention can be employed as a mutagenicity test and toxicity test (inclusive of a test relating to influence on reproduction) of medicaments and chemicals or as means for detection or environmental measurement of environmental hormones or endocrine disruptors and environmental assessment. Furthermore, the genes and genetic materials of the invention and respective method inventions contribute development of medical technologies on diagnosis, therapy and prevention of male infertility and development of diagnostic agents, therapeutic medicines or preventive medicines therefor, or contraceptive medicines.

Moreover, the invention of the application relates to methods for diagnosing male infertility wherein mutation or expression change of human male infertility-associated genes which are human homologues of mouse genes contained in the above MSGs; and wherein such a gene polymorphism as test targets. More specifically, the invention relates to methods for diagnosing male infertility wherein mutant polynucleotides derived from male infertility-associated genes characterized by point mutation or gene polymorphism, mutant polypeptides as the gene products thereof, and methods for diagnosing male infertility wherein these mutant polynucleotides and mutant polypeptides are used as targets. Moreover, similarly to the case of the above mouse MSG, the gene materials based on the information obtained from human homologues contribute to the development of medical technologies on diagnosis, therapy and prevention of male infertility and development of diagnostic agents, therapeutic medicines, preventive medicines, or contraceptive medicines there of.

BACKGROUND ART

Mouse Spermatogenesis Genes

Since proposal of the concept of endocrine disruptors (hereinafter sometimes referred to as "ED") (1997), the risk of a low sperm count and impaired reproductive function to be induced by the ED has widely been well known, a sense of fateful crisis of human being has been raised and also global environmental conservation measures by development of MSDS (material safety data sheet) and PRTR (pollutant release and transfer registers) have been accelerated, so that development of methods for detecting and measuring ED and confirmation of influence of ED on living organisms become urgent problems. Furthermore, the conventional test for "influence on reproduction" with regard to medicaments, chemical agents, chemical products, chemical substances, and the like is a test only for teratogenicity as a measure. However, in order to avoid and sweep away the risk of impaired reproductive function to be induced by the ED, it is defective and insufficient to carry out the conventional teratogenicity test alone; therefore it is necessary to add detection of "mutagenicity for spermatogenesis genes of mammalians or human homologous genes thereof" or test for influence on spermatoblasts and processes of their differentiation and spermatogenesis (e.g., toxicity test or assay using expression modulation, mutation, amino acid replacement, or the like of MSG in a mouse testis or in vitro as a measure), to the toxicity test including a test for "influence on reproduction". Thus, it is considered that the detection or test is considered to be a compelling problem to be necessarily solved.

However, heretofore, there are not known technologies on the toxicity test using expression modulation or mutation of spermatogenesis genes as a measure (test for influence on reproduction), the mutagenicity test, ED detection, and the like. The reason is that spermatogenesis genes usable as test targets are not identified.

Moreover, Western developed countries including Japan, it is known that about 10% of total married couple have experienced some forms of infertility problems and there is a possibility that about a half of them is attributed to factors at the male side. Part of the causes of male infertility suggested includes endocrine disorders, genetic factors including chromosomal abnormalities, environmental factors, anomalies including enorchima and varicocele (Rubio C, et al. Human Reprod 2001; 10: 2084-2092; Lee P A, et al. (2000) J Urol., 164(5), 1697-1701). However, most of the causes of male infertility are insufficient spermatogenesis and aspermatogenesis and the causes of the problems are not elucidated yet at present (Cram D S, et al. (2001) J Androl 22(5), 738-746). Moreover, among the cases of male infertility, there exist cases considered to be associated with various inherited factors (Thielemans B F J, et al. Eur. J. Obst Gynec 1998; 81: 217-225), but causative genes thereof are not always identified. Therefore, establishment of methods for diagnosing, treating, or preventing male infertility (e.g., genetic diagnosis and achievement of genetic therapy, drug treatment, and prevention based on a result of such a diagnosis) is a long-awaited problem to be solved, which provides significant good news for human being. Furthermore, when it is called to mind that high rates of birth may be accompanied by poverty, starvation and malnutrition, spread of infectious diseases such as AIDS, and the like in developing countries, development of contraceptives is also considered to be an important problem.

As mentioned above, in order to achieve effective detection of ED and the like by toxicity test or mutagenicity test, or to diagnose male infertility more reliably, a molecular biological approach targeting spermatogenesis genes is indispensable. However, heretofore, any spermatogenesis gene (group) usable in such tests has not been identified and, as a matter of course, there is no proposal of means for applying such a gene (group) to various tests.

The invention of this application is accomplished in consideration of the above circumstances and an object thereof is to provide mouse spermatogenesis genes (MSGs) usable in the toxicity test, the mutagenicity test, or genetic diagnosis relating to ED detection and the like, and purified polynucleotides, polypeptides, antibodies, and the like as materials for carrying out such tests.

Also, another object of the invention is to provide respective methods for toxicity test, mutagenicity test, and genetic diagnosis using MSGs.

Mutation of Human Male Infertility-Associated Genes

As a result of extensive investigations of the relation between human homologues of mouse genes belonging to MSGs and male infertility, the inventors of this application have found that specific mutation in human Scot-t gene and protamine genes is involved in male infertility. In this regard, with regard to the relation between Scot-t gene and protamine genes and male infertility, the following have been known.

Succinyl CoA:3-oxo acid CoA transferase (OXCT/SCOT) is one of important enzymes in the energy metabolism of a ketone body and the ketone body is produced in the lever and transported to peripheral tissues to be used as an energy source (Mitchell G A, et al. Clin. Invest. Med. 1995; 18: 193-216). Succinyl CoA transferase (SCOT) is localized in a mitochondria of some tissues and catalyzes formation of acetoacetyl CoA by transferring the CoA moiety from succinyl CoA to acetoacetic acid. The acetoacetyl CoA is further decomposed into two acetyl CoA molecules capable of entering tricarboxylic acid cycle (Williamson, D. H. et al. (1971) Biochem. J., 121, 41-47; Tildon J T et al. J Clinic Invest 1972; 51: 493-498). Although cDNA of Scot has been cloned from swine and human heart (Lin, T. W. and Bridger W. A. (1992) J. Biol. Chem., 267, 975-978; Kassovska-Bratinova S, et al. Am J Hum Genet 1996; 59: 519-528), the inventors of this application has hitherto been cloned a novel gene named scot-t encoding haploid germ cell-specific SCOT from a differential cDNA library of mouse testis (Koga M, et al. Biol. Reprod 2000; 63: 1601-1609). The SCOT-t is an iso-form of SCOT specific to germ cells, is present in haploid sperm and sperm mitochondria, and is considered to play a specific role also in spermatogenesis and energy metabolism of sperm. According to Northern blotting, Western blotting, and immunohistochemical analysis, expression of mouse scot-t is detected in testis, especially in late spermatid, but is not detected in the other somatic cells. The nucleotide sequence of mouse scot-t has homology of 63.4% and 62.7% to Scot of swine and human hearts, respectively and presumed amino acid sequence has homology of 68.0% and 67.4%, respectively. One to 39 residues at $NH_2$ terminal of SCOT-t form a signal sequence targeting mitochondria. Actually in immunofluorescent stain, localization of SCOT-t protein in mitochondria in immobilized sperm obtained from tail of epididymis is shown (Koga M, et al. Biol Reprod 2000; 63: 1601-1609). The amino acid sequence of SCOT-t contains one glutamic acid residue (the amino acid residue in position of 341th), which corresponds to glutamic acid 344 which is known to be conserved in all CoA transferases including SCOT (Rochet J C, Bridger W A, (1994) Protein Sci., 3, 975-81). The inventors of this application have also cloned and characterized human orthologue of mouse scot-t. Whole coding region of mRNA of human Scot-t and deduced amino acid sequence show homology of 75.4% and 75.8% relative to those of mouse scot-t, respectively. Similarly, the inventors have indicated that h-Scot-t is a single gene having no introns and is expressed specifically in testis (Tanaka H, et al. Mol Human Reprod 2001; 8: 16-23).

There are some reports on importance of mitochondrial enzymes in energy metabolism in motility and functions of sperm (Pascual, M. I., et al. (1996) Biosci. Rep., 16, 35-40; Yeung, C. H., et al. (1996) Mol. Hum. Reprod., 2, 591-596; Ruiz-Pesini, E. et al. (1998) Clin. Chem., 44, 1616-1620). The fact that Scot-t is specifically present is considered to show the presence of a novel metabolic system wherein a ketone body is utilized as an energy source for sperm motion. Furthermore, since Scot-t is specifically expressed in haploid spermatids, it is suggested that Scot-t may play some specific role in spermatogenesis.

Moreover, a remarkable reorganization in sperm nuclei occurs at a spermatogenesis stage. In this process, histone is removed and the nuclei undergo replacement by a specific nuclear protein and finally replaced by protamine having a high positive charge, whereby it is highly compressed (Wounters-Tyrou, D. et al. (1998) Biochimie, 80, 117-128; Sassone-Corsi P. (2002) Science, 296, 2176-2178). DNAs of human sperm are assembled in head of sperm in a highly condensed state by two kinds of protamines, i.e., protamine-1 and protamine-2. Protamine-1 is a single polypeptide molecule having 50 amino acids, on the other hand, protamine-2 is a complex of at least two different forms having 57 and 54 amino acids (Mckay, D. J. et al. (1986) Eur. J. Biochem., 158, 361-366). Protamine-2 family proteins are synthesized as precursors having 66 to 101 residues based on a single copy gene present in the 16th chromosome (Krawetz, S. A. et al. (1989) Genomics. 5, 639-645; Reeves, R. H. et al. (1989) J. Hered, 80, 442-446).

It is suggested that male infertility occurs as a result of the nuclear concentration disorder. In mouse, as a result of early translation of mRNA of protamine-1, immature nuclear concentration occurs to terminate differentiation of sperm (Lee, K. et al. (1995) Proc. Nat.l. Acad. Sci. USA, 92, 12451-12455). In various studies targeting infertile patients, decrease of content of protamine-2 has been reported (Balhorn, R. et al. (1988) Experientia., 44, 52-55; Belokopytova, J. A. et al. (1993) Mol. Reprod. Dev., 34, 53-57), and there is a report that completely selective protamine-2 deficit is observed in sperm nuclei of part of male infertile patients (de Yaba, L. et al. (1993) J. Biol. Chem., 268: 10553-10557). However, in the results of sequence analysis of protamine-2 gene obtained from these patients, the presence of mutation causing the detected decrease of protamine-2 is not observed (de Yaba, L. et al. (1993) J. Biol. Chem., 268: 10553-10557; Schlicker, M. et al. (1994) Hum Reprod., 9, 2313-2317). Moreover, it is suggested that decrease of protamine-2 occurs owing to incomplete processing of protamine-2 precursor molecules in part of infertile patients (dYebra, L. et al. (1998) Fertil Steril., 69, 755-759).

As mentioned above, it is pointed out that some mutation of Scot-t gene or protamine gene may be associated with male infertility but the reality of the situation is not at all elucidated. An object of the invention of this application is to provide Scot-t gene mutation and protamine-2 gene mutation as causal genes of human male infertility.

Also, another object of the invention is to provide a mutant polypeptide expressed with the above gene mutation, an antibody against the mutant polypeptide, and a method for diagnosing male infertility using these mutant gene and mutant polypeptide as test targets.

DISCLOSURE OF INVENTION

This application provides the following mouse spermatogenesis gene group and inventions utilizing the same as inventions for achieving the above objects.

Namely, the invention provides a group of mouse spermatogenesis genes, which is an assembly of 89 genes in total, wherein the respective genes transcribe mRNAs from which cDNAs having the respective base sequences of SEQ ID NOs:1 to 89 are synthesized.

The invention provides a cDNA library, which consists of cDNAs derived from the respective genes belonging to said group of mouse spermatogenesis genes.

The invention provides a group of DNA fragments each consisting of the base sequence of continuous 10 to 99 bases of the respective cDNAs belonging to said group of cDNA library.

The invention provides a group of primer sets for PCR amplification of DNAs of the respective genes belonging to said group of mouse spermatogenesis genes or the respective cDNAs belonging to said group of cDNAs.

The invention provides a microarray comprising one or more cDNAs belonging to said group of cDNAs or one or more DNA fragments belonging to said group of DNA fragments.

The invention provides a group of mouse spermatogenesis polypeptides, which is an assembly of 78 polypeptides in total, wherein the respective peptides have the respective amino acid sequences of SEQ ID NOs:90 to 167.

The invention provides a group of antibodies against the respective polypeptides belonging to said group of mouse spermatogenesis polypeptides.

The invention further provides a method for assaying toxicity or mutagenicity of a subject substance, which comprising detecting expression modulation or mutation of one or more genes belonging to said group of mouse spermatogenesis genes.

Furthermore, the invention provides a method for diagnosing reproductive ability of a subject individual, which comprises detecting expression modulation or mutation of one or more genes belonging to said group of mouse spermatogenesis genes.

Namely, the MSGs of the above invention is cloned by the following three kinds of methods based on the concept that "detection of expression modulation and mutation of spermatogenesis genes can be utilized to a toxicity test, especially a reproductive toxicity test and a mutagenicity test".

(a) Cloning Using Monoclonal Antibody

A monoclonal antibody specifically recognizing each processes of spermatogenesis was prepared and an objective gene (group) was identified. Namely, a cell extraction fraction was obtained from mouse testis and rats were immunized therewith. After thorough immunization, the obtained spleen cells were subjected to cell fusion with myeloma cells to prepare hybridomas. In order to search for a hybridoma which prepares an antibody specifically recognizing spermatoblast from the obtained respective hybridomas, the hybridomas were screened by reacting them with slices of the testis and investigating what kinds of antigens were recognized by antibodies produced in culture supernatants of respective hybridomas, whereby hybridomas producing spermatoblast-specific antibodies were obtained. Using the obtained monoclonal antibody, genes encoding antigen proteins recognized by the antibodies were cloned from a mouse testis library expressed in *Escherichia coli*.

(b) Cloning Using Polyclonal Antibody

A polyclonal antibody specifically recognizing spermatoblasts (inclusive of cells at all differentiation stage) was prepared and an objective gene (group) was identified. Namely, a spermatoblast extract fraction was obtained from mouse testis and rabbits were thoroughly immunized therewith. The obtained serum was injected into abdominal cavity of a castrated male mouse and antibodies recognizing cells other than spermatoblast were absorbed. A serum content of the mouse was collected and further reacted with a liver extraction fraction. Antigen genes recognized by the rabbit antibodies contained in the obtained serum were cloned from a mouse testis library expressed in *Escherichia coli*.

(c) Cloning Using Subtracted Library

A subtracted library containing a concentrated gene group specific to spermatoblasts was prepared and a gene group specifically expressed at each differentiation stage was cloned, followed by analysis of functions of each resulting clone. In particular, spermatid is a sole haploid cell which is present in an animal individual in a large number for a long period of time. Since the genes of the group specifically expressed in such spermatid each exhibits a specific function for spermatogenesis, these genes of the group were comprehensively cloned and phenomena specific to spermatogenesis were analyzed. Specifically, a subtracted library was obtained wherein mRNAs expressed in testis of a 17 day-old mouse having no spermatid were subtracted from a cDNA library of testis of 35 day-old mouse (C57BL/6) having spermatoblasts at all differentiation stages was prepared. From the subtracted library, a gene group specifically expressed at a morphogenesis stage of spermatid.

By the above methods (a) to (c), 89 clones in total of spermatoblast-specific gene cDNAs (MSGs cDNAs) were obtained. Then, basic sequences of respective cDNA clones were determined according to a known method, and it was confirmed that these cDNAs were composed of basic sequences shown in odd number sequences of SEQ ID NOS:1 to 89. Moreover, homology search thereof was carried out among various base sequences already reported and it was found that, in 89 of the MSG clone, known genes were about 26%, homologous genes were 32%, and especially, unknown gene were up to 42%.

Table 1 shows, from left to right, "Sequence Number", "Name of Gene" (known one), "Database (GenBank) Registry Number", "Sequence Number of Polypeptide" encoded by the gene, and "Coding Region" thereof, of 89 genes in total shown in SEQ ID NOS: 1 to 89.

TABLE 1

| | | | | |
|---|---|---|---|---|
| 1 | AKAP110 | | AF093406 | 90 | 292-2884 |
| 2 | | | | unidentified |
| 3 | Rbcc728 (human), Trim36 (human) | | 91 | 45-2202 |
| 4 | Nopp140 (rat) | | 92 | 401- |
| 5 | | | 93 | 1-302 |
| 6 | | | 94 | 12-573 |
| 7 | | | 95 | 109-889 |
| 8 | | | 96 | 543-861 |
| 9 | | | | unidentified |
| 10 | | | 97 | 1-372 |
| 11 | | | 98 | 1-319 |
| 12 | ATR | AF236887.1 | 99 | 168-606 |
| 13 | | | 100 | 396-546 |
| 14 | HSpb (mouse) | | | unidentified |
| 15 | | | | unidentified |
| 16 | Spergen-1 (rat) | AB047508 | 101 | 66-513 |
| 17 | | | 102 | 140-1445 |
| 18 | | | 103 | 1046-1994 |
| 19 | | | 104 | 362-1127 |

TABLE 1-continued

| | | | | |
|---|---|---|---|---|
| 20 | arylsulfatase A | X73230 | 105 | 642-2160 |
| 21 | | | 106 | 111- |
| 22 | | | 107 | 1-202 |
| 23 | | | 108 | 47-550 |
| 24 | Drctnnb1a | | 109 | 228-768 |
| 25 | | | 110 | 1-420 |
| 26 | | | | unidentified |
| 27 | | | 111 | 1-278 |
| 28 | | | 112 | 334-2719 |
| 29 | | | | unidentified |
| 30 | | | 113 | 165-462 |
| 31 | | | 114 | 242-695 |
| 32 | | | | unidentified |
| 33 | | | | unidentified |
| 34 | CDC14B (human) | | 115 | 1-534 |
| 35 | | | | unidentified |
| 36 | cystatin-related epididymal spermatogenic protein | AF090691 | 116 | 180-606 |
| 37 | | | | unidentified |
| 38 | | | 117 | 511-868 |
| 39 | | | 118 | 1-619 |
| 40 | pregnancy-induced growth inhibitor AY037158.1 (human) | | 119 | 287-698 |
| 41 | | | | unidentified |
| 42 | | | 120, 121 | 160-550, 618-957 |
| 43 | fatty acid coenzyme A ligase, long chain 2 | NM_007981 | 122 | 1-2098 |
| 44 | Fem | NM_010193 | 123 | 75-1956 |
| 45 | major 80,000 Mr fibrous sheath component | U10341 | 124 | 121-2668 |
| 46 | | | 125 | 14-566 |
| 47 | | | 126 | 46-655 |
| 48 | Glycerol phosphate dehydrogenase 1, mitochondrial | NM_010274 | 127 | 131-2312 |
| 49 | Lim domains containing 1 | NM_013860 | 128 | 527-2531 |
| 50 | oaz-t | AB016275 | 129 | 193-788 |
| 51 | pctp-1 | AB031550 | 130 | 325-1198 |
| 52 | testis-specific phosphoglycerate kinase | M18654 | 131 | 21-1272 |
| 53 | phospholipase C delta 4 | AF125974 | 132 | 26- |
| 54 | protamine 1 | X07625 | 133 | 1-145 |
| 55 | protamine 2 | NM_008933 | 134 | 82-388 |
| 56 | scot-t1 | AB022180 | 135 | 32-1592 |
| 57 | scot-t2 | AB049996 | 136 | 32-1592 |
| 58 | mitochondrial capsule selenoprotein | NM_008574 | 137 | 190-819 |
| 59 | SP-56 | U17108 | 138 | 80-181 |
| 60 | Sperizin | AB016984 | 139 | 113-1093 |
| 61 | oppo 1 | AB074438 | 140 | 83-917 |
| 62 | Gal beta-1, 3-GalNAc-specific GalNAc alpha-2, 6-sialyltransferase | X93999 | 141 | 67-1186 |
| 63 | suppressor of fused homolog (Drosophila) | NM_015752 | 142 | 148-1603 |
| 64 | t-actin 1 | AB023062 | 143 | 28-1282 |
| 65 | t-actin 2 | AB023063 | 144 | 64-1384 |
| 66 | t-complex Tcp-10a | X58170 | 145 | 897-2211 |
| 67 | tektin-t | AB027138 | 146 | 117-1407 |
| 68 | teek 1 | NM_009355 | 147 | 28-1129 |
| 69 | TP-2 | M60254 | 148 | 61-412 |
| 70 | tsec-1 | AB000619 | 149 | 211-1252 |
| 71 | tssk 1.2 substrate | AF025310 | 150 | 25-1603 |
| 72 | serine/threonine kinase 22B (spermiogenesis associated) | NM_009436 | 151 | 28-1099 |
| 73 | SCP1 | D88539 | 152 | unidentified |
| 74 | tsga2 | NM_025290 | 153 | 90-942 |
| 75 | Gapd-S | NM_008085 | 154 | 1-131 |
| 76 | meichroacidin | D88453 | 155 | 90-941 |
| 77 | halap-X | AB032764 | 156 | 1-805 |
| 78 | | | 157 | 158-1082 |
| 79 | Ssecks | AF326230 | 158 | 457-5194 |
| 80 | gsg1 | NM_010352 | 159 | 144-1056 |
| 81 | haspin | NM_010353 | 160 | 34-2296 |
| 82 | gsg3 | NM_007605 | 161 | 111-1008 |
| 83 | hils1 | NM_018792 | 162 | 241-649 |
| 84 | | | 163 | 14-1208 |
| 85 | | | 164 | 292-973 |
| 86 | shippo1 | AB067773 | 165 | 121-883 |
| 87 | putative lysophosphatidic acid acyltransferase | NM_018743 | 166 | 78-534 |
| 88 | | | 167 | 1-292 |
| 89 | | | | unidentified |

Furthermore, the following findings (1) to (4) were obtained in the above MSG clones group.

(1) With regard to the gene structure, most of 89 clones of MSG have no intron and, even if intron is present, most of them have very little one.

(2) Most of them have no known transcription-related factor-binding sequence such as TATA, CAAT, GC motif, and the like.

(3) Expression timing is specific to the spermatogenesis stage. For example, in the process of primordial germ cell->spermatogonium->spermatocyte->spermatid (haploid)->sperm->acquisition of reproductive ability in female genital tract, there are a number of genes specifically expressing only at the stage of spermatid->sperm.

(4) With regard to actions and functions of expressed products, there are observed those wherein an iso-form characteristic to germ cell against somatic cells is present and which exhibits considerably specific activity at respective stages of spermatogenesis. For example, those exhibiting the action only in the fertilization process are present.

Of these findings, the above (1) and (3) relating to intron are particularly important. Namely, the reasons are as follows: it is suggested that "the structures and transcription of the genes involved in spermatogenesis are (1) relatively simple and detection of mutation is not difficult and even when mutation occurs in the gene, the (3) expression occurs only in germ cells and the mutation character does not appear in somatic cells but appears only in germ cells to result in infertility" and it is judged that detection of the expression modulation and mutation is utilizable as a reproduction toxicity test and a mutagenicity test.

In this regard, part of the findings regarding Table 1 and the above MSGs are described in detail in the following literatures reported by the inventors of this application: Int. J. Androl. 20: 361-366, 1997; Gene 204: 159-163, 1997; Genomics 46: 138-142, 1997; Mammal. Genome 8: 873-874, 1997; Cytogenet. Cell Gent. 78: 103-104, 1997; Nature 387: 607-611, 1997; Dev. Biol. 197: 67-76, 1998; Biol. Reprod 58: 261-265, 1998; Gene 237: 193-199, 1999; J. Biol. Chem. 274: 17049-17057, 1999; FEBS Lett. 456: 315-321, 1999; Genomics 57: 94-101, 1999; Biol. Reprod. 62: 1694-1701, 2000; Biol. Reprod. 63: 993-999, 2000; Genes Cells 5: 265-276, 2000; Biol. Reprod. 63: 1601-1609, 2000; Gene 267: 49-54, 2001; Mol. Human Reprod. 7: 211-218, 2001.

Furthermore, this application provides an invention of mutation of a male infertility-associated genes among the genes contained in the above group of mouse spermatogenesis genes and inventions utilizing the genes' mutation.

Namely, the invention provides a polynucleotide (Scot-t mutant polynucleotide) or a complementary sequence thereof, which polynucleotide is complementary to mRNA transcribed from a human male infertility-associated gene Scot-t, and has one or more mutations selected from the following group:

"t" at 129th position is replaced by "c";
"t" at 870th position is replaced by "g";
"c" at 1071st position is replaced by "at"; and
"t" at 1667th position is replaced by "c", in the DNA sequence of SEQ ID NO:168.

The invention provides a Scot-t mutant oligonucleotide or a complementary sequence thereof, which is part of the above Scot-t mutant polynucleotide and is a DNA sequence consisting of continuous 10 to 99 bases containing the said mutation sites.

The invention provides a polynucleotide (Scot-t mutant genomic polynucleotide) derived from a human chromosomal DNA, which hybridizes the above Scot-t mutant polynucleotide or the above Scot-t mutant oligonucleotide or the complementary sequences thereof under a stringent condition.

The invention provides a primer set for PCR amplification of the above Scot-t mutant polynucleotide, the above Scot-t mutant genomic polynucleotide, or the mRNA transcribed from the Scot-t mutant genomic polynucleotide, wherein one of the primers is an oligonucleotide or a complementary sequence thereof which is a DNA sequence consisting of continuous 15 to 45 bases containing the mutation site.

The invention provides a polynucleotide (protamine-2 mutant polynucleotide) or a complementary sequence thereof, which polunucleotide is complementary to mRNA transcribed from a human male infertility-associated gene protamine-2, and "c" at 248th position is replaced by "t" in the DNA sequence of SEQ ID NO:173.

The invention provides an oligonucleotide (protamine-2 mutant oligonucleotide) a complementary sequence thereof, which is part of the protamine-2 mutant polynucleotide and is a DNA sequence consisting of continuous 10 to 99 bases containing the mutation site.

The invention provides a polynucleotide (protamine-2 mutant genomic polynucleotide) derived from a human chromosomal DNA, which hybridizes the protamine-2 mutant polynucleotide or the protamine-2 mutant oligonucleotide or the complementary sequences thereof under a stringent condition.

The invention provides a primer set for PCR amplification of the above protamine-2 mutant polynucleotide, the protamine-2 mutant genomic polynucleotide, or the mRNA transcribed from the protamine-2 mutant genomic polynucleotide, wherein one of the primers is an oligonucleotide or a complementary sequence thereof which is a DNA sequence consisting of continuous 15 to 45 bases containing the mutation site.

The invention provides a polypeptide (Scot-t mutant polypeptide), an expression product of the above Scot-t mutant polynucleotide or Scot-t mutant genomic polynucleotide, which has one or more mutations selected from the following group:

Leu at 38th position is replaced by Pro;
Leu at 285th position is replaced by Arg; and
Thr at 352nd position is replaced by Met, in the amino acid sequence of SEQ ID NO:169.

The invention provides a polypeptide (protamine-2 mutant polypeptide), an expression product of the above protamine-2 mutant polynucleotide or protamine-2 mutant genomic polynucleotide, which consists of the amino acid sequence of 1st to 49th positions of the amino acid sequence of SEQ ID NO:174.

The invention provides an oligopeptide (Scot-t mutant oligopeptide), which is a part of the above Scot-t mutant polypeptide and is an amino acid sequence consisting of continuous 5 to 30 amino acids containing the mutation site.

The invention provides an oligopeptide (protamine-2 mutant polypeptide), which is a part of the protamine-2 mutant polypeptide and is an amino acid sequence consisting of continuous 5 to 30 amino acids.

The invention provides an antibody (anti-mutant Scot-t antibody) prepared using the above Scot-t mutant oligopeptide as an antigen, and an antibody (anti-mutant protamine-2 antibody) prepared using the above protamine-2 mutant oligopeptide as an antigen, respectively.

The invention provides an antibody (anti-protamine-2 antibody) prepared using the oligopeptide consisting of the amino acid sequence of 50th to 91st positions of SEQ ID NO:174 or an amino acid sequence of 1st to 11th positions of SEQ ID NO:175 as an antigen.

The invention also provides a method for diagnosing male infertility, which comprises detecting presence of the Scot-t mutant genomic polynucleotide or protamine-2 mutant genomic polynucleotide in a chromosomal DNA isolated from a subject person.

In the above diagnostic method, a preferred embodiment comprises detecting whether a chromosomal DNA or an mRNA thereof isolated from a subject person hybridizes the Scot-t mutant polypeptide or protamine-2 mutant polynucleotide or the Scot-t mutant oligonucleotide or protamine-2 mutant oligonucleotide, or a complimentary sequence thereof under a stringent condition or not. Moreover, in the diagnostic method, another preferred embodiment comprises detecting presence of a PCR product when PCR is carried out using a chromosomal DNA or mRNA isolated from a subject person as a template with the respective primer sets.

The invention provides a method for diagnosing male infertility, which comprises detecting presence of the Scot-t mutant polypeptide or protamine-2 mutant polypeptide in a biological sample isolated from a subject person.

In the above diagnostic method, a preferred embodiment comprises detecting presence of a polypeptide reactive to the anti-mutant Scot-t antibody in a biological sample isolated from a subject person. Moreover, in the diagnostic method, another preferred embodiment comprises detecting presence of a polypeptide reactive to the anti-mutant protamine-2 antibody but not reactive to the anti-protamine-2 antibody in a biological sample isolated from a subject person.

The invention provides a DNA probe, which is labeled Scot-t mutant oligonucleotide or labeled protamine-2 mutant oligonucleotide.

The invention provides a DNA chip comprising the above Scot-t mutant oligonucleotide and/or protamine-2 mutant oligonucleotide.

The invention provides a labeled antibody, wherein the above anti-mutant Scot-t antibody, anti-mutant protamine-2 antibody, or anti-protamine-2 antibody is labeled.

Namely, as a result of analysis on DNA samples of 516 male persons (infertility: 255 cases, healthy persons: 261 cases) for Scot-t gene and 496 male persons (infertility: 226 cases, healthy persons: 270 cases) for protamine genes, the inventors of this application have found that nucleotide mutations and resulting amino acid mutations as shown in Table 2 are present in each cDNA (Scot-t: SEQ ID NO:168, protamine-1: SEQ ID NO:170, protamine-2: SEQ ID NO:173). They have found that one base replacement and amino acid mutation in Scot-t and a shortened protein caused by one base replacement in protamine-2 are particularly important as a cause of male infertility. In this regard, SEQ ID NO:168 corresponds to the base sequence of 4th to 1760th in known human Scot-t cDNA (GenBank/AB050193). SEQ ID NO:170 corresponds to the base sequence of 532-1089 in known human protamine-1 cDNA (GenBank/M60331). Moreover, SEQ ID NO:173 corresponds to a base sequence of 804-1629 in known human protamine-2 cDNA (GenBank/M60332). The positions of nucleotide mutations and amino acid mutations in Table 2 correspond to the base positions and amino acid positions in the sequence tables. Moreover, the sign of "-" means a non-coding region, "silent" means that the amino acid does not mutate with the nucleotide mutation, and the mark of "***" means mutation into a stop codon. In addition, "deletion" means deletion of a nucleotide and "addition" means addition of a nucleotide.

TABLE 2

| Nucleotide Mutation | Amino Acid Mutation |
|---|---|
| Scot-t | |
| t129c | Leu38Pro |
| t870g | Leu285Arg |
| c1071t | Thr352Met |
| t1667c | — |
| Protamine-1 | |
| c44: eletion | — |
| g73: addition | — |
| a133g | (silent) |
| c160a | (silent) |
| g363a | (silent) |
| c364a | (silent) |
| a431g | — |
| Protamine-2 | |
| c248t | Glu50*** |
| g398c or a | — |
| a473c | — |
| t493: deletion | — |

In each invention of this application, a "gene" is present in a genomic DNA and is a double-stranded DNA encoding a specific polypeptide (protein), and it contains a coding region (open reading flame: ORF) and expression-regulating region(s) (promoter/enhancer sequence, repressor sequence) according to the ORF.

In the invention of this application, the "polynucleotide" and "oligonucleotide" mean long-chain or single-chain nucleotide chains, respectively. A tentative criteria are that the polynucleotide contains 100 bp or more and oligonucleotide contains less than 100 bp, but there exist some exceptions.

In the invention, the "polypeptide" and "oligopeptide" mean long-chain or single-chain peptide chains, respectively. A tentative criteria are that the polypeptide contains 30 amino acids or more and oligopeptide contains less than 30 amino acids, but there exist some exceptions.

Moreover, in the following explanation, "influence on reproduction" means not teratogenicity but influence on spermatogenesis and fertility.

Furthermore, the other terms and concepts used in the invention may be explained in the description of Mode for Carrying Out the Invention and Examples. In this regard, various gene manipulating technologies and molecular biological technologies used for carrying out the invention are easily and surely practicable for those skilled in the art based on known literatures (e.g., Sambrook and Maniatis, in Molecular Cloning—A Laboratory Manual, Cold Spring Harbor Laboratory Press, New York, 1989; Ausubel, F. M. et al., Current Protocols in Molecular Biology, John Wiley & Sons, New York, N.Y., 1995, etc.) except for the technologies for which their sources are particularly indicated.

BRIEF DESCRIPTION OF THE DRAWINGS

FIG. 1 is a schematic illustration demonstrating human Scot-t genomic DNA and protein together with SNPs positions. Horizontal arrows show two pairs of primers.

FIG. 2 shows a genomic DNA sequence of protamine-1 and primers for PCR amplification and sequence analysis. Translation starting point, intron, and canonical poly A addition signal are shown by +1, an outline box, and shadowed characters, respectively. The primer sequences are underlined parts. The amino acid sequence of each protein is written with capital letters under the nucleotide sequence. Numerals in right margin show position numbers of nucleotide and amino acid (thick letters) sequences (the nucleotide position number is a number from the translation starting point (+1) and note that it is different from SEQ ID NO:170). SNPs are shown by thick letters. Asterisk shows difference of nucleotides possessed by 496 cases of human male patients of parent population in which infertility and reproduction ability are proved, from GenBank registered sequence (EMBL/DDBJ/GenBank/Y00443, M29706, M60331, M60332).

FIG. 3 shows, just as FIG. 2 shows, a genomic DNA sequence of protamine-2 and primers for PCR amplification and sequence analysis.

BEST MODE FOR CARRYING OUT THE INVENTION

The mouse spermatogenesis genes group (MSGs) is an assembly of 89 genes in total wherein cDNAs synthesized from mRNAs transcribed from the respective genes have the base sequences represented by SEQ ID NOS:1 to 89.

cDNAs can be identified by cloning methods of (a) to (c) as mentioned above or a combination thereof. These methods are all known methods and can be carried out by those skilled in the art without requiring undue experiment. For example, basic procedure of operations of the subtraction method in the method (c) is exemplified in general textbooks (Current Protocol in Molecular Biology 1:5.8.9-5.9.20, Green Publishing Associate and Willey-Interscience, 1987-). Namely, (i) after total RNAs and mRNAs are extracted from testis of mature mouse having spermatoblasts at all differential stages, e.g., 35 day-old mouse and purified, cDNAs corresponding to mRNAs are synthesized to prepare a cDNA library, and separately (ii) total RNAs and mRNAs are extracted from testis of immature mouse having undifferentiated spermatoblasts, for example, 17 day-old mouse and purified and the mRNAs are, for example, labeled with biotin. Then, (iii) hybridization is carried out between the above cDNA library and excess concentration of the biotin-labeled mRNAs, and hybrids formed from these both substances and remaining excess biotin-labeled mRNAs are removed by agglomeration with avidin to prepare a subtracted cDNA library. Thereafter, (iv) from the above subtracted cDNA library, for example, by Northern blotting using total RNAs of both 17 day-old and 35 day-old mice, cDNAs specifically reactive to the total RNAs of 35 day-old mouse are selected and collected (cloned) and thereby MSG clones can be obtained. In this regard, when the above cDNA library and subtracted cDNA library are formed in a form of the resulting transformants by inserting and linking the cDNAs to a vector and transferring it into a host *Escherichia coli*, subsequent amplification, preparation, and screening of the cDNAs are all facilitated.

The MSGs of the invention can also be defined as genomic DNA fragments which hybridize oligonucleotide probes synthesized based on the base sequence information of cDNA clones (SEQ ID NOS:1 to 89) identified by the above methods. Hybridization is carried out under "stringent conditions" wherein salt concentration, organic solvent concentration, and temperature, and the like are within certain ranges.

Thus identified gene DNA (genomic DNA) of the MSGs can be isolated by screening the mouse genomic DNA library which is cloned to a BAC (Bacterial Artificial Chromosome) vector, a cosmid vector, a phage vector, or the like, using the above probes. The isolated genomic DNA fragments can be also used as probes, for example, for diagnosing chromosome aberration by fluorescent in situ hybridization (FISH).

Moreover, determination of base sequence of the obtained MSGs clone cDNAs can be conducted by a known method and is usually conducted by a cycle sequence method (Current Protocol in Molecular Biology, 1: 7.4A.12-7.4A.13) using dideoxy method (Sanger method) as an elementary method. An advantage of the cycle sequence method is that a polynucleotide obtained from PCR amplification can be directly sequenced, which can be achieved using a commercially available Thermo Sequenase fluorescent labelled primer cycle sequencing kit [manufactured by Amasham (USA)] and a LC4000 autosequencer [manufactured by LI-COR].

In this regard, polynucleotides (DNA fragments and RNA fragments) can be also purified by known methods from genomic DNAs or mRNAs of respective genes belonging to MSGs. Such purified polynucleotides are useful, for example, as targets to be tested in the toxicity test and the like.

Furthermore, these polynucleotides and the above cDNAs can be used for detection and cloning of homogeneous genes. Namely, for example, homology search using the base sequences of SEQ ID NOS:1 to 89 enables detection of homologous genes of animals and plants other than mouse homologous to the MSGs, e.g., homologous base sequences in human genomic DNA. For the homology search, it is possible to use gene databases provided by, for example, DDBJ (http://www.ddjb.nig.ac.jp/), NCBI (http://www/ncbi.nim.nih.gov/), and the like. The homologous gene can be found in the form of a full-length base sequence, EST (expression sequence tags), STS (sequence tagged sites), GSS (genome survey sequence), SNP (single nucleotide polymorphism), or the like. Moreover, these homologous genes can be screened and cloned, for example, directly from human chromosomal DNAs (using DNAs extracted and prepared from chromosome of human sperm, leucocyte, etc.), or by hybridization using probes provided by the invention, RT-PCR with a PCR primer, or the like.

The DNA fragment group of the invention is an assembly of respective gene DNAs belonging to the above MSGs group or continuous 10 to 99 base fragments (sense chains or antisense chains) of respective cDNAs belonging to the above cDNA group. These DNA fragments are useful as probes in the hybridization assay for detecting mutation of gene MSGs, for example. Moreover, they can be used as probes for the reproduction toxicity test and preparation of a microarray for gene diagnosis of infertility.

These DNA fragments can be also prepared by synthesis in accordance with usual methods or optionally by cleavage of the above polynucleotides and cDNAs with appropriate restriction enzymes.

The primer set group of the invention is an assembly of synthetic oligonucleotides for PCR amplification of the above gene MSGs and cDNAs, and expression modulation and mutation of respective genes of MSGs can be detected by PCR using these primer sets.

These primer sets can be designed on the basis of the base sequences of SEQ ID NOS:1 to 89 and prepared via respective steps of synthesis and purification. In this regard, since success of PCR largely depends on the primer design and setting of various conditions, various ingenuity and trials are necessary to prepare an optimum primer. As points to keep in mind for the primer design, the following may be pointed out, for example. The size of primer (number of bases) is from 15 to 40 bases, preferably 15 to 30 bases in consideration of satisfying a specific annealing with a template DNA. However, in the case that LA (long accurate) PCR is carried out, the number is effectively at least 30 bases. In order to prevent annealing of one set of the sense chain (5-terminal side) and the antisense chain (3-terminal side) or one pair (two primers) of primers each other, use of a complementary sequence between two primers is avoided. Also, in order to prevent formation of hair-pin structure in the primers, it is tried to avoid use of self-complementary sequence. Furthermore, in order to assure a stable binding to the template DNA, GC content is made about 50% and localization of GC-rich or AT-rich may be avoided in the primers. Since annealing temperature depends on Tm (melting temperature), primers having a Tm value which is from 55 to 65° C. and which is close to each other is selected in order to obtain a PCR product having a high specificity. Moreover, it is necessary to take note so that the final concentration of the primer used in the PCR becomes from about 0.1 to about 1 µM. Furthermore, commercially available software for the primer design, for example, Oligo™ [manufactured by National Bioscience Inc., (USA)], GENETYX [manufactured by Software Development K.K. (Japan)], or the like may be employed. In this regard, the invention provides one or more sets of two oligonucleotides for PCR amplification of each cDNA in respective cDNA base sequences for SEQ ID NOS:1 to 89.

The microarray (DNA chip) of the invention is characterized in that the above cDNAs or one or more of continuous 10 to 99 base fragments of the cDNAs are provided as probes in a substrate. In this regard, two or more or five or more cDNAs are preferably provided. Such microarray may be a microarray wherein the DNA fragments are directly synthesized on the substrate or a microarray wherein the DNA fragments are spotted on the substrate coated with a material with which DNA can combine.

The spermatogenic polypeptide group of the invention can be obtained according to a method of isolation from mouse cells, a method of preparing peptides by chemical synthesis based on the amino acid sequences of SEQ ID NOS:90 to 167, or the like methods. In addition, the group can also be obtained in a large amount according to a genetic recombination method using polynucleotides such as cDNAs. Namely, polypeptides encoded by MSGs can be obtained in a large amount by inserting cDNA or an ORF region thereof into an expression vector for in vitro transcription or an expression vector suitable for prokaryotic cells such as *Escherichia coli* and *Bacillus subtilis* and eukaryotic cells such as yeasts, insect cells and mammalian cells, and by in vitro transcription or from transformant cells transformed with the expression vectors. The transformant cells can be produced by transferring the recombinant vectors into cells according to known methods such as electroporation, calcium phosphate method, ribosome method, and DEAE dextran method. Moreover, for isolation and purification of the polypeptides from culture products of the transformant cells, use can be made of known methods, for example, treatment with a denaturing agent such as urea or a surfactant, ultrasonic treatment, enzymatic digestion, salting-out or solvent precipitation method, dialysis, centrifugation, ultrafiltration, gel filtration, SDS-PAGE, isoelectric focusing electrophoresis, ion-exchange chromatography, hydrophobic chromatography, affinity chromatography, reverse phase chromatography, and the like. In this regard, the polypeptides of the invention include fused proteins with other any proteins. For example, fused proteins with glutathion-S-tansferase (GST), green fluorescent protein (GFP), or the like may be mentioned. Furthermore, proteins expressed in cells may sometimes undergo various modifications in the cells after translation. Accordingly, the modified proteins are also included in the invention. Such modifications after translation are elimination of N-terminal methionine, N-terminal acetylation, sugar-chain addition, limited degradation with an intracellular protease, myristoylation, isoprenylation, phosphorylation, and the like.

The thus obtained polypeptides are useful as immunogens for antibody preparation, target molecules for developing therapeutic agents for infertility, or the like.

The antibody group of the invention is an assembly of polyclonal antibodies or monoclonal antibodies which recognize the above MSGs polypeptides. The antibody group is useful as materials for carrying out the toxicity test and genetic diagnosis by investigating expression of MSGs polypeptides or mutants thereof in spermatoblast. The antibodies include all of the whole molecules capable of binding to epitopes of MSGs polypeptides, and Fab, F(ab')$_2$, Fv fragments, and the like. For example, in the case of polyclonal antibodies, such antibodies can be obtained from sera of animals after immunization of the animals using the above MSGs polypeptide or its partial peptide. Alternatively, they can be prepared by collecting sera of animals after the above expression vectors are transferred into muscle or skin of the animals by injection or a gene gun. As the animals, mouse, rat, rabbit, goat, chicken, and the like are used. Preparation of hybridomas by fusing B cells collected from spleens of immunized animals with myelonas enables production of monoclonal antibodies.

The methods for toxicity test, mutagenicity test, and genetic diagnosis according to the invention can be carried out, for example, in accordance with the following (A) to (I).

(A) Detection of ED (In Vivo)

For example, using an experimental animal such as mouse, guinea pig, or monkey reared under administration of an ED-suspected substance, chromosomal DNA is extracted from the leukocytes, tissue cells, and the like and purified (above Current Protocol in Molecular Biology 1:2.2.1-2.2.3). Using the DNA, an experimental animal DNA homologous to MSGs is amplified by PCR with the above primer set to prepare an analyte DNA. The base sequence thereof is determined and homology search is carried out between the analyte and normal gene DNA. As a result of the search, genetic diagnosis wherein mutation in the experimental animal, expression modulation induced by the mutation, and amino acid replacement are analyzed can be carried out on the basis of the resulting difference in base sequence and amino acid sequence between both DNAs. For the search, use can be made of, for example, a commercially available software for homology search (a program for homology search provided by the above DDBJ or NCBI, e.g., FASTA, BLAST, PSI-BLAST, SSEARCH, etc.). In this regard, points to keep in mind for homology search are described in, for example, a literature (Current Protocol in Molecular Biology 1:7.7.12-7.7.15). Furthermore, using RNA extracted from each organ (especially testis and sperm) of the above animal, it can be judged whether the suspected substance is ED or not by detecting change in expressed amount of mRNA by Northern blotting, RT-PCR method, microarray method, or the like with regard to MSGs.

(B) Detection of ED (In Vitro)

For example, using cell culture wherein an ED suspected substance is added to and mixed with a medium and culture is effected, tetrahymena, echinus fertilized eggs, microorganisms, and the like, morphological anomaly (e.g., abnormal cell division, cellular degeneration, etc.) under the cultivation is detected on a microscope and also a gene DNA (analyte DNA) homologous to the MSGs is prepared from the above culture product as in the above (A), followed by homology search. Thus, by investigating occurrence of mutation and change of expressed amount by Northern blotting, RT-PCR method, or the like, it can be judged whether the suspected substance is ED or not. In this regard, as the culture cell, a transformant with an expression vector obtained by cloning each polynucleotide (cDNA) of the MSGs of the invention can be employed.

(C) Mutagenicity Test/Toxicity Test

Using new drugs under development and environmental pollution-suspected chemicals as analytes, these tests can be carried out in a similar manner to the above (A) and (B).

(D) Test of Influence on Reproduction (In Vivo)

Using new drugs under development and environmental pollution-suspected chemicals as analytes, these tests can be carried out in a similar manner to the above (A) and (B).

(E) Test of Influence on Reproduction (In Vivo)

An expression vector to which an MSG gene (polynucleotide such as cDNA) is inserted and linked is constructed and then transferred into a host to prepare a transformant. The transformant is cultured in the presence of a new drug under development or an environmental pollution-suspected chemical. The present test can be carried out by judging whether the amount of its expression product or its function is normal or not. For example, Calmegin gene is expressed and the functional abnormality of the resulting Calmegin as shaperon is detected. Alternatively, by using such an expression vector, it is possible to detect or search substances which inhibit or accelerate its expressing ability and activity of an expressed product.

(F) Preparation of Experimental Animal

For the purpose of carrying out analysis of in vivo functions of the MSGs and homologous genes thereof, animals wherein these genes are knocked out can be prepared. Moreover, for the purpose of analyses of regulator gene loci of these genes and activity thereof and also functions of gene products in individuals, transgenic animals can be prepared. Such experimental animals also enable development of medicaments and medical technologies for gene therapy and prevention of male infertility as well as preclinical test in development of contraceptives.

(G) Test with MSG-Transduced Transformant

As in the above (F), an expression vector of an analyte gene DNA is constructed and its transformant is prepared. Then, abnormality of functions of its expression products is detected and also mutation of the analyte DNA and amino acid replacement induced by the mutation are analyzed. Contrastive analysis of both results thus obtained can creates meanings of correlation between function of an expressed product and the mutation.

(H) Amplified DNA by PCR

By PCR using the primers of the invention, DNAs of animals or cultured cells under various experimental conditions can be amplified using these DNAs as templates. The basic procedure of PCR is described in, for example, the above literature (Current Protocol in Molecular Biology 1:15.0.1-15.3.8). Moreover, the experimental group DNAs amplified by PCR and their fragments or restriction enzyme fragments can be used for analyses of SSCP (single strand conformation polymorphism), RFLP (restriction fragment length polymorphism), EST, STS, GSS, SNP, and the like and for SAGE (serial analysis of gene expression). For example, they can be employed as analytes for polyacrylamide electrophoresis, as probes for DNA microarrays or DNA chips, and as probes for hybridization after labeling.

The following will describe human male infertility gene mutations of the invention.

The Scot-t mutant polynucleotide of the invention is a polynucleotide having any one or more mutations selected from the following:

"t" at 129th position is replaced by "c";
"t" at 870th position is replaced by "g";
"c" at 1071st position is replaced by "t"; and
"t" at 1667th position is replaced by "c", in the DNA sequence of SEQ ID NO:168 or a complementary sequence thereof.

The Scot-t mutant polynucleotide can be isolated, for example, by screening a cDNA library prepared from whole mRNAs of a male infertile person using a Scot-t mutant oligonucleotide to be mentioned below as a probe. Also, the polynucleotide can be isolated by RT-PCR with the total mRNAs of a male infertile person as a template using the primer set of the invention to be mentioned below. Alternatively, it can be also obtained by transducing the above base replacement into wild-type Scot-t cDNA using a commercially available mutation kit or the like. The thus obtained cDNA can be amplified, for example, by conventional gene amplification methods such as PCR (polymerase Chain Reaction) method, NASBN (Nucleic acid sequence based amplification) method, TMA (Transcription-mediated amplification) method, and SDA (Standard Displacement Amplification) method.

The Scot-t mutant polynucleotide of the invention can be employed in the method for diagnosing male infertility according to the invention. Moreover, it is also used as a material for preparing the Scot-t mutant polypeptide of the invention to be mentioned below in a gene engineering manner.

The Scot-t mutant oligonucleotide of the invention is an oligonucleotide which is part of the above Scot-t mutant polynucleotide and which is composed of a continuous DNA sequence of 10 to 99 containing each mutation site, or a complementary sequence thereof.

The Scot-t mutant oligonucleotide can be prepared chemically by a known method. Moreover, it can be also prepared by cleavage of the Scot-t mutant polynucleotide with an appropriate restriction enzyme.

The Scot-t mutant oligonucleotide can be also employed in the method for diagnosing male infertility according to the invention. Alternatively, it is also used as a material for preparing the Scot-t mutant oligopeptide of the invention in a gene engineering manner.

The Scot-t mutant genomic polynucleotide of the invention is a polynucleotide (genomic DNA) derived from human chromosomal DNAs, which hybridizes the Scot-t mutant polynucleotide or Scot-t mutant oligonucleotide or a complimentary sequence thereof under stringent conditions. The stringent conditions mentioned here are conditions which enable a selective and detectable specific binding between the polynucleotide or oligonucleotide and a genomic DNA derived from a chromosome. The stringent conditions are defined by salt concentration, organic solvent (e.g., formamide), temperature, and the other known conditions. Namely, stringency is increased by reducing the salt concentration, increasing organic solvent concentration, or elevating hybridization temperature. For example, a stringent salt concentration is usually about 750 mM or less of NaCl and about 75 mM or less of trisodium citrate, more preferably about 500 mM or less of NaCl and about 50 mM or less of trisodium citrate, most preferably about 250 mM or less of NaCl and about 25 mM or less of trisodium citrate. A stringent organic solvent concentration is about 35% or more, most preferably about 50% or more of formamide. A stringent temperature condition is about 30° C. or higher, more preferably about 37° C. or higher, most preferably about 42° C. or higher. The other conditions include hybridization period of time, concentration of a washing agent (e.g., SDS), presence or absence of carrier DNA, and the like. By combining these conditions, various classes of stringency can be set. As one preferable embodiment, hybridization is carried out at 30° C. under conditions of 750 mM of NaCl, 75 mM of trisodium citrate, and 1% of SDS. As a more preferable embodiment, hybridization is carried out at 37° C. under conditions of 500 mM of NaCl, 50 mM of trisodium citrate, 1% of SDS, 35% of formamide, 100 µg/ml of denaturated salmon sperm DNA. As the most preferable embodiment, hybridization is carried out at 42° C. under conditions of 250 mM of NaCl, 25 mM of trisodium citrate, 1% of SDS, 50% of formamide, 200 µg/ml of denaturated salmon sperm DNA. In addition, conditions for washing after hybridization also affect stringency. The conditions for washing are also defined by salt concentration and temperature, and stringency at washing is increased by decrease of salt concentration and elevation of temperature. For example, stringent salt conditions for washing are preferably about 30 mM or less of NaCl and about 3 mM or less of trisodium citrate, most preferably about 15 mM or less of NaCl and about 1.5 mM or less of trisodium citrate. A stringent temperature condition is about 25° C. or higher, more preferably about 42° C. or higher, most preferably about 68° C. or higher. As one preferable embodiment, washing is carried out at 25° C. under conditions of 30 mM of NaCl, 3 mM of trisodium citrate, and 0.1% of SDS. As a more preferable embodiment, washing is carried out at 42° C. under conditions of 15 mM of NaCl, 1.5 mM of trisodium citrate, and 0.1% of SDS. As the most preferable embodiment, washing is carried out at 68° C. under conditions of 15 mM of NaCl, 1.5 mM of trisodium citrate, and 0.1% of SDS.

The Scot-t mutant genomic polynucleotide can be isolated by screening a genome library, which is prepared from chromosomal DNAs of a male infertile person, by stringent hybridization as above using Scot-t mutant oligonucleotide as a probe and washing treatment.

The Scot-t mutant genomic polynucleotide may be a detection target in the method for diagnosis according to the invention.

The Scot-t primer set of the invention is a primer set for PCR amplification of the Scot-t mutant polynucleotide, a double-stranded polynucleotide composed of the Scot-t mutant genomic polynucleotide and its complementary sequence, or mRNA transcribed from the Scot-t mutant genomic polynucleotide. In these primer sets, one oligonucleotide primer is composed of a continuous DNA sequence of 15 to 45 nt, preferably 15 to 30 nt containing at least one nucleotide mutation site of SEQ ID NO:168 (Scot-t cDND) or a complementary sequence thereof. Another primer may be any continuous DNA sequence at 5'-side or 3'-side of each mutation site of SEQ ID NO:168 or a complementary sequence thereof.

These primer sets can be prepared by a known process for DNA synthesis based on SEQ ID NO:168 containing each mutation site. Moreover, at the terminal of the primer, a linker sequence or the like may be added. Furthermore, for designing the sequence, commercially available software, for example, Oligo™ [manufactured by National Bioscience Inc., (USA)], GENETYX [manufactured by Software Development K.K. (Japan)], or the like may be employed.

The Scot-t primer sets of the invention can be employed in the method for diagnosing male infertility according to the invention.

In the protamine-2 mutant polynucleotide of the invention, c at 248th position in SEQ ID NO:173 (protamine-2 cDNA) is replaced by t.

The protamine-2 mutant oligonucleotide, mutant genomic polynucleotide, protamine-2 primer sets of the invention can be obtained and used in the same manner as in the case of the above invention relating to Scot-t.

The Scot-t mutant polypeptide of the invention is a polypeptide which is an expression product of the Scot-t mutant polynucleotide or mutant genomic polynucleotide of the above invention and which has one or more mutations selected from the following group:

Leu at 38th position is replaced by Pro;
Leu at 285th position is replaced by Arg; and
Thr at 352nd position is replaced by Met, in the amino acid sequence of SEQ ID NO:169.

Namely, in these Scot-t mutant polypeptide, amino acids in the normal (wild-type) polypeptide (SEQ ID NO:169) are mutated as above by missense mutation in the Scot-t mutant polynucleotide of the above invention.

The protamine-2 mutant polypeptide is a short-chain polypeptide which is an expression product of the protamine-2 mutant polynucleotide of the above invention and which is composed of an amino acid sequence of 1st to 49th positions in the amino acid sequence of SEQ ID NO:174. Namely, the polypeptide is a short-chain polypeptide which is formed by mutation of 50th glutamic acid codon into a stop codon by one base replacement (c by t) at 248th position of the protamine-2 mutant polynucleotide and as a result of no expression of the following protein-encoded region from the position.

These mutant polypeptides are obtained by a process for isolation from a biological sample of a male infertile person according to a known method, a process for preparing peptides by chemical synthesis based on an amino acid sequence of SEQ ID NO:169 or 174 containing each mutant amino acid residue, or a process for production by a recombinant DNA technology using mutant polynucleotide (mutant cDNA) of the above invention. These mutant polypeptides may be employed as test target in the method for diagnosing male infertility according to the invention.

The mutant oligopeptides of the invention are oligopeptides which are parts of the respective mutant polypeptides of the above invention and which have an continuous amino acid sequence of 5 to 30 containing each amino acid mutation site. These mutant oligopeptides can be prepared by a process of chemical synthesis based on a predetermined amino acid sequence or a process of digesting the above mutant polypeptides with an appropriate protease. These oligopeptides can be employed, for example, as antigens for antibody preparation according to the invention.

The anti-mutant Scot-t antibody, anti-mutant protamine-2 antibody, and anti-protamine-2 antibody of the invention are polyclonal antibodies or monoclonal antibodies prepared using the oligopeptides of the above invention as antigens and include all of whole molecules capable of binding to epitopes of the mutant polypeptides of the invention, and Fab, F(ab')$_2$, Fv fragments, and the like. Such antibodies can be prepared in a similar manner to the case of antibodies described for the MSGs invention. Moreover, these antibodies can specifically recognize the above mutant polypeptides and thus employed in the methods for diagnosis according to the invention.

The method for diagnosis according to the invention is a method for diagnosing whether a subject person suffers from male infertility or not. Namely, chromosomal DNAs are isolated from a biological sample of the subject person and, in the case that the mutant genomic polynucleotide of the above invention is present in the DNAs, the subject person is judged to be a high-risk person of male infertility. The subject person may be an infertile male person or a boy having an infertile male person in relations on his mother's side, but is not limited thereto. The mutant polynucleotide can be also detected by a method of directly sequencing it but the following methods are preferable.

First, it is detected whether chromosomal DNAs isolated from the subject person or mRNAs thereof hybridize the Scot-t mutant polynucleotide and/or protamine-2 mutant polynucleotide or respective mutant oligonucleotides under stringent conditions. In the case that the subject person possesses a gene mutation associated with male infertility, the chromosomal DNAs or the mRNAs and mutant polynucleotides or mutant oligonucleotides hybridize even under stringent conditions. The hybridization can be detected by a known method. For example, the detection can be carried out conveniently and at a high accuracy using the DNA probe or DNA chip of the invention. As a hybridization method using a labeled DNA probe, specifically known methods, for example, Allele-specific Oligonucleotide Probe method, Oligonucleotide Ligation Assay method, Invader method, or the like can be adopted. Moreover, the DNA chip may be a chip wherein the mutant polynucleotides and/or mutant oligonucleotides are directly synthesized on a substrate or a chip wherein the oligonucleotides are spotted on a substrate coated with a material to which nucleotides may bind. Nucleotide mutation in a test sample DNA can be identified using presence of hybridization of the labeled test sample DNA and the oligonucleotides on the substrate as an indicator.

In the second preferable method, presence of a PCR product is detected in the case that PCR is carried out with a primer set of the above invention using chromosomal DNA or mRNA isolated from the subject person as a template. When the subject person possesses gene mutation associated with male infertility, a PCR product of the polynucleotide defined by the primer set is obtained. PCR or RT-PCR can be carried out by a known method. Nucleotide mutation may be detected by, other than a method of direct sequencing of a PCR product, PCR-SSCP method, PCR-CFLP method, PCR-PHFA method, or the like. Moreover, a known method such as Rolling Circle Amplification method or Primer Oligo Base Extension method can be also employed.

In the application of another method for diagnosing male infertility of the invention, in the case that the Scot-t mutant polypeptide and/or protamine-2 mutant polypeptide of the above invention is present in a biological sample isolated from a subject person, the subject person is judged to be a high-risk person of male infertility. Although the polypeptides can be detected by various known method, one preferable method is a method of detecting the Scot-t mutant polypeptide using an anti-mutant Scot-t antibody. Moreover, it is a method of combined use of an anti-mutant protamine-2 antibody and an anti-protamine-2 antibody (an antibody prepared using an oligopeptide composed of an amino acid sequence of 50th to 91st positions in SEQ ID NO:7 or of 1st to 11th positions in SEQ ID NO:8). Namely, in the case of short-chain protamine-2 mutant polypeptide, the anti-mutant protamine-2 antibody reacts but the anti-protamine-2 antibody prepared using long-chain protamine-2 polypeptide does not react.

In the case of the method for diagnosis using the above antibodies, a convenient and highly accurate detection is possible especially by using a labeled antibody in this invention. For the labeling, an enzyme, radioactive isotope, or fluorescent dyestuff can be employed. The enzyme is not particularly limited as far as it satisfies requirements that it has a large turnover number, it is stable even when combined with an antibody, it specifically colors a substrate, and the like. Use can be made of enzymes usable for usual EIA, for example, peroxydase, β-galactosidase, alkaline phosphatase, glucose oxidase, acetylcholine esterase, glucose-6-phosphorylation dehydrogenase, malate dehydrogenase, and the like. Moreover, an enzyme-inhibiting substance, coenzyme, and the like can be also employed. The combination of the enzymes with an antibody can be effected by a known method using a crosslinking agent such as maleimide compound. As the substrate, a known substance can be employed in accordance with the kind of enzyme to be used. For example, 3,3',5,5'-tetramethylbenzidine can be used in the case that a peroxidase is used as the enzyme, and p-nitrophenol can be used in the case that alkaline phosphatase is used as the enzyme. As the radioisotope, those used in usual RIA, such as $^{125}I$ and $^{3}H$ can be employed. As the fluorescent dyestuff, those used in usual fluorescence antibody methods, such as fluorescence isothiocyanate (FITC) and tetramethylrhodamine isothiocyanate (TRITC), can be used. In the case of using an enzyme, enzyme activity is determined by adding a substrate which is decomposed by the action of the enzyme to develop color and then optically measuring the decomposed amount of the substrate, the activity is converted into an amount of bound antibody, and an amount of the antibody is calculated based on the comparison with standard values. In the case of using a radioactive isotope, amount of radiation emitted by the radioactive isotope is measured by a scintillation counter or the like. Moreover, in the case of using a fluorescent dyestuff, an amount of fluorescence may be measured by a measuring equipment combined with a fluorescent microscope. Furthermore, a sandwich method using a primary antibody and a labeled secondary antibody ("ELISA method" in the case of using an enzyme as a label) can be also preferably employed.

EXAMPLES

The following will specifically describe embodiments and compositions and advantages of the invention with reference to Examples and Use Examples but the invention of this application is not limited these examples.

Example 1

Preparation of Mouse Total RNA

Each testis was excised from the following two groups of mice (C57BL/6), 19 mice of 17 days old and 5 mice of 35 days old and collected into one capsule per group. Thereto was added 50 ml of 5.5M GTC solution (pH 7.5; 5.5M guanidine thiocyanate, 25 mM sodium citrate 2H$_2$O, 0.5% (W/V) sodium lauryl sarconate, and 0.2M 2-mercaptethanol), and then the mixture was passed through a syringe with a 18 G needle to break the cells. Then, the mixture was subjected to low-speed centrifugation and the supernatant was collected to remove precipitated cell fragments. Fifty milliliters of the collected supernatant was transferred into two tubes, in which 14 ml of CsTFA (cesium trifluoroacetate) solution was placed, in an amount of 25 ml each, followed by ultra-centrifugation (25,000 rpm, 15° C., 24 hours). RNA precipitated by the ultra-centrifugation was dissolved in 600 µl of 4.4M GTC solution/tube and then precipitated with ethanol. The precipitated RNA was dissolved in TE [10 mM Tris-HCl (pH 7.5), 1 mM EDTA], and then recovered by re-precipitation with ethanol to obtain total RNA of each of both groups of 17 day-old and 35 day-old mice.

Example 2

Preparation of Mouse mRNA[Poly(A)+]

Each of the total RNA in two tubes (two groups) in an ethanol-precipitated state obtained in Example 1 was rinsed with 70% (V/V) ethanol, and then 500 μl of the above TE/tube was added to dissolve the RNA, followed by heating at 65° C. for 5 minutes and rapid cooling on ice. Then, 500 μl of 1M NaCl/tube was added thereto and the resulting mixture was loaded on an oligo(dT)cellulose column [Type 3; manufactured by Collaborative Research] equilibrated with TE/NaCl (TE: 1M NaCl=1:1) beforehand. Each column was washed with 8 ml of the above TE/NaCl and then each was eluted with 0.5 ml of TE to achieve fractionation. This fractionation was repeated 5 times in total and a portion of each fraction was taken out and mixed with EtBr (ethidium bromide). Thereafter, the second fraction from which fluorescent radiation was observed under UV irradiation was adopted as an mRNA fraction. On the second fraction, the above operations from heating at 65° C. for 5 minutes to column fractionation was repeated again. After precipitation of the resulting fraction with ethanol, the precipitate was rinsed with 70% (V/V) ethanol and dissolved in 10 μl of TE. A portion thereof was taken out and quantitative determination was conducted on an absorptiometer.

Example 3

Preparation of cDNA Library of 35 Day-Old Mouse Testis

It was prepared according to the procedure described in the following (1) to (6).

(1) Synthesis of First Strand (Preparation of Single-Stranded, ss-cDNA)

Seven micrograms of mRNA of 35 day-old mouse obtained in Example 2 was weighed out and distilled water was added thereto to make the total amount 7.5 μl, followed by heating at 65° C. for 5 minutes and then cooling with ice. Thereafter, the following reagents were added and mixed: 2.5 μl of 10×1st strand buffer [500 mM Tris-HCl (pH 8.3), 750 mM KCl, 30 mM MgCl$_2$], 2.5 μl of 0.1M DTT (dithiothreitol), 1.5 μl of 1st strand methyl nucleotide mixture (10 mM dATP, dGTP and dTTP; and 5 mM 5-methyl-dCTP), 1 μl (1.6 μg) of linker primer [(GA) 10ACGCGTCGACTC-GAGCGGCCGCGGACCG(T) 18], 0.5M1 of RNase inhibitor, and 7.5 μl of H$_2$O. The whole was left on standing at room temperature for 10 minutes to effect annealing and then 2 μl of a reverse scriptase [manufactured by Seikagaku Corporation (Japan)] was added thereto, followed by reaction at 37° C. for 40 minutes. Then, 2 μl of Super Script [manufactured by BRL (USA)] was added and mixed and then the whole was allowed to react at 50° C. for 40 minutes to obtain a single-stranded first strand (ss-cDNA).

(2) Synthesis of Second Strand (Preparation of Double-Stranded, ds-cDNA)

To the first strand solution obtained in the above (1) was added the following reagents on ice and the whole was mixed: 20 μl of 10×2nd strand buffer [188 mM Tris-HCl (pH 8.3), 906 mM KCl, 46 mM MgCl$_2$], 7.5 μl of 0.1M DTT, 3 μl of 2nd strand nucleotide mixture (10 mM DATP, dGTP and dTTP; and 25 mM 5-methyl-dCTP), and 135 μl of H$_2$O. The whole was cooled with ice for 5 minutes and then 1.5 μl (2 units) of RNase H and 6 μl (50 units) of *Escherichia coli* DNA polymerase I were added and mixed, followed by reaction at 16° C. for 180 minutes. After completion of the reaction, cDNA was extracted with 200 μl of phenol/chloroform (water-saturated phenol:chloroform=1:1 mixture) and chloroform, successively, and then was dissolved in 30 μl of 1/10 TE to obtain a double-stranded second strand (ds-cDNA).

(3) Blunt End Formation (Preparation of Blunt End ds-cDNA)

To 30 μl of the ds-cDNA solution of the above (2) was added the following reagents, and the whole was mixed: 10×T4 DNA polymerase buffer [500 mM Tris-HCl (pH 8.3), 100 mM MgCl$_2$, 500 mM NaCl, 100 mM DTT], 2.5 mM dNTP mixture, 1 μl (10 units) of T4 DNA polymerase, and 54 μl of H$_2$O; the total amount was 100 μl. Then, after a reaction at 37° C. for 30 minutes (keeping the period strictly), cDNA was extracted with 100 μl of the above phenol/chloroform and chloroform, successively, and then was dissolved in 20 μl of 1/10 TE to obtain a blunt ended ds-cDNA.

(4) Linkage of Adaptor

To 4 μl of the blunt ended ds-cDNA solution of the above (3) was added the following reagents, and the whole was mixed and then cooled with ice for 5 minutes: 2 μl of 10× ligase buffer [500 mM Tris-HCl (pH 8.3), 70 mM MgCl$_2$, 10 mM DTT], 2 μl of 10 mM ATP, 1 μl (0.35 μg) of an adaptor, and 9.5 μl of H$_2$O; the total amount was 18.5 μl. The above adaptor is a 1:1 (W/W) mixture of BamH I(Bgl II)-Sma I[d(GATCCCCGGG)] [manufactured by Takara Shuzo Co., Ltd.] and pSma I linker[d(pCCCGGG)] [manufactured by Takara Shuzo Co., Ltd.] and was prepared by dissolving them in a buffer [10 mM Tris-HCl (pH 7.5), 1 mM EDTA, 10 mM MgCl$_2$] to have a concentration of 0.35 μg/μl. Then, 1.5 μl (4 units) of T4 ligase was added and mixed. After a reaction at 8° C. overnight, the whole was heated at 70° C. for 30 minutes and then centrifuged at 15,000 rpm at 4° C. for 5 seconds, the supernatant being obtained as an adaptor-linked ds-cDNA.

(5) Preparation of Restriction Enzyme Fragments of ds-cDNA and Fractionation by Spin Column To the adaptor-linked ds-cDNA solution of the above (4) was added 27 μl of Not I buffer [278 mM NaCl, 8 mM MgCl$_2$, 1.8 mM DTT, 0.01% (W/V) BSA (bovine serum albumin), 0.018% (W/V) Triton X-100] and 3 μl of Not I (10 units), respectively and the whole was mixed, followed by a reaction at 37° C. for 150 minutes. After completion of the reaction, 5 μl of 10×STE [1M NaCl, 100 mM Tris-HCl (pH 8.3), 10 mM EDTA (pH 8.0)] and 10 μg of tRNA were added and mixed. The resulting mixture was placed in Chroma Spin columns [manufactured by Clontech (USA)] in an amount of 10 μl/column and centrifuged at 4° C. at 1,800 rpm for 5 minutes and then a fraction of restriction enzyme fragment at a bottom of the centrifugal tubes was collected. Then, the fragment was extracted with equivalent amount of phenol/chloroform and chloroform, successively, and then 10 μg of tRNA was replenished and the total amount is made 250 μl with adding water. Furthermore, precipitation with ethanol was carried out and the precipitate was rinsed with 70% (V/V) ethanol and then slightly dried to obtain a restriction enzyme (Not I/Bgl II) fragment of the adaptor linked ds-αDNA.

(6) Insertion and Linkage of ds-Restriction Enzyme into a Vector

To the slightly dried product of the ds-DNA restriction enzyme (Not I/Bgl II) fragment of the above (5) was added the following reagents, and the whole was mixed and then cooled with ice for 5 minutes: 3 µl of the above 10× ligase buffer, 3 µl of 10 mM ATP, 1 µl (1 µg) of a plasmid vector pAP3neo (restriction enzyme Not I/Bgl II cleavage), and 22 µl of H$_2$O. Then, 1 µl (4 units) of T4 DNA ligase was added and mixed. After a reaction at 12° C. overnight, the whole was heated at 70° C. for 30 minutes. After extraction with phenol/chloroform and chloroform, successively, the product was dissolved in 20 µl of TE to obtain a solution of a plasmid vector to which the ds-cDNA was inserted. Then, using the whole amount of the solution, ds-cDNA-inserted plasmid vector was transferred into a competent cell, *Escherichia coli* by electroporation to effect transformation. The resulting transformant was provided as a cDNA library of 35 day-old mouse testis, for the preparation of a subtracted library in Experiment 4 to be mentioned below.

Example 4

Preparation of Subtracted Library of Mouse

According to the procedures (1) to (5) described below, a subtracted library was prepared by subtracting expression genes (mRNA:B) in 17 day-old mouse testis from the cDNA library (A) of 35 day-old mouse testis obtained in Experimental Example 3 by hybridization. In order to remove also genes over expressed prior to the appearance of haploid by the subtraction, the reactant ratio of A/B=1/40 was adopted in the hybridization.

(1) Conversion of cDNA Library (A) of 35 Day-Old Mouse Testis into Single-Stranded Ones The transformant (*Escherichia coli*) of the cDNA library obtained in (6) of Experiment 3 was cultured at 37° C. for 1 hour in 4 ml of SOC [2% (W/V) Bacto-tryptone, 0.5% (W/V) yeast extract, 10 mM NaCl, 2.5 mM KCl, and 20 mM glucose] medium. Thereafter, it was transferred into 100 ml of LB/Amp [1% (W/V) Bacto-tryptone, 0.5% (W/V) yeast extract, 0.5% (W/V) NaCl, 50 µg/µl ampicillin] medium and further cultured at 37° C. for 4.5 hours to amplify the cDNA. Among 100 ml of the resulting culture solution, 50 ml thereof was transferred into another vessel and 1 ml of a helper phage (R408; 2×10$^{12}$ pfu (plaque-formation unit)/ml) was added thereto, followed by culturing at 37° C. for 10 hours. The remaining 50 ml of the culture solution was frozen and stored under addition and mixing of DMSO at a final concentration of 7% (V/V) after the culture at 37° C. without further treatment. After completion of the culture, fungi were removed by centrifugation and collected supernatant was filtrated through a filter having a pore size of 0.2 µm to remove *Escherichia coli* debris completely. Then, to 50 ml of the culture filtrate was added the following reagents, and the whole was mixed: 5 ml of Dnase I solution [0.1M Tris-HCl (pH 7.5) and 0.1M MgCl$_2$] and 5 µl of Dnac I. The whole was reacted at 37° C. for 30 minutes and then 20% (W/V) PEG (polyethylene glycol; solvent was 2.5M NaCl) was added to a quarter of the whole and mixed, followed by further reaction at room temperature for 20 minutes. Then, the phage was collected by ultracentrifugation at 4° C. at 10,000 rpm for 10 minutes and, after supernatant was discarded and PEG was completely removed, the phage was suspended in 400 µl of TE. Thereto were added 25 µl of Proteinase K solution (solution composed of 2 mg of Proteinase K, 800 µl of TE, and 200 µl of glycerol) and 4 µl of 10% (W/V) SDS (sodium dodecyl sulfate), and the whole was mixed, followed by a reaction at 42° C. for 1 hour. After completion of the reaction, extraction was carried out with phenol, phenol/chloroform, and chloroform, successively, and precipitation with ethanol was carried out. The precipitate was rinsed with 70% (V/V) ethanol and then dissolved in 100 µl of TE, a portion of which was quantitatively determined using a ultraviolet spectrometer.

(2) Biotinylation of 17 Day-Old Mouse Testis mRNA

Distilled water was added to a tube containing 40 µg of 17 day-old mouse testis mRNA obtained in Experimental Example 2, and the total amount was made 20 µl. Thereto was added 30 µl of biotin (photoprobe biotin 1 µg/µl aqueous solution)[manufactured by Vector Laboratories (USA)], followed by mixing. After thorough pipetting, the tube was placed on ice with the cap off and labeling was carried out by irradiating the tube with a mercury lamp (BHRF100/110 v/60 W) from 10 cm above the tube for 20 minutes. After completion of the labeling, 50 µl of 0.1M TE (pH 9.5) was added thereto and, after thorough pipetting, 100 µl of water-saturated butanol was added and excess of biotin was removed. Furthermore, 100 µl of chloroform was added to remove butanol, and then precipitation with ethanol and rinsing with 70% (V/V) ethanol were successively carried out, followed by dissolution into 20 µl of distilled water. The above labeling operation was repeated again and finally the product was dissolved in 10 µl of distilled water to form a biotinylated mRNA aqueous solution.

(3) Hybridization

The following reagents were added to a PCR tube and mixed together carefully so as not to contain bubbles: 1.5 µl (0.5 µg) of ss-cDNA prepared in the above (1), 5 µl (20 µg) of the biotinylated mRNA obtained in (2), 12.5 µl of 2×HB [80% (W/V) formamido, 100 mM HEPES, 2 mM EDTA, and 0.2% (W/V) SDS; prepared just before use], 2.5 µl of 2M NaCl, and 1 µl of Poly A (1 µg/µl aqueous solution) [manufactured by Pharmacia (Sweden)], 2.5 µl of distilled water. It was reacted at 65° C. for 10 minutes and further at 42° C. for 43 hours to effect hybridization.

(4) Recovery of ss-cDNA by Reaction with Avidin

Into another tube was transferred 25 µl of the reaction solution obtained in the above (3), and then 400 µl of SB [50 mM HEPES (pH 7.5), 2 mM EDTA, and 500 mM NaCl], and 10 µg of streptoavidin [manufactured by Gibco BRL (USA)] were added thereto and the whole was mixed. After a reaction at room temperature for 5 minutes, ss-cDNA not hybridized was extracted with 400 µl of phenol/chloroform (1:1 equivalent mixture). The above operations from the avidin-addition to extraction with phenol/chloroform was repeated again. Thereafter, further extraction with chloroform was carried out and purified ss-cDNA was recovered by millipore filter. Then, it was dissolved in 30 µl of 1/10 TE and then 15 µl thereof was transferred into another tube (the remainder was stored at −20° C.) and concentrated (not completely dried) by vacuum drying for 10 minutes.

Furthermore, the above operations from hybridization to vacuum drying were repeated twice. The composition at the second and third hybridization was as follows: ss-cDNA concentrated by the above vacuum drying, 5 µl (10 µg) of the biotinylated mRNA, 12.5 µl of 2×HB, 2.5 µl of 2M NaCl, and 1 µl of Poly A, total amount of which was made 25 µl by adding distilled water. Moreover, of 30 µl of ss-cDNA obtained by second hybridization, 15 µl was used for third hybridization and the remainder was stored at −20° C.

(5) Conversion of ss-cDNA into Double-Stranded One

Fifteen microliters of PNK reaction mixture was added to and mixed with 15 µl of the ss-cDNA solution obtained in the above (4), followed by a reaction at 65° C. for 10 minutes. The PNK reaction mixture was prepared by reacting the following composition at 37° C. for 30 minutes: 1 µl of primer oligonucleotide for double strand formation, 3 µl of 10× ligation buffer [500 mM Tris-HCl (pH 7.5), 70 mM $MgCl_2$, and 10 mM DTT], 3 µl of 10 mM rATP, 2 µl of PNK (T4 polynucleotide kinase; 10 units/µl) [manufactured by Toyobo Co., Ltd. (Japan)], and 21 µl of distilled water were added and the total amount was made 30 µl. After completion of the reaction, the mixture was cooled to room temperature and then the following reagents were added to 30 µl of the reaction solution and the whole was mixed, followed by further reaction at 65° C. for 1 hour: 5 µl of 10× BcaBEST Buffer [manufactured by K.K. Takara (Japan)], 10 µl of 1 mM dNTP, 0.5 µl of single strand DNA binding protein (2.1 µg/µl) [manufactured by USB (USA)], 2 µl of BcaBEST DNA polymeraze [manufactured by K.K. Takara (Japan)], and 3 µl of distilled water were added and the total amount was made 50 µl. After completion of the reaction, extraction with 100 µl of phenol/chloroform and chloroform was successively carried out and purified ds-cDNA was recovered by filtration through millipore filter. Then, it was dissolved in 20 µl of TE and a portion thereof was transferred into *Escherichia coli* (XL-1 Bleu) by electroporation to effect transformation. The thus obtained transformant was used for MSG cloning as a subtracted library, i.e., MSG-candidate cDNA library.

Example 5

Cloning of MSG

Northern blotting was carried out between ss-cDNA prepared, in a similar manner to the description in (1) of Experimental Example 4, from the culture solution of transformant containing the MSG-candidate cDNA library of the subtracted library prepared in Experimental Example 4 and total RNA of both testis of 17 day-old and 35 day-old mice obtained in Experimental Example 1, and cDNA whose signal was detected only in 35 day-old mouse was screened and collected. As a result, 79 MSG clones were obtained in total. Moreover, when clones obtained by cloning with monoclonal antibody and polyclonal antibody were combined, 89 MSG clones were obtained in total.

Example 6

Determination of Base Sequence of MSG Clone DNA

After MSG clones/vectors were amplified by culturing respective transformant of MSG library obtained in Example 5, respective vectors (plasmids) were extracted and purified by alkali method. Then, based on dideoxy method (Sanger method), sequences of respective cDNAs of 89 MSG clones in total obtained in Example 1 were determined. The results are shown in SEQ ID NO:1 to 89.

Example 7

Investigation of ED Action Against MSG

As one model of ED discharged into the environment, change in expression of MSG gene by administration of DES having estrogen action was investigated using mouse.

To a 8 week-old C57BL/6 male mouse, DES was intraperitoneally injected twice every two days. After two days, both testes were taken out and one was subjected to tissue observation while RNA was extracted from another one to compare a gene expression level.

Material: mouse: 8 week-old C57BL/6 male mice

Administration DES Concentration and Number of Mice
  1: no treatment (two mice)
  2: 0 µg DES in corn oil (two mice)
  3: 1 µg DES in corn oil (two mice)
  4: 10 µg DES in corn oil (two mice)
  5: 50 µg DES in corn oil (three mice)

Experimental Schedule

On the first day, no treatment or each amount of DES dissolved in 20 µl of corn oil was intraperitoneally injected. On the third day, the same treatment was conducted as in the first day. On the fourth day, testes were taken out. One of them was fixed with Buan and embedded in paraffin, and then subjected to HE stain, followed by tissue observation. Another one subjected to RNA extraction with Trizol and the gene expression level was compared by Northern hybridization.

Analyzed gene: OAZt (Ornithin decarboxylase antizyme-t): SEQ ID NO:50

Results

It was impossible to detect morphologically evident change. However, as a result of Northern hybridization on a spermatid-specifically expressing gene OAZt, individual difference was very large but, as a whole, the treated group showed a low level.

OAZ-t is a gene exhibiting a haploid spermatid-specific expression. It was suggested that initiation of the expression was suppressed by DES. In spit of such a low concentration and a short-term DES treatment that no morphological anomaly was observed, difference was detected at a gene expression level. This fact indicates that the method of the invention is sufficiently applicable as a highly sensitive detecting system at an individual level of influence of estrogen on male germ cells.

Example 8

Functional Analysis of Mouse Haspin

Haspin (SEQ ID NO:81) is a protein kinase which is spermatid-specifically expressed. It has various functional domain (nucleus-transferring signal, leucine zipper, transcription factor-like structure) including a kinase domain and is involved in various spermatid functions, so that it is considered to play important roles in spermatogenesis. Furthermore, when haspin gene is expressed in cultured cells, it is also known that the protein transfers into nuclei and growth of the cells was stopped at G1 stage (J. Biol. Chem. 274, 17049-17057, 1999).

The following are revealed about the haspin.

Analysis of Hapsin-Knockout Mouse

Using thymidine kinase (TK) gene and neomycin (neo) resistance for selection, haspin gene of an ES cell was broken and a haspin gene-defective (haspin KO) mouse was prepared by preparing mouse embryo from the ES cell. The individual of the KO mouse normally developed and grew but male mouse exhibited infertility and fertility was observed in female mouse. Moreover, no apparent disorder was observed in spermatogenesis and morphologically not abnormal sperm was produced but it was confirmed that the mouse exhibited male infertility owing to dysfunction.

Analysis of Expression Regulatory Region of Hapsin Gene

A transgenic (TG) mouse was prepared using a reporter gene wherein GFP gene was linked to 192 bases at upstream of haspin gene. As a result of the analysis of the TG mouse, GFP was expressed in a haploid spermatid specific manner, so that it was confirmed that the region comprising the 192 bases was a promoter which regulates the specific expression of haspin gene.

Analysis of Interactive Protein with Hapsin Molecule

From the experimental results of yeast 2 hybrid system, it was revealed that there exist at least 8 kinds of intratesticular proteins interacting with haspin molecule. These proteins play important roles in spermatogenesis through interaction with human (Mol. Hum. Reprod. 7, 211-218, 2001) or mouse haspin.

Based on these results, the following may be applicable. Namely, since it was confirmed that genetic deficit of haspin causes male infertility, 1) it is possible to cause male infertility by dysfunction of haspin itself or dysfunction of a protein interacting therewith;

2) it is possible to cause infertility by inhibiting interaction between haspin and the other molecule; and 3) it is possible to cause infertility by inhibiting transfer of haspin to nucleus.

Namely, the inventors have found out a protein directing the specific transfer to nucleus (importin alpha) among molecules interacting with haspin. Dysfunction of the importin alpha can inhibit the transfer of haspin to nucleus and cause functional deficit of haspin.

4) it is possible to cause infertility by the action of an inhibitor against kinase activity of haspin.

Namely, since specific inhibitors against various kinases have hitherto been developed, it is highly probable to develop an inhibitor against a highly specific kinase such as haspin.

Moreover, the haspin promoter identified as above specifically expresses only in haploid spermatid, but by activating the promoter in somatic cells, it is also possible to regulate the growth of abnormally growing cells. The activation of the promoter can be achieved by introduction of a specific transcription factor effective thereon or a gene thereof. Alternatively, it can be achieved by a method of activating gene expression of its transcription factor.

Example 9

Detection of ED in Mouse

A 10 day-old mouse (male) was reared for 200 days with continuous administration of an ED-suspected analyte (Bisphenol A or the like) orally. Irrespective of observed anomaly on reproduction function, behavior, or appearance thereof, cellular RNA and chromosomal DNA were extracted from the testis of the reared mouse using an RNA extraction kit (e.g., TOLIzol: GIBCO BRL) and a DNA extraction kit (e.g., DNAzol BD Reagent: Oriental Yeast (Japan)). The RNA was investigated on change of expression level by Northern blotting and with regard to the DNA, amplification of spermatogenesis gene(s) was carried out using the PCR primer obtained in Example 5. Thereby, when the amplification was impossible, it was judged that the gene(s) possess a large mutation. When the amplification is possible, the amplified DNA fragments were directly sequenced or, after fragmentation with an endonuclease which recognizes and cleaves a specific DNA base sequence, the fragments were subjected to agarose gel or polyacrylamide gel electrophoresis and then analyses of SSCP, RFLP, EST, STS, GSS, and SNP were carried out to detect mutation. A DNA fragment in which mutation was detected was further subjected to determination of its base sequence and then judged on the following points by computer analysis: whether the mutation is polymorphism or not; whether the mutation causes modulation during the process of regulation, duplication, and transcription of the gene(s); and whether the mutation induces a large disorder on the function of translation product(s) (protein(s)). Based on these change in RNA and DNA, ED was detected.

Example 10

Analysis of Human Scot-t Gene and Protamine Gene

1. Methods 1-1. Subject Person and Extraction of Genomic DNA

For the analysis of Scot-t gene, a total of 255 cases of male infertility patients were classified into a plurality of subordinate groups in accordance with spermatology. 152 cases (60%) were nonobstructive azoospermia, 72 cases (28%) were severe oligospermia (from 0.1 to $3 \times 10^6$ cell/ml), 27 cases (11%) were low sperm motility, and 4 cases (2%) were idiopathic infertility wherein number, morphology and motility of sperm were normal. As a control group, the subjects were 261 cases of reproducible male persons who were husbands of pregnant wives visited maternity hospitals.

For the analysis of protamine genes, a total of 258 cases of male infertility patients were classified into a plurality of subordinate groups in accordance with spermatology. 153 cases (59%) were nonobstructive azoospermia, 73 cases (28%) were severe oligospermia (number of sperm: less than $5 \times 10^6$ cell/ml), 28 cases (11%) were asthenozoospermia where sperm motility was low, and 4 cases (2%) were idiopathic infertility wherein number, morphology and motility of sperm were normal. As a control group, the subjects were 270 cases of healthy persons as mentioned above.

Genomic DNA of each of the above infertile patients and healthy persons was extracted by a known method using a protease and phenol (Sambrook and Maniatis, in Molecular Cloning—A Laboratory Manual, Cold Spring Harbor Laboratory Press, New York, 1989) and used.

1-2. Identification of Mutation in Human Scot-t Genomic DNA

Since human Scot-t contains a pseudo-gene having 19 bp deletion (18 nucleotides of 745th to 762nd and one nucleotide of 778th intervening 15 nucleotides) at the central part of a coding region (Tanaka H, et al., Mol Human Reprod 2001; 8: 16-23), two kinds of PCR primers containing the deleted region were prepared so that the pseudo-gene was not amplified. Namely, For the amplification of 5' half, use were made of 25 oligonucleotide (tgctctgtgacgcgcggcccgaggc: SEQ ID NO:176) at upstream of presumed transcription initiation site and 26 oligonucleotide (cctccacgatctcttccacctccacc: SEQ ID NO:177) of from 770th to 745th, 24 oligonucleotide (cggtggaggtggaagatcgtgg: SEQ ID NO:183), and 25 oligonucleotide (tccattcctcaccactgcacacctg: SEQ ID NO:178) at downstream of presumed transcription unit (cf. FIG. 1).

Determination of the total sequence of the h-Scot-t DNA except for 35 nucleotides located around the internal primer sequence (730-764) around the central part was able with using 2 kinds of PCR amplification fragments covering the left side and the right side of the n-Scot-t gene (FIG. 1).

1-3. Introduction of Various SNP Types of Genes into Recombinant h-Scot-t cDNA and Analysis of Succinyl CoA Tranferase Activity On 72 hours after transfection of each cDNA using $CaPO_4$, HEK 293 cell was lysed. Each cell lysis solution (5 mg protein) was subjected to a chromatographic treatment using HPLC to separate into exogenous SCOT-t and endogenous SCOT-s, followed by analysis of enzyme activity. Standardization of succinyl CoA transferase activity was carried out using a relative amount of h-SCOT-t protein evaluated on a densitometer from Western blotting signals using anti-SCOT-t antibody.

SCOT enzyme activity was carried out by a method described in a literature (Marcondes, S, et al. (2001) Proc. Natl. Acad. Sci. USA. 98, 7146-7151) with slight modification. Namely, content of the analyte mixture were 50 mM Tris-HCl (pH 8.5), 0.2 mM succinyl CoA, 5 mM lithium acetoacetate, 5 mM $MgCl_2$, 5 mM iodoacetamide, and an h-SCOT-t fraction. Spectroscopic analysis of SCOT activity was carried out by measuring formation of acetoacetyl-CoA absorption at 313 nm. Protein concentration was measured by Bradford method using bovine serum albumin as a standard substance.

1-4. Identification of Mutation of Protamine-1 and Protamine-2 Genomic DNA

Genomic DNA was isolated from blood by a known method using a protease and phenol. Two kinds of polymerase chain reaction (PCR) primer sets in both of 5' and 3' lateral regions were constructed and genomic DNAs of these protamines were amplified. For protamine-1 (Domenjoud, L. et al. (1990) Genomics, 8, 127-133), 24 oligonucleotide (P1A; cccctggcatctataacaggccgc: SEQ ID NO:179) from −42 to −19 upstream from the transcription initiation site was used as the 5'-primer, and 24 oligonucleotide (P1B; tcaagaacaaggagagaagagtgg: SEQ ID NO:180) from 492 to 515 downstream from canonical PolyA addition signal AATAAA was used as the 3'-primer. For protamine-2 (Domenjoud, L. et al. (1990) Genomics, 8, 127-133), PCR amplification was carried out using 24 oligonucleotide (P2A; ctccagggcccactgcagcctcag: SEQ ID NO:181) from +49 to +72 as the 5'-primer, and 24 oligonucleotide (P1B; gaattgctatggcctcacttggtg: SEQ ID NO:182) from 625 to 648 as the 3'-primer. By these primer setting, 557 polynucleotide (SEQ ID NO:170) from −42 to 515 and 599 polynucleotide from 49 to 648 of protamine-1 and protamine-2 genes, respectively can be amplified in the PCR (FIG. 2). PCR conditions were as follows: for protamine-1, 40 cycles of denaturation at 96° C. (45 seconds), annealing at 66° C. (45 seconds), and extension at 72° C. (1 minute) were conducted, and for protamine-2, 40 cycles of denaturation at 98° C. (10 seconds), annealing at 68° C. (45 seconds), and extension at 72° C. (45 seconds) were conducted. The fragments amplified by PCR were purified using SUPREC PCR spin column (Takara, Siga, Japan) and thermal cycle sequence analysis (ABI, CA, USA) was carried out. Determination of DNA sequences was carried out using the same PCR primers.

2. Results 2-1. Sequence Analysis of Human Scot-t DNA

By the PCR primer setting described in the above 1-2, pseudo-gene DNA was not amplified and only true Scot-t genomic DNA was amplified, so that male persons having a risk of infertility and control male persons whose reproducibility was proved were compared.

As a result, four sites of single nucleotide polymorphism: SNP were observed as shown in Table 2. In 516 cases of male persons in total of 255 cases of infertile patients and 261 cases of volunteer persons whose reproducibility was proved, one site was present in the 3'-noncoding region (t1667c), and the other sites were present in the coding region and alterations at 38th, 285th and 352nd amino acids were induced (FIG. 1). With regard to t129c SNP located at 38th amino acid (L38P) within consensus mitochondrial target sequence domain, in reproducible control group and infertile patients, respectively, 94% (246 cases) and 96% (246 cases) were major homozygous leucine type (t/t), 5.4% (14 cases) and 2.7% (7 cases) were heterozygosity (t/c), and 0.4% (1 case) and 0.8% (2 cases) were minor homozygosity, which was observed to cause an amino acid alteration to proline (c/c). With regard to t870g SNP located at 285th amino acid (L285R), in reproducible control group and infertile patients, respectively, 80% (208 cases) and 80% (204 cases) were major homozygous leucine type (t/t), 19% (50 cases) and 15% (39 cases) were heterozygosity (t/g), and 1.1% (3 cases) and 4.7% (12 cases) were SNP minor-type homozygosity (g/g), which was observed to cause an amino acid alteration to arginie (g/g). With regard to c1071t SNP located at 352th amino acid (T352M), in normal control group and infertile male persons, respectively, 96% (250 cases) and 93% (238 cases) were major homozygous leucine type (c/c), 3.1% (8 cases) and 4.3% (11 cases) were heterozygosity (c/t), and 0.8% (2 cases) and 2.4% (6 cases) were minor homozygosity (c/c), which was observed to cause an amino acid alteration from threonine (c/c) to methionine (t/t). With regard to the expression rate of homozygous SNPs causing amino acid alterations at three regions, parent population of infertile patients exhibited significantly two to four times higher value as compared with the value of the reproducible control group. Furthermore, in this case, very interesting SNP (t1667c) was found in the 3'-coding region. In normal control group and infertile male parent population, respectively, 80% (206 cases) and 80% (200 cases) were major t-type homozygosity (t/t), 19% (49 cases) and 15% (38 cases) were heterozygosity (c/t), and 1.2% (3 cases) and 4.8% (12 cases) were c-type minor homozygosity (t/t). All the cases of the minor homozygosity were double SNPs and in both of the normal reproducible control group (3 cases of male persons) and infertile patients (12 cases of male persons), respectively, genotype in t870g was minor g-type homozygosity, but one exception was observed in the infertile cases (the above were shown in Tables 3 and 4).

TABLE 3

Background of clinical survey for 255 cases of infertile male persons and mutation in h-Scot-t gene (SNPs)

|  | Ratio(%) | L38P | L285R | T352M | t1667c |
|---|---|---|---|---|---|
| Azoospermia | 152 (60) | 2 | 6 | 3 | 6 |
| Aevere oligospermia | 72 (28) | 0 | 5 | 2 | 5 |
| Asthenozoospermia | 27 (11) | 0 | 1 | 1 | 1 |
| Idiopathic infertility | 4 (2) | 0 | 0 | 0 | 0 |
|  | 255 (100) | 2 | 12 | 6 | 12* |
| Reproducible control | 261 | 1 | 3 | 2 | 3** |

*Total case number: 250 cases (azoospermia 147 cases)
**Total case number: 258 cases

TABLE 4

Expression rate of 3 sites of SNPs in coding region and 1 site in non-coding region in infertile and reproductive ability-proved parent populations

| Type & position of SNPs | Genotype | Reproducible control | Infertile case | Increase ratio in infertile case | statistical significance |
|---|---|---|---|---|---|
| t129c (L38P) | t/t | 246(94) | 246(96) | | |
| | t/c | 14(5.4) | 7(2.7) | | |
| | c/c | 1(0.4) | 2(0.8) | x2 | p < 0.54 |
| t870g (L285) | t/t | 208(80) | 204(80) | | |
| | t/g | 50(19) | 39(15) | | |
| | g/g | 3(1.1) | 12(4.7) | x4 | p < 0.018 |
| c1071t (T352M) | c/c | 250(96) | 238(93) | | |
| | c/t | 8(3.1) | 11(4.3) | | |
| | t/t | 2(0.8) | 6(2.4) | x3 | p < 0.17 |
| t1667c | t/t | 206(80) | 200(80) | | |
| | t/c | 49(19) | 38(15) | | |
| | c/c | 3(1.2) | 12(4.8) | x4 | p < 0.018 |

2-2. Succinyl CoA Transferase Activity of Recombinant h-SCOT-t Having SNPs

In order to investigate influence of SNPs on h-SCOT-t enzyme activity, a recombinant protein having 3 sites of SNPs inducing amino acid replacement was expressed in HEK 293 cell and analysis of succinyl CoA transferase activity was carried out in vitro. All the minor-type SNPs located at t129c (L38P) and c1392t (T352M) exhibited a similar level of enzyme activity to that of major-type SNPs. Contrarily, the minor-type (g/g) SNP located at T870G (L285R) diminished the enzyme activity by half in vitro as compared with the major-type (Table 5). Based on this result, it is shown that the succinyl CoA transferase activity of h-SCOT-t is a prerequisite for male infertility and the SNPs diminishing the enzyme activity contain some cause of male infertility.

TABLE 5

Sccinyl CoA transferase activity at inside of HEK 293 cell transformed using recombinant h-Scot-t cDNA having SNPs

| | Major-type | L38P | L285R | T352M |
|---|---|---|---|---|
| Activity ratio | 100+− | 100+− | 50+− | 100+− |

Each assay was conducted three times.

2-3. Sequence Analysis of Human Protamine-1 DNA

A DNA fragment containing 557 bp amplified by PCR contained an intron composed of 91 nucleotides of from 204th to 294th (SEQ ID NO:170, FIG. 2). SNPs in 509 bp within each primer was identified by sequence analysis of a DNA fragment having 557 bp (FIG. 2). Since all DNA samples amplified about the same amount of PCR products, it was confirmed that the SNPs were by no means contained in primer sequence region. The expression rate of SNP was evaluated on male infertile patients as targets, and was compared with the case of volunteers whose reproductive ability was proved. In a total of 528 cases of male subject persons (infertile patients 258 cases and target volunteers having reproductive ability 270 cases), SNPs were found at 5 sites and 4 sites of them were present in the 133th, 160th, 320th and 321st coding region and 1 site was present at 431st of 3' non-translation region (FIG. 2 and Table 6). All the observed SNPs did not induce alteration of amino acid (silent mutation). All of the 3 sites of SNPs located at a133g, c160g, and g320a and SNP located at 14th and 46th amino acids (FIG. 2) were major homozygosity and heterozygosity and no minor homozygous SNP was observed (Table 6). With regard to the other c321a SNP located at 47th amino acid, in infertile parent population and control parent population having reproductive ability, respectively, 56.6% (146 cases) and 47.8% (129 cases) were homozygous major c/c type, 34.5% (89 cases) and 43.3% (117 cases) were heterozygosity (c/a), and 8.9% (23 cases) and 8.9% (24 cases) were homozygous minor type (a/a) SNP. In addition to a431g SNP in the 3'-non-coding region, all these SNP did not induce any amino acid alteration and also it was not shown that occurrence rate in infertile patients was significantly higher than that in volunteers who were proved to have reproductive ability (Table 6: the positions of nucleotides in Table 6 corresponds to the positions of nucleotides in FIG. 2).

TABLE 6

Expression rate of SNPs in protamine-1 and protamine-2 genes in infertile and reproductive ability-proved parent populations

| | Position | | | Number of SNP (%) | |
|---|---|---|---|---|---|
| | Nucleotide | Amino Acid | Genotype | Infertility group | Reproductive ability-proved control |
| Protamine-1 | 133 | 14(R) | a/a | 250(96.9) | 268(99.3) |
| | | | a/g | 8(3.1) | 2(0.7) |
| | 160 | 23(R) | c/c | 258(100) | 269(99.6) |
| | | | c/a | 0(0) | 1(0.4) |
| | 320 | 46(R) | g/g | 257(99.6) | 270(100) |
| | | | g/a | 1(0.4) | 0(0) |
| | 321 | 47(R) | c/c | 146(56.6) | 129(47.8) |
| | | | c/a | 89(34.5) | 117(43.3) |
| | | | a/a | 23(8.9) | 24(8.9) |
| | 431* | | a/a | 257(99.6) | 269(99) |
| | | | a/c | 1(0.4) | 1(1) |
| Protamine-2 | 248 | 50(Q) (Ter)*** | c/c | 257(99.6) | 270(100) |
| | | | c/t | 1(0.4) | 0(0) |
| | 398** | | g/g | 148(57.4) | 127(47.0) |
| | | | g/c | 88(34.1) | 118(43.7) |
| | | | g/a | 0(0) | 1(0.4) |
| | | | c/c | 22(8.5) | 24(8.9) |
| | 473** | | a/a | 146(56.6) | 127(47.0) |
| | | | a/c | 90(34.9) | 118(43.7) |
| | | | a/c | 22(8.5) | 25(9.3) |
| Total | | | | 258 | 270 |

The meanings represented by added asterisk symbol are as follows:
*3'-non-coding region
**Intron
***Ter: Stop codon (tag)

2-4. Sequence Analysis of Human Protamine-2 DNA

SNPs in 551 bp within each primer were identified by sequence analysis of DNA fragment (SEQ ID NO:173) in 599 bp (FIG. 3). Since all PCR amplified about the same amount of DNA determined on agarose gel electrophoresis, it was confirmed that the primer sequence region did not contain SNPs. In this case, 3 sites of SNPs were observed in 599 nucleotides in protamine-2 gene, and 1 site was present in exon and two sites in intron (FIG. 3). One site of heterozygous SNP in 248th nucleotide changed c into t, which changed glutamine into stop codon. This change was observed only one case of infertile patient among 153 cases of azoospermia patients and also was not found inn 270 cases of reproducible control parent population (Table 6). There is a possibility that this change is associated with a cause of azoospermia even in hemizygous state. Furthermore, 2 sites of SNPs of g398c and a473c were observed within intron. With regard to g398c, in infertile parent population and reproducible control parent population, respectively, 57.4% (148 cases) and 47.0% (127 cases) were major-type homozygosity, 34.1% (88 cases) and 43.7% (118 cases) were heterozygosity (g/c), and 8.5% (22 cases) and 8.9% (24 cases) were minor homozygous (c/c) type. Furthermore, the presence of different heterozygous SNP which was g/a type was observed in 1 case of the control group. With regard to another SNP of a473c, in infertile parent population and reproducible control parent population, respectively, 56.6% (146 cases) and 47.0% (127 cases) were major-type homozygosity, 34.9% (90 cases) and 43.7% (118 cases) were heterozygosity, and 8.5% (22 cases) and 9.3% (25 cases) were c-type minor homozygosity. There was no significant difference in expression rate of these intron SNPs between in the case of infertile parent population and in the case of reproductive ability-proved volunteers.

INDUSTRIAL APPLICABILITY

As precisely described in the above, the invention of this application provides 89 clones of mouse spermatogenesis genes (MSG) and full-length cDNA base sequences of these MSGs. Moreover, the invention provides a method for genetic diagnosis and methods for toxicity test and mutagenicity test using expression modulation and mutation of MSGs as measures. These test methods enable genetic diagnosis directly using male infertility gene DNA and analyses at a molecular level of environmental toxicity as influence of minute amount of chemical substances released into the environment on sexual differentiation and germ cell differentiation and influence of substances having reproduction toxicity and mutagenicity on the living body, especially influence on gene group exhibiting germ cell-specific expression. Furthermore, the invention contributes to detection and measurement of ED having a risk of inducing a low sperm count and reproductive dysfunction as well as global environmental assessment relating to ED. In addition, in the conventional test for "influence on reproduction" purposing detection of teratogenicity, the invention provides an additional novel assay for "mutagenicity against MSGs" and hence remarkably contributes improvement of international standard for assuring safety of medicaments and chemicals.

Moreover, the invention provides Scot-t gene mutation and protamine-2 gene mutation which cause hereditary male infertility. Furthermore, it provides a method for diagnosing male infertility targeting these gene mutations, mutant polypeptides derived from the gene mutations, and the like.

The invention claimed is:

1. A isolated polynucleotide which is the cDNA of human male infertility-associated gene Scot-t and consists of the nucleotide sequence of SEQ ID NO: 168, and has the following mutation:

"t" at 870th position is replaced by "g".

* * * * *

SEQUENCE LISTING

<160> NUMBER OF SEQ ID NOS: 183

<210> SEQ ID NO 1
<211> LENGTH: 3080
<212> TYPE: DNA
<213> ORGANISM: Mus musculus

<400> SEQUENCE: 1

```
agaacatccc agcatcttca ttgactttaa aagtatattc tggagtcttc tgtggttccc      60
tataacagag cttcagaggt tctccgattt taagaaagat gagctgcctg gaattacaaa     120
tgggcaggac ttttctattc actctttcaa caggaaaatt actaagcacc aacgttaaag     180
agtccttata tattacatgg caggaggggt gggtagactt agggatagtg aagacaccaa     240
taaggctcat tcggagtctt ccttgtatct caaaacccat cctcaataag gatggcggat     300
agggttgact ggttacaaag tcaaagtggc gtttgcaaag ttggtgtcta ttcacctgga     360
gacaaccaac accaagactg gaaaatggac acatcaacag atcctgtccg agtgctcagc     420
tggctccgca aagacctgga gaaaagtaca gcgggcttcc aggactcgag gttcaagcct     480
ggagagtcat cgtttgtgga ggaagtggct tacccagtgg accaacgaaa aggtttctgt     540
gttgattatt acaataccac caacaagggc agtccaggaa gattgcattt tgagatgtct     600
cacaaggaga acccttccca gggcctcatt tcccatgttg gtaatggggg ttccatagac     660
gaagtttcct tctatgccaa ccgcctcaca aacctagtga tcgccatggc ccgaaaggag     720
atcaatgaga agatccacgg cgctgaaaac aaatgtgtcc atcagtcatt gtatatgggg     780
gatgagccca cacccacaa aagcttgagt acagtggcct ctgagctcgt gaacgagaca     840
gtcaccgcat gttccaagaa catttccagt gacaaagctc ccggctctgg agacagggcc     900
tcggggtcgt cacaggcccc tggtctaaga tacatgagca ctctgaagat caaggagagt     960
acaaaggaag gcaagtgtcc agacgacaag cccggcacta agaagtcttt cttctataag    1020
gaagtgtttg agtcccggaa tgcaggagat gccaaggagg gcgggaggtc cttacccgga    1080
gatcaaaaac tgttcaggac cagccccgac aacaggcctg atgactttc aaactctatc     1140
```

```
agtcaaggga tcatgaccta cgccaacagc gtggtgtctg acatgatggt ctccatcatg   1200
aagacgctga agatccaggt gaaggacaca accatcgcca cgattctgct gaagaaggtg   1260
ctgatgaagc atgcaaagga ggttgtctcc gacctcatcg actccttcat gaagaacctc   1320
cacggcgtca cgggaagcct catgactgac acagactttg tctcggccgt gaaacgaagt   1380 ttttttctc atggaagcca aaaggccaca gatatcatgg atgccatgct gggcaagcta   1440
tacaatgtga tgtttgccaa gaaattccct gagaacatcc ggagagccag ggacaagtcg   1500
gagagttact cccttatctc cacgaaatca cgggctggtg acccaaagct ctcaaatttg   1560
aactttgcga tgaagtcaga atcaaagctg aagaaaaatt tgttttctac atgcaaacta   1620
gagaaagaga agacgtgtgc cgaaactctg ggtgagcata ttattaagga gggactgcac   1680
atgtggcaca agagtcagca aaatctcct ggcttggagc gtgccgcaaa actgggtaac   1740
gctccacagg aggtctcctt tgagtgccca gatccttgtg aggcaaaccc tcctcaccaa   1800
cctcagccac cagagaattt tgcaaatttt atgtgtgact cagactcctg ggccaaggac   1860
ctgattgtat ctgccctgct tctgattcag tatcacctgg cacagggagg aaagatggat   1920
gctcagagct tcctggaagc tgctgccagc accaattttc ccaccaacaa gccacctcct   1980
ccttctcctg tagttcagga tgagtgcaaa cttaagtctc ctccccacaa gatatgtgac   2040
caagaacaaa cagaaaagaa agatctgatg agtgtcatct tcaatttat ccggaactta   2100 ctcagcgaga ccatattcaa gagtagccgt aactgtgaat ccaatgtgca tgagcagaac   2160
actcaggaag aagagataca cccgtgtgaa aggcctaaga ctccatgtga aaggcctatt   2220
accccgcctg ccccgaaatt ctgtgaggat gaggaggcca ctggtggtgc cttatctggg   2280
ctaaccaaga tggttgccaa ccagctagac aactgtatga tgggcagat ggtggagcac   2340 ctgatggact cggtgatgaa gttatgcctc attattgcca agtcctgtga ctctcccctg   2400
tcggagctgg gagaggaaaa gtgtggggat gccagccggc caaattctgc cttcccagat   2460
aacttatatg agtgcctacc agtcaagggc acagggacag ctgaagccct cctgcagaac   2520
gcctacctca ccatccataa tgaactgaga ggtttgtcag acagcccccc cgagggctgt   2580
gaaatcccca aggtgatcgt cagcaaccac aatctggctg acaccgttca gaacaagcaa   2640
ctgcaagctg tccttcagtg ggtggctgcc tcagagctca atgtccctat tttgtacttt   2700
gctggtgacg atgaaggaat ccaggagaag ctgcttcagc tctcagccac tgccgtggag   2760
aaaggccgca gcgttgggga ggttctgcag tcggtgctga ggtacgagaa ggagcgacag   2820
ctggatgaag cagtgggaaa tgtcacgcgg ctgcagctgc tggactggct gatggcaaac   2880
ctgtgattgg ggcctaccct gagttccctc agcgggccga gtccccgccc cctcagcccc   2940
ctccatgccc cacagagccc taagtcccc tccatgccac ccacactaaa cacgccatct   3000
aacgctactc actggatttt gcagattttc ttgtccatgc gagcaaggac ataaatgaaa   3060
agattacagt taaagggcaa                                               3080
```

```
<210> SEQ ID NO 2
<211> LENGTH: 935
<212> TYPE: DNA
<213> ORGANISM: Mus musculus
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
```

```
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t

<400> SEQUENCE: 2
ctgtccttgg atccgctttc tcaggctggt gctgaaggtc ctaagtcagc ctcaccagcc      60
agctctgttt accwggaccc acatgagcgt tcacaggcca cacgaccctc cactccctgt     120
gcagacccct ctgagcctgg gctcaccggc tgatccattg tcaaccggag ctcattaagc     180
ccccctcatc tgtcccggag cctacagagc ccttcccaga gccctctggg cgngctctgc     240
atccgcgtgg gagcgggtga cccaactccc acataccttc actgctgccc ttaactgact     300
tccacagttc atacccacgg agagggtggg aaatgagagc tcaggttggc gctgagcctg     360
ggccttgtgt ggtagggttg tccaagacag gaggaggcct attgagggtg ggatcctagg     420
actgaagagc ttgtcaggac cgcagaagga gcgccccctg cgaggaaaag cagaccaggt     480
ggttcggtga gagcagagaa ggctaggcta gcatctattt ctaggctact gctgtccctg     540
gggggatgct ggtgcggagg ataatggcca caagacctgg gagagaaagt cacaagggac     600
cccgctactc ggcaagagta gtcactaggt agaaggcggc ccagcagggn ctgccatcat     660
ctgctttagg gatctgccgt ggcagcagga accctgctca gttcccttcc tgcaccttgc     720
cccacagccc tagtcgaggg aactgcaacc tgctgtactt agagatggac agcaggcaac     780
agcgccccca gaggaagacg ctacagtggc agcttgctca agagcaaaga caacagtcac     840
ccccacaggg nctttgnctg tggnctncag ncagncagac accaagagca agcctcagga     900
cgacttgcga cccaagactg ggtgtgtgag nctca                                935

<210> SEQ ID NO 3
<211> LENGTH: 2301
<212> TYPE: DNA
<213> ORGANISM: Mus musculus
<220> FEATURE:
<221> NAME/KEY: misc_feature
<222> LOCATION: (40)..(40)
<223> OTHER INFORMATION: b is c, g, or t
<220> FEATURE:
<221> NAME/KEY: misc_feature
<222> LOCATION: (121)..(121)
<223> OTHER INFORMATION: n is a, c, g, or t

<400> SEQUENCE: 3
```

-continued

```
ggggtaaaga ctccgtggtt aatgtcaccc ggcggagggb tgcgatggag ggggatgcct      60
cagactctca ggtgactatt aagaatatcg aaaaggagct tatttgccca gcgtgcaagg     120
ngctgtttac ccacccgctg atccttccct gccagcacag cgtctgtcat aagtgtgtga     180
aagaactttt actgtctctt gatgactcgt tcaatgatgt ggcgtcagac agctcaaatc     240
agagcagccc taggctccgg ctcacctccc ctagcatgga taaaatcgac aagattaaca     300
gaccaggctg gaagcgtaat tcactgaccc cgagaccaac cacgttccct tgtcctggct     360
gtgaacatga tgtggatctt ggagagcgag gagtcagtgg tctgtttcga aatttcactt     420
tggaaacgat tgtcgagaga taccggcagg ccgctagggc agccacagcc attatgtgtg     480
acctttgtaa acctccaccc caggaatcta caaagagctg catggattgt agtgcaaggg     540
gctactgcaa tgaatgcttc aaaatttatc atccctgggg cactgtaaaa gcccagcatg     600
agtatgtggg ccccaccact aatttcagac ccaaggttct aatgtgccca gaacatgaga     660
cagagagaat aaacatgtac tgtgaactat gcagaaggcc agtttgccac ctctgtaagt     720
tgggtgggaa tcattccaat caccgggtaa ccaccatgag cagtgcctac aaaaccttaa     780
aggagaaact ttcaaaagac attgatttcc ttattggcaa ggaaagccag gtgaagagtc     840
aaatttctga actaaacttg ctaatgaaag agacagagtg caacgtagag agggcgaagg     900
aagaagcgct ggcgcatttt gaaaagctct ttgaaatcct ggaagacagg aagtcgtctg     960
ttctgaaagc catagatgcc tctaagaaac taagactaga caagtttcac actcagatgg    1020
aagagtacca aggccttcta gagaataacg ggctcgtggg gtatgctcag gaagttgctg    1080
aaggagacgg atcagtcttg cttttgtgcag acggcgaaca gctccatctc agaatacaga    1140
aagctacgga gtccctgaag agctttagac ctgcagccca ggcttctttt gaagactatg    1200
ttgttaacat atcgaaacaa acagaggtgc ttggagagtt gtcctttttc tccagtggca    1260
tagacattcc tgagatcaac gaggaacaga gtaaagtgta taataacgcc ttgatagact    1320
ggcatcatcc agaaaaggac aaagccgaca gctatgttct agaataccgc aagattaata    1380
gagacgaaga aatgatatca tggaatgaga tagaagttca cggcacaagt aaagttgtct    1440
ccaaccttga aagcaacagt ccctatgcgt tccagtgag agcttacagg gggttctatc     1500
tgcagtccct gcagcagaga attgatcctg catactcctc cagctccagt tttcagttt    1560
cctgttcgat gagaagtgtg gctacaacac tgagcacctc ttgctgggac ctgaagagag    1620
accgggtgga gagcagagct ggatttaacg tcctcctggc tgcggagcgc atccaagtgg    1680
gccattacac aagcttagac tacatcatcg gggatgtcgg agtcacgaaa ggtaaacact    1740
tctgggcctg ccgcgtggaa ccgtattcat acctggtgaa agtgggagtt gcttccagcg    1800
acaaactgca agagtgcgtg cgctctcccc gagatgcagc tagtccaaga tatgagcaag    1860
acagtggaca tgacagtgga agcgaggacg cctgttttga ttcttcacag cccttttacat    1920
tagttactat aggcatgaag aaatttttta tacccaagtc acctacttcc tctaatgaac    1980
cagaaaacag agttctcccc atgccaacga gtatagggat tttccttgac tgtgataaag    2040
gcaaagtgag cttctatgat atggaccaca tgaaatgcct gtatgagcgc caggtggact    2100
gttcgcatac aatgtatccg gcctttgcct tgatgggcag cggaggaatt cagcttgagg    2160
aagccatcac agcaaagtat ctggaatatg aagaggatgt gtagcttgga cacccacgt    2220
gactgatgag gataagaacc gtgaacaaag ccatgccttg atgttaatct aattacatat    2280
catttacgtc tctgtcacca a                                             2301
```

<210> SEQ ID NO 4
<211> LENGTH: 892
<212> TYPE: DNA
<213> ORGANISM: Mus musculus

<400> SEQUENCE: 4

| | | | | | | |
|---|---|---|---|---|---|---|
| gcgactccat | gaacacagcc | aaactgaagt | gcctcgtcct | ccctcgctgg | ctctgctccc | 60 |
| accctgtgcc | cgcgctcagc | cccctctgcc | tatctgagag | ccttctgctc | ccaaagaggg | 120 |
| ccagagacac | caagagatca | tagagagcgt | gaggggctgc | cagcttccag | aatgttctta | 180 |
| gacctcccaa | cctcggctcc | cgtacccctg | ctggggctct | gtgccgagca | actgtccacg | 240 |
| catcctacac | aaagccagtg | gaaggttttg | taatgcagta | ctgacgaact | tcagctcgag | 300 |
| agtcggtccc | aacttgttcc | cccagagttc | ttgtcacagt | gggtcccagc | tgaggggtca | 360 |
| ggggacatga | gctgtttgtc | agctgggaat | acctcgccct | atgcccagct | ccagaatggg | 420 |
| tctcaacccc | cagctgggca | gacagtcccc | gatcccccag | aatggccttt | gcttccatcc | 480 |
| aaagaacacc | gccaacacac | acacctccga | ccccgagacg | tcctgcgttg | atctcggctc | 540 |
| tccggaggac | gcagaattcg | gttctgaagg | aaagtgggag | ggtacttctg | ctgagggatg | 600 |
| tctgatgggg | acccgggtgg | aacctctcgg | gaaggttgta | ggcagaacca | ccctggggcc | 660 |
| agagcttaga | gcgaggctgg | tgctgtcccc | tttgccccgt | gctttggtca | gcatgctggt | 720 |
| cttgtcttca | gcctggcttt | ctaggcagag | aggagaccag | gcttcttatg | agtctgcatt | 780 |
| gtccctcagt | gggtgcaaga | ggccatgtgg | gtcatcagcc | catgcctcac | cctggcagtg | 840 |
| tgctctaact | gaggctcctc | tacccaactg | aataaactg | gaagctgaaa | aa | 892 |

<210> SEQ ID NO 5
<211> LENGTH: 690
<212> TYPE: DNA
<213> ORGANISM: Mus musculus

<400> SEQUENCE: 5

| | | | | | | |
|---|---|---|---|---|---|---|
| gaattcgacg | tctagatccc | cgggctctcc | agcgttgtgc | tacattccgt | gctttgggcc | 60 |
| ggatcctagt | ttaaacttgg | cccaaacctc | accgtcttcc | gggtcaaacg | tgccattcct | 120 |
| cagccccggg | ttccgcttcc | tccctagaaa | cccaatccct | cccgacgtcg | ccagcacccc | 180 |
| tacccccaaa | ctatggcccc | tagctaagtg | gccaagtggc | tggagcgggg | aggcggasag | 240 |
| ctgggagagc | tgtgggcggg | tcggactcgc | gtgcctccac | agggtcagga | acctgtggag | 300 |
| gtgacacctt | tggaggagga | ctctggatgg | ccctagcgg | cgcccaggt | cctcgaggct | 360 |
| acgtcccaag | tgctttggaa | gcccatggtt | atttcagaaa | ccatgaagct | ggttcctggt | 420 |
| gtgagtatgt | ggaaccgggg | aacccaggag | ctgctcaatc | ctgctgtcat | ccggaaggag | 480 |
| gctgaagaag | gcaccccca | ggcgcctgag | cagcaaccca | tccagacagg | tgtgtccaag | 540 |
| cctcaggtga | ttatgaaaca | gataaggaac | gagaccccca | aagcctggct | gctcccacc | 600 |
| aagcctgtgc | cccactctgg | gtcctgagcc | tccacactgg | gaaatggacc | ttgctcaaaa | 660 |
| ataaacgaat | tgccgcagaa | aaaaaaaaaa | | | | 690 |

<210> SEQ ID NO 6
<211> LENGTH: 725
<212> TYPE: DNA
<213> ORGANISM: Mus musculus

<400> SEQUENCE: 6

| | | | | | | |
|---|---|---|---|---|---|---|
| aggctgtttg | catggaccga | gctgacacaa | tatatgattt | caaaggtatt | aaacaagaag | 60 |

```
ggctactcat cagaaaaggg atgacgcggg agctgaagaa cgaactcagg gaggtgagag      120
aacaactcac ggaaaaaatg aagagataaa acagataaa ggatataatg acaaagatt       180 tcgataaact ttatgagttt gtggaaatta tgaaggaaat gcagcaggat atggacgaaa      240
agatggatgt tttaattaat aatcagaaga acaacaagct tcccttcaa aaccaagcca      300 aggagcagca gaaattctgg cagctaggaa agatggacaa aggctcccaa gccatgatca      360
cagaagaacc cgatggagca ccattggctt gtgacaagaa tgtggtgcca ccaaaaccaa      420
cgaggaatcc actggagtcc ctccatccat gtcagagttg ctgcgagacc ttcacaccat      480
gcctgggtgc cttttcacc cttgtcgtct ggagctgctt tctaatttat ctgtacttca      540
acttcgccga ggtggagcat gtgctgccga cctagcacag ccatggagcc taccaccagc      600
tccaactcat catctcctga ctcctgagct acacagcaga cttttctgcc ctcttaaaca      660
ccctccaacc cccacccctg cccaggcttc cacctggaaa ttaaagaatc tcatttaaag      720
caaaa                                                                  725

<210> SEQ ID NO 7
<211> LENGTH: 1045
<212> TYPE: DNA
<213> ORGANISM: Mus musculus

<400> SEQUENCE: 7
gggacttcca ggcggaggtg gtgggctatt taggggaggg gtagtcacag atgtccagca      60
ggagtccttg agaggcaaag cacactcag catccctgag accctaccat gttcctcttc       120
tcccggaaga ccaagacccc catcagcacc tacagtgact cctacagggc tcctacctcc      180
atcaaggagg tctataagga cccaccacta tgggcctggg aagccaacaa gtttgtgacc      240
ccaggtctga ctcagactat gcaccgccac gtggaccctg aggccctgca aagatgacc       300 aaatgtgccg cacaggacta cacctataag agttccatat caggtcaccc ttatttgcct      360
gagaaatact ggctctctcc agatgaagag acaaatgct gtccgagcta cctggacaat       420
gaccggtaca acacgtggaa gacgagtcct tgcagcaact actggaacaa gtataccggc      480
tgtcttcctc gactgtccaa ggacaccggg atggagtcag ttcgaggaat gccgttggaa      540
tatcctccta gcaggagcg cctcaacgcc tacgagcgcg aggtagtggt gaacatgctg      600
aactcgctgt ctcggaaccg gactctgccg cagattgtac cccgctgtgg gtgcgtggac      660
cctctcccgg gccgattgcc ataccaagga tatgaaagcc cttgctccgg ccgccactac      720
tgtctgcgcg ggatggacta ctgcaccacc cgggagccta gcacagaacg ccgcctgcgc      780 cttttgtgctc gcagcagccg actgagtgtg tcgcccttcg gtcaccggcc aggaatgcaa      840
tgtgctgtta caactccccc gcccatcatt ttacccgtat cccaaccta gatgggacac       900 aagtcacttc aagaagactg gtggttccag agaaacaact atgtagtcca tcctgagttt      960
gtgtctgaga ctgtctgtct accttcctag taagcttgac aggcaaggga ggagtgctca      1020
ataaactctt cacacaaaaa aaaaa                                            1045

<210> SEQ ID NO 8
<211> LENGTH: 932
<212> TYPE: DNA
<213> ORGANISM: Mus musculus
<220> FEATURE:
<221> NAME/KEY: misc_feature
<222> LOCATION: (37)..(37)
<223> OTHER INFORMATION: s is c or g
<220> FEATURE:
<221> NAME/KEY: misc_feature
```

<222> LOCATION: (38)..(38)
<223> OTHER INFORMATION: b is c, g, or t
<220> FEATURE:
<221> NAME/KEY: misc_feature
<222> LOCATION: (39)..(39)
<223> OTHER INFORMATION: n is a, c, g, or t

<400> SEQUENCE: 8

```
ttaacctcac taaagggaac aaaagctgga gctccasbng gtggcggccg ctctagaact    60
agtggatccc ccgggctgca ggaattcgat atcaagctta tcgataccgt cgacctcgag   120
ggggggccct taggacgcgt aatacgactc actataggga attcgacgtc tagatccccg   180
gggtccgagc caagatacaa catacttgct ggatgcccta agaagaggac aattttcttc   240
ttctgttgca gggctgttat cacacaaggc tctgaggaaa atattaata atgttaaatt    300
tttgcagtcc attttgaaac gaacaaggct ttcatgatac atcttgtctt tgaagatgag   360
aatacaagaa gacaggtaaa cacaagacgt gaagagtagt gaaagggact agtgcttgcc   420
aaaggggcct gagagggaag cctggtcagc accgtgtgga cagccctgca ctgttttcca   480
aagatgctct tgaagtagtc ctcattaaca cagcttgcct tcacctgcca aagctcttca   540
tcatgggctg catgaagtca aggaaacgt tcccatttcc taccacattg gacattgaca    600
agctgcatga gagtgaggag gcctttattc cagatgacag cagtcaatat aggacacctt   660
ctccaggtga acaacagcaa gtccaggaag taaagaaact cccagagccc ggtgctgtga   720
tcggtgccct gatccttgaa ttcgcagacc gtctggccag tgaaattgtg gaggatgcct   780
tgcagcagtg ggcatgtgaa acatccagt actacaacat cccatacatc gagagtgagg    840
gctcagacac caccattaat tgatgatact caactgtgct ctggatgtag tcggtgctag   900
ttaaatacat aagttttcaa ataaaaaaaa aa                                 932
```

<210> SEQ ID NO 9
<211> LENGTH: 861
<212> TYPE: DNA
<213> ORGANISM: Mus musculus
<220> FEATURE:
<221> NAME/KEY: misc_feature
<222> LOCATION: (3)..(3)
<223> OTHER INFORMATION: s is c or g
<220> FEATURE:
<221> NAME/KEY: misc_feature
<222> LOCATION: (4)..(4)
<223> OTHER INFORMATION: d is a, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (8)..(8)
<223> OTHER INFORMATION: k is g or t
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (11)..(11)
<223> OTHER INFORMATION: r is a or g
<220> FEATURE:

```
<221> NAME/KEY: misc_feature
<222> LOCATION: (12)..(12)
<223> OTHER INFORMATION: d is a, g, or t
<220> FEATURE:
<221> NAME/KEY: misc_feature
<222> LOCATION: (13)..(14)
<223> OTHER INFORMATION: s is c or g
<220> FEATURE:
<221> NAME/KEY: misc_feature
<222> LOCATION: (16)..(16)
<223> OTHER INFORMATION: r is a or g
<220> FEATURE:
<221> NAME/KEY: misc_feature
<222> LOCATION: (18)..(18)
<223> OTHER INFORMATION: r is a or g
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (22)..(22)
<223> OTHER INFORMATION: s is c or g
<220> FEATURE:
<221> NAME/KEY: misc_feature
<222> LOCATION: (23)..(23)
<223> OTHER INFORMATION: m is a or c
<220> FEATURE:
<221> NAME/KEY: misc_feature
<222> LOCATION: (24)..(24)
<223> OTHER INFORMATION: b is c, g, or t
<220> FEATURE:
<221> NAME/KEY: misc_feature
<222> LOCATION: (26)..(26)
<223> OTHER INFORMATION: s = c or g
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (36)..(36)
<223> OTHER INFORMATION: h is a, c, or t
<220> FEATURE:
<221> NAME/KEY: misc_feature
<222> LOCATION: (37)..(38)
<223> OTHER INFORMATION: r is a or g
<220> FEATURE:
<221> NAME/KEY: misc_feature
<222> LOCATION: (40)..(40)
<223> OTHER INFORMATION: n is a, c, g, or t

<400> SEQUENCE: 9
ctsdntnkyw rdsstrcrga nsmbasctnt acgtthrrgn gagctggacc tagcaagcag      60
aggatattgg acctctttt ttaaaaaaaa agaggcatgg accatgctaa gaaaaagtgt      120
atttctaatc caaactgtga ctctgaagac aagccatgta aaaacaaaat gtttaacacc    180
atttaccata accagaacaa accaaagcct catttgtgac caaggtcgat caatcacaat    240
atatttggac ttactaccat tcctgcacag atcactgaca tcagatcata gattgtgaat    300
ctcatcaatg ataatctgga aactccttgt gtaccactat ggtttgtggg ctgcatctgg    360
cattcttcca aaagaggcaa gatctcatat cagttgtgtt aagaccatat cattgctttc    420
aagtggtcac gcatgaacat aacaaggaga caccttggaa tcaaaggtgt gggagctcca    480
ctcagaaatt ctctgttccc aggtcttcct agatgagacc ctttagagtc aaggagaagc    540
tgacctcaag tatgacctga gccatacccca ctactccagg aaggttggac acagtttaac   600
cacaaggaga gctggtctga taaatgcaat gatggcaaaa gccataaagt gacatcagtg    660
ggatcctggc agccttctga ctacagagta ccctgggtcc agcttaactt caagagtgta    720
tgggccacac tctttctttt tatgatcttg gacaatcttc actacaaggt agccttgtag    780
```
ccttacatta ttctttagca ggcatttcat gccctagcat tgtgtatcta gttttcaata    840 aataataactt tcatttncaa a    861

<210> SEQ ID NO 10
<211> LENGTH: 460
<212> TYPE: DNA
<213> ORGANISM: Mus musculus
<220> FEATURE:
<221> NAME/KEY: misc_feature
<222> LOCATION: (3)..(3)
<223> OTHER INFORMATION: s is c or g
<220> FEATURE:
<221> NAME/KEY: misc_feature
<222> LOCATION: (4)..(4)
<223> OTHER INFORMATION: d is a, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (8)..(8)
<223> OTHER INFORMATION: k is g or t
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (11)..(11)
<223> OTHER INFORMATION: r is a or g
<220> FEATURE:
<221> NAME/KEY: misc_feature
<222> LOCATION: (12)..(12)
<223> OTHER INFORMATION: d is a, g, or t
<220> FEATURE:
<221> NAME/KEY: misc_feature
<222> LOCATION: (13)..(14)
<223> OTHER INFORMATION: s is c or g
<220> FEATURE:
<221> NAME/KEY: misc_feature
<222> LOCATION: (16)..(16)
<223> OTHER INFORMATION: r is a or g
<220> FEATURE:
<221> NAME/KEY: misc_feature
<222> LOCATION: (18)..(18)
<223> OTHER INFORMATION: r is a or g
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (22)..(22)
<223> OTHER INFORMATION: s is g or c
<220> FEATURE:
<221> NAME/KEY: misc_feature
<222> LOCATION: (23)..(23)
<223> OTHER INFORMATION: m is a or c
<220> FEATURE:
<221> NAME/KEY: misc_feature
<222> LOCATION: (24)..(24)
<223> OTHER INFORMATION: b is c, g, or t
<220> FEATURE:
<221> NAME/KEY: misc_feature
<222> LOCATION: (26)..(26)
<223> OTHER INFORMATION: s is c or g
<220> FEATURE:

```
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (36)..(36)
<223> OTHER INFORMATION: h is a, c, or t
<220> FEATURE:
<221> NAME/KEY: misc_feature
<222> LOCATION: (37)..(38)
<223> OTHER INFORMATION: r is a or g
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
```

```
<220> FEATURE:
<221> NAME/KEY: misc_feature
<222> LOCATION: (377)..(378)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (382)..(383)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (395)..(397)
<223> OTHER INFORMATION: n is a, c, g, or t
<220> FEATURE:
<221> NAME/KEY: misc_feature
<222> LOCATION: (399)..(400)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (413)..(414)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t

<400> SEQUENCE: 10
```

```
ctsdntnkyw rdsstrcrga nsmbasctnt acgtthrrgn cctctaccac ctgccagcac      60
ctgcaggatc tcgagctgtg acctgtgacc cagccccagg acctcctacc cacctgccca     120
gcatctgcag gatctccaag atcttcagct ctgaccctaa gatcaccac cctggacctc      180 ccacccacct gcccagcacc tgcaggatct cgagctgtga ccctgtgacc ccagccccag     240
gacctnctac ccanctgncc agcacctgna ggatctngag ctgtgactnt gtgaccccga     300
ccctggaacc tncnaccnag ntgaccagca cctgnagtat ccnaggatct nagntgtgac     360
cctgtgaccc cnanccnnan cnngggacct ncnannnann tgancagnan ctnnagaatn     420
tncaggatct tnagtttggt ntncataann anagtgtgnt                            460
```

<210> SEQ ID NO 11
<211> LENGTH: 654
<212> TYPE: DNA
<213> ORGANISM: Mus musculus
<220> FEATURE:
<221> NAME/KEY: misc_feature
<222> LOCATION: (652)..(652)
<223> OTHER INFORMATION: n = a ,c, g, or t
<220> FEATURE:
<221> NAME/KEY: misc_feature
<222> LOCATION: (654)..(654)
<223> OTHER INFORMATION: n = a,c, g, or t

<400> SEQUENCE: 11

```
ggcaacacac tggagggcag agtgaagaaa gaccagtcac aaccactgaa agaactggga      60
cgtgtcacca ctggagacag ggaacaaagg gatggccatg ataccagcga ccccaggagg     120
aaaaggggat cgggaccggg tagtcctacg cgcgcacaga tccatccaca gaaaatggaa     180
gggttcgttt cagacctttg gaaggatgt gtgcatcacg ggtcagtcgg tgtcctccgg      240
cctccgcact gttccccagg agtatgcgtg ttgccaattc tacaccaagt tttggggcca     300
cctgcctgtt ccccgggctg atgcactgct gccctactgg gtgcctttt tcctgagacc      360 acgatagcag gtctcgaaga tgatgcggtg ttacatcccc agagccatga agtcctgccg     420
gttctccttc cacttctttt ggggccgcct tccgatgccc agggacaggt ctgttatgcc     480
ctactggttg ctccatgtgc tgatgtcaca gatgatggtt ttgatgaggc tggagaattt     540
tgaagatact ccaggttgcc cccaggtctc atgcagatgg tatggttgct ggtggttttt     600
tggaaccaac atcttctcct tatgttgcag cagctccagg tccttttaa gntn           654
```

<210> SEQ ID NO 12
<211> LENGTH: 696
<212> TYPE: DNA
<213> ORGANISM: Mus musculus
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t

<400> SEQUENCE: 12

```
agtattcacc atgacggtct ccaagcccag gatgtagcca accattgaca tgactgcagt      60
```

| | |
|---|---|
| agagcggcaa tatgcagatc tgctactgta ccatgatgta ggatcaggga atgttctgcc | 120 |
| agactcccag ggcccatgct tccacctgat gaatgatggc ctgaactatg agctcacggg | 180 |
| actatatgaa cacttccgtg caggagcctc ctcttgacta ctccttcaaa agcgtccaaa | 240 |
| tggtccaaga tctggtaacc gaggagccaa ggacaggtct acgaccggtg aggcactcaa | 300 |
| agtcaggaaa gttactgacc cagtccctgt ggctcaacaa caatgtccta aatgatctga | 360 |
| aagatttcaa ccaggtggtt tcacagcttc tacagcatcc agagaatttg gcctggattg | 420 |
| atctatactt caatgacctg actaccattg accctgttct aacaacattc ttcaacctaa | 480 |
| gtgtcctcta ccttaacggc aacggaatcc atcgactagg ggaggtgaat aaggtagctg | 540 |
| tacttcatcg ttttcggaga ctgatcttcc atgggaaccc catagaggaa gaaaaggggt | 600 |
| acaggtaagt ggctggtttt aaggtccaga tgagttttct aaggtacaag gggggagggg | 660 |
| aaaagatatt taagaccatt ttttgtnana ngngga | 696 |

<210> SEQ ID NO 13
<211> LENGTH: 830
<212> TYPE: DNA
<213> ORGANISM: Mus musculus

<400> SEQUENCE: 13

| | |
|---|---|
| ggtgatgagg atggcaagaa agagcggagg gcgatggacc cggtggctta agaaggagg | 60 |
| gaaaggtgga agaggaggct ggaaaagaag agggaagaga ggwggagggg ggagaggagg | 120 |
| aggaagtcac ctccgaaacc ctgcgtggca aaccccgacc tctgcccatc tcagcactac | 180 |
| cagctttcag ctacatccca ccaaggcacc agggccccaa ggagcgcagc tacttcagtc | 240 |
| gcgagggcca gacagggatt gtctccctct atgactgtgt ttttaagagg agactagatt | 300 |
| ataaccagaa attacaccga gatgacagag aacatgcaaa gaacctgggg ctccatatta | 360 |
| atgaggagga acaagaaagg actgtgccag tgctgatgtc ctctgtctat gggaaacgca | 420 |
| tcaatcagcc cattgagccc ctaaacagag actatggcca tgtgagccac gtgaagaccg | 480 |
| acttctacag gaagaacgag atccccagca tcaaggggcc cggctttggg cacatcaatc | 540 |
| cagcctgaag aagtcgtgtg gtttctaggg cactctgagg taccctatca gcaagtgatg | 600 |
| tagtatacga accattttcc tgttcatgtc acctgtagct gtaagaatgt tctttgactg | 660 |
| caggaggata agcacgtgca tatctaaggt ggtcctggct cagaacctgg aaaagcacct | 720 |
| ttccttatgt tgaaagcttt agggtaagga ttttcactgg acttatttaa aatgacactg | 780 |
| actgattcat tctgagacct gaataaaaga aaagcttgcc tcccaaaaaa | 830 |

<210> SEQ ID NO 14
<211> LENGTH: 690
<212> TYPE: DNA
<213> ORGANISM: Mus musculus

<400> SEQUENCE: 14

| | |
|---|---|
| tttttttttt tttttttttaa acaaacaaaa cctgcacctt taatgcttcg gtgatggcgg | 60 |
| gtaggaagca gtttctccac cgggcagcgc gaacccgggg aaaaccgggt agcttcccga | 120 |
| tgtcccagcg tggcccttgc tgaacggaat caagtggcca ctctaccagt gaggctgctc | 180 |
| agggatgagg tgcaggcaa tggctgtgag caaccaagtt tccaaataaa ggtggatgcc | 240 |
| caaggtttcg ctccggagga cttggtggtg cggataggsg gccagaatct gacggtgacc | 300 |
| ggccagcggc aacacgagtc gaatgacccg agcaggggcc gtaccgcatg gagcagagtg | 360 |

```
ttccccgaca aatgcagctc ccgccgacct tagatcctgc agccatgacc tgcagcctga      420
ccccctctgg ccatctgtgg ctcagggggac aaaacaagtg cctacctccc cctgaagctc     480
aaacaggcca gtcccagaaa cccrggaggg gagggcctaa gagctcctta caaaacgaaa      540
gtgtgaagaa tccttagagt ctcttagcgt tcttctgcgg grgaagagtt gaagcccaaa      600
cagactcggc cctgagactc aggaggggag gccctaggca ctacaaccta ccctaatgta      660
ttaaaccgag gtgtgcagca aaaaaaaaaa                                       690

<210> SEQ ID NO 15
<211> LENGTH: 720
<212> TYPE: DNA
<213> ORGANISM: Mus musculus

<400> SEQUENCE: 15
tccgggctga agcacccatc tggcaggctg gtgtgtctgt gggctgctgg agagtcgtgg       60
agtcctgttt cagtggctcc gttccccgg ttaccgagtg agccgcactt cccccagggt      120
tgggctgtcc aggcataggt gccagtttca aacggccag agggagttcc taagtgccca      180
atttcggcct tcagggtctc tctgtgtact tgttgctacc ctggaaatca gatcaagctg      240
gccttgaact cataaagaga cccactggcc ctctacctcc tggttgccag agagaaaagc     300
aacacaccca gggaccacca gtcagcagtg tggttgtaag gcccaccact caggacctct     360
ggggctgtgg cacgaaagag ctgctagctg gagaaggtag tctactcagc actcaagcct    420
atacttggag gacccacacc caaatccttc gcatccatag gaacccaaat aaccgtctct     480
gcttcctact gccttctcag atctgtggaa acttcttgag atccttgctc aacttaagag     540
aaaagactta actctacctt tacatcacgg tggatgatac ccaagtcgtg gagatagcct    600
gtggagaaca gtgggcatgg gtgtgtctgc cagtttcttt gtagccccta tctctcctct   660
atcctgactt ccaaaattaa atattaattc tgtttctcct ccccactaaa aaaaaaaaa      720

<210> SEQ ID NO 16
<211> LENGTH: 703
<212> TYPE: DNA
<213> ORGANISM: Mus musculus

<400> SEQUENCE: 16
gacagcttca atggaaggag ggagccaagg agtccctctg taagtctgaa gatgatcatt       60
acaacatgga ttatgtacat ctttgcccgg aaaaccgtag gctacccttc ccaccaaggg     120
tgaactcgga cattgaagtt gaagaaagcg aagctgtatc cgttgtgcag cactggttga    180
acaaaacgga agaggaggct ctcggagca taagggagaa gatgtccatc aacgactctc     240
ccacccatgg acatgacata catgtgacca gagatttggt gaaacaccat ctctcaaagt    300
ctgatatgtt aacagacccg agtcaagaag tcctggagga agaacaagg atccagttta    360 taagatggag ccacacccgt atcttccaag tgccaagtga agtgatggat gacgtcatgc    420
aggaacgaat agatcaagtg agacgaagcg tatctcatct catgtgtgac tcgtacaatg    480
atccaagctt caggacttct tgctcagaat gctaaggttg aaggactcca gggtcgatga   540
acagcctgtg tccaaagagt gtccacctca tgttttgacc tgaagggtga ccagacttga    600
gaagagagac tctaaacgct gagcccttgg ttaccaccat gacaatgctg gaaacttctt     660
actgaagtgc taataaagag acatcttatt taccaaccaa aaa                       703

<210> SEQ ID NO 17
<211> LENGTH: 1590
```

<210> SEQ ID NO 17
<211> LENGTH: ...
<212> TYPE: DNA
<213> ORGANISM: Mus musculus

<400> SEQUENCE: 17

```
agaagaggca gaggaggtcc ggtctgaccc ggagccccca gcgcccaccg cccgccgcga      60
tgggggcagg gccaacgggc agggctatgt gcagctagaa gggtaggcag tggaattgaa     120
gtggttacca agttgagcta tggagaagcc ggagtctctc gcacctgtta gtggcctcag     180
tgcagaatcc cctgggggggg tttctagggc agtacctggc agtgccagag gtatgcaaac    240
agacaccgga ttaccccccg gagtagcctt gcttcgcggt cctggctccc tcttgcattc     300
cgggaaccct gtagtccgca gtcctggtcc aattcagccc tctgaagggg cagtgaccct     360
caattcagga cccgctccgc aacttcagga ggttgcaagc cttgggtcca gcacatcccc     420
tggcactgga actggtgcaa ctaaggcgtc caccccggg ccggaggagg ctaaagtgta      480
cagctcggag agtagtacac actccgggac atctttcacg gagcggcctc ggagcatcct     540
aaaaaacagc agctccattt tgataaagaa acccccggt tcggagaaga agtctcagcg      600
ctgggatgaa atgaacatct tggctaccta ccaccctgct gacaaagact atggctttat     660
gaaggcggat gagcccagaa ccccctacca caggctgcag gacaccgatg aggacccatc     720
tgcagaatct tctctcaagg tgactcctca gtcagtggca gagaggtttg ccacaatgga     780
caatttcctc cccaaggtcc tccagtacgg agacaacaaa aactcaaagg acacagacaa     840
ctttgccaag acatactcca gtgattttga caagccaccga aagatacact acagtgaagg    900
gaagttccta aagtccccaa aaaacctgcc cactgaggaa gagagcattg ggctagtgc      960
cagcatcagc agcagtaatc aagctgtggc gacagacctg aagcctaggc ctgtggagaa    1020
aggctgggca ggaagactgg ccacaggagt caaaaatgac actgtcctga tgactgatag    1080
ccatgtctta agcaccaacg attctgctac ctatagaaac cagttcccat cagcctcaga    1140
ctcttccatg gggcagctgg ctaatctaca gcgcaaggaa tactacagca aggaaggta     1200
tctgaggtcc ggctcccgcc cagagctcgg agaggatata aagatgaag aacaggatag     1260
tccttcaggt ttgacctggg ttactgagaa tccgaaaggc actccagtca atgggtcaca    1320
ggtgacgccc aactgttggg ctaaggggcc aaggtgccga agtccaggga gctcagaaaa    1380
ggaacatgga agtaaccaga accctccaag ctggaatggg cgcagacgtg agcctgggcc    1440
aagatgaaag cttgcggctc cagtggactc agaaaaaaga acgtagacct tggaaaatgt    1500
agtcaacgag gagtggggtg aggggttgcct tccctgtctc cactctaatg gacaataaag    1560
agaacatcag gaatctgaaa aaaaaaaaaa                                      1590
```

<210> SEQ ID NO 18
<211> LENGTH: 2494
<212> TYPE: DNA
<213> ORGANISM: Mus musculus

<400> SEQUENCE: 18

```
ggggacaaca ctagaatctt tggacactag agaagcagtc ccagcacttt ggctaatgac      60
ttttttctgct tttccttaga aaattagacc gtaccaatat atttaagcaa tttgcttcac    120
tctatggctt tccccctact aatggtgata attcaattaa gaaccaagat cctggagaga    180
tgagtcagtg ggcaaaatgt gtgctgtaca agcacggggc cagagtgaac ctccaggatc    240
cattgagaaa tctgtggagg ttcttgcctc taaatccagc atttgggttg agaagagac     300
agactgacag gtcagtggtt tatcagacac agaaagctcc aggctcaatg aggggccttg    360
```

```
gctcaaaaac taaagtggag agtgatacag aaagatacac aacagaaaag cgaataggaa      420
accatcttgt ttccctaaca aaatatattg ttgaagatga atttctctcg tgacttaagc      480
tcagtgtgat taagtaaaaa aactacacag actagttcag aggtgtttgt caacgttttt      540
gagcaaaaat atttaggcat atgtcagcta tcagtgacgt aaggtggggc attggtggag      600
caactgaaat gagtattact catgatctct gtgttggaag gagcatagaa gtcttactag      660
ttgggtataa gttgtatttt tgtaaattac accaatctcg tttcctgcta aaagttttct      720
tttaaaggaa gctgtactat attgctgcct gtgccctgga gtacttgcca cctgaccccta     780 cctgtccttg ggcgttggag gtgagatggc acagagtcaa tgacacagac tccatgagca     840
gatcttggag acatctaagg tttaatgggg ctttcccaca ttccggactg ctgccctcca     900
atgacgctct gagtcattga tccaagtact ggcaacatgt ggaagcccag gacaggtcag     960
cgtcactagc ctccagtcta agcaacagcc gagaaccagt gtggtctgaa actccagcaa    1020
gtactagaca aagcctcctc tgttcatgga aagcggaaat gaaggatttt ccagccaatc    1080
acaaggaact atccacctct ccaaagagcc caccttcctt atccagcagg ctaccctgcc    1140
gagtgacctc cattcaaccc ttctgcagga acacagtgt ggcggtctaa ccaaaaacat     1200
aaaggccaac actcagaaaa ggcgtccggg aacagtgatt ctatcaaaac gctcaagtcg    1260
aattatgtca gaaacccagc ctagacccc tgtgatccca tcccgcaggc cagggttccg     1320
gatatgctat atttgtggcc gagaattcgg gtcccagtca cttgccattc atgagcccca    1380
gtgcttggag aagtggcgca ctgagaacag caaactaccc aagcacctga ggaggccaga    1440
acctccaaac cgcagcccat cggtggcact gactcccaca gccttcaggc agccaatgag    1500
gaagcatttc agagtgctca ggctcagctg ctgccctgtg aaaactgcgg ccgcacgttc    1560
ttgccagacc gtctcctggt tcaccagaga agctgcaagc caagggtga gaaccctgga     1620 ccaccaagca tgggtagttc taatgttcct actggtctca agaaagcttc tagcggcatc    1680
ccagcccgac caaggactct catctgttac atttgtggta gggaatttgg cacgctgtcc    1740
cttcctatcc atgagcccaa atgcttggaa aagtggaaaa ttgagaatga ccaactccct    1800
agagagctgc gtcggccaca gccccagaag cctcaacccc ttccagctgg acagtccagc    1860 caagagggg cgagtcaagc cgcacttgtg ccttgcccaa attgtggccg gacttttgct     1920
gtggaccgcc tacctgtaca ccagagaagt tgtaaatctc aacctagtgg accaaaaact    1980
tcaaattcga acatagaaag gaaggcggt ccaaatccac ccactaattc caagcaacag     2040
aggaacatgg aagcacccaa tggggacaag gtaactggtg tcatttaaga tgaagtaggt    2100
ggactgggga cacactacat cttcaaaagg atgagagaac tattcctaga gtcagccacc    2160
tcagccccaa cgatggtttc taccaaagcc ttacttgtgt ctcaaagcag cctgtccaag    2220
tggctctcct tttggactcc aggggctgag tgtgtgtcta ttttgcaaa gtagacctaa     2280 cagaatcctt gtctggcttg ttcataatcc tcttcagtcc tacagcctaa aagaaatgga    2340
ctgttttctc tgatccctcg tcccagtaat ccctgggaga gactgttact taaaatgagt    2400
cattaatgct gtgtctacat tacagagata tgattcccaa cccaacaaaa aaaaaaaaa    2460 aaaaaaaaaa aaaaaaaaa aaaaaaaaa aaaa                                  2494
```

<210> SEQ ID NO 19
<211> LENGTH: 1260
<212> TYPE: DNA
<213> ORGANISM: Mus musculus

<400> SEQUENCE: 19

```
gaattcgacg tctagatccc cggggcggaa tggagctggg gagagcaagg gtctcctctc    60
ccttcctcta gatcatcggc tatgagctcc aaggaagacc catcctttct gttaccacca   120
gagaaagacg ccattaccaa atggtggtaa gacatccaac caaaagctgg cgtcaagatt   180
atgctgatta actccaagtc ccaagactct tgttggctgg aaaccaagtt tcacagcaaa   240
ggagcttaag gacaaaaaca cagagcttac catctagcag tttcatgtga cttcttcctc   300
aaacacatca ccatcggctc gggaaggaca tccttcaaat acactcccat acttcgagac   360
catggccaaa ggagggaaag gccccaaggg caaaaagatc accccttaatg tggcaaagaa   420 ctgcatcaaa atcacatttg atgggagaaa acgccttgac ctgagcaaga tgggtatcac   480
caccttcccc aagtgtatct tgcggctcag tgatatagat gagctagatc ttagccggaa   540
tatgatcaga aaaattcccg actccatcgc caagttccag aacctgcgat ggctcgacct   600
gcacagtaac tatattgaca agctccctga atccattggc cagatgacct ccttgctctt   660
cctcaatgtg agcaacaaca ggctgaccac caacgggctt cctgtggagc tgaaccaact   720
caagaacatc cgcaccgtga atctgggcct taaccacctg gacagcgtgc ccaccacact   780 ggggggccctg aaggagctcc atgaggtggg gctgcatgac aatctgctga ctaccatccc   840
cgccagcatc gccaagctcc ccaagctgaa gaagctcaac ataaagagga accccttccc   900
aaatgcagat gaatcggaga tgttcgtaga ctccatcaaa aggctagaaa acctctatct   960
ggtggaagag aaggatatgt gttcatcctg tctgcagaga tgccaacagg ccagggacaa  1020
gttgaataaa atcaagagca tggcccccct ctgcaccgaga aaggccctct tttccaattt  1080
ggtttcaccc aactcaacag ccaaggatgc ccaggaagaa tggaggtgac ctgggaccct  1140
gaggcaggag ggagaaagga gggaagacga gacagtaggc tgtacccaaa ggagagggct  1200
cttgtattac tgtgggagcc tttccacccca agccataaaa caccattccc taaaaaaaaa  1260
```

<210> SEQ ID NO 20
<211> LENGTH: 2919
<212> TYPE: DNA
<213> ORGANISM: Mus musculus
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 20

```
tctccagcct caccctatcc cgccccggtc ccaggtccgc agcagcccca cccggaaggt    60
tcccataggc acacaaaccc gcttggctcg gctccccagc tccgcctcgn ccggtccag   120 ctccacctat cccgactct gtgccgccca gtnccagagc ccgccccttc tgggtcagcc   180
aattgtcacg tgaccgcggg cgtatccgag actgcctgag atcgacgctg tctaccacca   240
gttcctcctc aatttcgaac cgccttgtc ccatggcnct ggagcctccc gggtcaatgt   300
gaagtgactt ctgctcctga tnccaagcct gtgctggcac ctctgggtga acagggtcag   360
```

```
atccccgctc gtgacgttaa tgaagccctg gtccttttagg ggctctgtgg agttacaccc    420
caggccaccc ccttccgagt tctgacagat tcgctgagc ttcagagagt ggacctacag    480
acagaaggat tatttgggtc tggcggctca ggggaggagg agggctcggg actggggcct    540
caggtagggg ctggcctggg cgctcaagga acgagcctgc tggaatcgct ctgccttccc    600
taccaaggga ctgaggacac aggcccatct gtatctctgt catggccctg gggaccctct    660
ttttggcatt ggctgcaggc ctgagcactg ccagcccacc taacatcctg ctgatctttg    720
cggatgacct gggctatggg gacctcggct cctatgggca ccccagttct accacccta    780 acctggatca gttggctgaa ggtggactac ggttcacaga tttctatgtg cctgtgtctc    840
tgtgcacgcc atctcgggcc gccctcctga ctggccggct cccagttcga tcagccatgt    900
accctggagt tctggggccc agttcccaag ggggcttgcc cttggaggag ttgactttag    960
ccgaagtcct ggctgctcga ggctaccta caggatggc tggcaagtgg catcttggag    1020
tggggccaga gggggccttc ctgccccgc atcagggctt ccaccgattc tgggcatcc    1080 catattccca tgaccagggt ccctgtcaga acctaacgtg cttcccacca gacatcccct    1140
gcaaaggtgg ctgtgaccaa ggccttgttc ccatcccact actggccaac ctgacagtgg    1200
aggcccagcc cccttggctg cctggactgg aggcccggta tgtgtctttc tcccgagacc    1260
tcatggctga tgcccagcgc cagggccgac cgttcttcct gtactacgct tcccaccaca    1320
ctcactaccc tcagttcagt ggacaaagct tcaccaagcg ctcaggccgt gggccatttg    1380
gggactcctt gatggagctg gatggagctg taggggcctt gatgacaact gtgggggacc    1440
tcggtctgct ggaagagaca ctagtcatct tcactgcaga taacggtcct gagttgatgc    1500
gcatgtccaa tggcggctgc tctggcctct tgagatgtgg aaaaggaaca acttttgaag    1560
gtggcgtccg agagcctgcc ttggtctact ggccaggtca cattactcct ggtgtaaccc    1620
atgagctggc cagctctctg gacctgctgc ccacccctggc agccctgacc ggggctccgc    1680
tgcccaacgt caccttggat ggtgttgaca tcagcccctt gctgctaggc acaggcaaga    1740
gcccacggaa gtctgtcttc ttctacccgc cctacccaga cgagatccat ggggtctttg    1800
ctgttcggaa tgggaaatac aaggctcatt tcttcaccca gggctccgcc cacagtgaca    1860
ccacttcaga tcctgcctgt catgctgcca acgtctgac ggctcatgag cccccactgc    1920
tctacgactt atctcaggac cctggggaga actacaatgt tttggaaagt atagagggg    1980 tctccccaga agccctccag gctttgaaac acatccaact cctcaaggcc cagtacgatg    2040
cagccatgac ctttggcccc agccagatag ccaagggcga ggaccctgcc ctacagatct    2100
gctgtcagcc gagctgcact ccccacccctg tctgctgcca ctgcccaggc tcccagtcct    2160
gaggggactg gagaaatcac gggggtcctt caagggtagc ccaggacccc tagccctgtc    2220
ctgagtgtgt gatggttcac cagagggaca gggacaagtg tgtagtttgt atctggtaat    2280
gtaataacac cagctgagac ttgagacgtg ctaattcatc tagtccttgt ggtaactctg    2340
aggtcagtac tattctgctg tgctacaaga caaggacatt gacgcatagg gaatctcgtg    2400
gacctttcca gtccgatgc caccttacca gaaagagctt gagctaggat ttgaacccag    2460
gcaccctggg tttaaaattt gtcccaccct ggtgatctgc gtgtgttcca tggacacacc    2520
gctgaagcaa gacatgtccc ttcacagaaa ccggtaatga gttcaagtgc caggaactgg    2580 gggtggggggg agtggtgagg gcagaggaac cctaaagatg caaagcacct ggaagacagg    2640 cttttcctcaa gaagcaatgc cagaggccct ggaactggtc agcttggttc tttaaagaaa    2700
tcagctgtct ggagttaggt gataaactga tcattccggg tagagttaaa ggacctgggg    2760
```

```
acctgctag atcccaggaa ggaccatcag cagcttctga gactgcctca tggggctcac    2820
ttgtctctca agctctgaat ttctcctttg tgcatacttc aagtaatttt ctacaaaaaa    2880
aaataataaa aataaataaa ataaaataaa gttgtctac                          2919
```

<210> SEQ ID NO 21
<211> LENGTH: 1040
<212> TYPE: DNA
<213> ORGANISM: Mus musculus
<220> FEATURE:
<221> NAME/KEY: misc_feature
<222> LOCATION: (74)...(74)
<223> OTHER INFORMATION: k is g or t
<220> FEATURE:
<221> NAME/KEY: misc_feature
<222> LOCATION: (102)...(102)
<223> OTHER INFORMATION: k is g or t
<220> FEATURE:
<221> NAME/KEY: misc_feature
<222> LOCATION: (698)...(698)
<223> OTHER INFORMATION: w is a or t
<220> FEATURE:
<221> NAME/KEY: misc_feature
<222> LOCATION: (702)...(702)
<223> OTHER INFORMATION: y is t or c
<220> FEATURE:
<221> NAME/KEY: misc_feature
<222> LOCATION: (842)...(842)
<223> OTHER INFORMATION: w is a or t

<400> SEQUENCE: 21

```
ggggcacttc caggccggag tgtgggctat ttaggggaag ggtagtcac agatgtccag       60 caggagtcct tgakaggcaa agcccactac agcatccctg akaccctacc atgttcctct    120
tctcccggaa gaccaagacc cccatcagca cctacagtga ctcctacagg gctcctacct    180
ccatcaagga ggtctataag gacccaccac tatgggcctg ggaagccaac aagtttgtga    240
ccccaggtct gactcagact atgcaccgcc acgtggaccc tgaggccctg cagaagatga    300
ccaaatgtgc cgcacaggac tacacctata agagttccat atcaggtcac ccttatttgc    360
ctgagaaata ctggctctct ccagatgaag aggacaaatg ctgtccgagc tacctggaca    420
atgaccggta caacacgtgg aagacgagtc cttgcagcaa ctactggaac aagtataccg    480
gctgtcttcc tcgactgtcc aaggacaccg ggatggagtc agttcgagga atgccgttgg    540
aatatcctcc taagcaggag cgcctcaacg cctacgagcg cgaggtagtg gtgaacatgc    600
tgaactcgct gtctcggaac cggactctgc cgcagattgt accccgctgt gggtgcgtgg    660
accctctccc gggccgattg ccataccaag gatatgawag cycttgctcc ggccgccact    720
actgtctgcg cgggatggac tactgcacca cccgggagcc tagcacagaa cgccgcctgc    780
tgcctttgtg ctcgcagcag ccgactgagt gtgtcgctct tcggtcaccg gccaggaatg    840
cwatgtgctg ttacactccc cgccatcatt ttacccgtat cccaacctta gatgggacac    900
aagtcacttc agaagactgg tggttccaga gaaacaacta tgtagtccat cctgagtttg    960
tgtctgagac tgtcctgtct accttcctag taagctttgc caggccaagg gaggaagtgc    1020
tcataactct cacacaaaaa                                                 1040
```

<210> SEQ ID NO 22
<211> LENGTH: 324
<212> TYPE: DNA
<213> ORGANISM: Mus musculus

<400> SEQUENCE: 22

```
tcttcaggtt tgactgggtt actgagaatc cgaaaggcac tccagtcaag ggcacaggtg      60
acgcccaact gttgggctaa ggggccaagg tgccgaagtc cagggagctc agaaaaggaa     120
catggaagta accagaaccc tccaagctgg aatgggcgca gacgtgagcc tgggccaagg    180 caagggggatg aaagcttgcg gctccagtgg actcagaaaa agaacgtag accttggaaa    240 atgtagtcaa cgaggagtgg ggtgagggtt gccttccctg tctccactct aatggacaat    300
aaagagaaca tcaggaaaaa aaaa                                             324
```

<210> SEQ ID NO 23
<211> LENGTH: 697
<212> TYPE: DNA
<213> ORGANISM: Mus musculus
<220> FEATURE:
<221> NAME/KEY: misc_feature
<222> LOCATION: (560)...(560)
<223> OTHER INFORMATION: n is a c g or t

<400> SEQUENCE: 23

```
gtacgccaca gcgtatgatg cgtaaagtcc ctggagagct ccgctatggc tcagatggcc      60
aagaaagtcc actggtctag cgcagcagca ggagcagccg ctgctgccaa aatttcgaag    120
cttgagaaga ccaccaaaag attcaaactt attaagaagc gaaaccctag ttctaagctt    180
cccaagagat cttcacactc tttactttgt tctctttctc gttcctgttg ttgctgtcgc    240
tgtcgttgtt gctgttactg tcgttgctgt cgttgttgct gtagtcgttc tcgtcgtttt    300
cgtagcagaa ctacattaaa gttctttcag attacgagaa aggggagca atcacttcaa    360 agaagaatta ggagacaatt gacgcggagc caactggagc tgatcgaacc ggaaccgacc    420
atggctttgg agccaagcga gattacagtg gcattcttct ctcataagaa tgccaatgtg    480
tctgatccag aggaagttcc accatgcctt gacagtgacc catttccgaa tggagacttg    540
gccagttcct agaccccgan cgggtccaaa gtcccatgaa acatcagtgg acgggtctgg    600
gagctgagct gtggtcctgt caaggaaact cttcaccaca aactaatttg aatgatggtg    660
aaaataatca gatgtgaaaa taaaaaaaaa aaaaaaa                              697
```

<210> SEQ ID NO 24
<211> LENGTH: 848
<212> TYPE: DNA
<213> ORGANISM: Mus musculus

<400> SEQUENCE: 24

```
gggagctggc ggcagtggcg gctgtccggg ctgggttgtc agtcagagag aggagggaag      60
atggctcgcc cggactcgtg ctgctagaag gagaggggca ggtggcgcgg ctgccggcgg    120
acacagtcgc ccggtcgccg tggtcgccgt ggtcgccgtg gtcgtggggg gaggccgcgg    180
taggtccgga gctgctctgg ttgaaggttt gaaacaaatg tggaaagatg ttcacctcag    240
agataggagt tgtggaagaa tggctgtcag aatttaagac actcccagaa acatctttgc    300
caaattatgc cacaaatttg aaagacaaga gttctttagt tacatctctc tataaagtta    360
tccaggagcc acagagtgag ttactagagc ccgtgtgtca ccagctcttt gagttctacc    420
gcagtgggga ggagcagctg ctgcgcttca ctctgcagtt cctcccggag ctgatgtggt    480
gctacctcgc cgtgtcggcc agcagagatg tgcacagcag cggctgcatt gaggctctcc    540
tgctgggggt ttacaacctg gaaatagttg acaaacacgg acatagtaaa gtattgagtt    600
ttacaattcc atctttatcc aaaccatctg tatatcatga accttccagc attgggctca    660
tggcgctgac ggagagtgcg ctgtcccagc atggcttatc aaaagtcgtg tacagtggac    720
```

```
cccatcctca acgggagatg ctgacagcac agaacagttt gaagtattga cattccttct    780
ctgtgttaca atgctgcctt aacctacatg cccagtgtct ctcttcagtc actgtgtcag    840
atttgttc                                                              848
```

<210> SEQ ID NO 25
<211> LENGTH: 776
<212> TYPE: DNA
<213> ORGANISM: Mus musculus

<400> SEQUENCE: 25

```
caaagaagag actggcttca cggaagagtc taccaagaat cccattgtct tccagccgcc     60
tcacaggcct ttcctgggga ccctgtcttc atccaggacg gagtatcacc aagtcagact    120
acctccctgt aactcaccct cagggaagtg atttcctccc tgtgctgtcc agaggctctg    180
atcgggacac tggattcagc cgagtgaatg aaaggacctt gaaccccaga gtgcctactc    240
cagccccaca gtctgccagc atgagccaca ggtcctacca gcctcccag cggatgcaac     300 agacaaatgt tgccctgctt ggcaggagtc tgtgggaac aaggagccca cagggttcac     360
tcttaacaac cccagctatg ttcggagttc ctatgaacag acagagatc agcggtacct     420 gaccacctac aaccaagggt acttcgagaa tatcccaag gggctggatc gagaaggctg     480
gactcgaggt ggcatccagc cccagaaagc aggagcctac gccctcagtg agctgaataa    540
ccataccctc atggactcca ccccaaatcc cacggagacc ctgaggcacc tgcacccca    600 tgtgggaaga accctggctt cagttgaccc cttctatcga gacatgctta tagcagccgt    660
acccagcttc agttgagtct gcagggtttg gcatgacggg acaagctcct ccctcgtccc    720
aagattgcct cggtaacttt actaaggatt aagaacact gaaccagcaa aaaaaa        776
```

<210> SEQ ID NO 26
<211> LENGTH: 509
<212> TYPE: DNA
<213> ORGANISM: Mus musculus
<220> FEATURE:
<221> NAME/KEY: misc_feature
<222> LOCATION: (20)...(20)
<223> OTHER INFORMATION: s is c or g
<220> FEATURE:
<221> NAME/KEY: misc_feature
<222> LOCATION: (21)...(21)
<223> OTHER INFORMATION: k is g or t
<220> FEATURE:
<221> NAME/KEY: misc_feature
<222> LOCATION: (27)...(28)
<223> OTHER INFORMATION: w is a or t
<220> FEATURE:
<221> NAME/KEY: misc_feature
<222> LOCATION: (35)...(35)
<223> OTHER INFORMATION: r is a or g
<220> FEATURE:
<221> NAME/KEY: misc_feature
<222> LOCATION: (37)...(37)
<223> OTHER INFORMATION: r is a or g
<220> FEATURE:
<221> NAME/KEY: misc_feature
<222> LOCATION: (42)
<223> OTHER INFORMATION: y is c or t
<220> FEATURE:
<221> NAME/KEY: misc_feature
<222> LOCATION: (44)...(45)
<223> OTHER INFORMATION: w is a or t
<220> FEATURE:
<221> NAME/KEY: misc_featrue
<222> LOCATION: (55)...(55)
<223> OTHER INFORMATION: r is a or g
<220> FEATURE:

```
<221> NAME/KEY: misc_feature
<222> LOCATION: (59)...(59)
<223> OTHER INFORMATION: m is a or c
<220> FEATURE:
<221> NAME/KEY: misc_feature
<222> LOCATION: (82)...(82)
<223> OTHER INFORMATION: r is a or g
<220> FEATURE:
<221> NAME/KEY: misc_feature
<222> LOCATION: (169)...(169)
<223> OTHER INFORMATION: m is a or c
<220> FEATURE:
<221> NAME/KEY: misc_feature
<222> LOCATION: (286)...(286)
<223> OTHER INFORMATION: w is a or t
<220> FEATURE:
<221> NAME/KEY: misc_feature
<222> LOCATION: (300)...(300)
<223> OTHER INFORMATION: m is a or c
<220> FEATURE:
<221> NAME/KEY: misc_feature
<222> LOCATION: (306)...(306)
<223> OTHER INFORMATION: m is a or c
<220> FEATURE:
<221> NAME/KEY: misc_feature
<222> LOCATION: (366)...(366)
<223> OTHER INFORMATION: m is a or c
<220> FEATURE:
<221> NAME/KEY: misc_feature
<222> LOCATION: (447)...(447)
<223> OTHER INFORMATION: h is a c or t
<220> FEATURE:
<221> NAME/KEY: misc_feature
<222> LOCATION: (455)...(455)
<223> OTHER INFORMATION: y is c or t

<400> SEQUENCE: 26
caacactggg ctgagcagas kgcttcwwag gagtrargcc aycwwgaggc aaggrcctma      60
aaattctcat ccttccaaag argcgcgccc agggccaaga agaccggaag cattagattc     120
tcggaagatc ttagaggctg agaaatgagt acatcactac caacacccmc agacaacagc     180
acggccaaca catgcgcgaa gtcctgcagg ggatcagcca tagtctcaca ggccagaagg     240 gaagggagg ggacagactg ggacgatggg gaggttccgg tctgcwggcc ctcagggagm     300
aggccmagcg ggaccccgga aggggcccga gctgtgtctg tcctctcctg catacgctgc     360
aaggcmaccg cctgcgctca tcgatgctga tgtaccagcg acttcctggg cgcctgagta     420
ccagaggctc acacacccag tctgggghctg caagycgtcc tgaggcttgc actaggtgtc     480
tggctggctg gaggccacgg caagcccct                                       509

<210> SEQ ID NO 27
<211> LENGTH: 500
<212> TYPE: DNA
<213> ORGANISM: Mus musculus
<220> FEATURE:
<221> NAME/KEY: misc_feature
<222> LOCATION: (54)..(54)
<223> OTHER INFORMATION: r is a or g
<220> FEATURE:
<221> NAME/KEY: misc_feature
<222> LOCATION: (74)..(74)
<223> OTHER INFORMATION: r is a or g
<220> FEATURE:
<221> NAME/KEY: misc_feature
<222> LOCATION: (116)..(116)
<223> OTHER INFORMATION: r is a or g
<220> FEATURE:
<221> NAME/KEY: misc_feature
<222> LOCATION: (121)..(121)
<223> OTHER INFORMATION: r is a or g
<220> FEATURE:
<221> NAME/KEY: misc_feature
```

<222> LOCATION: (133)..(133)
<223> OTHER INFORMATION: r is a or g
<220> FEATURE:
<221> NAME/KEY: misc_feature
<222> LOCATION: (230)..(231)
<223> OTHER INFORMATION: w is a or t
<220> FEATURE:
<221> NAME/KEY: misc_feature
<222> LOCATION: (283)..(283)
<223> OTHER INFORMATION: r is a or g
<220> FEATURE:
<221> NAME/KEY: misc_featrue
<222> LOCATION: (295)..(295)
<223> OTHER INFORMATION: w is a or t
<220> FEATURE:
<221> NAME/KEY: misc_feature
<222> LOCATION: (298)..(298)
<223> OTHER INFORMATION: m is a or c
<220> FEATURE:
<221> NAME/KEY: misc_feature
<222> LOCATION: (302)..(302)
<223> OTHER INFORMATION: r is a or g
<220> FEATURE:
<221> NAME/KEY: misc_feature
<222> LOCATION: (389)..(389)
<223> OTHER INFORMATION: w is a or t
<220> FEATURE:
<221> NAME/KEY: misc_feature
<222> LOCATION: (399)..(399)
<223> OTHER INFORMATION: w is a or t
<220> FEATURE:
<221> NAME/KEY: misc_feature
<222> LOCATION: (410)..(410)
<223> OTHER INFORMATION: w is a or t
<220> FEATURE:
<221> NAME/KEY: misc_feature
<222> LOCATION: (453)..(453)
<223> OTHER INFORMATION: y is c or t

<400> SEQUENCE: 27

```
actaacaaat aagagttgtc acgcacaggg atcagaactg cagcccccca agtrctacca      60
gatagctagc tgtrtgactc cagatgagtc tcttaacctc tcggtagctg aaactrgagg     120
rcgacgccct ggrtgtgcat ctgataccca gagccagcca cttcgaggac cttcccgccc     180
ttctttgcac tctaggtcca ccgggaccct ggcgggaccg ggacgtagcw wccattcctc     240
agtccacacc tttcctacac gcacccgggt gcgaccctga gtrgctgaga ctccwgcmcg     300
crgactggct actgttaaga cccggagatg tgctccgggc tgaagtccct gcatgtgaca     360
gacacaggtg catagaccct gtggcagcwg caacgtccwt gagcatcgaw cttcgccacc     420
aaaggaggat acaggacggc ttccggagcg gayaaggctg gagcagcttt agaaactggt     480
gcacatttct ggccaaaaaa                                                 500
```

<210> SEQ ID NO 28
<211> LENGTH: 2961
<212> TYPE: DNA
<213> ORGANISM: Mus musculus

<400> SEQUENCE: 28

```
gcctccgggc aagatgaagg aggaacactg gaagtggagc gcctgaacac acggcgagac      60
tctgaaagct attaacattg tttgggcggt tagggcggtt ggcggcaact cgccggaggg     120
cggcagttgc gtggcacccc gtaagcgtgc ctaggcgcac gctcccctcc gctcctccac     180
tcagagagca aagtggggc ggaggggag ggggaagaac gcgaagggcg gtggaactac        240
aactcccgca aggccttgcg cgtccagggt gctttacaat agaagctcgg ttggcgaggt     300
ctgcggagag gtgtcggaac tgccgtttcc ggcatgttca ggtctacgag aacgaccgat     360
```

```
cagtggaggg tgggggagag actccaatgc ccagcgggcc atgcgcgggc agcgcttgcg    420
cgaaccgcgg acgggggggc ggtcgggcca tttaaatgtg tgtttgtggg tgaaatggct    480
gcgcaggtcg gagcggttcg cgtagtacgg gcggtggcgg cgcaggagga gccggacaaa    540
gaagggaagg agaaacccca tgttggggtt tcgccgcggg gagtgaagcg gcagcgccgg    600
gcgagcagcg ggggttctca ggagaagcgg gggcggccga gccaggaccc ccctctcgct    660 cccctcatc ggcggcgtcg tagccgccaa catcccgggc cgctgcctcc aacgaatgcc    720
gccccaaccg tcccgggccc tgttgaacct ctgctcctgc cgcctccgcc gccaccgtcg    780
ctggcacccg ccgggcccac tgtcgctgcc ccgctcccgg ccccgggcac ctcggccctc    840
ttcaccttct cgcctctgac ggtgagcgcg gccgggccca agcataaggg ccacaaggag    900
cggcacaagc accatcacca ccgcggctcc gatggtgacc ccggcgcctg cgttccgggc    960
gatctcaagc acaaggacaa gcaggaaaac ggcgaaagga gcggaggggt gcctctgatc   1020
aaggccccca agagagaaac agcagatgaa atggtaaaa cccagagagc tgatgatttt    1080
gtcttgaaga aaataaagaa gaaaagaaa aagaaacatc gagaagacat gagaggaaga    1140
cgccttaaaa tgtacaataa ggaagtacaa accgtctgtg ctggcctgac ccgcatcagc   1200
aaagaaattc tcacccaagg acagctaaat agcacttcag gagttaataa ggagtccttc   1260
aggtatttga aggatgaaca gctgtgcaga ttaaatttgg gcatgcaaga atatcgggtg   1320
ccccagggag tacagacacc ttttacaacg caccaagaac attctattcg cagaaatttc   1380
ttaaaaacag gtactaaatt tagcaacttt attcacgaag aacaccagtc caatgggggt   1440
gctcttgtcc ttcatgcata catggacgaa ctctcatttt tgtctccaat ggagatggag   1500
agattttctg aggagtttct tgctttgaca ttcagtgaaa atgagaaaaa cgctgcgtac   1560
tatgcgttag caatagtgca tggagcggcc gcttatctcc cagacttctt ggactacttt   1620
gcttttaatt ttcccaacac tccagtgaaa atggaaattt tgggcaagaa agatattgaa   1680
acaaccacca tttcaaattt tcatactcag gtcaacagga catattgctg tggtacctac   1740
cgagcaggtc ctatgcggca gataagtctt gttggagcag tagatgaaga agttggtgat   1800
tatttcccag agttcctaga tatgctagaa gaatcaccat ttctgaaaat gactttgccc   1860
tggggtacac tttccagcct ccagctacaa tgtaggtctc agagcgatga cgggcctata   1920
atgtgggtga ggccaggaga acagatgatc cctacagcag atatgccaaa gtcacccttc   1980
aaaagacgac gatcaatgaa tgaaattaaa aatctccagt acctacctcg gacaagtgaa   2040
ccccgagaag tcctctttga agacaggacc agagctcatg ctgatcatgt aggtcagggg   2100
tttgactggc aaagtacggc tgctgttggg gttttgaagg ctgtacaatt cggtgaatgg   2160
agtgatcagc ctcgcataac caaagatgtg atttgttttc atgctgagga ttttactgat   2220
gttgtacaga gacttcagtt agaccttcat gaacctccag tttctcagtg tgtacagtgg   2280
gtggatgaag caaaactaaa ccaaatgagg cgagaaggca ttcgctatgc tagaattcag   2340
ctttgcgaca atgatatcta cttcatccct agaaatgtca ttcatcagtt caaaacagtg   2400
tcagcagtat gcagcctagc ctggcatata aggcttaaac aataccaccc tgttgtggaa   2460
accgctcaaa acacagagag caattccaac atggattgtg tttagaagt tgactcccag    2520 tgtgtgagaa taaaaactga atctgaggaa agatgcacag atgcagct tttgacaact    2580 gcttcaccgt cttttcccacc tccatcagaa cttcatctac aggatctgaa gactcagcct   2640
cttccagttt tcaaggtgga gagcagactg gactctgacc agcaacacag tctgcaggca   2700
catccaagca ctcctgtgtg acatatccga tttccccacc tcccacttgc catccagcag   2760
```

```
atgccatcct gtcatctaag ctggtcatta ctaatacaca aggagactgt ctcctgacag    2820
ccagcactgt gcaatcactc aggaaccagc ggatctgcaa agacctacaa tcaaacgcaa    2880
atctccattt tccttttaca aagcattcta ccctcacttc cagtataaac atattaaaag    2940
aatataaaaa tgttaaaaaa a                                              2961

<210> SEQ ID NO 29
<211> LENGTH: 330
<212> TYPE: DNA
<213> ORGANISM: Mus musculus

<400> SEQUENCE: 29
agctctccat tttctcagac tactatgacc tgggctacac atgcgatcca acttgtttca      60
aggcccaccc caggagacaa agagcctcat gaaggcttcc tacacgcccg aagtgataga     120
gaagtcggtg agggatgtgg aacactggca caggaggaag acggatgacc tggaccggtg     180
gcaccggaag aatgctatga acatgaactt gcagaaagcg ctggaagaga atacggaga      240 gaagagcaga tccaaggcca agtagttgaa aggacattgg gaggaagctt gagaatgttg     300
ccaataaaga aataaaggct gtggtcaaaa                                     330

<210> SEQ ID NO 30
<211> LENGTH: 786
<212> TYPE: DNA
<213> ORGANISM: Mus musculus

<400> SEQUENCE: 30
caagaacggg acggaacgtg gagctcaagt ttgtcgactc atccggcggc agtttgagtt      60
agcgtggact ctttcagatc atcctagatt ctttgctctt tttctatgac tgctccggca     120
atcccatctc cgagcatttc caccccacag tgatcgggga gagtatgtac ggggattttg     180
aggaagcctt tgaccatctt cagaacaggc tgatcgccac caagacccct gaagaaatcc     240
gaggtggggg tctccttaag tacagcaacc tccttgtgcg ggacttcagg cctgccgacc     300
aggaggagat caagaccctg gagcgttaca tgtgctccag atttttcatc gacttccccg     360
acatcctgga acagcagagg aagctggaga cctaccttca gaaccacttc tcggacgagg     420
agagaagcaa gtacgactac ctcatgattc tccgcaggtt gtgaacgaga gcaccgtgtg     480
cctcatgggg cacgaacgca ggcagaccct gaacctcatc tctctcctgg ccttgcgtgt     540
gctggcagaa caaacatca tccccagtgc caccaacgtc acctgttact accagccagc     600
tccttacgtc agtgatggca acttcaacaa ctattacatt gcgcaccctc caattaccta     660
cagccagcct tatcctacat ggctgccctg taactaacct gaagacctga gggtttccac     720
agtgggaact cggttagggc aggggctctc aggtaggaga gcctctttct agatgtaggt     780
gtttgg                                                               786

<210> SEQ ID NO 31
<211> LENGTH: 770
<212> TYPE: DNA
<213> ORGANISM: Mus musculus
<220> FEATURE:
<221> NAME/KEY: misc_featrue
<222> LOCATION: (104)..(105)
<223> OTHER INFORMATION: n = a, c, g, or t

<400> SEQUENCE: 31
cgttggaagc tactgtttcg ggctcttgta cctgcctgag ttaacgtctc tggtggctgt      60
```

```
tttctggctt tctctgcata gcgattgctg acagaacgtg agtnngaatt tcactccaga    120
gacccaagag ccaaagcctg gcagaagaca gcacaatctt tcacaggaag aggcttttcc    180
tttcgaggtg taccacgtac actttgggca gcaggacact tggcttcaag tcaactcccg    240
gatggagcca gaatccatag aaatttgtcc ttataaccct caccaccgaa tcccgctcag    300
caggttccag taccacctgg cgtcatgcag gaagaagaac cccaagaaag ccaaaaagat    360
ggccagctgt aaatacaacg cctgccacgt ggttcccatc agaaagctgg ctgaacatga    420
agctacctgt gtcaacagga gctccgtgga ggaagaggac acattaggcc ctctgcaagt    480
cagcctccca cagccgcaga accaggacac actacaggtt cgttggcttt ccaaccctga    540
catttggaat gttgacggcg ccaactgtca cccaatgttc gtccttaaga gttttgttcc    600
ccaaaaactt gtttgtgaaa gtgacatcca agagtcacgg ggaggagacc aatgcccaga    660
agatcctcag actaggacca ggaaggcaaa cttctagcag gaggaagagg gctctcaaat    720
gcgtggatgg atcgcgcatc tcatctgaat aaaaacctgc aaagtaaaaa              770

<210> SEQ ID NO 32
<211> LENGTH: 379
<212> TYPE: DNA
<213> ORGANISM: Mus musculus

<400> SEQUENCE: 32
aaaacgtcga tgtgtaatca ctgagcttag agttaaacat tgtggtcaag tgcttgggtt     60
ccgtctgtag atttaagtgc tgacgttgta tctctcagta attttagatg tcttttaaaa    120
aatctgaaca agtgttagac ccgtgtgtgc gttggtgggc actcaagcat cccgtgggtg    180 acccccattct ttccccttcc tctgcgccac gccctcctg ccccgcccat ccccacctgc    240
ctccacccgg gaccctcacc ttgctgtggt ctttatctgc ctattactca gcctaaggaa    300
acaagttcac tctacacacg cataaaggaa agcaaatgtt attttaaga aaatggaaaa    360 taaaaacttt ataaacacc                                                 379

<210> SEQ ID NO 33
<211> LENGTH: 380
<212> TYPE: DNA
<213> ORGANISM: Mus musculus
<220> FEATURE:
<221> NAME/KEY: misc_feature
<222> LOCATION: (26)..(26)
<223> OTHER INFORMATION: n is a, c, g, or t

<400> SEQUENCE: 33
tgaaatagca aagactgtcg cctggnagtc ccttgtgcac agtggttctg tgtgcccacc     60
actcttacca tagacttcag gagaaagtta aaacataccc agcagacagt gtctagagaa    120
ccatctttcc tttgactcaa gaggcatcgg gagaggcctt gctctcttca gctcatagaa    180
ctcagtagca cggacttcgc tgagggcact cgagtcctcc actgaatgtg tgagggctc    240 cataaagata agtgattgtt ttacctctaa atgttgagaa cggaaaccat cctgttgcta    300
caccagtgga agcattcgtt cggcacgtgt ctgtcggtct catggaggtg aaacgataaa    360
tatgtgtgtg cttaaaaaaa                                               380

<210> SEQ ID NO 34
<211> LENGTH: 815
<212> TYPE: DNA
<213> ORGANISM: Mus musculus
<220> FEATURE:
<221> NAME/KEY: misc_feature
```

```
<222> LOCATION: (21)..(21)
<223> OTHER INFORMATION: w is c or t
<220> FEATURE:
<221> NAME/KEY: misc_feature
<222> LOCATION: (28)..(28)
<223> OTHER INFORMATION: w is c or t
<220> FEATURE:
<221> NAME/KEY: misc_feature
<222> LOCATION: (30)..(30)
<223> OTHER INFORMATION: w is c or t
<220> FEATURE:
<221> NAME/KEY: misc_feature
<222> LOCATION: (482)..(482)
<223> OTHER INFORMATION: m is a or c
<220> FEATURE:
<221> NAME/KEY: misc_feature
<222> LOCATION: (561)..(561)
<223> OTHER INFORMATION: m is a or c
<220> FEATURE:
<221> NAME/KEY: misc_feature
<222> LOCATION: (603)..(603)
<223> OTHER INFORMATION: h is a, c, or t
<220> FEATURE:
<221> NAME/KEY: misc_feature
<222> LOCATION: (622)..(622)
<223> OTHER INFORMATION: m is a or c
<220> FEATURE:
<221> NAME/KEY: misc_feature
<222> LOCATION: (640)..(640)
<223> OTHER INFORMATION: m is a or c
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_featrue
<222> LOCATION: (657)..(658)
<223> OTHER INFORMATION: w is c or t

<400> SEQUENCE: 34
ataatacaag agcgatttct wgccttcwgw gggcccattc aagatccagg ctggaaagtg      60
gttaccacca acattctccg gagacttata ttccatattt taagaatcac aatgtaacta     120
ccattattcg tctgaataaa aggatgtatg atgctaagcg ctttacggat gctggattcg     180
atcaccatga tcttttcttt ccggatggca gcacccctgc tgagtcaatt gtccaagaat     240
ttctggatat ttgtgaaaat gtcaaggggtg ccattgctgt gcattgcaaa gctggccttg     300
gtcgaacagg cactctgata ggctgctacc tcatgaagca ttacaggatg acagcagctg     360
agagcattgc ctggctcaga atctgtagac ccggctcagt aattgggccc cagcaacagt     420
ttctggtcat gaaacaatca agcctctggc tagaaggcga ctatttccgt caaaagttaa     480
gmgggcagga gatggccccc tcagagaagc cttctccaac cctttcgga tgctgatgac     540 ctgtccttaa atggggcttg mgatcaagac aatcagagcc tggccgtata gtgatgatgg     600
tghgtcagtg gatgccccag gmgcagactt cgggccctgm naagccggga cagccgwwgc     660
cagcgctatc cccctcacca tgtctgcgtg gctttgtcgg cttctgggtg atcgtgttct     720
gtccaacggg aatggccgtg tgggctgctg tctcgggctg taccttctag ccggctattg     780
tgggggctgg gggccgcggg cctggcctcc cgccc                                815

<210> SEQ ID NO 35
<211> LENGTH: 705
<212> TYPE: DNA
<213> ORGANISM: Mus musculus
<220> FEATURE:
<221> NAME/KEY: misc_feature
<222> LOCATION: (695)..(695)
<223> OTHER INFORMATION: n is a, c, g, or t
<220> FEATURE:
```

<221> NAME/KEY: misc_feature
<222> LOCATION: (704)..(704)
<223> OTHER INFORMATION: n is a, c, g, or t

<400> SEQUENCE: 35

```
gtcagaggtt gaactttatt aattatcaat aataatgatt aaaataaaag ctgtgatgcg      60
gtgtttgctt ccagcctacc accacagttt ggcatggtga atggggagga gttcgttggg     120
gttgcggcac tcgctcgcag ctccccaggg aaacgtgagt tttatttttc atctcttcta     180
aagtttaagt aaaatcttca tttcttccaa aagaaaaat acttgagaca agactttaaa      240
cccgcctccg ggagtgagca tgtgcagatt cccaatcctg ttcttgtcgc ctcaggggac     300
cacgtcggca aaagttcaaa tgtaaaaact gagaacaggt accttagtgg ttaagggcac     360
aaactgttct cccaaaggtc atgagtttga attacagcag gtgctgtgat attttgtacc     420
ttcttttggt ggctgaatag atgaccacga attctggctc actcttgtgg cctccgggtt     480
taaacgcagg cagaattcac tctgtgtccc atcatcatca aaaggcctcg ctcaggttgt     540
gagctgaatg gggcgccgag gagcagagct tgggcagggt tggggtgtct ttgggtcagg     600
agtcacacgg tggggtgtaa ctgtgtcaca atggcagtta tgggtgacag gatcagggca     660
tctgggggcta ttgtgaagcg tcgactcgag cgccnccttt agtna                    705
```

<210> SEQ ID NO 36
<211> LENGTH: 693
<212> TYPE: DNA
<213> ORGANISM: Mus musculus

<400> SEQUENCE: 36

```
aaacccagaa gaaccacaag ctggggtggc cagagtgagg aaggagccca gcaggacgag      60
caggtgggag agtcacagaa agttcagcag acctacagag gcagcagtga ctgctcctct     120
gaagctcaag ccctgaggaa acatagagga catcttttgt acctttttgac tgagggacca     180
tggcaaaacc cttgtggctc tccttgatcc tcttcatcat tccagtggcc ctggcagttg     240
gtgtggatca gtccaagaat gaagtgaagg cacagaacta ctttggatcc attaatatct     300
ctaatgccaa tgtgaagcag tgtgtttggt ttgccatgaa agaatacaac aaggaaagtg     360
aggacaaata tgtcttcctt gtggacaaga tactccatgc caaacttcag atcacagacc     420
gaatggaata ccaaattgat gttcagatct cccgcagtaa ttgcaaaaaa cctttaaaca     480
atactgaaaa ctgcatccct caaaaaaaac ccgaactgga aaaaaaaatg agttgcagct     540
ttctggtagg agcacttccc tggaatggcg agttcaacct gttgagcaaa gaatgtaaag     600
atgtctaagg gtgtcttgga gcacccctcc cacttctggg tctgcttttc tctgtaataa     660
agagcaacct gtggttcaag tctgtcacca acc                                  693
```

<210> SEQ ID NO 37
<211> LENGTH: 940
<212> TYPE: DNA
<213> ORGANISM: Mus musculus

<400> SEQUENCE: 37

```
cgggctctgc aatcttccag attagcaagt ctctgatgcc atagttaagg ttcaagcaga      60
acaagaaaaa tagcagatta acttttaataa aggttgtctt gcagtttctt ttgcattaag    120
tctggcgtat gctgcagccg ttcagttcct gttgtttcct gtgaaccaga cgcacctcgg     180
tggttgatgc agaggggggac gttttcgagc atgttctcaa tcgtttcgga aagacgctca     240
gaactgggaa cccccccctcc cccaggaaaa tgattgatgt gctccgtata agatcagaca     300
```

| | |
|---|---|
| ggaaccttta tcacagagtt ctaaatcatg gagacccatc ctcaagggct agcgtccgga | 360 |
| tgccgcctgc ctccgctcac ctctggccat ctgatggaag tggaggcctg taggctacgc | 420 |
| cttccacttg ttgtaagcct tgcttcagtc atgaagagtc ttgcttgcca tttctgcact | 480 |
| gtactgactc ggccagaggt cccttctcac gtgtccccct ccttccgccc gagttgcagt | 540 |
| ttttaatgga ggcactttgg agaagttgca atattaaatt gaggataatt tacaattaca | 600 |
| gaagagtctg aagctttcct gccgacagaa cacagacagc aaacgaagca atgaagcatt | 660 |
| ttcctttata ccggcccagg acttgtgatt tcttttacat taagattttc ttccaaagtg | 720 |
| accctccctc cttctgtggt ttggtaactt taataaaggt catttaaaga gtggacattt | 780 |
| tacagcctcc ctacccaaga cagagttaaa aacagccatg ggagagttgg gggaccctga | 840 |
| ctgtatatgt catttatatt gtgtctaaat tactatgcca tgggctattt tagtgttttg | 900 |
| ggaaaataat aaaatctgtt ctttagcata ataaaaaaa | 940 |

<210> SEQ ID NO 38
<211> LENGTH: 970
<212> TYPE: DNA
<213> ORGANISM: Mus musculus
<220> FEATURE:
<221> NAME/KEY: misc_feature
<222> LOCATION: (75)..(75)
<223> OTHER INFORMATION: s is c or g
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t

<400> SEQUENCE: 38

| | |
|---|---|
| gtcggtctga ggggcggtcg ggtgtattct gcgctcatca caccgcgagg cccgcgcgcc | 60 |
| cgaccaacgg cgggsgcnca gcgcctcccc tggcaccgct cgctcctcgc tggggcggga | 120 |
| cgaggcccga cggctccggt cactatgagt gaaaatcttt caacctaata tcagaaaaat | 180 |
| gtgacattct atccattctt cgggatcatc ctgaaaacag gatttaccag aggaaaatcc | 240 |
| aggaactcag caaagattcc acctcgatcc ggaagaccaa aggagacgga aactgcttct | 300 |
| acagggcctt aggctattcc tacctggagt ccttgctggg caagagcaga gagatcctca | 360 |
| agttcaaaga gcgtgtgcta cagaccccaa atgaccttct ggctgccggc tttgaggaac | 420 |
| acaagttcag aaacttcttt aatgcttttt acagtgtggt tgagctggta gagaaggata | 480 |
| gctcagtgtc cagcctgctg aaggtgttca atgaccagag ttcctcggac cgaatcgtgc | 540 |
| agttcttacg cctcctcacg tcggccttca tcaggaaccg agctgacttc ttccgacatt | 600 |
| tcattgatga gagagatgga catcaaagac ttctgcactc acgaagtaga gcccatggcc | 660 |
| atggagtgtg accacgtgca gattacagcc tgtcgaggca ctcaacattg ctctgcaggt | 720 |
| agagtacgtc gacgagatgg aaacgctctg taccacatgt gttcccgagg ctgcatnctt | 780 |
| tcggtttatc tgctctataa aacatccact acaacatgct ttaacgcagc cgagaaaact | 840 |
| gaatantttt gggccatgtg gagacggtaa tcgatggatt gattatgaat ggatatcctg | 900 |
| cttggaattt tttgagtgat tagaaattag gaaatatagc tctgggtaag caaattgaat | 960 |
| gggaaaaaaa | 970 |

<210> SEQ ID NO 39

<211> LENGTH: 1020
<212> TYPE: DNA
<213> ORGANISM: Mus musculus

<400> SEQUENCE: 39

```
cgggcggttc tggagcaact ggactcatca aaagcttcgt gggcctggct acagcgccgg      60
ggccttatac ctgctgtaca aggccgtcag actggcttaa aatgtcatcc gccactctgc     120
tccaactcgc cgatctgcat tgcccgcctg gccatcgaga gagagcgcca cgggcgggac     180
tccggtgaga ttcgaagact tctcaactct ctagactgca aacaggatga gtataccagg     240
agcatgatcc ttcataacat cacccgctgc gtgtacttgc tggaggctga ggcctcttct     300
tgtactatgg atgacatcga cttggtggct gacatgctag atgagaagga caacagtgta     360
aaaatccaag ctctgaatgc acttaaagct ttctctggca tcaggaaatt caggctcaaa     420
atccaggagc attgcatcaa ggtactggaa ctgatttcca ccatctggga cttggaattg     480
cacgtagctg gtctccgatt gctcaacaac ctcccgctac ctgactatgt gcacccacag     540
ctgcggcggg tgatgcctgc cctgatggag atcatacagt cagactgcat cctggcacag     600
tacaagctgt ccgcctcctg agttacctgg cacagaagaa cgaccttctt tatgacattc     660
tcaactgtca ggtgcgtccc aacttcctga acctcttcca gtcttcacag ccgggcagtc     720
tgctgttcga ggtgctggtg tttgcggaac acttgagtga aggtcggaac gccacccact     780
accgagcggt caaatggcat tacaacgagc aatccctgca cgaagccctc tttggggatg     840
agtcagactg gcagaccgac tgctctcccc tggtcatcca ccctgaggag gaagttcaga     900
tccaggcctg caagtcatag tgagcttgca gtgtcccagg actggatccg acctcttctg     960
cgactagcat tctgcttaaa cgggagtgag taggagatca taatgcgtag ggagggaaaa    1020
```

<210> SEQ ID NO 40
<211> LENGTH: 1070
<212> TYPE: DNA
<213> ORGANISM: Mus musculus

<400> SEQUENCE: 40

```
cggctgcggg ccgtaatgtg gtactggcca caggcaccct tgacagccca gccatgctag      60
gcatcccagg agagaccctg cccttttgtcc accacgacct gtcagccctg gaggcagccc     120
ttcggcaggc actgtgaacc caacctcaga cccggtgctg attgtgggag cagggctatc     180
tgcagccgat gctgtcctct ttgcccgtca ctacaacatc caggtgatcc atgctttccg     240
ccgtcccgtg catgaccccg gcctggtatt caaccagctg cccaagatgc tatccctga     300
gtaccacaaa gtgcagcaga tgatgcgcga tcagtccatc ttgtctccta gcccctatga     360
gggctaccgc agcctccctg agcaccagcc actgctcttc aaagaggacc accaagcagt     420
gttccaggac ccacaggggg gccagcagct cttgggggtc tccatggtgc tggtcctcat     480
tggctcccac cccgacctct cctacctccc caggcaggt gctgacttgg tcatagaccc     540
agatcagcca ctgagtccca agaggaaccc cattgacgtg gacccttca cccatgagag     600
cactcaccag gagggcctgt atgccctggg gccgttggct ggggacaact tgtgagatt     660
tgtccagggc ggggcctggc tgctgccagc tccctgctga agaaggagac caggaagcca     720
ccttaacatt agcctggcac cctgacaccc aggccctgaa gaggaagagg gcttatcaca     780
gcccagcggg acgtgagcca tctaaagatt tcccatttgg gaaccagtct cccagcaga      840
aggggaagac ttgagccatg tggatggact atctgcccca gaggcatggg gaacacaggc     900
tgcctaccct caggcgagat gaggccccag gtgggagcag tagccataga caggggggccc     960
```

```
cttgaaactg tcagtgtgtg ctggagtcac aggggcagct gagtgtcaaa ttggagggcc    1020
caggcaactt ttcacatcag atctgtaata aacagctgtg ctcacaaaaa              1070
```

<210> SEQ ID NO 41
<211> LENGTH: 640
<212> TYPE: DNA
<213> ORGANISM: Mus musculus
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (44)..(44)
<223> OTHER INFORMATION: v is a, c, or g
<220> FEATURE:
<221> NAME/KEY: misc_feature
<222> LOCATION: (45)..(45)
<223> OTHER INFORMATION: n = a, c, g, or t
<220> FEATURE:
<221> NAME/KEY: misc_feature
<222> LOCATION: (117)..(117)
<223> OTHER INFORMATION: w is a or t

<400> SEQUENCE: 41

```
ttgcgcccga gtggagtgag ccgagcctng cttaccagca tctvncctcc gcacaccgcg     60
aaggcgccca attggaggtg cggccacggc cggggcaggc ggcacaacgc cgtcagwaaa    120
gggaagaaag ggaaaggccg gcccaagacc tccgggaaga agcagaagct gaagaagcag    180
gaagtggaca tcatgagccc cgcagccatg ctgaacctgt attacattgc tcacaatgtt    240
gcggactgcc tgtacctgcg aggcttcccc tggccagggg ctcccaaagg gaaaggggg    300 aaaaaataag atttaggtga tagaattcaa agcacgcctt ggtctcaaag aacagaaagt    360
aggagaatgc atttaggata actcaaggac ttcggccaaa cgggctctaa aagacaagcg    420
gaaacacaga gccactgtgc ttttctgtgc taagcaatag caaacgccgt ttttttattt    480
ccgaagctaa gccaggcact aggtaagcca ctttggtttt tcagaagtaa tcaggaaaag    540
tagttcataa aggttaccct ggcactggta gtaatttttt ttaaatatta taatcataat    600
tctagactga attaaacctt gatctcagaa ggcaaaaaa                          640
```

<210> SEQ ID NO 42
<211> LENGTH: 1061
<212> TYPE: DNA
<213> ORGANISM: Mus musculus
<220> FEATURE:
<221> NAME/KEY: misc_feature
<222> LOCATION: (22)..(22)
<223> OTHER INFORMATION: r is a or g
<220> FEATURE:
<221> NAME/KEY: misc_feature
<222> LOCATION: (58)..(58)
<223> OTHER INFORMATION: d is a, g, or t

<400> SEQUENCE: 42

```
attctctatg ctttgctgat gratctgtac tgagctgtgg gaagtcgtca cctgggadct     60
acatttaatg aaagaagtga tttgtattcc agtcctggat taacagccaa acaaagtgtc    120
gagttgcttc tggaaattca gaaacaagtt aacagagcga tggagacgct tccacctcca    180
aaacaagaga ccaaaaaagg gcataatggg agcaaaagag ctcagccacc gatcactggc    240
aaggtatctc accttggctg tttaaccatc aactacgacg ccatagagca gccactgctg    300
ctgcttcagg ggatctgctc aaacctgggg ttggaactgg gagtgaactt ccatctagcc    360
```

-continued

| | |
|---|---|
| atcaactgtg ctgggcatga gctgatggac tacagtaaag ggaagtacga agtgatggtg | 420 |
| ggcacccaca aaagcgcact gaagatggtg gagctctacg tggacctgat caacaagtat | 480 |
| ccttccataa tcgccttaat tgatcctttc aggaaggagg cgccgcttcc gggagtgtct | 540 |
| ctaaactcct agagtgcaga aatataagca ccctgaaatc ccacggactg atcataaagc | 600 |
| acacaaacca aaccacaatg tctgacttgg tggaaataac ccatcttatc aacggtaaga | 660 |
| agctcctggc cgtctttgga agcacagact cggagtcctc tgatgacagc cttgtcgatt | 720 |
| tggctgttgg attcggtgcc cggtttatca agttgggggg tctttctcgg ggtgaacgga | 780 |
| tgaccaaata caaccgcctt cttgctatag gaagaact catccagagg ggagtatggg | 840 |
| gtttcagtga agaacacaat ttttctttct ttcaagagga tgctactgcc acaatggctg | 900 |
| aggaactctt gggctcctgg actccatctt cccacagagg tgatagagga atcggctaaa | 960 |
| acatgagcct ccctcccggt tctggactcc cagggcacag ccactccacc agtgtggcca | 1020 |
| gctggtgtga atgcctccac gtgtgctcgc tctgaatcac t | 1061 |

<210> SEQ ID NO 43
<211> LENGTH: 2100
<212> TYPE: DNA
<213> ORGANISM: Mus musculus

<400> SEQUENCE: 43

| | |
|---|---|
| atggaagtcc atgaattgtt ccggtatttt cgaatgccag agctgattga cattcggcag | 60 |
| tacgtgcgca cccttccaac caacaccctc atggggtttg ggcttttgc agcgctcacc | 120 |
| accttctggt atgccaccag gcctaaggcc ctgaagccac catgtgacct ctccatgcag | 180 |
| tcagtggaaa tagcgggtac cactgatggt attcgaagat cagcagtcct tgaagatgac | 240 |
| aagctcttgg tgtactacta cgacgatgtc agaaccatgt acgatggctt ccagaggggg | 300 |
| attcaggtgt caaataatgg tccttgttta ggttctcgga agccaaacca gcccatgag | 360 |
| tggatttcct acaaagaggt ggcagaactg gctgagtgca taggctccgg gctgatccag | 420 |
| aagggggttca agccttgctc cgagcagttc atcggcctct tctctcaaaa cagacccgag | 480 |
| tgggtgatcg tcgagcaagg atgcttctct tactcaatgg tggtcgtccc gctctatgac | 540 |
| acccttggag ctgacgccat cacctacata gtgaacaaag ctgaactctc tgtgattttt | 600 |
| gctgacaagc cagaaaaagc caaactctta ttagaaggtg tagaaaacaa gttaacacca | 660 |
| tgccttaaaa tcatagtcat catgactcc tacggcagtg atctggtgga acgaggcaag | 720 |
| aagtgtgggg tggaaatcat cagcctcaaa gctctggagg accttggaag agtgaacaga | 780 |
| gtgaagccca gcctccaga acccgaagat cttgcgataa tttgtttcac aagtggaact | 840 |
| acaggcaacc caaaggagc aatgatcact caccaaaaca ttataaacga ctgctcaggt | 900 |
| tttataaaag caacagagag tgcattcatc gcttccacag atgatgtgct gatatctttc | 960 |
| ttgcctctcg cccatatgtt tgagaccgtt gtagagtgtg taatgctgtg tcatggagct | 1020 |
| aagataggat ttttccaagg agatatcagg ctgcttatgg acgacctcaa ggtgcttcag | 1080 |
| cccaccatct tccctgtggt tcccaggctg ctgaaccgga tgttcgacag aatttttgga | 1140 |
| caagcaaaca cttccttgaa gcgatggctg ttggactttg cctccaaaag gaagaggcg | 1200 |
| gacgttcgca gtggcatcgt cagaaacaac agcctgtggg ataaactcat cttccacaag | 1260 |
| atacagtcga gcctgggtgg gaaagtccgg ctgatgatca caggagcagc cccggtgtct | 1320 |
| gccacagtgc tgacgtttct gaggacagcg ctcggctgcc agttctatga aggctacgga | 1380 |
| cagaccgagt gcactgctgg ttgctgcctg agcttgcccg gagactggac ggcaggccat | 1440 |

```
gttggagccc ccatgccttg caattatgta aagcttgtgg atgtggaaga aatgaattac    1500
ctggcatcca agggcgaggg tgaggtgtgt gtgaaagggg caaatgtgtt caaaggctac    1560
ttgaaagacc cagcaagaac agctgaagcc ctggataaag atggctggtt acacacgggg    1620
gacattggaa aatggctgcc aaatggcacc ttgaagatta tcgacaggaa aaagcacata    1680
tttaaactag cccaaggaga gtacatagca ccagaaaaga ttgaaaatat ctacctgcgg    1740
agtgaagccg tggcccaggt gtttgtccac ggagaaagct tgcaggcctt tctcatagca    1800
gttgtggtac ccgacgttga gagcctaccg tcctgggcac agaagagagg cttacaaggg    1860
tccttcgaag aactgtgcag gaacaaggat atcaataaag ctatcctgga cgacttgttg    1920
aaacttggga aggaagccgg tctgaagcca tttgaacagg tcaaaggcat tgctgtgcac    1980
ccggaattat tttctattga caacggcctt ctgactccaa cactgaaggc gaagaggcca    2040
gagctacgga actatttcag gtcgcagata gatgaactgt acgccaccat caagatctaa    2100
```

<210> SEQ ID NO 44
<211> LENGTH: 2020
<212> TYPE: DNA
<213> ORGANISM: Mus musculus

<400> SEQUENCE: 44

```
gtggacgcgg cctccggggg cgcaaggcag cagcagcggt ggcgaccaaa cgggtgttgg      60
agttggcggc ggccatggag ggcctggctg gctatgtgta caaggcggcc agcgagggca     120
aggtgctcac tctggctgcc ttgctcctta accggtcaga gagcgatatc cgctacctgc     180
tgggctatgt cagtcagcag ggaggacagc gctccacacc cctcatcatc gcagcccgca     240
atgggcacgc caaggtggtg cgcttgctgt tagaacacta ccgtgtgcag acccagcaga     300
ccggcaccgt ccgcttcgac gggtatgtca ttgacggtgc cactgctctt tggtgtgctg     360
cgggagccga acattttgaa gttgttaaac ttccagtcag ccatggagcc aacgtgaacc     420
acaccacagt cactaactca actccattgc gggcagcatg ctttgatggc agactggaca     480
ttgtgaaata tttggttgaa aataatgcca atatcagcat tgccaacaag tatgacaaca     540
cctgcctaat gatcgcagca tataaagggc acactgatgt ggtcagatac ctcttagaac     600
aacgtgctga tcccaatgct aaagcacact gtggagccac agctttgcac tttgcagccg     660
aagctggtca cattgacatt gtgaaagaac tgataaaatg gagagctgca atagtggtga     720
atggccatgg gatgacacca ttgaaggtgg ccgctgaaag ctgtaaagct gatgtcgttg     780
aactgttgct ctctcatgct gattgtgacc gcagaagtcg gattgaagcc ttggagctct     840
tgggtgcctc ctttgcaaat gatcgtgaga actatgacat catgaagaca taccactatt     900
tatatttagc tatgttggag agatttcagg atggtgacaa cattcttgaa aaagaggttc     960
tcccacccat ccatgcttat gggaacagaa ctgagtgtag gaaccacag gaattggagg    1020 ctattcggca agacagagat gctcttcaca tggagggcct tatagttcgg gaacggattt    1080
taggtgctga caacattgat gtttcccacc ccatcattta cagaggggct gtctatgctg    1140
ataacatgga gttcgagcag tgcatcaaat tgtggctcca cgcactacac ctgaggcaga    1200 aagtaacag gaatacccac aaagatctgc ttcggtttgc tcaagtcttc tctcagatga    1260
tacacctcaa tgaagctgtg aaggcccag acatagagtc cgttttgaga tgcagtgtct    1320
tggaaataga gcagagcatg aacagagtta aaaatatctc cgatgccgac gtccacagtg    1380
ccatggataa ctatgagtgt aacctctata cctttctgta cctcgtgtgc atctccacca    1440
```

| | |
|---|---|
| agacacagtg tagcgaagaa gatcagtgca gaattaacaa gcagatctac aacctgattc | 1500 |
| acctggaccc cagaacacgg gaaggttttt ccttgctaca cctggctgtc aactcgaaca | 1560 |
| caccagttga tgatttccat actaacgatg tctgcagctt tcccaacgct ctggtcacaa | 1620 |
| agctcctgct ggactgtggc gctgaggtaa atgcagtgga caatgagggg aacagtgccc | 1680 |
| tccacattat cgtccagtac aacaggccca tcagtgattt tctgactttg cactccatca | 1740 |
| tcatcagcct tgtggaggct ggagctcaca ccgacatgac aaacaagcag aataaaactc | 1800 |
| cgctagacaa agtacaact ggggtgtctg aaatactact taaaactcag atgaagatga | 1860 |
| gcctcaagtg cctggctgcc cgagcagttc gggctaatga cattaactac caagaccaga | 1920 |
| tcccccggac tcttgaagag tttgttggat ttcattaagt gactggatgt gtaaaatcgt | 1980 |
| ttaatgtggt gctaaaaagt aaaggacttt aatcacagac | 2020 |

<210> SEQ ID NO 45
<211> LENGTH: 2860
<212> TYPE: DNA
<213> ORGANISM: Mus musculus

<400> SEQUENCE: 45

| | |
|---|---|
| gggcacgagt aggcttcagg agagtatgga gggttgaaga aagacctaac atcttgaggc | 60 |
| agactggaag agtcatcgca gcatccaaat tctccaaaag aaaacatcca aaggtccaaa | 120 |
| atgattgcct actgtggtac tacaacgatg tctgacgata ttgactggtt acacagccgc | 180 |
| agaggcgtgt gcaaggtaga tctttacagt ccaaaaggac aacaagatca ggaccgaaaa | 240 |
| gtgatatgct ttgtggatgt gtctaccttg aatgtggaag ataaagattc caagggtgct | 300 |
| gctggttcca ggtcagaagg cgagttaaat ctggagactc tggaagaaaa agagattatc | 360 |
| gtaatcaagg acactgaaaa acaagaccag tctaagacgg agggatctgt gtgccttttc | 420 |
| aaacaagctc cctctgatcc tataagtgtc ctcaactggc tcctcaatga tctccagaag | 480 |
| tatgccttgg gtttccaaca tgcattaagc ccctcagcct ctagctgtaa acataaagtg | 540 |
| ggagacctag agggtgacta tagcaaaata ccatctgaga actgctacag tgtgtacgct | 600 |
| gatcaagtaa actttgatta tttgaacaaa ggaccctcaaa accttcgcct agaaatggcg | 660 |
| gcatccaaaa acaccaacaa taaccaaagt ccctcaaatc ctgcaaccaa atctcctagc | 720 |
| aatcagaggt cagttgccac tcctgaggga gaatgttcta tggacgacct ttccttctat | 780 |
| gtcaaccgat tgtcatctct ggtaatccaa atggcccgta aggaaatcaa ggacaaattg | 840 |
| gaaggtggaa gcaaatgtct ccatcattcc atgtatacat caggagataa agggaaaacc | 900 |
| agcccccgga gtgctgtcag caaaattgct tcggagatgg cccatgaagc tgttgaactg | 960 |
| acctcatcag aaatgcgtgg caatggagag gattgcagga tggccggaa aaccttttg | 1020 |
| tatagtgaaa tgtgtaacaa gaacaagtgt ggcgaaaagc agcagatgtg cccaaaagac | 1080 |
| agcaaagaat ttgcggattc catcagcaag gggcttatgg tttatgcaaa tcaagtagca | 1140 |
| tctgacatga tggtctctgt tatgaaaact ttgaaagtac acagctgtgg gaagccaatt | 1200 |
| ccggcttgtg tggtcctgaa gagggtacta ttgaagcaca ccaaggaaat tgtatctgat | 1260 |
| ctgattgatt catgtatgaa aaacttgcat aacataacag gagtcctgat gacagactca | 1320 |
| gacttcgttt ctgctgtcaa gaggaatctt ttcaatcatg gtaaacaaaa tgcagcggac | 1380 |
| atcatggagg ccatgctaaa gcgtctggtc agtgctcttc ttggtgagaa gaaggagact | 1440 |
| aagtctcaaa gtctggccta tgcaaccctt aaagctggaa ctaatgatcc gaaatgcaag | 1500 |
| aatcagagcc ttgagttctc agctatgaaa gctgaaatga aaggaaaaga taaatgcaaa | 1560 |

```
tccaaagcag atccatgctg caaatcgttg acaagtgctg agagagtcag cgagcatatc    1620
ctcaaagaga gccttactat gtggaacaac cagaagcaag gaaaccaagg caaagtgact    1680
aacaaagttt gctgcaccag taaagatgag aagagagaaa agatcagtcc ttccacagat    1740
tcactggcca aggatctaat tgtctctgcc cttatgctca ttcaatacca tctgacccaa    1800
caagccaagg gcaaagatcc atgtgaagag gagtgccctg gttcctccat ggggtatatg    1860
tcccaaagtg cacaatacga aaaatgtgga ggtggccaaa gttctaaatc actttcaatg    1920
aagcattttg aaactcgtgg agctcctgga ccatctacat gtatgaagga aaatcaactg    1980
gagtcccaga gatggatat gtcaaacatg gttctgtccc tgattcagaa actcctgagt    2040
gagagccctt tcagttgcga tgaactaact gaaagtgaca ataagcgttg ttgtgatcct    2100
agatcaagca aagcagctcc catggccaag agacctgaag agcaatgcca agacaatgca    2160
gaactagact tcatcagtgg gatgaagcaa atgaaccgcc agtttataga tcagctggta    2220
gaatccgtga tgaaactctg cctgatcatg gctaagtaca gcaacaatgg agcagccctg    2280
gctgagctgg aagaacaagc agccctggta ggcagtggct ccagatgtgg ccgtgatgct    2340
atgatgtcac aaaattattc tgaaactcct ggccctgaag ttattgtcaa caatcagtgc    2400
tctacaacta acttgcagaa gcagctgcag gctgtcctgc aatggattgc agcctctcaa    2460
ttcaatgtgc ccatgctcta cttcatggga gacgatgatg gacaactaga gaagctccct    2520
gaagtttcag ctaaggctgc agagaagggg tacagtgtag agatcttct tcaggaggtc    2580 atgaagtttg ccaagaacg acaactggat gaagccgtgg gcaacatggc tagaaagcag    2640
ctgctagact ggcttctcgc taacctgtaa gctgagaatt cctttgactc ccctccatcc    2700
atcctccccc ccagcagcaa ttccaccccca gctggagcca ccctcaccat caggctggtg    2760
aactgcacaa ttgggatcac atttaccaat acatctgagc agttgcactg tgaaaatact    2820
gggtgccctc ctgggcaaca tgaataaaaa aattcaaaaa                          2860
```

<210> SEQ ID NO 46
<211> LENGTH: 620
<212> TYPE: DNA
<213> ORGANISM: Mus musculus
<220> FEATURE:
<221> NAME/KEY: misc_feature
<222> LOCATION: (168)..(168)
<223> OTHER INFORMATION: m is a or c

<400> SEQUENCE: 46

```
cgtggcaggc ttgatgtcta cctgtccact cccaacttgt tatgaatcaa aagacttgac     60
tagtctctat gacgtacaat catttccaaa gatcacagac actaaaaaga cagatgattt    120
gtactggaga cagctggaga tgaagcccct ccccatatcc tgctctamgt caaaccatta    180
cattgactat gaaccactta agtctgccta ccgtgaccca tatgctatgt gtccaaaccc    240
tgttcgcctc agtaagtcta atattcttca aaacaaaaca gatacggctg atttcacttt    300
tgacaacttt ttaagtaaac cagaattttt gggcatgaac atggaaagca atgaagaaac    360
aagacctctt ttagattgga tccctagagc tggagtgccc aagcatcatt ccaacctgcg    420
aaatcttagg aacacattct caaagtccat ggcacagaag cgtctgcata actccattca    480
agaagaacaa aaagacctcc gagataaact gcagtgtggg atgagacatc aatttttgg    540 ctacaatggc catcatttct ataattgaga ttcccttgag acccagtctc ttgcaagaaa    600
taaaatatgt cacagagaaa                                                620
```

-continued

```
<210> SEQ ID NO 47
<211> LENGTH: 1086
<212> TYPE: DNA
<213> ORGANISM: Mus musculus
<220> FEATURE:
<221> NAME/KEY: misc_feature
<222> LOCATION: (12)..(12)
<223> OTHER INFORMATION: y is c or t

<400> SEQUENCE: 47
tcgactcggt gycgtctgaa catctgaagc tggggccctc ccaccatgga acttgatcaa      60
gataagaaaa aggaaacacc agaagaaaca gaaaacgtta acgaggtgca actagagaag     120
caaaaccaag atgaagaaac tgaagctgaa gctgaagagg cagataaagc cattcttgag     180
aggagtgatt cagtgaaaac ggaatgtccc ccccaggcag agaagcaaaa ccaagatgaa     240
gaaactgaag ctgaagctga agaggcagat aaagccatac ttgagaggag tgattcagtg     300
aaaacggaat gtccccccca ggcagagaag caaatccaag aagagaaatg tgaaactcaa     360
gaggcagata gatctgaggg aaccgagttg gggaaacttc actctcagct agatcagctg     420
cctgataacg tcatgctggc aggcgtcaag atccaggcct ggtggcgagg cacactggtg     480
cgccgaaccc tgctgcttgc agccctcaac gcttggacca ttcagtgctg gtggagagag     540
gcaaaggcca ggctgcaggg gaggaagtta catgaggtga tgcgctacag actgagaaac     600
ctaaacctaa agtccatcag caagcgaaaa caacccaacc aaagctcctt cctttaaaac     660
aacccaagga ctcgaggata aaaagaccc gagcagccaa aagatccag gccttgtggc     720 gcggattcct ggtgaggcaa actctgctgg ctgctgcctc aatgtctggg tgattcagtg     780
ctggtggaga agcatcctcc acagacaggt acttaaacgg cggctggcct gctgaggata     840
tacgtcattg aggaagaggc agccgtcagt ccaggcctgg gttcgcatgt ggaattgccg     900
tcgatacttc aatcagatat gcaatcaaat atgcaacaca ctctgtgtgt cccagtccgc     960
cgaaaacagc tttaccttcc agacgatgac attttgcagg ttcatatgaa gttgtttcca    1020
ggcaccagag ttcacattga attctatcca tctaaggccg cagcacaaga gttgctcatt    1080
gctaat                                                               1086

<210> SEQ ID NO 48
<211> LENGTH: 2432
<212> TYPE: DNA
<213> ORGANISM: Mus musculus

<400> SEQUENCE: 48
atcccggcgc gctcgccgcg agctcagggc cactctggtt ctcggtgagg ccgactccgt      60
tctggctgga ggatcctgac tcccttgctc gccgaccct tgcgcgtgac gaccgatctc      120
aggctgagca atggcgtttc aaaaggcagt gaaggggact attcttgtgg gtggaggagc      180
tctggccact gttttgggac tctctcagtt tgctcattac agaaggaagc aagtgagcct      240
ggcatatgtg gaagcagcag gatacctcac ggagcctgtg aacagggaac ctcccctccag     300 agaagctcag ctcatgactt tgaagaacac acccgaattt gacatccttg ttatcggagg      360
cggagccaca gggtgtggct gtgcactaga tgccgtcacc agaggactga aacagccct      420 tgtagagaga gatgacttct catcgggac tagcagtaga agcactaaat tgatccacgg      480
tggtgtgcga tacctccaga aggctatcat gaacttggat gttgagcagt ataggatggt      540
gaaagaagcc cttcacgaac gtgccaactt actagaaatc gctcctcatt tatcagctcc      600
ggtgcctatc atgcttccac tttacaagtg gtggcagtta ccttattact gggtgggaat      660
```

```
caagatgtat gacctggttg cagggagtca atgcctgaag agcagttacg tcctcagcaa    720
atcccgagcc ctggagcatt tcccatgct ccagaaggac aagctggtag gcgccattgt     780
ctactatgac ggacaacaca acgatgcacg gatgaacctc gccatcgccc tcactgctgc    840
caggtacggg gctgccacgg ccaattacat ggaggtggtg agcttgctca agaagacaga    900
ccctgaaacc ggcaaagagc gagtgagcgg tgcgcggtgc aaggatgtgc tcacagggca    960
ggaatttgac gtgagagcca atgcgttat caatgcctcc ggcccttca cagactccgt     1020 gcgcaaaatg gatgataaaa acgttgttcc catctgccag cccagtgccg ggtccatat    1080 tgtgatgccc ggatactaca gccctgagaa catgggactt cttgatcctg caaccagtga   1140
tggcagagtg attttcttct tgccttggga aagatgaca attgctggca ccactgatac    1200
gccaacggac gtcacgcacc atcctattcc ttcagaagaa gacattaact tcatcctgaa   1260
tgaagtgcgg aactacctga gttctgacgt tgaagtgaga agaggggatg tcttggcagc   1320
ctggagtggt atccgtcccc ttgttaccga tcccaagtct gcagacactc agtccatctc   1380
tcgaaatcat gttgtggaca tcagtgacag cggactcatc acaatagcag gtgggaagtg   1440
gaccacctac cgctccatgg cagaagatac cgtggatgca gctgtcaagt tcacaacttt   1500
gaatgcggga ccgagtagga ctgttgggct gttccttcaa ggaggcaaag actggagccc   1560
cacactctac atcaggcttg tccaggatta tgggcttgag agcgaggttg cacaacatct   1620
ggccaaaacc tatggtgaca aggctttcga ggtggccaaa atggcaagtg tgactggaaa   1680
gcggtggcct gttgttggag tgcgtcttgt gtcagaattt ccatacattg aagcagaggt   1740
gaaatacggg attaaggagt atgcctgcac tgcagttgac atgatctcac ggcgcacccg   1800
cctggccttt ctcaatgttc aggctgcaga ggaagccctg cctaggattg ttgaactaat   1860
gggaagagag ttggactgga gtgaattgag gaaacaggaa gaacttggaa cagccacgag   1920
atttctgtac tatgaaatgg gctacaagtc tcgaacagaa caacttacag atagcactga   1980
aatcagcctg ctgccttcag acatcgatag gtacaagaag agatttcaca gtttgatga    2040 agatgaaaaa ggcttcatta ccattgttga tgttcagcgt gtcctagaga gtatcaatgt   2100
acaaatggac gaaaacacac tgcatgaaat tctctgcgaa gtagatttga caaaaatgg    2160 acaggttgag ctgcacgagt ttctgcagct gatgagcgca gttcagaaag gaagggtctc   2220
tggaagccga cttgccatcc tgatgaaaac tgccgaggag aacttggacc gcagagttcc   2280
aatccccgtg gaccgtagtt gtggaggatt gtgagtctga ccagtaaatc cgccaccagc   2340
aagcatagga cagccagcgc tatgtacaac cagagatgac ttaaactcta aatagtgga    2400 tctcgtagct gccttttta aaacaaacaa ac                                  2432

<210> SEQ ID NO 49
<211> LENGTH: 4806
<212> TYPE: DNA
<213> ORGANISM: Mus musculus

<400> SEQUENCE: 49
cagccggcca gcgagctccc gggactgacg acccgcgcgc tcacttccgc gtcccgccgc     60
cggccgccgc catcggacaa tgggccgcgc gccgcgtgca gtgagctctg ctggatccgg    120
ccaccggccc aggccagggg ctgcccggtg tgtttgcaag ttcgattgtt cgacgtggat    180
gtgagtttac tttttttctg tggacgttct ctgtcttctt tcgcctgttt tgggttttgt    240
gacttggaga agagaacttt tctaagcagg ccgggcaccg tgaaggctgc tctgccccca    300
```

```
cgtggacgct ccccggggga aaagaagtct gaaagtaaac ttagcccgc tggcctgaag    360 gctcaactct ggctggactg tgagttttgg agtcatgacc ttcttgctgg gcaggtggga    420
atctttatct gccttaggct ggacctgaaa cctcggccag cacccaaatc tcccccacca    480
cattcacacc ttgaaccagg gctaggcccg gacactgatc tacaacatgg ataaatacga    540
tgatctgggc cttgaggcca gtaagttcat cgaggacctg aacatgtatg aggcctccaa    600
ggatgggctc ttccgggtgg acaagggtgc tggcaacaac ccagaatttg aggaaactcg    660
aagggtgttc gcgaccaaga tggccaaaat ccacctccag cagcagcaac agcagcagct    720
cctacaggag gaggccctac ctagggcagg cagaagcccg gtcaacggtg gaaccgtca    780 gggtgcgagc ggcaagctgg ctgcagatgg ggccgctaag cctcctctgg ctgtgccaac    840
agtggcacct ggattagcta ctaccactgc ggccgcgca ccctcgtacc catctcagga    900
gcagaggatc aggccatctg cccatggtgc aaggcctggc agtcagaact gtggttccag    960 ggagggcct gtgagttccc agagacctgc tttacacggc ctgagtccct cctgtgaaga   1020
cccttcctgc ctcactcacg gagactatta tgacaatttc tctttggcaa gcccacagtg   1080
gggtgataaa cctgaagggt gccccagcgt gagtctgggt gtaggaagtg gatggcctgg   1140
ttgcccaggg aatgactcca cattgcccaa atcctgtgga gaccatcacc cttaccagcc   1200
acagctctcc acagtgtgct ctggcaggtc ttttgaaagt ggcatcagtg gccaggacgg   1260
tggcattggt ggccatagca gcgagaagcc aacaggcctt tggtccactg cctcctctca   1320
gcgagtgaac ctcggttttt cttccatggg cttggagaat gggacctccg ctcaacccaa   1380
gggcacaact gtttcagcac cgatggtccc tagcagcgcc agccaaggag cttgtccgaa   1440
aagagattca ggtctgggat atgaggcttc aggcagggtc ttcaaacccc ttgtggacac   1500
tcagccttgg ctgcaggatg ggcccaagtc ttacctctca gtttctgctc cattatcctc   1560
gacagctggc aaggacagta cccagccagg tatgaccacc gggctggatc ctaagtttgg   1620
atgcgtggag tctggcacta gtcccaagcc cagccccacc agtaacgtcc atccggtaat   1680
gtccactcca tctgagttat cttgtaaaga gagttctccc agctggtcca ctgcacagtag   1740 tctggaacct gtgctcccag ggagtcccac ccctccagg gtgagattgc cctgccagac    1800
cctcgcaccg ggccctgagc ttggacccctc cactgcggaa ttgaagttgg aagccctcac   1860
ccagcgtctg gagcgagaga tggatgctca ccccaaagcg gactacttcg gttcctgtgt   1920
gaaatgcagc aaaggggtgt ttggagctgg ccaggcctgt caggccatgg gagatctcta   1980
ccacaatgcg tgcttcacct gtgcagcctg cagcaggaag ttaagaggaa aggccttcta   2040
ttttgtcaat ggcaaagtat tctgtgagga agacttttg tattctggct ttcagcagtc    2100
tgcggacagg tgttttcttt gtggacacct gatcatggac atgatcctac aggccctagg    2160
gaagtcctat caccccggct gtttccgctg cgtcatctgt aatgaatgtc tggatggggt    2220
tcctttcacc gtggactctg agaacaagat ctactgtgtc cgagactatc acaaggtgct    2280
ggcccccaag tgtgcagcct gtggccttcc catccttccg ccagagggtt cagacgagac    2340
catcagagtt gtgtccatgg acagggacta ccacgtagag tgctaccact gtgaggactg    2400
tggtctggag ctcaatgacg aggacggtca ccgctgctat ccactggagg accacctgtt    2460
ctgtcactcc tgccatgtca agagactgga gaaggaccc tcacctgcac ccctccacca    2520
gcaccacttc tagcaaggag acacagtgga gatacgggc cagcctgctg ggggaaatgt    2580
ctgtgtagca cttctgagct ccccccacagc tggggcacag gaagaggagg ggcaggaggt   2640
caagttcctg tgtgtgtgag tgtgtgtgcg cgtgtgaaga gggtatcttc cttctaaccg   2700
```

-continued

```
cagcagtgtg cactccccat ccagtccatg tgttttcaaa gtgcttttct ctattgccac    2760
actctcgctg aatcactcag gaagatgctc cagcttgcac gtggcccctg acacaagatg    2820
gggcttttgt gactggacac atcctagtcc ctggaaagca ggttttcagg ttgtgttgag    2880
cacattccac agtgtcccta agagaaaacc ttgatagagg tgagcagcac ttcctctggg    2940
cgagcacctg cacccggata accctcacac agcccatggt gtgacttaac agttcagtcc    3000
acttcagagc tttagctctt ctgagaatac ttcaaacact tgactgcatt gcagctagaa    3060
agaggctctg catatgcttt gtacattgga gtttgcttgg tgaaggagag ccaagcttgg    3120
acatctggga ggctgggtct ccctgctgtg cctctgcctt tcctcctgca cctaagacag    3180
tggggttggg gcagaggctt gcctgtccta tgcagccagc tcagagagaa ctggtgcagg    3240
cgccaggctt ctcgtccatg cttggtgctg tgttttcatt gcttcctcca gtctgtgaca    3300
ttggagttgc ttcctcaagg tgagtctgag gcttcctcat atccctgtca ccttgttcaa    3360
ctcatttgaa catgaccgtt gggaatccca gtccatatcc tgggagagag ctacttctaa    3420
aaggaaagtt ttgtgtgtga gatctcagag ctagcaccag agggagtgcc cgagcttgtt    3480
tcagcggact tgtatctctc tggtcctctt ctcagcacag acatttgctt ggtttgagga    3540
aactaatata aggtacactg cttttgtctg ttttttttaaa cgtcattctt tctctctacc    3600
ttttcccaca cacaaaacat acctcacaga tagttttcac caaatcacag atcaaagagg    3660
aattcatcca tcctattgga gactgttggt gtatcagcag tggccgtttt ccaactcttg    3720
aactacagct aagcagtaca gtcgcaacac aaggtcttct gagactagct gcaactgaag    3780
tcatgagttc actctggcct catgtgcctc tgcatgctgg ctcccgaggt tgccaggcta    3840
agatggagac cacatgctgt caatattaag accacttctg aggtggatat gtggacatac    3900
ccgtcctccc aacatttgag agcctgaagt ttgtgaagaa ggagtttaag gctgtcctca    3960
actacatgag gtcatgatct cactcaaaaa aaaaaaaaaa aaaacttaaa agagaaagaa    4020
aaaaacccca cccagcattg aagaacataa ttaactttgc ctatcacttc ccgaggccag    4080
aggtcagtgt ctccttggaa gttcaaatgg gtaaaactgg aaaaacaaaa atgaaatggg    4140
tttccatctg ctgtcttatc ttcagggagt gtcccgtgac ttgtggcagg aaggctgcag    4200
tgtcttactt cagcagtcag gctgggtacc cagcagctgg cttgggtggt gaagcaaggc    4260
cggtagagct cctgccacat gtgaatgtgg actcttgact aggcctcagc tagacctggt    4320
agctactgca atcctgctga cctccattgc ctatgagaag ttcagaacta gcactgtgga    4380
tcaggagcat cttttcatt tttatcaggt tccttctgtt gggatccttt ggccagatgt    4440
tactcgtttc ctgttctaga cagaggcccc cttaaaaaaa aaaagctat gaatgtatgg     4500 ggtcaccgag atagaccctg agaccagcgc tgttttctct ctttggtttc ccgggctggc    4560
tttggcaagg gtgcaggga aaggagaaaa cacaatgtct ttgccttcct ggaggctctg     4620
gtagagtcta attttgtgtc aagatgattg atgaagattg cagtggaatt agtgtctgag    4680
gtagatggga tttgtttgca aattgaataa tttaaaactc tgtgattaat ttttaaatga    4740
aattaaatga aattcctgat tgaagtgatt cagatctgtt tgcaaatact acattttata    4800
ttatca                                                               4806
```

<210> SEQ ID NO 50
<211> LENGTH: 894
<212> TYPE: DNA
<213> ORGANISM: Mus musculus

<400> SEQUENCE: 50

```
cttatccgct gaacctcact ttgccgcagg aggcactgaa cagagaaact gccttgtaac      60
aggtcccgcc cctctctcta ctcccttct tatatcaaga ggggaaaaac acggaactat     120
ctctatccat tctggtcacc attcgccat tacctctact gttacaaata ccggatcacc     180
ctccgggaga agatgctgcc ttgttgttac aaaagcatca cttacaagga acaggaggac    240
ctgactctcc ggccccattg ctgcctcccg tgctcctgcc tcccgtgctc ctgcctccag    300
tgctcctgag tccctaggag gcctccaggt gggtaggagc actgcacagg aaaaagacca    360
cagccagctt aaagaactct attcagctgg aacctgaca gtgctatcaa ctgaccccct     420
gcttcaccaa gatccagttc agttagactt ccactttcgt cttaccccc attcctctgc     480
tcattggcac ggccttctgt gtgatcaccg actcttcctg gatatcccat atcaggcctt    540
ggatcaaggc aaccgagaaa gcttgacagc aacactggag tatgtggagg agaaaaccaa    600
tgtggactct gtgtttgtga acttccaaat cgatcggaag acagaggtg ccctgctgcg     660
agcctttagc tacatgggct tcgaggtggt tagaccagat catcctgccc tccctccctg    720
ggacaatgtc atcttcatgg tgtatcccct tgaaagggac cttggccacc ctggcagtga    780
gcctccctaa acatgttcca tctctgtgag gggttggaaa ctcaacacac gggactctga    840
ggccaggatg tgatttaaga tacttccatc ctaggaataa agggtagtgc aatc           894
```

<210> SEQ ID NO 51
<211> LENGTH: 1380
<212> TYPE: DNA
<213> ORGANISM: Mus musculus

<400> SEQUENCE: 51

```
catccttagc ggcagacagg gctaccccag gaggaaggtg gggaaaaggg gcccgtgggg     60
gtaatttatc atccaaagac ctccgtccat ctgtctgtct gtctagatgg gtccccgcgc    120
ggcccccggt cgcccgggca gcggaggcag cggcggcggc ggaagagctc gcacaccggc    180
cccggcgggc cccggcagag aagcccgcac aggtcccagg aaggtggcgt cacatctgca    240
gccgcgtcga cgttgtctga gcctccgcgg aggacccagg agagtcggac taggaccagg    300
gccccgggcc tccccacgct ccctatggaa aagccagctg cctcaacaga accccaaggg    360
tctcggcccg ccttgggccg tgaaagtgtc caggtgcccg atgaccagga cttccgcagt    420
ttccggtcag agtgtgaggc cgaggtgggc tggaacctga cctacagcaa ggccggcgtg    480
tctgtgtggg tgcaggctgt ggagatggat cgaactctgc acaagatcaa gtgtcggatg    540
gaatgctgtg acgtgccagc tgagacgctc tacgatgtcc tgcatgacat agaatacaga    600
aagaagtggg acagtaatgt cattgagact ttcgacatcg cccgcttgac tgtcaacgct    660
gacgtaggat attattcctg gaggtgtccc aagcccctga gaaccgtga tgtcatcacc     720
ctccgctcct ggctccccat gggcgctgat tacatcatta tgaactactc agtgaaacac    780
cctaaatacc cacctcggaa agacttggtc cgagctgtgt ccatccagac gggctacctc    840
atccagagca cggggcccaa gagctgcgtc atcacctacc tggcccaagt ggaccccaaa    900
ggctccttac ccaagtgggt ggtgaataag tcatctcagt tcctggcccc caaggccatg    960
aagaagatgt acaaggcctg catcaagtac cccgagtgga agcagaaaca ccagcctcat   1020
ttcaagccat ggctgcaccc ggagcagagc ccattgccca gcctggcgct gtcagagttg   1080
tcggtgcaac atgcagactc actggagaac atcgatgaga gtgcagtgac agagagccgc   1140
gaggagcggg caggcggtgc gggaggagag ggcagcgacg atgacacctc gctcacctga   1200
```

-continued

```
gtgaccggct ctctgcaagg accaagacca gactggggtg gaaccctggg gcactgagcc      1260
ttctgcactt cctcccttcc cccacctgcc ttctgggggg gcactgggct cctgcccagg      1320
tggctgcggc atggctggac atggcccaa  taaatgaacc acacagcccc agccaaaaaa      1380
```

<210> SEQ ID NO 52
<211> LENGTH: 1530
<212> TYPE: DNA
<213> ORGANISM: Mus musculus

<400> SEQUENCE: 52

```
ctgttgtgca taccatcaag atggctcttt ctgctaagtt gactctggac aaagtggatc        60
ttaagggaaa aagagtaatc atgagagtag acttcaacgt tcccatgaag aataaccaaa       120
ttacaaacaa ccagagaatc aaggctgcca tcccaagtat caagcactgt ctggacaatg       180
gagccaagtc cgtagttctc atgagtcacc tcggtcggcc tgatggtatc cctatgccag       240
acaagtattc attagagcct gttgctgatg agctcaagtc cctgctgaac aaggacgtca       300
tattcttgaa ggactgtgtg ggccctgaag tagagcaagc ctgtgccaac ccagataatg       360
ggtctatcat cctgctggag aacctgcgct tccatgtgga ggaagaaggt aagggtaaag       420
attcttctgg aaaaaagatt agtgctgacc ctgctaaagt agaagccttc caagcatcac       480
tgtctaaact tggcgatgtc tatgtcaacg atgcatttgg cactgcacat cgggctcaca       540
gttctatggt cggagtaaat ttgccccaga aggcatctgg tttccttatg aagaaggaac       600
tggattattt ttccaaggct ttagaaaagc cagagaggcc cttcctggct atccttggtg       660
gagccaaagt gaaagacaag atccaactca ttaaaaatat gttagacaaa gtcaatttca       720
tgattattgg tggtggaatg gcttacacct tcctgaaaga actcaagaac atgcagattg       780
gtgcttcctt gtttgatgaa gagggagcca cgattgttaa agagatcatg gaaaaagcag       840
aaaagaatgg tgtaaagata gttttttcctg ttgactttgt tactggtgac aagtttgatg       900
agaatgctaa agttggacaa gccactatag aatctggtat accatctggt tggatgggct       960
tggactgtgg ccctgagagc attaaaatca atgctcaaat tgtggcccaa gcaaagctga      1020
tagtttggaa tggacctatt ggggtatttg aatgggatgc cttttgctaaa ggaaccaaag      1080 ctctcatgga tgaagttgta aaggccacct ccaatggctg tgtcaccatt ataggaggag      1140
gagatactgc tacttgctgc gccaaatggg gcactgaaga caaggtcagc catgtgagca      1200
caggaggtgg ggcaagtctt gagcttctgg aaggtaaaat ccttccaggg gtagaggccc      1260
tcagcaacat gtaattgtca taatgtactt gcttcctgtt tcctgcgcac aggaccagaa      1320
ccaactcaac ctaacctata tctcaacatt tgttaacctc tactatgaat caagacgccc      1380
gtatgtgctg cgtgtgccat caatatcaca ttcagcaagt cttaattctg tcatcatcat      1440
ttgttagtct cttcaagatc tcatcaggat ttcccacagt ccttcctagg gaggaaacat      1500
tctcatgtca actattaaag aagtgagcta                                      1530
```

<210> SEQ ID NO 53
<211> LENGTH: 443
<212> TYPE: DNA
<213> ORGANISM: Mus musculus
<220> FEATURE:
<221> NAME/KEY: misc_feature
<222> LOCATION: (129)..(129)
<223> OTHER INFORMATION: r is g or a
<220> FEATURE:
<221> NAME/KEY: misc_feature
<222> LOCATION: (146)..(146)

<223> OTHER INFORMATION: y is c or t

<400> SEQUENCE: 53

| | | | | | |
|---|---|---|---|---|---|
| tgactctggc | accagctggt | ggagcagtgg | gtgatgacat | ctcagattca | agacctacta | 60 |
| gccactgatc | aggacctgct | gctgatccag | aaggcaacaa | tgatgcgcaa | ggtgaggacc | 120 |
| aaaagctgra | agaagctaag | atactycaga | cttcagaatg | acggcatgac | agtctggcat | 180 |
| ggaagtcaac | cagaaagcat | gcccaagccc | acttttttcga | tctctgatgt | ggagaggata | 240 |
| cgtaaggggc | aggattctga | gttgttgcgc | tatctggtgg | aggagtttcc | cctggagcaa | 300 |
| gggttcaccg | ttgtctttca | agtgcgccgc | cccaacctgg | acctagtggc | caacagtgtt | 360 |
| gaagaggccc | agatttggat | gcgaggactc | cagctgttgg | tggatcttgt | tgccagcatg | 420 |
| gaccaccagg | agcaaatgga | tca | | | | 443 |

<210> SEQ ID NO 54
<211> LENGTH: 309
<212> TYPE: DNA
<213> ORGANISM: Mus musculus

<400> SEQUENCE: 54

| | | | | | |
|---|---|---|---|---|---|
| atggccagat | accgatgctg | ccgcagcaaa | agcaggagca | gatgccgccg | tcgcaggcga | 60 |
| agatgtcgca | gacggaggag | gcgatgctgc | cggcggagga | ggcgaaggat | gctgccgtcg | 120 |
| ccgccgctca | tacaccataa | ggtgtaaaaa | atactagatg | cacagaatag | caagtccatc | 180 |
| aaaactcctg | cgtgagaatt | ttaccagact | tcaagagcat | ctcgccacat | cttgaaaaat | 240 |
| gccaccgtcc | gatgaaaaac | aggagcctgc | taaggaacaa | tgccacctgt | caataaatgt | 300 |
| tgaaaactc | | | | | | 309 |

<210> SEQ ID NO 55
<211> LENGTH: 651
<212> TYPE: DNA
<213> ORGANISM: Mus musculus

<400> SEQUENCE: 55

| | | | | | |
|---|---|---|---|---|---|
| ggtgggcagg | cctccgccct | cctcccctac | tccagggccc | actgcagcct | cagcccagga | 60 |
| gccaccagat | ctcccaacac | catggtccga | taccgcgtga | ggagcctgag | cgaacgctcg | 120 |
| cacgaggtgt | acaggcagca | gttgcatggg | caagagcaag | gacaccacgg | ccaagaggag | 180 |
| caagggctga | gccgtatgca | cgtcgaggtc | tacgagagga | cccatggcca | gtctcagtat | 240 |
| aggcgcagac | actgctctcg | aaggaggctg | caccggatcc | acaggcggca | gcatcgctcc | 300 |
| tgcagaaggc | gcaaaagacg | ctcctgcagg | caccggagga | ggcatcgcag | aggctgcaga | 360 |
| accaggaaga | gaacatgcag | aaggcactaa | gcttcctggg | cccctcaccc | ccagctggaa | 420 |
| attaagaaaa | agtcgcccga | aacaccaagt | gaggccatag | caattcccct | acatcaaatg | 480 |
| ctcaagcccc | cagctggaag | ttaagagaaa | gtcacctgcc | caagaaacac | cgagtgaggc | 540 |
| catagcaact | cccctacatc | aaatgctcaa | gccctgagtt | gccgccgaga | agcccacaag | 600 |
| atctgaagtg | aaattgtgca | aagtcacctg | cccaataaag | cttgacaaga | c | 651 |

<210> SEQ ID NO 56
<211> LENGTH: 1750
<212> TYPE: DNA
<213> ORGANISM: Mus musculus

<400> SEQUENCE: 56

| | | | | | |
|---|---|---|---|---|---|
| gtccggagct | gggagcccgt | ggccgtggac | gatggcggcg | ctgaggcttc | tggcctgggc | 60 |

```
gctcccacgt ggggtatctg ctctccgccc accaccogcg ctgccccacc gccttatccg    120
ccgctatgtt tcggaccgca gcgggagtgt ccatttctac acggaccogg tgaaggcggt    180
ggagggcgtc aaggacgggt ctaccgtcat gctcgggggc ttcgggctct gcggcatccc    240
cgagaacctg atcggtgcgc tgaagaccaa gggcgtgaag gacctgaaga tcgtcagcag    300
caacgtgggc gtggacgact tcggcctggg catcttgctg gcctccaagc aggtcaggcg    360
cgtggtgtgc tcctacctgg gggagaacgc gctctgcgag aagctctacc tggcgggcga    420
gctggaactg gagatgacgc cgcagggaac tttggccgag cgcatccgcg cgggtggcac    480
tggcgtgccc gccttctaca cgcccacagg ctatggaacg ctggtgcagg aaggggggctc    540
tccaatccgg tacgcgcccg atggccacct gattactcta agtgagccgc gagaagtacg    600
cgagttccag ggccgcttct acctgctaga gcacgctatc cgcgctgact tcgcactgat    660
caagggctgg aaggccgacc gctccggcaa cgtgatcttc aggggcagcg cgcgcaactt    720
caatgtgccc atgtgcaagg ccgcggacat ctcggtggtg gaagtggagg agatcgtgga    780
cgtgggtact ttcgccccgg aagacatcca cgtccccaac atctatgtgg accgcgtgat    840
caaggggccg aagttcgaga gcgcatcga gcgcctaacc acacgtgaca gcaagcccgc    900
gcccgggagc aaagacaatg acccttccag gacgcgcatc atcaagcgcg cggctctgga    960
gttccaggac ggcatgtatg ccaatctggg catcgggatc cctgtcttgg cgagcaacta   1020
catcagcccc aagatgaccg tctacctgca cagtgaaaac ggaatcctgg gcttgggccc   1080
gttcccttg aaaaatgagg tagatgccga cgtcatcaac gcaggcaagc agacagtgac   1140
ggtggttccc gggggctgtt tcttcgccag cgatgactct tttgccatga tccgtggcgg   1200
acacctccaa ctgaccatgc ttggggccat gcaggtttct caatacgcg acctggccaa   1260
ctggatggtg ccaggcaaga aggtgaaggg catgggcggg ccatggact tggtgtctag   1320
taaaaagacc agagttgtag tcaccatgga acactgcacc aagacaaagc agcccaaaat   1380
cttgaagaaa tgcaccatgc cattgaccgg caagcgctgc gtggacctca tcatcactga   1440
gaaggcagtg tttgaagtga accactcaaa ggggctgaca ctggtggagc tgtgggaggg   1500
ctcgtcggta gatgacatca aggccaccac agcctgttca tttgccgtgt cccccaacct   1560
caagcccatg cagcagatta aacttgatgc ttgaggagcc ctccagggct aatttgccag   1620
ttagtgacaa ctggacatcc ttagcagcac ctgaccactg tgccacactg gctcctccag   1680
cttccttctg ctagatggtg tctatcgaga gccatgtgac cttaattaaa aaccctaact   1740
tgaaaaaaaa                                                          1750
```

```
<210> SEQ ID NO 57
<211> LENGTH: 1750
<212> TYPE: DNA
<213> ORGANISM: Mus musculus

<400> SEQUENCE: 57
```

```
gtccggagct gggagccgat ggctgtggaa gatggcggcg ctgaggcttc tggcctgggc     60
gctcccacgt ggggtctctg ctctccgccc acgacctgcg ctgccccacc gccttatccg    120
ccgctatgtt tcggaccgca gcgggagtgt ccatttctac acggaccogg tgaaggcggt    180
ggagggcgtc aaggatgggt cgaccgtcat gctcgggggc ttcgggctct gcggcatccc    240
cgagaacctg atcggtgcgc tgaagaccaa gggcgtgaag gacctgaaga tcgtcagcag    300
caacgtgggc gtggacgact tcggcctggg catcttgctg gcctccaagc aggtcaggcg    360
```

| | |
|---|---|
| cgtggtgtgc tcctacctgg gggagaacgc gctctgcgag aagctctacc tggcgggcga | 420 |
| gctggaactg gagatgacgc cgcagggaac tctggccgag cgcatccgcg cgtgtggcac | 480 |
| tggcgtgccc gccttctaca cgcccacagg ctacggaacg ctggtgcagg aaggggctc | 540 |
| tccaatccgg tacgcgcccg atggccacct gattactcta agtgagccgc gagaagtacg | 600 |
| cgagtttcag ggccgcttct acctgctaga gcacgctatc cgcgctgact tcgcactgat | 660 |
| caagggctgg aaagccgacc gctcgggcaa cgtgatcttc agaggcagcg cgcgcaactt | 720 |
| caatgtgccc atgtgcaagg ccgcggacat ctcggtggta gaagtggagg agatcgtgga | 780 |
| cgttggtact ttcgccccgg aagacatcca catccccaac atctatgtgg accgcgtgat | 840 |
| caaggggccg aagttcgaga gcgcatcga gcgcctaacc acacgtgaca gcaagcccgc | 900 |
| gcccgggagc aaagacaatg acccttccag gacgcgcatc atcaagcgcg cggctctgga | 960 |
| gttccaggac ggcatgtatg ccaatctggg catcggatc cctgtcttgg cgagcaacta | 1020 |
| catcagcccc aagatgaccg tctacctgca cagtgaaaac ggaatcctgg gcttgggccc | 1080 |
| gttcccttg aaaaatgagg tagatgccga cgtcatcaac gcaggcaagc agacagtgac | 1140 |
| ggtggttccc gggggctgtt tcttcgccag cgatgactct tttgccatga ttcgtggcgg | 1200 |
| acacctccaa ctgaccatgc ttggggccat gcaagtttct caatacggcg acctggccaa | 1260 |
| ctggatggtg ccaggcaaga aggtgaaggg catgggtggg gccatggact ggtgtctag | 1320 |
| taaaaagacc agagtggtag tcaccatgga acactgtacc aagacaaagc agcccaaaat | 1380 |
| cttgaagaaa tgcaccatgc cgttgactgg caagcgctgc gtggacctca tcatcactga | 1440 |
| gaaggcggtg tttgaagtga accactcaaa ggggctgacg ctggtggagc tgtgggaggg | 1500 |
| ctcgtcggta gatgacatca aggccaccac agcctgttca tttgctgtgt cccccaacct | 1560 |
| caagcccatg cagcagatta aacttgatgc ttgaggagcc ctccagggct gattttccag | 1620 |
| ttagtgacaa ctggacatcc ttagcagcac ctgaccactg tgccacactg gctcctccgc | 1680 |
| cttccttctg ctagatggtg tctagtgaga gccatgtgac cttaattaaa aaccctaacc | 1740 |
| tgaaaaaaaa | 1750 |

<210> SEQ ID NO 58
<211> LENGTH: 848
<212> TYPE: DNA
<213> ORGANISM: Mus musculus

<400> SEQUENCE: 58

| | |
|---|---|
| gtcagaagac tttgacttct gatagccatg gactcactag actgctgagg aagacccagc | 60 |
| atctattcaa tctgctgaaa catccaggaa actacttta acaccgagaa tcaagtatgg | 120 |
| aaatgctgaa ctaagaagag cccaaggaag aactgtgttg ccagatcagg aactccaact | 180 |
| ctaaagaaga tgagtgatcc atccaaaacc aaccagtgcc ccctccatg ctgcccacca | 240 |
| aaaccatgtt gccacctaa accgtgctgt ccacagaaac caccttgctg tcccaaatcc | 300 |
| ccatgctgcc cacccaagtc cccatgttgc cctccaaagc cctgtccctg tcctcccccc | 360 |
| tgtccctgtc cctgtccagc cacctgtcct tgtccgctga aaccaccatg ctgcccacag | 420 |
| aagtgttcgt gctgccccaa aaagtgcacc tgctgcccac agccacctcc ttgctgcgct | 480 |
| caacctacct gctgctcttc agagaacaag actgagtcag attctgatac atctggccaa | 540 |
| actctggaga agggctctca atcaccacag tccccaccag gtgctcaagg caactggaac | 600 |
| cagaagaagt caaacaaata gactgtccct gacaccatgc ccttttttcaa agggtatagg | 660 |
| attactacag gtcaggctaa gactatgttg taaagatgct gttttcacaa taaccaacaa | 720 |

```
gtccactcaa ccataagcta ccatttcgac ctaactgtag gctactattg caactggaaa    780
tggaaggtag aaaaggatag aaacatcttg tctagtgatc ctgacattta gatagcaaag    840
aaataaaa                                                              848

<210> SEQ ID NO 59
<211> LENGTH: 2026
<212> TYPE: DNA
<213> ORGANISM: Mus musculus

<400> SEQUENCE: 59
ggcacgagga ggggcgaaaa acccaaggca acactagagt cttcctacgt cttattcaga     60
tacctacaga aaagggagaa tgataacctg gtccttcatt gatctgtgga gaacctctca    120
ttcaactctg ttccaaatga ccttggccac tgttctgatg gctcctgttc ttggtgattg    180
tggacctcca cccctttttac cgtttgcttc tccaaccaac cagttgtatg agtcaacaac    240
cttcccatct ggaactgtcc tgaaatatac ctgccatcac ggcttcaaga gagtcaattc    300
aagccatctt tcttgtgatg agaatggttc atgggtctat agtaccttt  gtgccaggaa    360 acgatgcaag aacccaggcg agttggtcaa tgggaaagta gaaattccat ctgaccttt     420 ggtaggctca atcatagagt tcagctgctc aaagggctat cttctgattg gctcagcaac    480
tagtcggtgt gaggtccaag gtaaaggagt tgactggagt gattctctcc cagaatgtgt    540
aattgccacg tgtgagcccc ctccgcccat cagcaatggg aagcacagtg ggagagatga    600
tgacctgtac acgtttggct ctgtagtcat ctacaattgt gatcccacct tcacactcct    660
tggcaatgcc tccattgtct gcactgtggt gaacaggaca gtaggtgttt ggagaccaca    720
ccctcctgcc tgtcaaaaaa tcgtctgcca tcggccgcag attccgaagg gatacttggc    780
ccctggattt cgacagttct atgcgtacag agacgctctt gagatccgat gcaagaaggg    840
ttttatcctc agaggcagca gtgtgatcca ctgtgaagca aatggcgagt ggtttccttc    900
tatccccacc tgtgaaccca atggttgtac caatatacca gatatttcct atgcttcctg    960
ggagggatat aagtttccat taagaaattt tgaagtattt gaaattgggg ccaaattgaa   1020
ataccagtgc aagcctggtt atcgagcaag tcttaacgat ccccagactg tgacttgtca   1080
ggaaaatctg acttggtcat ctactaatgg atgtgaaagg atatgttgcc caacaccaga   1140
tatggagaaa atcaaaattg tgagtgaaag gagagatttc actggcacat gcatctatgc   1200
ctatggagac tatgttttct acatttgtaa tgaaggctct tacccctatgt ctacggatgg   1260 aaggagttca tgtcaagcag atggaaagtg ggaccctgca ataccatcat gtcaggcaga   1320
ctcaggcctg caaaaccgtc ttgctctttt caccttccca aacatatcag aaaccaatgt   1380
gacaaacaaa acctatctat ttggtcatga agaaaactca accgagcatg ccatgaaagg   1440
tgtgtgtctc aaaccaatgg tcataaatgg aaacctgtct gtggagagag ttatctatgc   1500
tgaactggaa aatatcacca ttcaatgtga tcctggatat accatagttg gttcaccaaa   1560
catcatttgt tcaaacagaa cgtggtaccc tgaggtaccc agctgtcaga tggaggtcct   1620
agaagactgc agaatagtga gcagaggcgc acaactcttg cattgcctct caagcccaga   1680
agatgtgcac agggccctga aggtgtacaa gctgtttcta gagatcgaac gattggaaca   1740
tcagaaagag aagtggatac agttacacag gaaacctcag tctatgaaaa ttaataggtc   1800
atttagactt tgcaattagt ggacagagtc tccacgcagc agctggcctg acacacacca   1860
ccactcctgt taaaaggttt tggggccaga agaacttagg ttgtgttttt ttttttctg    1920
```

| | |
|---|---|
| ttttgttttt gaaactatgt cattcattag tgtctagcca ttgtggttca atttgtctac | 1980 |
| ttggctggac tcactgaaat agttaaatat aaactgtcaa atgtca | 2026 |

<210> SEQ ID NO 60
<211> LENGTH: 1167
<212> TYPE: DNA
<213> ORGANISM: Mus musculus

<400> SEQUENCE: 60

| | |
|---|---|
| gggcgctccc acccggccac gaatccccgc gtggctccgg agatgcccga ggggcttcag | 60 |
| taccgtccca ccagggactc atcggagctc gggagccgga gtagggactg ccatggcgcg | 120 |
| gtttgcgtgg acccgggtag ccccagtggc cctggtgact ttctggctgg tcctgtccct | 180 |
| gtcgcccacg gacgctcagg ttaacttgag ctctgtggac ttcttggacc tcccggcgct | 240 |
| gcttggggtt cctgtggacc ccaagagggc acgcggatac ctgctggtgg cccggccggc | 300 |
| cgacgcctgc cacgccatcg agggccctgg ccccgacaac cactcactgg acccactagt | 360 |
| gctggtccgg cccctgggct gctcctggga gcaaacaggg cggcgagcac agagagctgg | 420 |
| agccacagca gcctcagtgg gccctgaggc cccaggggcag ctgcgcgagt ttgaggactt | 480 |
| ggaggtgacc gtacgctgcg accagccagc ccgcgtgctg ctgcctcacg cggaaccctg | 540 |
| ccccgacccc gagtgtcacc ctgtagtggt tgcatcctgg gcgctcgccc gagccctggc | 600 |
| cctggccgca tctacgctgt tcgtgctgcg gcagctgtgg ccgtgggtcc ggggcttggg | 660 |
| tagccggggc accgcggtga agacgcagac atgccagaag gcacaggtgc gcacgttcac | 720 |
| gcgcctcagc gacctgtgcg ccatctgcct ggacgactac gaggaggggg aacggctcaa | 780 |
| gatcctgcct tgcgcacatg cgtaccactg tcgctgcatc gacccctggt tctcgcgcgc | 840 |
| cggagcttca tgcccctgt gcaaacagtc agtggccagc actcacgacg gttccacgga | 900 |
| cggcagcgta ggcggcgagg aaccaccct ccccggacac cgcccgccca tctgggccat | 960 |
| ccaggcccgg ctgcgctccc gcaggctcga gctgctagcc cggacagtcc cctgccgtcg | 1020 |
| ctgcagcagc accacgtctc tgggggtggc ggagaacgtg gcgcagtcag aagcgacttc | 1080 |
| cgagctctcc tgaccccaac tgacgcggga agggcggaaa ccaggcaggg gaggttgggg | 1140 |
| gtgcccaata aagcgtgttt gaatctg | 1167 |

<210> SEQ ID NO 61
<211> LENGTH: 1080
<212> TYPE: DNA
<213> ORGANISM: Mus musculus

<400> SEQUENCE: 61

| | |
|---|---|
| tggggagaat gccttctctt ggatctggag ctcaggtgcc tgaaaagagg tcccccattc | 60 |
| ttgctcagac actaggcctg tgatggaacc tgacttgaat gaggaagaat ccgagaggat | 120 |
| aaggaccagc aggaacaggc ggtcactgga gcatcgtcgc aactccctat tgcccttcta | 180 |
| atggaaagca acaaacaact ctcgctggat ggcccaggtg gtggcctcag agttcagcct | 240 |
| ggtggccttc ctcctgctcc tagtcatggt cttctccaag aaatggttgt atccctctaa | 300 |
| gagtcgtttc catcagcgct accccaaaa tgtcaccaag agagtctaca cctccatcca | 360 |
| cagtatgtcc acagggctcc tgtacatctg cgtatctaaa agctgcccca gctcagacaa | 420 |
| cggagaagac aattttaaga tgtggacaat ccatccagtt tttggggtgg ctaagataag | 480 |
| tttcaccctg gccatagggc tgggtttgt cctcaccacc tggctgcacc tgccctacct | 540 |
| gccctgcttg cagagaatgc ctttctttgg cctgattgga atcatcctga gcttctgtga | 600 |

```
agtcaccttaa attttcctca ccctcctgtt gttccctgtt aacctctgga tctacgagct      660
gaggaagaat atatcggttc ccatcggctg gagctatttc attggttggc tggtgctcat      720
cctgtatttc acttgtggga ttctttgcta cctcaaccat aaaaactact ggagtctgat      780
aatgagcagc accaccatca acactgcttg cagcagctta gggccagagt ctctggtgag      840
tccctcccag accccagcag ccaggagaac agccaggagt ctcctaagga tgaccaaaag      900
catcagtcca gataagtagt ctcaccaccc agccagacac cactggctag gactgtcctc      960
atcgtgacca ggaggagcaa aggaggattt ggggaccagc tttgcattcc tcttcctcaa     1020
cttggcttgt ctgtggctca ggtgatgtgg aataaattgc catgtcttca aaaaaaaaaa     1080
```

<210> SEQ ID NO 62
<211> LENGTH: 2000
<212> TYPE: DNA
<213> ORGANISM: Mus musculus

<400> SEQUENCE: 62

```
acggtcctct ccggccgggg gctcggtgag cagggcggca gacgggcgca ccccggccag       60
gctcacatgg acctcccgcg ccgctggctc tttcggatgt tgttgctcgt tgccaccagc      120
tctgggatcc tcctcatgct gtactcctcg gcggggcagc agtcccctga gacccaggtt      180
cccgccagga acatggcgta cccacagcat ttctttgacc ccaaaccacc gaattcggaa      240
aacagaaaga gccgactttg ccaacactcg ctgtccctgg ccattcagaa ggaccgtcgc      300
ttccgcagcc tgtttgacct ctccacccccg gtgctgctgt ggagggcct cttcactcag      360 gaactctgga ataatctgag ccagcacaaa gtccctacg gatggcaggg gctctcccac      420
gaagtcattg cctctaccct gagacttctg aaaagcccgg agagcgggga gctgtttggt      480
gcccccagga aactacctct aagctgtatt cgctgtgccg tggtgggtaa cggaggtatt      540
ctgaatgggt cccggcaggg ccagaaaatc gatgctcatg actatgtctt cagactcaat      600
ggcgccataa ccgaagcttt tgagcgcgac gtgggcacta agacctcctt ctacggtttc      660
accgtgaaca ccatgaagaa ctcactcatc tcctatgcca aactgggctt cacctctgtg      720
ccacaagggc agaacctgcg ctacatcttc atcccctcca gcatccgtga ctacctgatg      780
ctgagatccg ccatcctggg tgtgcctgtt ccagaaggtc ctgataaagg gacaggcct      840 cacacctatt ttggaccgga aacctctgcc agtaaattca agctcctgca cccagacttc      900
atcagctacc tgacagagag gtttctgaaa tccaagctga ttaacacacg atttggagac      960
atgtatatgc ctagcacggg agcgctcatg ctgctgacag ccttgcacac ctgtgaccag     1020
gtcagtgcct acggattcat cacaaacaac taccagaaat actcagacca ctatttcgaa     1080
cgagaaaaga aaccactgat attctacgca aaccacgacc tgtccctgga agcttcgcta     1140
tggcgagacc tgcacaacgc cggcatcctt tggctgtacc aacgctgacc caaagtacc     1200 ggatttctgt gcctcaaaag cacttttttt gacctttcaa cttctggaag aggcaacact     1260
ccccttggcc ctctacttcc caacagaggg tattgagaca agacccgtca cataatacca     1320
gagcctgttc aatgcacgac actgtcacgg gtcaagacaa ctcttctgag gcttagccga     1380
gggagggaag actgctttgt aggattcgtt ttaaaactga acattaaatg agacaatgat     1440
gctcaccagc aaacaggcgg gcaggcacat ctcagagcta agtagtccaa agccagcacc     1500
tggccctggg caactagaaa cattgatgga accactcagg gctatccagg aacctcgatc     1560
gagcagagct gaaaccaatg gcatgttgag tcccaaatgc caaagccatt caacctagaa     1620
```

```
caccttaggc attataggaa caggacactt ctgcctcctg atagaggatg agaaacagag    1680
gcagaatgta gtttgaagct agataatagg gtgtgatgga tgaccatttt gtcttttttg    1740
tgttggtaga gtagaagaca caaactccaa ggtggtgtgt ctggagggaa ggggtgtggc    1800
ggcactcagg acagagtttg gtggcacctg caccgaggtt caggctagga gtacctagca    1860
ccaaagagac aaactttgtg taagtcgcca ccactgagtc tcactggaga ggcacattag    1920
tccttgtcac aacaggaaa ctgagtgatg gaccctcact tcacagcttc aataaacagc    1980
acctgatgca gtccaaaaaa                                                 2000

<210> SEQ ID NO 63
<211> LENGTH: 1669
<212> TYPE: DNA
<213> ORGANISM: Mus musculus

<400> SEQUENCE: 63
gaattcaagc cggagcctcg tgcgcaggcg cggagttaga cctcgccgta gcccccatcg      60
cctcggggag tctcatccac agtgggtccg ctggccatag gggcgctttc cctcctctac     120 tcccggggttc tcggccctac ggccccaatg gcggagctgc ggcctagcgt cgcccccggt    180
cccgccgcgc cccggcctc tggccctagt gcccctccgg cctttgcttc actcttttccc     240 ccgggactgc acgccatcta cggagagtgt cgccgcctct accctgacca gccgaacccg     300
ctccaggtta ccgctatcgt caagtactgg ttgggtggtc cggacccctt ggactatgtt     360
agcatgtaca ggaacatggg gtgtccttct gccaacatcc ctgagcactg gcactacatc     420
agctttggcc tgagtgatct ctatggtgac aacagagtcc atgagtttac aggaacagac     480
ggaccaagtg gatttggctt tgagttgacg tttcgtctga agagagaaac tggggagtct     540
gccccaccaa catggccagc agagctgatg cagggcctag cccgatatgt cttccagtca     600
gagaacacct tctgtagcgg ggaccatgtg tcttggcaca gccctttgga taacagtgag     660
tcaagaattc agcacatgct gctgacggag gacccacaga tgcagcctgt gcggacaccc     720
tttggggtag tgactttcct ccagattgtt ggtgtctgca ctgaggagtt acattcagcc     780
caacagtgga acgggcaggg catccaggaa ctactacgga cagtgcccat tgctggcggt     840
ccctggctga taactgacat gcggcgggga gaaaccatat ttgagatcga tccgcacctg     900
caacaggaga gagttgacaa aggcattgag acagacggtt ctaacctgag cggcgtcagt     960
gccaagtgtg cctgggatga cctcagccgg cctccggagg atgaagagga tagccggagc    1020
atctgcctcg gcacacagcc tcggaggctg tctggcaaag acacagagca gatccgggag    1080
accctgaggc ggggactgga gattaacagc aaacctgtcc ttccaccaat caattctcag    1140
cgacagaacg gcctcaccca cgacagggct ccgagccgca aggacagttt gggcagcgac    1200
agctccacgg ccatcatccc ccacgagctg atccgcacac ggcagctcga gagcgtgcat    1260
ctaaaattta accaagagtc gggagccctc atccctctct gcctaagggg cagactccta    1320
catggccggc acttcaccta caagagtatc acaggcgaca tggccatcac gtttgtgtcc    1380
acgggagtgg aaggcgcctt tgccactgag gaacacccgt atgcagctca cggaccctgg    1440
ttacaaattc tgttgacaga agagtttgta gagaagatgt ggaggactt agaagatcta    1500 acctctccag aggaatttaa acttcccaaa gagtacagct ggcctgagaa gaaactcaaa    1560
gtgtccattc tcccgacgt ggtgttcgac agtccactgc actagcctgg ctgtgcctgc    1620
aggggccaag aggagcccag ctgctcctgg tgacttccag tgtgacagg              1669
```

<210> SEQ ID NO 64
<211> LENGTH: 1380
<212> TYPE: DNA
<213> ORGANISM: Mus musculus

<400> SEQUENCE: 64

```
atgtaggaag gtgaggaagg gaggcagatg gcgacaaaga acagccctag ccctaagccc      60
atgggcacag cgcagggcga ccctggagag gcaggaacac tgccagcacc cgaggctgct     120
ggcatccggg acacaggttc cactcaactg aagacaaaac ccaagaaaat acggaagatc     180
aaggcgctgg tcattgacct gggttcccag tactgtaagt gcggctatgc aggagagccg     240
aggcccacct atttcatctc ctctaccgtg ggcaagcgca gcgctgagat ggctgcggat     300
gctggagaca acttcaagga gacatacgta ggccatgagc tgctcaacat ggaggcatct     360
ctgaagctgg ttaacccact gaagcacgga gttgtggtgg actgggattg tatccagaac     420
atctgggagt acatcttcca caccgctatg aagatcatgc cggaagagca tgcggtgctg     480
gtgtccgacc ctccgctcag ccccaccagc aaccgggaga agtacgctga gctcctgttc     540
gagaccttcg gcatccctgc catgcatgtg acctcccagg cgctgctgtc catctactca     600
tatggcaaga cctccggctt ggtggtggag agcggacacg gcgtgtcgca tgtggtgccc     660
atctctgaag ggaccctgct gccgggcctg cccagccgtg tagactatgc gggctgcgac     720
ctcaccaact acctcatgca gctactcaat gaggcaggcc acaagttttc agacgatcac     780
ctgcacatca tagaacacat caagaagaag tgctgctatg ctgcgctgct gcccgaggag     840
gagatgagcc tgggcctaga cgagctgcat gtggactacg agctcccaga tgggaagatc     900
atcaccatcg gccaggagcg cttccgctgc tctgagatgc tcttcaagcc ctccctggtg     960
ggttgcaccc aacctggcct ccccgagctc acggcgacct gcctggcccg ctgccagggc    1020
actggcttca aggaggagat ggctgctaac gtgctgctgt gcggtggctg caccatgctg    1080
gatggtttcc ccgagcgttt ccagagggag ttgagtctcc tctgcccagg agacagcccc    1140
acggtggccg ctgctcccga gaggaagaca tcagtgtgga ccggcggctc catcctggcc    1200
tccttgcaag ccttccagca gctttgggtc agcaaagaag agtttgagga gcggggctgt    1260
gcagccatct acagcaagtg ctaagggcag gccccccagg caaaagctgg agagcagagg    1320
cccctctttg ggccactcta tacctttaca gaatttcgca taaaagttta acctgtaaaa    1380
```

<210> SEQ ID NO 65
<211> LENGTH: 1523
<212> TYPE: DNA
<213> ORGANISM: Mus musculus

<400> SEQUENCE: 65

```
gtcctctgat ttaagtcttt caggccttgt agccagcagg atcgagagct ttctgagagc      60
agtatgtctc tggatggtgt gtgggctcca cagacagcaa acattgggga cggacctgcc     120
aagaaagcta gtgaccaggc ctccatgcag acacaggtcc tccaaaccgc ctccctaaaa     180
gatggcccag caaaagggc ggtatgggtc cgtcgggaca atgctgagac agaagaccct     240
gttaagtcaa ctatgtccaa ggataggcca agactagagg taaccaaagc agtggttgtg     300
gacctgggca ctggcttctg taaatgtggc tttgctggcc tgccaaagcc cactcataag     360
atctcaacaa cagtgggcaa gccctacatg gagacggcca gacggggga taatcgcaaa     420
gagacctttg tggggcacga gctctttaac ccagatatac atctcaagct ggtcaacccc     480
ctgcgccatg gcatcattgt ggactgggac acagtacagg acatctggga atacctcttc     540
```

| | |
|---|---|
| cgacaggaga tgaagatcgc cccagaggaa cacgcggtcc tggtttcaga cccacccctg | 600 |
| agtcctcata ccaacagaga gaagtacgcc gagatgctgt tgagaccttt caacacacct | 660 |
| gcaatgcaca tcgcctacca atcccgcctg tccatgtact cctacggacg cacctctggc | 720 |
| ctggtggtgg aggttggaca tggtgtgtcc tatgtggtcc ccatctatga gggttatcct | 780 |
| ttgcccagca tcacggggag ctagactac gcaggttctg acctaacgac ctacctgatg | 840 |
| aacctgatga acaactctgg aaaacacttc tctgaggacc atctcggtat tgtggaggac | 900 |
| atcaagacga ggtgctgctt cgtggccctg acccccattg aagagaagaa aatccctgcc | 960 |
| cctgaacatg agatccatta tacctgcct gatgggaaag agatccgtct gggtcaggag | 1020 |
| aggttcctct gctcggagat gttctccaag ccatctctaa tcaagtccat gcagctgggc | 1080 |
| ctccacaccc agacagtgtc ctgccttaac aaatgtgaca tagcactcaa acgagacctc | 1140 |
| atggggaaca tcctgctctg tgggggcagc actatgctca ggggtttccc taaccgtctg | 1200 |
| cagaaggagc tgagcagcat gtgccccaac gacaccccc aggtcaatgt gctgcccgag | 1260 |
| agagacactg cagtctggac tggtgggtct atcctggcct cactccaggg ctttcaacca | 1320 |
| ctgtgggtcc atcgcctgga gtacgaggaa catgggcctt tcttcctcta cagaaggtgc | 1380 |
| ttctgagcag acacagcatg ctcaccgtgg tggcaatgcc agctttactg tgtgagggct | 1440 |
| gaaccttcta caagtggtgt tgagttggca tgttcatttc tgtagcatta aaaccctc | 1500 |
| gtgtctgtcc ccttaaaaaa aaa | 1523 |

<210> SEQ ID NO 66
<211> LENGTH: 2588
<212> TYPE: DNA
<213> ORGANISM: Mus musculus

<400> SEQUENCE: 66

| | |
|---|---|
| ctagctgtgt agagggcaca gagagctgtt gggatatggc ctagatgagg aatgtcctgg | 60 |
| tagaagtcac catcttaggc taggtgaagt gactggctgg ggggcgcaga aggagggtac | 120 |
| tccctggtga gaagggctta ggatccaatg ctggggaata gagtcctcct tctgagaagc | 180 |
| catggatgcc agtctacccc tgcagaaaac catggggccc gggccagatg aaggtgcagt | 240 |
| gggttatgaa taagctctgc tataggtgcc tttgactctc agggtgaaat accttgtctc | 300 |
| cagtcagatc ccctaccaca gtggctaagc ctctcattct tgtttctata cagcctaggt | 360 |
| tggtgagtac aagtgtttat gtgtagaaac aggaaatgtg ctgttatatt tgtgatttgg | 420 |
| ggtaaggaca ttcccaaagg ctctgcctgg aaatccctgc cactcaccca tcctcacacc | 480 |
| ccctcccaca ggccagtcag aggctaccat tctctacatt ggtaagggtg tggcaattag | 540 |
| ctgcaaaggg gctttagtag tggtagaggg gttgatttag ttattggtgt catatgccgt | 600 |
| gctctccttt ggaaggctgc tcttccattt tttctctcca ctcaactgtc tcccactggg | 660 |
| ctcctccccc acggctccaa gtctcaggtt ccataagtcc tccttctttg tcatcctttt | 720 |
| aggttatgga gttgtaggtt gggggcgagg ggtttgtcct gatgagaggc agggaaacct | 780 |
| tccacagcaa aggtctgacg aaggactaag acatcccagg cgccctctca aggccctgtt | 840 |
| cacctcaaga atgcttactg gtcacctcga ggctaaatag tcagcagaga caagccatgt | 900 |
| tggaggatct gagtcaagga aaggggtcca accatgagaa aggaagatg gagagcacag | 960 |
| cccagatcac tgaggaagac agcaagcttg atgaggttgt ggggctgcag aagcagattt | 1020 |
| gtgaccttgg gacagagctc acaagacaat catctttgtg gtgcgtagct cacaaagacc | 1080 |
| tccaaagcca gatcgatgct ctgataaagg agaaccagga gatccgtgcg gagctgaaga | 1140 |

```
ccttgaagaa gcaggatgca gaggccacca aagcctgtat aggctcaccc acccggcaa    1200 gagcaagcaa cactctgcca gtgtacataa agatagaggg aattgattcc gagaggacaa   1260
cctcatggga tgaaagagat gagctttctg gaagtcctcc aaacagaagc acaatggcca   1320
ccggaagaac agactcccag gatgaaaggc tgtcttttac atctgtggat gaaaaggtta   1380
tacacatgtc ttccaaattt ctacaaagaa gctttggcag aatgtcacca gaaccactgt   1440
ctgacagcac attcctggac aaagagtcac tggctgacat ctggtcctca aatccagaga   1500
cttcggacag tgaacttctc ctgcatgctc aagcaagcag ggtcatccct tgttttccc    1560 caaatgcact gtgggtgcag aatattccaa caaagtcaag agctcctaaa gaaatacagc   1620
aaacctcgga cactacaaag actgatgaga caaggaaaa gcgacaccca aacggcaagg    1680
tggagcgaat gctcagcgac gggcgaacca tcatcacctt ccccaatgga accaggaagg   1740
agatcagtgc tgacaagaag accaccctca tcaggttttt taatggtgac atgaagaaga   1800
tcaagtccga tcagaaagtg atttattatt atgcggacgc acaaacaatg cacacaacct   1860
acccagatgg tgttgaagtg gtgcagtttc ctaacaagtg gactgaaaaa ttctacccgg   1920
atggctccaa ggaaaccgtg tttcctgatg ggacagtgaa acagcttaag gatggatgtg   1980
aagagacggt gttccccgat gggacatttg tgacagtgaa gaggaacgga gacaaaacca   2040
tcatgttcag caacggagag aaagaaatcc acacggccag gttcaagcgg aaggaattcc   2100
cagatggcac catcaagact gtgtattgca atggctgcca ggagaccaag tatgcctcag   2160
ggagggtcag ggtcaaagat gagaagggaa ctgtcatcct ggactggaag tagtgcatcc   2220
aacagactca aggccaggca gtaggctcca atctccaaat atagttttga ccaaaacaga   2280
caaagcgact cacgattccc ttgacaatcc tggagatccc ctgcacatga ggagtaaaga   2340
gacatccaaa aattgtaaag aaagagacca tgtagccacc accatcttgg gagagaggtc   2400
agagaagcag tagccagaaa tgaggtcctg gacatggctt ccgtggcctt gtacagacca   2460
tgccttctgt cggagtctgg ccctagagca gagggtacaa tgggagcaac gtgaccactg   2520
ccagctagtt cctgggagca gccgttaaca acgctggctc cgtgtttttt gttggccaac   2580
acctgcct                                                           2588
```

<210> SEQ ID NO 67  
<211> LENGTH: 1500  
<212> TYPE: DNA  
<213> ORGANISM: Mus musculus

<400> SEQUENCE: 67

```
cagggctttg tgcctgaaga cagaccactg aggaaataca gcttgattgc taatacctca     60
caggaggtgg cgatctggaa caggcctaag gggttcagac cttcgtctcc ttagccatgg    120
cgacactaag tttcaagccc agcgaacgct accggctctc cgactggcgc accaacagct    180
acctattgtc caccaatgca gagcggcagc aggatgcttc ccaccaaatc cgccaggagg    240
cccggatcct tcgcaatgag acaaacaatc agattgtatg ggatgaacat gacaatagga    300
cccgcctggc tgagaggatc gacactgtca accggtggaa ggagacgctg acaagtgtc     360 tgacagattt agatgctgag atcgatagct tggcacaggc caagaatcg gcggagcaaa     420 acctgcaggc caagaacctg cccctggatg tggccatcga gtgcctgact ctgcgagaga    480
gccggcgaga cattgatgtg gtgagggacc ctgtgaggga agagctgctg aaagaggtgg    540
aagtcattga agccaccaag aaggtcctac aggagaagat cagccaggcc ttccagcacc    600
```

-continued

| | |
|---|---|
| tctgtctcct gcaggaaatt cggcagcaac tcaactctga ccaccgggac aaaatggaga | 660 |
| cactggagat cgacaggggc tgcctctctc tcaacctcac ttccccaaac atctctctga | 720 |
| aagtcaaccc cacacgcatc cccaaagact ccaccacact gcagcagtgg gatgaattta | 780 |
| ctcgattcaa caagaaccgg gcagaggccg aaatgaaagc gtccatagag ttgagggaag | 840 |
| ccattgccct agctattgct cagaccaaca atgaactgga cgctcagagg gttgcaacag | 900 |
| aattcacctt caggaagcgg cttcgggaaa tggagagttt ttacagtgag ctcaagtggc | 960 |
| aagagaaaaa taccttagaa gagatagccg agctgcaggg agacattcgg cgcctggagg | 1020 |
| aggacctgcg tagaaagatg atgaacttga agcttgcaca tacccggctg gagtccagaa | 1080 |
| cctaccggtc caatgtggag ctctgccggg accagacaca gtatggcctc attgatgaag | 1140 |
| tccaccagtt agaggcaacc atcaatacca tgaagcagaa gctggcccaa acacagaacg | 1200 |
| ctttggatgc cctgttcaag cacctggccc ggatacaggc tgatatcgcg tgcaagacca | 1260 |
| acaccctgct cttggacacc aagtgtatgg acacccgacg caagctgacg gtgccggctg | 1320 |
| agaaatttgt gccccaggtg gacaccttca cgcgcacgac aaaccgcaca ctgagtccac | 1380 |
| tcaaaatctg ccagctggag ctaacctagg cttttggcggc tgaggaaga cacaagattg | 1440 |
| gtgggagggg ggagtagtga ggggacagta aaataataaa aatggagttc tcaaaaaaaa | 1500 |

<210> SEQ ID NO 68
<211> LENGTH: 1246
<212> TYPE: DNA
<213> ORGANISM: Mus musculus

<400> SEQUENCE: 68

| | |
|---|---|
| gacccatata cagggcggcc agatgccatg tggggttcca gggcccaaca atcaggtccg | 60 |
| gacaggggcg gagcctgcct gctggctgct ttcttactct gtttcagcct cttacatgct | 120 |
| caggactaca cgccctcaca aacacctcca cccacatcga acacctcgct caaaccaaga | 180 |
| ggccgggtcc agaaggagtt atgtggcaag accaaattcc aagggaagat ctatggcggt | 240 |
| cagattgcaa aggctgagcg gtggccgtgg caggccagtc tgatctttcg tggcaggcac | 300 |
| atctgtggag cagttctcat cgacaaaacc tggctactca gcgctgccca ctgcttccaa | 360 |
| aggtctctca caccatctga ctaccggatc ctgctagggt acaaccagct gagcaacccc | 420 |
| tccaactaca gccggcagat gaccgtgaat aaggtcatct tgcatgagga ctatagcaag | 480 |
| ctcagccgtc tggagaagaa cattgtcctg atccagctgc accacccgt gatctacagc | 540 |
| acccacattt tcccagcctg tgtccctgac ggcaccacga aggtttcccc taataatctc | 600 |
| tgctggataa gcggctgggg aatgctctca gcggacaagt tcctgcaagc acctttccct | 660 |
| ctgctggacg cggaggtctc tcttattgat gaagaggaat gcacgacctt tttccagaca | 720 |
| ccagaagtca gcatcacgga atatgatgtt ataaaagacg atgtgttatg tgccggagat | 780 |
| ctcaccaatc agaaatcctc ctgccgagga gactctgggg gccccctggt ctgcttcctg | 840 |
| aatagcttct ggtacgtggt agggctggcc aactggaatg gagcatgtct tgaaccaatc | 900 |
| cacagcccca acatcttcac caaggtctcc tacttttctg actggatcaa gcagaaaaag | 960 |
| gcaaacacgc ctgccgctga tgtctcctca gcaccccttg aggaaatggc gtcatccctg | 1020 |
| agaggctggg ggaattacag tgcaggcatt accctcaaac ccaggatctc cacaaccttg | 1080 |
| ctgtcttctc aggccctcct cctgcaatcg atttggctca ggattctgtg atttgtctac | 1140 |
| tgatctattc accaagagcc actttgcacg cttccatctg tgggctcacc tgtcccatct | 1200 |
| gaggccacac cagctccagg cctgaccgaa taaaacaact aaagac | 1246 |

<210> SEQ ID NO 69
<211> LENGTH: 555
<212> TYPE: DNA
<213> ORGANISM: Mus musculus

<400> SEQUENCE: 69

```
aaagccgggc ctgctgggag gaggaggagg aggaagtctc tgccccgagt gtggcctccc    60
atggacacca agatgcagag ccttcccacc actcatcccc accccacag ctcctcgcgg    120
cctcaaagtc acaccagtaa ccagtgcaat cagtgcacct gcagccacca ctgccggagc    180
tgcagccagg caggccacgc gggctctagc tccagcccca gccctggccc gcccatgaag    240
cacccccaagc catccgtgca ctctcgacac tcacctgcaa gacccagcca ccgcgggagc    300
tgccccaaga acaggaagac cttttgaaggg aaagtgagca agagaaaggc cgtcaggagg    360
cggaaacgga ctcacagagc taagaggcgt acgtcagggc gaagatacaa gtgacgcact    420
ccaggatgtt cctgtgtcca tttgatccca aaatgagata gccatcacta ggggactgtt    480
gggatgatgt cacaggaaca tgtcactgca gcaatttcta tgcaacatgg attaaagctt    540
gtaccctgga agact                                                    555
```

<210> SEQ ID NO 70
<211> LENGTH: 2053
<212> TYPE: DNA
<213> ORGANISM: Mus Musculus

<400> SEQUENCE: 70

```
gcacgaggaa gtattgtggc cttgtggtaa ctcttgatgt ctgatagcac agaggactcg    60
caggtttgtg gattaaagcg ctagtctcaa tgggtgaagg gaacccagga gctgctggtc    120
aaagcctatg caaaagctgt tcgaggtgga gacagaagag gctgccctt ggcgggaggc    180
tgcccgagac ctgagaactc tcgcgggaag atgtacggtc accacggcaa ccgcatcgcc    240
ccggggttgg taaagatggc ggggcgaagt gttagagtgc cgagacgcgg ttctgcaggt    300
acccagtcgc gcgggcagct tgcagctgga cgggacctcc tcgcccggga caagagtac    360
aagcgtttaa atgaagaatt ggaggcaaaa actgctgatc tggttcgaca agctgaggaa    420
gtaataagag agcagcaaga agtgcgagcc aggcctttct cagcactaac tacatcatgc    480
aaagaggaag gtggttccag ttcgagagat ctgttgtcat ctgaagggac tcatccatgg    540
acagaaacca agccaaagac caaaaacact ggtcctgtaa acaagattca aaacagactc    600
cactctgcag ataaagaaag gaaaacaaat tcaagtgcta aactgaaata tcctgatgcg    660
cagactgcca acgatgtggc catcccagac gatttctcag acttctccct tgccaagacg    720
attagcagga ttgaagggca gctggacgag gacggcttgc ccgagtgtgc agaggacgac    780
agcttctgtg gtgtgagtaa ggacattggc acagaggctc agatccgatt tctaaaggcc    840
aagctccatg tgatgcaaga ggagctggac agcgttgtgt gtgagtgcag taagaaggag    900
gataaaattc aggacttaaa gtccaaggtg aaaaatttgg aagaagactg tgtgcgacaa    960
cagcgaacag ttacatccca gcaatcccaa atagaaaaat ataagaatct ttttgaagaa   1020
gcaaataaaa aatgtgatga attacagcag cagctgtcat cagtgaacg ggaattagaa   1080
agtaaaagaa gattacaaaa acaggctgcc tcaagtcaga gtgccacaga ggtccgtctg   1140
aatcgagctc ttgaagaagc agaaaagtat aaagtggagc tgagtaaaact caggcaaact   1200
aacaaggaca atcagtacct taacaatgac ttagagaaa gagcctcaaa ctgaaggagg   1260
```

-continued

```
gaactcaagt gagcagtcgt catgatggaa gaaactgaga tgaagacaac tcattatctg    1320
tacttaaagg atagaagaac ctttaagttg acctctgagc agttgcagaa gctaaaaaag    1380
cacttggaga cagaccatta ccctaagaag gaaactctgc aggccttggc tgaggagctc    1440
atactgtgga aagaagtcat cagatcctgg ttcttcactc agcatcaaga gagatgaggc    1500
acagatggtt tttaatgggc tacagggttg gataacgcac tgtcactact gtacaacaag    1560
aaggactgcc aggcagaaga actccaagga gtgtcctcag aatggcgttg gactccccga    1620
agcgttggaa gccttaaaga ggctcaagct ctcttctggt taccaaagca gagatggcat    1680
gtcacaggat ttctgacttt tcaacttctt tgttggggca ggtgtctgtc tatggaagaa    1740
ggatattaca aatgaagacc atcaaaaaat tgaagtgttg aaatcagaaa acaaaaaact    1800
agaaagacaa aaaggagaat taatgatatt ttcaagaagc agttgaaatt gattgacatt    1860
ttgaaaaggc agaagatgca tattgaagct gccaagatgc tgtctttcag cgaggaggag    1920
tttatgaaca gctcttgagt ggggcagttc atgagtgagc aactgcattg ggatgctcat    1980
ttgatatcaa gtgtagtctt cttgctgttc atgagtaata gaacatttg tgaaataaaa     2040 gagttagata atg                                                      2053
```

<210> SEQ ID NO 71
<211> LENGTH: 1814
<212> TYPE: DNA
<213> ORGANISM: Mus musculus

<400> SEQUENCE: 71

```
acctgggagc aggcccccccg caccatggca agcgtggtgg tgaagacaat ctggcaatcc    60
aaagagatcc acgaagcggg ggacccacct gcggggtag aaagccgtgc ccagctggtc     120
cccgaggctc ccgggggggt gaccagccct gccaaaggga taacgaaaaa aaagaaggct    180
gtgtccttcc atgggtgga gccccggatg tcccacgagc cgatgcactg gtgcctgaac     240
ctcaagcggt cctctgcctg caccaacgtg tccttgctca acctggctgc cgtggagccc    300
gactcctcgg gcacagactc gaccacagag gacagtggtc cactggcact gccagggaca    360
cctgcttccc ctacaacacc ctgggctcca gaggaccctg acatcacaga actactgagt    420
ggggtcaaca gtggattggt acgtgccaaa gactccatca ccagcttgaa ggaaaagacc    480
acgcgggtta atcagcacgt tcagactctg cagagcgagt gctctgtgct gagtgagaat    540
ctggaaagaa gacggcagga ggcagaagag ttggaggggt actgcagtca gttgaagggc    600
ccccgccctg atgtcctgac ccaggagaac tgccgcaagg tgacccgttc agtggaagac    660
gctgaaatca aaaccaatgt cctgaagcag aactctgcct tgctggagga gaagctaaga    720
tacctccagc agcaactgca ggatgagacg ccccggagac aggaggccga gttgcaggag    780
ttggagcaaa aactggaggc tggcctctcc cgacatggtc tgagccctgc cactcccatt    840
cagggctgct cgggtcctcc tggcagcccc gaggaacccc cgcggcagcg aggcctgtcc    900
ttcagtggct ggggcatggc agtccgcaca gggagggac cctcgctgag cgagcaggag    960
ttgcagaagg tctccaccgg cctggaggag ctgaggaggg aggtgtcctc gctggcagcc    1020
cggtggcatc aggaggaggg ggcagtgcag gagcccctga ggttgctggg aggccttggc    1080
ggccgtctgg atggcttcct gggccagtgg gagcgcgcgc agcgggaaca ggcacagtcc    1140
gcaaggggct tgcaggagct gcgagcacga gcagatgagt tgtgcactat ggtggagagg    1200
tcagcagtgt ctgtcgcctc actgaggagt gaactggagg cactgggccc agtaaaaccc    1260
attctggagg agctgggacg gcaacttcag aactcccgga ggggagctga ccatgtcttg    1320
```

```
aacttggatc ggtctgccca aggccctgt gcgcgctgtg ccagccaggg gcagcagtta    1380
tccacggagt ccctgcagca gctgctggaa cgtgcgctga ccccgctggt ggatgaggtg    1440
aagcagaagg gtctggctcc tgccagcccc agttgccaga ggctacacaa gaagattctg    1500
gagctggagc gccaggcctt ggccaaacac gtcagggcag aggccctgag ctccaccttc    1560
ggttggccca agacgaggcc gttcgggcca agaacctact gctgacggac aagatgaagc    1620
cggaggagaa ggtggccact ttggactata tgcatttgaa gatgtgctcc ctccacgacc    1680
aactcagcca cctgccactt gaggggtcca cggggcaatg gggggaggaa gcaatggagg    1740
ggctccccct aaacgtggga gtccaggctc tgaacaataa atggcctctc atgctggcat    1800
gaaaaaaaaa aaaa                                                      1814

<210> SEQ ID NO 72
<211> LENGTH: 1318
<212> TYPE: DNA
<213> ORGANISM: Mus musculus

<400> SEQUENCE: 72
tgttccgcac cggccgctcc tggcagcatg gacgatgcgg cggtcctaag gaagaagggt      60
tacatcgtgg gaatcaatct gggcaagggc tcctacgcaa aagtcaaatc tgcctactca     120
gagcgcctca gttcaatgt ggcagtcaag atcatagacc gaaagaaaac acccactgac     180
tttgtggaga gattccttcc tagggagatg gacatcctgg cgacggtcaa ccaccgttcc     240
atcattaaga cctacgagat cttgagacc tctgatggac gcatctacat tgtcatggag     300
ctgggcgtcc agggcgacct cctcacgttc attaagtgcc gaggagccct gcatgaggat     360
gtgggaggca agatgttccg ccaggtctcc tcagccgtca agtactgcca cgacctggat     420
gtcgtccacc gagacctcaa atgtgagaac cttctgcttg acaaggactt caacatcaaa     480
ctgtctgact tcggcttctc caagggctgc ctgcgggacg ggagtgggcg catcgtcctc     540
agtaaaacct tctgtgggtc agcagcttat gcagcccccg aggtgcggca ggggattccc     600
taccagccca aggtgtatga catctggagc ctgggtgtga ttctctacat catggtctgt     660
ggctccatgc cctacgatga ctctgacatc aaaaactgc gcatccagaa ggagcaccga     720
gtggacttcc cacgctccaa gaacctaact ggtgagtgca aggacctcat ctaccgcatc     780
ctacagccag atgtcaaccg gcggctgcac attgatgaga tccttagcca ctcatggcta     840 cagccccca agcccaaagc catgtcttct gcctccttca agggagg ggaaggcaag     900 tatcgagctg attgcaagtt ggatactcga ccaggctcca gacccgaaca ccggcctgac     960
cacaagctgg cgaccaaacc ccagcaacgg atgctggtga cacccgagaa tgaagacagg    1020
atggaagaca ggctggctga gacttccaga gctaaagacc atcacatttc tggagctgag    1080
gtggagaaag caagtaccta gtggtggaga gggccctggg ggtatcgtgg tgtgcagtct    1140
gcacccacat aagctaagta ggcaggtagg agctgaagaa gcacaggtgc aaggaacaag    1200
taaaattcgt caattaaacc actatttga ttacgttcta ttagctttct tccacttagt    1260
agcaaagcca ttaattactg accaccaaat aaaccacaaa gtgtatacaa gtaaaaaa     1318

<210> SEQ ID NO 73
<211> LENGTH: 2081
<212> TYPE: DNA
<213> ORGANISM: Mus musculus

<400> SEQUENCE: 73
```

```
gaattcagag ccaatgagca gactgtattc aaagctgtat aaagaggctg aaaagataaa      60
aaagtggaaa gtgagcatag aatctgaact gaagcagaaa gaaaataagt tgcaagaaaa     120
cagaaagata attgaagccc agcgaaaagc cattcaggaa cttcagtttg aaaatgaaaa     180
agtaagcttg aaattagaag aagaaattca agaaataaaa gatttaataa aggagaataa     240
tgctacaata cattggtgta atctactcaa ggaaacctgt gctagatctg cagaaaagac     300
aaataaatat gaatatgagc gggaagaaac cagacaagtt tatgtggatc taaatagcaa     360
cattgagaaa atgatactag cttttgagga acttcgtgtg caagctgaga atgccagact     420
ggaaatgcat tttaagttaa aggaagatca tgaaaaaatc caacatcttg aagaagaata     480
tcagaaggaa gtaaacaaca aggaaaatca ggtatcagaa ctgttgatcc aaagtgctga     540
gaaagaaaat aaaatgaaag atttaacatt tctgttagag gaatccagag ataaagctaa     600
tcaattagag gaaaaaacaa aattacaaga tgaaaactta aaagaattaa gtgaaaagaa     660
ggatcattta acatcagaac ttgaagatat taaaatgtct atgcaaagaa gtatgagcac     720
tcagaaagct ttagaggaag atttgcagat agcaacaaaa acgatttctc agctcactga     780
agtaaaagaa gctcaaatgg aagaactcaa caaagctaaa actactcact catttgtggt     840
gactgaactt aaagctacta catgtacctt ggaggaatta ctgagaacag aacagcaaag     900
gttggaaaaa aatgaagacc aactgaaact gattactgtg gaactccaga gaaaatcaaa     960
tgaactagaa gagatgacta aatttaaaaa taacaaagaa gtggaacttg aagaattgaa    1020
aaacatattg gcagaagatc aaaaacttttt agatgaaaag aaacaagttg agaagcttgc    1080
tgaagaatta caagagaaag aacaagaact aactttcctt ttggaaacca gagagaaaga    1140
agtccatgat ttgcaagaac aagtaactgt cactaaaaca agtgaacagc attatttaaa    1200
acaggttgaa gaaatgaaaa ctgagcttga aaagagaaa cttaagaata ctgaattaac    1260
tgcaagttgt gacatgcttt tgcttgagaa caaaaaattt gtacaagaag caagtgatat    1320
ggccctagaa ctcaagaaac atcaagaaga tatcattaat tgcaaaaagc aagaagaaag    1380
gctgttgaaa caaatagaaa atttggaaga aaaagaaatg catttaaggg atgaactgga    1440
atcagtaaga aaagagttca tacagcaagg agatgaagtt aagtgtaaat tggacaagag    1500
tgaagaaaat gctcgaagca ttgaatgtga agttttaaag aaagaaaagc agatgaagat    1560
attagaaagc aagtgtaata atttaaagaa acaagttgaa aataaaagca gaatattga     1620 agagcttcac caggagaata aaaccttgaa aaaaagagt tcagcagaaa tcaaacaact    1680
gaatgcatat gagataaagg tcagtaaatt agagttggaa ttagaaagta ccaagcaaag    1740
atttgaagaa atgactaaca attaccagaa ggaaattgag aacaaaaaga tatcggaagg    1800
aaagcttttg ggagaggttg agaaagccaa agcaacagtt gatgaagctg taaagttaca    1860
gaaagaaatt gatttacgat gccaacataa aatagctgaa atggtagcac ttatggaaaa    1920
acataagcac caatatgata agattgttga agaaagagac tcagaattag gactttataa    1980
aaacagagag caagaacagt catcagcgaa gattgctttg gagactgaac tatctaatat    2040
cagaaatgaa cttgtatccc ttaagaagca acttgaaata g                        2081

<210> SEQ ID NO 74
<211> LENGTH: 1148
<212> TYPE: DNA
<213> ORGANISM: Mus musculus

<400> SEQUENCE: 74
gtctccatga cgacgcggga cgcgcgtggg ggtggctggt aactgcttga tagagacgtt      60
```

```
gctcctgaga tcctgtctga aaccagatca tgtcggacct gggctctgag gagttagagg      120
aggagggaga gaacgacctt ggggagtacg aaggggagcg caatgaggtg ggagaacgac      180
acggacatgg gaaagcacga ctgtccaacg gggacacata tgaaggaagc tatgagtttg      240
gaaaaagaca tggtcagggg acttacaaat ttaagaatgg ggcccggtac accggagact      300
atgtcaaaaa taaaaagcac ggccaaggca cctttatcta tccagatgga tccagatatg      360
aaggggagtg ggctgatgac cagaggcacg gccaaggcgt gtactactat gtcaacaatg      420
acacctacac aggggagtgg ttcaatcatc aaaggcacgg gcaaggcacc tacctctacg      480
cagagaccgg cagtaagtat gtcggtacct gggtgcacgg acagcaggag ggtgccgccg      540
agctcatcca cctaaaccac aggtaccagg gtaagttcat gaacaaaaat cctgtgggcc      600
ctggaaagta cgtatttgat attggatgcg aacagcacgg tgaatatcgc ctcacagata      660
cggaaagagg agaagaggag gaggaggaag agacattagt gaacatcgtt ccaaaatgga      720
aagctctcaa catcacagaa ttggccctgt ggactccaac cctctccgag gagcagcctc      780
cccctgaggg ccaaggccag gaggaaccgc agggacttac tggcgtgggt gacccctcag      840
aagacatcca ggcagaaggt tttgagggcg agctggagcc gagggggggcc gatgaagacg      900 tagacacgtt caggcaggag agccaggaga acagtacgac atagaccagg gaaacttgaa      960
ctttgatgaa gaaccgtcag acctccagga ttaagatagt ggaggcagaa gaccacagac     1020
acaccaggcg tgccttagtt aacaccagtc agctagggct ggtatccacc acctgtcaat     1080
ctctctctct tagctgttaa gttgtttttt cggttaacaa ataaatctc caggtgttca     1140 gtgttgac                                                              1148
```

<210> SEQ ID NO 75
<211> LENGTH: 1317
<212> TYPE: DNA
<213> ORGANISM: Mus musculus

<400> SEQUENCE: 75

```
atgtcgagac gtgacgtggt ccttaccaat gttactgttg tccagctacg gcgggaccga       60
tgcccatgcc catgcccatg tccatgccca tgccctgtga tcagaccacc tccacccaag      120
gttgaggatc caccacccac ggttgaagaa cagccaccgc caccgccgcc gccacctcca      180
cctccaccac cacctcctcc tcctcctcca ccccagatag agccagacaa gtttgaagag      240
gctccccctc cccctccccc tcctcctcct cctccccctc cccctccccc accactccaa      300
aagccagcta gagagctgac agtgggtatc aatggatttg gacgcattgg tcgtctggtg      360
ctgcgagtct gcatggagaa gggcattagg gtggtagcag tgaatgaccc attcattgat      420
ccagaataca tggtttacat gttcaaatat gactccacac atggtagata caaaggaaac      480
gtggaacata agaatggaca actagttgtg gacaaccttg agatcaacac gtaccagtgc      540
aaagacccta agaaatccc ctggagctct atagggaatc cctacgtggt ggagtgtaca      600
ggcgtctatc tgtccatcga ggcagcttcg gcacatattt catctggtgc caggcgtgtg      660
gtggtcactg caccctcccc cgatgcaccc atgtttgtca tgggagtgaa cgagaaggac      720
tataaccctg ctctatgac cattgtcagc aatgcatcct gtaccaccaa ctgcctggct      780
cctctcgcca aggttattca tgaaaacttc gggatcgtgg aagggctaat gaccacagtc      840
cattcctaca cagccactca gaagacagtg atgggccat caaagaagga ctggcgaggt      900
ggccgcggcg ctcaccaaaa catcatccca tcgtccactg gggctgccaa ggctgtaggc      960
```

```
aaagtcatcc cagagctcaa agggaagcta acaggaatgg cattccgggt gccaacccca   1020
aacgtgtcag ttgtggacct gacctgccgc ctggccaagc ctgcttctta ctcggctatc   1080
acggaggctg tgaaagctgc agccaaggga cctttggctg catccttgc  ttacacagag   1140 gaccaggtgg tctccacgga ctttaacggc aatccccatt cttccatctt tgatgctaag   1200
gctggaattg ccctcaatga caacttcgtg aagcttgttg cctggtacga caacgaatat   1260
ggctacagta accgagtggt cgacctcctc cgctacatgt ttagccgaga gaagtaa     1317

<210> SEQ ID NO 76
<211> LENGTH: 1153
<212> TYPE: DNA
<213> ORGANISM: Mus musculus

<400> SEQUENCE: 76
gtctccatga cgacgcggga cgcgcgtggg ggtggctggt aactgcttga tagagacgtt    60
gctcctgaga tcctgtctga aaccagatca tgtcggacct gggctctgag gagttagagg   120
aggagggaga gaacgacctt ggggagtacg aaggggagcg caatgaggtg ggagaacgac   180
acggacatgg gaaagcacga ctgtccaacg gggacacata tgaaggaagc tatgagtttg   240
gaaaaagaca tggtcagggg acttacaaat ttaagaatgg ggcccggtac accggagact   300
atgtcaaaaa taaaaagcac ggccaaggca cctttatcta tccagatgga tccagatatg   360
aaggggagtg ggctgatgac cagaggcacg gccaaggcgt gtactactat gtcaacaatg   420
acacctacac aggggagtgg ttcaatcatc aaaggcacgg gcaaggcacc tacctctacg   480
cagagaccgg cagtaagtat gtcggtacct gggtgcacgg acagcaggag ggtgccgccg   540
agctcatcca cctaaaccac aggtaccagg gtaagttcat gaacaaaaat cctgtgggcc   600
ctggaaagta cgtatttgat attggatgcg aacagcacgg tgaatatcgc ctcacagata   660
cggaaagagg agaagaggag gaggaggaag agacattagt gaacatcgtt ccaaaatgga   720
aagctctcaa catcacagaa ttggccctgt ggactccaac cctctccgag gagcagcctc   780
cccctgaggg ccaaggccag gaggaaccgc agggacttac tggcgtgggt gaccccctcag   840 aagacatcca ggcagaaggt tttgagggcg agctggagcc gagggggggcc gatgaagacg   900 tagacacgtt caggcaggag agccaggaga acagtacgac atagaccagg gaaacttgaa   960
ctttgatgaa gaaccgtcag acctccagga ttaagatagt ggaggcagaa gaccacagac  1020
acaccaggcg tgccttagtt aacaccagtc agctagggct ggtatccacc acctgtcaat  1080
ctctctctct tagctgttaa gttgtttttt cggttaacaa aataaatctc caggtgttca  1140
gtgttgacaa aaa                                                     1153

<210> SEQ ID NO 77
<211> LENGTH: 1678
<212> TYPE: DNA
<213> ORGANISM: Mus musculus
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
```

```
<222> LOCATION: (280)..(280)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (365)..(366)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t

<400> SEQUENCE: 77
ggctcccctg acccagaccc caccactcct gactacttga cctccttgct ggcctttnga      60
gactttcagg tcacaggtag tngccactgt ccctacagta ctgctcagna ggctgtgggc     120
aaggacaact tcactctgat ccctgagggt gtcaatggta tagaagagcg gatgaccgtt     180
gtctgggaca aggcagtggc tactggcaag atggatgaga accagtttgt agccgtcacc     240
agcaccaacg cagccaagat cttcaacctg tacccgaggn aaggtcggnt cnctgtnggc     300
tccgatgctg acgtagtcct ctgggaccca gataagatga agaccataac agccaaaagc     360
catanntcaa ctgtggagta caacatcttt gagggcatgg agtgccacgg ctcccccctg     420
gtggtcatca gtcagggcaa gattgtcttt gaggatggaa acatcagtgt cagcnagggc     480
atgggccgct tcatccctcg gaagccattc ccagagcatc tctaccagcg tgtcaggatc     540
agaagcaagg ttttcgggtt gcatagtgtt tccaggggca tgtacgatgg gcctgtgtac     600
gaggtgccag ctacacccaa acatgctgct cctgctcctt ctgccaaatc ctcgccttct     660
aaacaccaac ccccacccat ccggaacctc caccagtcca acttcagctt atcaggtgcc     720
cagatagatg acaacaatcc aaggcgtaca gggcaccgca ttgtggcgcc cctggtggc     780
cgctccaaca tcaccagcct cggttgacct cagatgagcc agatatgcaa gagtgaagga     840
ttatgggaaa acgtccattc cttttccgtg tttttgaagc ccacagtttt agttggtact     900
gacggagggg agattgagcg atgctctttc cttctctgtt taggaagaag tggtactagt     960
gtggtgtgtt tgcctggaag tccctcgccc acagtgtgtg ttcacaccga ctccacctca    1020
gagcatggtg cctccgtttt cccttcctag tgacccagg tttagcatcg tcctatactg     1080
ttccctccac tcctccatga ccctctgagt gatggttctt ttgcgccctg tagctgttct    1140
aggataggat gcatgttagt aagttacgta tgcaagtctg agcgcgcgcg gctgatggac    1200
atcgtcgagg accgacatag acccgatgcc aagaccttag ccccaagggg agatttccaa    1260
actcttaaaa atgaaggctc ccatgagtct tcactagaaa gatgtggtcc ccatccccac    1320
cctgactgag acctgtgaag atgcagagtg gcagggaagg tcacggagct ccaccaccca    1380
tgtcctgtgt caacaacccg gtccctgtgg cacctgtaac tggccatagt gtctttctgg    1440
tctgtgtgtt cttccagcca gccttgggct ttgggcccag ccaggctcac acccagaaag    1500
gggtgtcctg acaccccacc caggccttga ggacggtgcg gtaatgactg cccaggctgc    1560
ctgagtctct gaccctctga ggagttcgag cagggcagtc agattttaa agttttgtac      1620
```

```
agttttcctt tgtattcact tccattttta cttaataact gacttgttgg tggctccc       1678
```

<210> SEQ ID NO 78
<211> LENGTH: 1087
<212> TYPE: DNA
<213> ORGANISM: Mus musculus
<220> FEATURE:
<221> NAME/KEY: misc_feature
<222> LOCATION: (39)..(39)
<223> OTHER INFORMATION: k is g or t

<400> SEQUENCE: 78

```
tgactgaact gaccaagagc agggagagtc tggactttka ccaaggatgc ttttcaagag      60
agtctatgga ggtgttcaga gcctcaactg caaggtatga aactcaagga actgacttca    120
cagccacaaa tgcaggatca gacctgtga tcacctcatg tttgaaacac caaagtctaa     180
acctgtaact gtagccaaaa cacaagggat ccgaggagta aatttgtag atttcacctc     240
aacacaacaa gggtgtcaag agatggcacc catggactta atcttaagt ctagacagga    300
tgaccagata actgtaaagt cactggagtg gaaggtggg attttcgacc aacagaaaaa    360
acagcttgaa tcagaaaata cattgcccat ggagtcagat caagaaccca acctgcaga    420
tatgcacccc atagagatcc aatctaaact acaattcaaa gatacagcct catttgaatt    480
ggctcctgag ccagttgttc aaagtgtaaa agctaaagag ttccaaaatg aactacaggt   540
gccaagtatg aaaccttgcc agttgatccc agtgtcccag atgcaccaag agaaagctgt    600
ggagtcaacg ttggacccac aacttcaagg tgtggaaact gtggcactaa ttacagaacc    660
ccaaattgaa agcacaaagt ctattcaatg gataccaata tctgagtttc aaagtgagaa    720
aggtataggg tcaaactcaa agtcacagtc tcaagaagcc agacccacag aactgaagcc    780
acctgtgcta tggagaggtg tgaggtcacc tgaactgact gccaggtcaa aaattcaagg   840
agaaaaatct gtggcatttc atcttgagcc acagttacgg gctcaagaac caaaaacgtt    900
caacttgact tcagagccac agcctcaagc catcacaact gaggagctaa acaaagaact   960
acagactgaa agtgtaagat ctgtccagtg gctatctcaa caggagttcc ccagtgtgaa   1020
gtttttaaga tccaaaagtt ggtcaccatt tcagggcgcc ccggaattcc aattcgccct   1080
atagtga                                                             1087
```

<210> SEQ ID NO 79
<211> LENGTH: 6197
<212> TYPE: DNA
<213> ORGANISM: Mus musculus

<400> SEQUENCE: 79

```
tgtgttctca gcaggatcgt ggagagcggg tgctcctcac cccttagtcc ctgtggtcct     60
gggcgcacat ctcctcgccc ctctgcttct ccgcggtccc aggaagacgg ctagccggcg   120
agagtaggaa agccactgag ccatgggtgc aggcagttcc accgagcagc ggaccccgag   180
cagccggcgg agagcgacac gccgagcgag ctggagctca gtggccatgg gcccgcagcg   240
gaagcgtcgg gagcagctgg gatcccgct gacgcggacc ccgccaccaa gctcccacag   300
aagaatggtc agctgtctgc cgtcaatggt gtagctgaac aagaagatgt ccacgtccaa   360
gaggaaagcc aggatgggca agaggaagaa gtcactgttg aagatgttgg acagagagag   420
tcagaagatg tgaaagaaaa agaccgagct aaagaaatgg cagccagttc cacagttgtt   480
gaagatatca caaggacga gcaggaggaa cacccgaaa taatcgaaca gatccctgct    540
tcagagagca atgtggaaga atggcgcag gctgctgagt cccaagctaa tgacgtcggc    600
```

```
ttcaagaagg tatttaaatt tgttggtttt aaattcacgg tgaagaagga taaaaacgaa    660
aagtcagata ccgtccagct actcactgtc aagaaggatg aaggcgaagg ggcagaagcc    720
tccgtcggag caggagacca ccaagagccc ggagtggaga ccgtcggcga atcagcatcc    780
aaagaaagtg agctgaagca atccacagag aagcaagaag gcaccctgaa gcaagcacag    840
agcagcacag aaattcccct tcaagccgaa tctggtcaag gaccgaggga gaagcagcc     900
aaagatggag aagaaaaccg agagaaagaa cctaccaagc ccctagaatc tccgaccagc    960
cctgtcagca atgagacaac atcttccttc aagaaattct tcactcacgg ctgggccggc   1020
tggcgcaaga agaccagctt caagaaacca aaggaagatg atctggaaac ttccgagaag   1080
agaaaggagc aagaggctga aaagtagac gaggaagaag gggaaaagac agagccagcc    1140
ccagccgagg agcaggagcc tgcagaaggc acagaccagg ccaggttgtc agccgactat   1200
gagaaggtgg agttgccttt ggaagaccag gtcggtgacc tggaggcatt gtcggagaag   1260
tgtgctcctt tggcaacgga agtgtttgat gagaagacgg aagcccacca agaagttgtt   1320
gcagaggtcc acgtgagcac cgtggagaag atgacgaaag gcaaggagg agcagaggtg    1380
gaaggggatg tggtggtgga aggatcggga gaatccttgc cccctgagaa actggctgag   1440
acccaggagg tccccagga agctgagcct gtggaggagc tgatgaagac caaagaagta    1500
tgcgtctctg ggggtgacca tactcagctg acagatctaa gtcctgaaga agatgcta    1560
cccaaacacc ccgaaggcat tgtcagtgag gtggagatgc tgtcctctca ggagagaatc   1620
aaggtacagg gaagtcccct gaagaagctc ttcagcagtt cgggcttaaa gaagctctcc   1680
gggaagaagc agaaggggaa gagaggagga ggcgggggag atgaagagcc aggagaatac   1740
caacacattc aaaccgagtc cccagagagt gctgacgagc agaagggaga gagctctgcc   1800
tcttcccctg aagagcccga ggagatcgcg tgtctggaga aggggccatc ggaagcaccc   1860
caggaagcgg aagctgagga aggagcgact tccgacggag agaagaaaag ggaagggatc   1920
accccctggg catccttcaa aaagatggtg acacccaaga aacgggtccg aagaccttct   1980
gagagcgaca aggaagaaga gctggataag gtcaagagtg ccaccttgtc ctccacggag   2040
agcacggcgt ctggaatgca ggatgaggtc agagcggttg gcgaggagca aggtcagag    2100
gagccaaagc gcaggtgga tacttcagtg tcttgggagg cgttgatttg tgtcggatcg   2160
tccaagaaga gagcgaggaa ggcatcctct tcagatgatg aaggagggcc aagaacactg   2220
ggaggggatg gccacagagc ggaggaggct agcaaagaca agaagcaga tgctcttcct    2280
gccagcaccc aggaacaaga ccaagcgcac ggaagttcct cacccgagcc agctggaagc   2340
ccttctgaag gggagggcgt ctccacctgg gagtcattta agagattagt cactccacga   2400
aaaaaatcca agtcaaaact ggaagagaga gccgaagact ccggtgcaga gcagttggcc   2460
tccgagatcg aaccaagtag agaggaatct tgggtttcca ttaagaaatt tattcctgga   2520
cggcggaaga aaagggcaga tgggaagcaa gaacaggccg ccgttgaaga ctcggggcca   2580
ggagagatca atgaggacga ccccgacgtc ccagctgttg tgcctctgtc tgagtacgat   2640
gcggtagaga gagagaagct ggaagcgcag cgagctcagg agaacgtgga gctgcccag    2700
ctgaaggggg ctgtgtatgt gtctgaggag cttagtaaga ctctggttca caccgtgagt   2760
gtcgcggtca ttgatgggac cagggcagtc accagtgccg aagagcggtc ccttcgtgg    2820
atatctgctt ccatgacaga acctcttgag cacgcagagg gagtggccac accgcctgtt   2880
ggagaggtca ctgaaaaaga catcactgca gaagcaactc ctgcactcgc ccagacttta   2940
```

```
ccaggggggca aagatgccca tgacgacata gtcaccagtg aagtggattt tacctcagaa   3000
gcagtgacag ccgcagaaac cacagaggcg ctccgcgctg aagaacttac cgaagcatca   3060
ggggcagaag agaccacaga catggtgtct gcagtttccc agctgtccga ctccccggac   3120
accacagagg aagccacccc agttcaggag gtagagggtg gcatgctaga tacggaagaa   3180
caggagcgcc agacgcaggc cgtcctccaa gccgttgcag acaaagtgaa agaggactcc   3240
caggtgcctg caacccagac tctgcagaga gcagggccga agcactgga gaaggtggag   3300 gaggtagagg aggactccga ggtgctggct accgagaaag agaaggatgt tgtgccggaa   3360
ggacccgtgc aggaagctga aactgagcat cttgcacagg gctccgagac tgtacaggct   3420
accccagaga gccttgaagt tcctgaagtc acagaggatg tagaccgtgc caccacatgc   3480
caggttatca agcaccagca gctgatgaaa caggctgtgg cccctgagtc atctgaaacc   3540
ttgacagaca gtgagacaaa tggaagtact cccctcgcag attcagacac tccaaacggg   3600
acacagcaag acgagaccgt tgacagccag gacagtaatg ccattgccgc cgtcaagcag   3660
tcacaggtca ctgaagagga ggcagctgct gctcagacgg aggggccttc aacaccatct   3720
agttttccag cccaggaaga acacaggaa aaaccaggaa gggatgttct agaacccaca   3780
caagcgctgg ctgccggggc agtgcctatt ctggcaaagg ctgaggtggg tcaagagggt   3840
gaggctggcc agtttgatgg agaaaaagtc aaagacggac agtgtgttaa agaactggag   3900
gtgcctgtgc acactggacc caacagtcaa aagactgctg acttgacacg tgacagtgaa   3960
gtaatggaag tggccagatg tcaggaaact gagagtaatg aagaacagag tattagcccg   4020
gagaaaagag agatgggaac cgacgttgaa aaggaggaaa cagagaccaa gacagagcaa   4080
gccagtgaag aacatgagca ggaaacagct gctcctgagc atgaaggaac ccaccctaag   4140
ccagtcctga cagctgacat gcctcactca gagagggggaa aggcactggg cagccttgaa   4200
ggaagccctt ctctcccaga ccaagacaaa gcagattgca tagaggttca agttcaaagc   4260
tcagacacac cagtcactca aacaaccgaa gctgtgaaaa aggtcgaaga aactgtggca   4320
acttcagaga tggatgaaag tttggagtgt gcaggtgcgc aatcattacc agctgagaag   4380
ctctccgaaa ccggtggcta cgggactctt cagcatggag aggacaccgt gccccagggg   4440
cctgagtctc aggcagagtc catcccaata atagtaactc ctgctcctga aagcatccta   4500
cattctgacc ttcaaagaga agtgagcgca tcccagaaac agagatcaga tgaagataac   4560
aagccagatg ctggtcctga tgctgccggc aaggagagtg cagcaagaga gaaaatcctc   4620
agggctgaac ctgagatctt ggaacttgag agtaagagca ataagattgt ccagagtgtc   4680
atccagacag ccgtcgacca gtttgcacgt acagaaacag cccccgaaac ccacgcttct   4740
gatttacaga atcaggttcc tgtgatgcag gctgacagcc agggagcaca acagatgctg   4800
gacaaagatg aaagcgacct tcaagtctcc ccccaagatg aacactcag tgccgtagcc   4860 caggaaggac ttgcggtttc tgatagttct gaaggcatga gcaaggcttc agaaatgatc   4920
accacgcttg cagttgaaag tgccagtgtc aaagaaagtg ttgagaagct gcctcttcag   4980
tgcaaagatg aaaaggaaca tgctgctgac ggcccccagc accaaagctt agccaaggca   5040
gaggcggatg cctctggaaa tctaaccaaa gagtccccag acaccaacgg accaaagcta   5100
accgaggaag gagatgccct gaaagaagaa atgaacaagg cccagacaga gaggacgac   5160 ctacaggagc caaagggaga cctgacagaa tcctaagacg tgagttgctc attgtaaaac   5220
tagaatgtga agtgaagtca cggaacaaga tgctgctgtt gggaccttga gaccaaaatt   5280
tcagagccct tgaggtgcag agagcagagc cgtccaatga tttcaaccct gcagagcacc   5340
```

| | |
|---|---|
| ccgacaatcc tgaggctgca tcgggagcta gagccagcta acatttcctc ttttcaagac | 5400 |
| tgcccttgat ttgccccttg gtgccatgta tttcagagtt aaggtcctgc tttctccacc | 5460 |
| tggaaccaat gtcggcaata cctagtccca cttctcaaac tggagcctcc tcctttatgt | 5520 |
| atttatatgt atgttttatg tagtcctcct cctgtaccta ttgtatattt tttttctaag | 5580 |
| gtttaagcac atgcctttg tattatgcag tatataatgg gtgtgcagcc atagcgaagc | 5640 |
| tttgagaagc cccaagcctc aactgtaacc tgcagcaaac agagaaataa cattcctggc | 5700 |
| aggaagatac aagtcttttt aaagtttact gatgcttaac tctgtgggct cgtagtcctc | 5760 |
| tgaaagtggt tgttttccta tgcacagtga gctcagaaat aaaaactcca ttttgagaca | 5820 |
| ttcagaatgt cccaacatta cgacaacatt ttttttttt ttttctaatc cagtccaggt | 5880 |
| tggaaagaag tctccttagt gtcagattaa gccccatctc ttaacaatat ggacagatga | 5940 |
| gtgtgccatg gccatgagct atttcctaac gcagaaggaa tttgttgtta cttttttggat | 6000 |
| tgtactcttc taggctggac cgaattcata tgcagattga agtgagacct gctctttaca | 6060 |
| gatggtattt tgatagatac tggagttgt ctgtattata tctgtgcccc ttcttttaag | 6120 |
| aacaatgtta cattatgttc ctttggataa attgtgattt gacaactgat ttcaataaaa | 6180 |
| atatttgctt cacttat | 6197 |

<210> SEQ ID NO 80
<211> LENGTH: 1310
<212> TYPE: DNA
<213> ORGANISM: Mus musculus

<400> SEQUENCE: 80

| | |
|---|---|
| gcaactaaga cctgtcagag cagaagctga gacacatttt caactcctgt cagctgactc | 60 |
| aaaatgtttg tctcacccag gagatcttca gaacaaaact gtagaggact ccccacctct | 120 |
| cccgccagcc cttggggaag cagatggagt tccagaaggg ttcctctgac cagcggacct | 180 |
| tcatttctgc catcctcaac atgttatcac tcggcctctc cacagcatcc ttgctcagca | 240 |
| gcgagtggtt tgtgggcaca cagaaggtgc ccaagcccct gtgcgggcaa agtctggcag | 300 |
| ccaagtgctt tgacatgccg atgtccttgg atggggcat cgccaacaca tcagcccagg | 360 |
| aggtggtaca atacacctgg gagactgggg atgaccggtt ctccttcctt gcttccgca | 420 |
| gtggcatgtg gctatcctgt gaggaaacca tggaagagcc aggggagaag tgcagacgtt | 480 |
| tcattgaact cacaccacca gcccagagag gtgagaaagg actactggaa tttgccacgt | 540 |
| tgcaaggctc atgtcacccc actctccgat ttggagggga gtggttaatg gagaaggctt | 600 |
| ctctcctcca cctcccttgg gggcccgtgg caaaggtctt ttggctgtca ctgggagccc | 660 |
| agactgccta tatcggactt caactcatca gcttcctcct gctactgacg gatctgttgc | 720 |
| tcaccacgaa ccctggctgt gggctcaagc taagcgcgtt tgcagccgtc tccttggtcc | 780 |
| tgtcaggact tctggggatg gtggctcata tgctatattc acaagtcttc caggcaactg | 840 |
| ccaacttagg tccggagctg gagaccacac tcttggaatt acggctgggc cttctacaca | 900 |
| gcgtgggttt ccttcacctg ctgcatggcg tcacggtcac caccttcaac atgtacacga | 960 |
| ggatggtgct ggagttcaag tgcaggcaca gcaagagctt taacaccaac cccagctgcc | 1020 |
| tggcgcacac caccgctgtt tccttcctcc tccgctgacg tgcacaaccc acgcagggga | 1080 |
| acctttgtcc agctgccatc agtacccag ccatcccatc cgctctgtct ctgaagctat | 1140 |
| tgacctctac tcggcgctac aggacaaaga atttcaacaa gggatcagcc aggagctaaa | 1200 |

-continued

| ggaagtggtc gagccatctg tagaagagca gcgttaggag ttaagtgggt ttgggaagca | 1260 |
| ggctaagtcc taccataggt gtcgctcact atcaacatct gcttaagcaa | 1310 |

<210> SEQ ID NO 81
<211> LENGTH: 2827
<212> TYPE: DNA
<213> ORGANISM: Mus musculus
<220> FEATURE:
<221> NAME/KEY: misc_feature
<222> LOCATION: (2813)..(2813)
<223> OTHER INFORMATION: n is a, c, g, or t
<220> FEATURE:
<221> NAME/KEY: misc_feature
<222> LOCATION: (2823)..(2823)
<223> OTHER INFORMATION: n is a, c, g, or t

<400> SEQUENCE: 81

| gtttctgttt gaaacgccgg gcgggcgctc gctatggcac aggctcaccc gcggtcgggt | 60 |
| acccggctct ttcgaacgta cgcggcgagg ggcgtccggg ggtcgcagcg cagcctggc | 120 |
| gggctggctg agcaatggtt ccagccgccg aacctgaagc gcgccttcag cagcagcctc | 180 |
| agcgacagta acgagtcgcc ggctgtcgct tccgacgacc cggacgaccc cgacttcccc | 240 |
| ggcagcctcg tgggccagcg gcggaggcgt cctcggggca gcggctcccg gaaccagcgg | 300 |
| accctgacaa acactccaag agtccaaagg ctgcgacctc ggctcccgca gaagtgcagc | 360 |
| accccgtgca gccggctgcg accgccacct ttccccaact gcagcccggg ctgcctcggg | 420 |
| tcggaccaca gtgtgtgcat ccagtccagg gacagcaacg agctgggcac cagtgcctcc | 480 |
| ctcttcagct ctccggcctc gcccggagcc cccgacccct tgtatgctga ctctgcagtc | 540 |
| cccgggagct tccacttgcc ggcagcctcc ctaagtgaac cgtctgtgcc ctgccccag | 600 |
| gtggcagcaa ccggtgacag gtacaccggg agggccctcc gagccgaagc cagcttcagg | 660 |
| tcatctctct ttagccttgt gaactcaggg gccacagaag agaacaagtt tgggacagat | 720 |
| ggggagaatg tgaaggaatc gtgttgtgaa agaagacagc agatgggaaa cagactaacg | 780 |
| gaccctgatc tgacaagccc gggaaagaga aggccgcgt gtaaaaaggt tgtgtcccaa | 840 |
| ggagtcgacc agagagacta tgaggagtcc agtgcttgca aagaccttcg tgtaccaggg | 900 |
| gaaatcagca ggcctaagag aactgggcca ctccggaaga ggaaacagca agaagcaacg | 960 |
| ggaacccctc cccgccacta ccaccaatct aagaagaaaa ggaaagcgtc agtctcctta | 1020 |
| tggaacttga atactagcca gagggattct tggaccaaaa ccagagcctc cttcggtttc | 1080 |
| cacaagaaga aaattataac cagtgtgata gaggtatgca gttctgttgc cagttcttcc | 1140 |
| tccaggtccc tcctgtctga atgttcgacc cctcctatca agaacagagc acaccttact | 1200 |
| gtttcttctc gatgctcttc tgtgtatttg ctaagtccct taaagaccct gcatgtcaca | 1260 |
| gaccaaaggc catcttatgc tgaaaaggtt tatggggagt gtaatcagga agggcccatc | 1320 |
| cccttagtg attgcctttc cacgaaaaa ctggaacggt gtgagaagat tggggaagga | 1380 |
| gtgtttggag aagtgtttca gataattaac gaccaagcac ctgtagccct aaaaatcatt | 1440 |
| gctattgaag ggttagattt agtcaatggg tccaccagaa aacctttga ggaaatcctg | 1500 |
| ccggagatca ttatctccaa agagctgagt ctcttgtcta gtgaggccta caaccgcaca | 1560 |
| gaaggcttta ttgggctgaa ctcagtacac tgtgttcaag gctttaccc tcccttgctg | 1620 |
| ctgaaagcct gggatcacta aacacaacc aaaagatctg ccaatgaccg gcctgacttt | 1680 |
| ttccaggaag accagctctt tattatcctg gaatttgagt ttggtggggt tgacttggag | 1740 |
| cgaatgaaaa ccaagctgtc ctctgtggcg actgcaaaga gcattctcca ccagatcact | 1800 |

```
gcatctctgg ctgtggcaga agcatccctg cactttgagc accgggactt acactgggga    1860
aatgtgctct taaagaaaac caacctcaaa gaactccgct acaccctcaa tgggaaaacg    1920
agcaccattc ccacccatgg gctacaggtc aacatcattg actacaccct gtcccgcttg    1980
gagcgggatg ggattgtggt tttctgtgat atctccgctg aagaggacct atttacaggt    2040
gagggtgact accagtttga gatctacagg ctcatgagga aggagaacaa aaactgctgg    2100
ggtgagtatc acccttacaa taatgtgctg tggctgcatt acctcacaga caagattctg    2160
aataagatga aatttaagac taaatgccag agcgcagcca tgaagcaaat aaggaaaaac    2220
ctgcaacatt tccacaggac tgtactgagt ttcagctctg ccacggacct gctctgccaa    2280
cacagtctat ttaggtaagc caggaactta gactttcaga gcctctttaa gtacactttt    2340
aggcctctgg tactaatctc tgccactaga gccagatgga ggtgaaagca catccttaag    2400
agttcctgtc agcttcttaa aagagaactg tgttttttcaa aaggtaaccca aaacatttgt   2460
tgacatgatt aaacttgctt ttaacaaatg ttcctctttt ttaaaaaaaa aataaaacta    2520
gacagaggac aagtggacac atctttaagt cctcgtcctg tcagcagagt ctacaagtct    2580
gatgttgctg gttttggagc cttgatactg ggtgtaggat gagcaaaacc aagcctcagc    2640
tgtggtccctt actgctcttg atgctgttgt caagatgcag agcagagagc aagagactag    2700
agagtccaaa ccaagagaaa gtatggaaaa tgtttatccg gttcactccc caatcacagg    2760
agcagaattt atagaatttc aacaggaaaa taaatgtctc tgtggctctc ccnaaaaaac    2820
ccnaaaa                                                              2827

<210> SEQ ID NO 82
<211> LENGTH: 1028
<212> TYPE: DNA
<213> ORGANISM: Mus musculus
<220> FEATURE:
<221> NAME/KEY: misc_feature
<222> LOCATION: (14)..(14)
<223> OTHER INFORMATION: n is a, c, g or t

<400> SEQUENCE: 82
ctagatcccc gggngagtaa caccttgaat gggcaaggta tcccatggac cgttttctca      60
ccctgtgagc acccttcatt tcagaagctt tgcttctgct gccactggcc atgtcactca     120
gcgtcttgag taggaaagag aaagagaaag tcatccacag gctcttagtc caggctcctc     180
ctggggaatt tgtgaatgcc tttgacgatc tctgtctgct tatccgagat gaaaagctta    240
tgcaccatca gggtgagtgc gcaggccatc agcactgcca aaatactgt gtcccactct      300
gcatcgacgg caacccagtc ctcctgtctc accacaatgt gatgggtgac ttccgcttct     360
ttgactacca gagcaaactt tctttcaggt ttgacctact ccagaatcaa ctgagggata    420
tccaaagtca cggaatcatt cggaatgaga ccgagtaccct aagatccgtt gttatgtgtg   480
ccttaaaact ctatgtgaat gatcactacc caaatggaaa ttgcaatgtg ctgagaaaaa    540
cagtcaaaag caaagaattc ttaatagctt gcattgaaga ccacagctat gacaatggag     600
agtgttggaa cggtctttgg aagtctaagt ggatcttcca ggtaaacccg tttctaaccc    660
aagtcacagg gagaattttt gtgcaagctc acttctttag gtgtgtcaac cttcatattg    720
aagtctccaa ggacctaaag gagagcttgg aggtggtcaa tcaagcccag ttggctctca    780
gtttcgcaag gcttgtggaa gaacaagaga ataagtttca agctgctgtc atagaagaac    840
tacaggagtt gtctaacgaa gccctgagaa aaatattacg gagggatctt ccagtgacac    900
```

```
gcactttgat tgactggcaa cggatcctct ctgacttgaa tctggtgatg tacccccaagt    960 tagggtatgt tatttactca agaagtgtgt tgtgcaactg gataatataa aaggttgctg   1020
ctcctggt                                                             1028
```

<210> SEQ ID NO 83
<211> LENGTH: 817
<212> TYPE: DNA
<213> ORGANISM: Mus musculus
<220> FEATURE:
<221> NAME/KEY: misc_feature
<222> LOCATION: (489)..(489)
<223> OTHER INFORMATION: n = a, c, g, or t

<400> SEQUENCE: 83

```
tgaggccaat cgtgggtgat gatcctcagt cctctctctg gccgaggtgt ggcccagacc     60
cccctagaga ggcgcctctg agggaagcag aagccagaac acagcccact cactaccgag    120
aggaaccagg tggactttgc cagctgccat cctggagtat ctagcacctg gagtttctac    180
agcagtcttg gaagagaat cagagagctg tgccgctggt gtcaccatac gcagcctcaa    240
atggctcaaa tggtgctgg agaccaagat gccggcacac tgtgggtccc aagccagagt    300
gagagtcaaa ctgagtccga catcagtacc caaagcctgc ggaagcccac catgtcgtat    360
gtgattctga agactttggc tgacaagcgg gtacataatt gtgtgtccct tgctaccttg    420
aagaaagctg tgtctatcac agggtacaat atgacccata cacctggcg cttcaagcgt    480 gtgctccana atctactcga taaaggcatg atcatgcatg tgacctgctg caagggtgcc    540
tccggctccc tctgcctgtg caaggagcgg gccctcaagt ccaaccacag ggccaagaga    600
tgccaggaca gacagaagag ccagaagcct cagaagcctg ggcagcgttg agtctgaacc    660
atgccaattg ctactaagct ccaaaaagaa gaatgaccag cttttcaaag gagtccgtag    720
ggtggccaaa ggcaaccgcc attgccatta ttaaggcagg tcaggcgggg tgccaggctt    780
gccaccaagt gggaataaaa cgcaacttat ttcacaa                             817
```

<210> SEQ ID NO 84
<211> LENGTH: 1316
<212> TYPE: DNA
<213> ORGANISM: Mus musculus

<400> SEQUENCE: 84

```
gggaagcggg gccatggctg aggctgtcca gcccagtggg gaatcccaag gcgcagaact     60
tacgatccag atccagcagc ctgcagagag agccctgaga acgccagcca agcgggtac    120 gcagtcagtg ctcagagtgt cccagctgct gctcagggcc attgctggcc accagcacct    180
gactctggat gcgctcaaga aggagctggg aaacgccggc tacgaagtgc gccgggagat    240
ctcctctcac cacgaggga agtccaccag gttggagaaa ggcacgctcc tgagggtcag    300
tggcagcgac gctgctggct acttcagggt ctggaagatt tcaaagccga ggaaaaggc    360 gggacaatcc cggttgacgc tgggcagcca ctcttctggg aagaccgtgc tcaaatcccc    420
cagaccactc aggcccgct cgcgtcgcaa ggcagccaag aaggccagag aagtctggag    480
acgcaaggcc agggctttga aggcaaggtc caggagggtc agaacaaggt ccacatcagg    540
ggccagatca aggaccaggt caagagcctc ttcaagggcc acttcaaggg ccacatcaag    600
ggccagatca agagcccggt caagggccca gtcaagtgcc agatcaagcg ccaggtcaag    660
cgccaagtca agcgccaagt caagcaccag gtctagcgcc aagtcatggg ccaggtcaaa    720
ggctaggtca agggcaaggt ctagagctaa ggacctagtg cgttccaaag cccgggaaca    780
```

| | |
|---|---|
| ggctcaggcc agggaacagg ctcatgccag agccagggaa caggctcatg ccagagccag | 840 |
| gacacaagac tgggtcaggg ccaaggcaca ggagtttgtc agtgccaaag agcagcagta | 900 |
| cgtcagagcc aaggagcagg agcgtgccaa ggccagggaa caggtgcgta tcggagccag | 960 |
| ggatgaagcc aggatcaagg caaaagatta acacagagta cggcctacaa aggaagacac | 1020 |
| cagtcctagg ccagcagagg agaagagttc aaactccaaa ctcagggaag agaagggaca | 1080 |
| ggaacccgag aggccagtaa aacagaccat ccagaaacca gctctggaca acgctcccag | 1140 |
| catacaagga aaagcatgca caaagtcttt taccaaaagt ggtcagcctg ggacactga | 1200 |
| gtctccttaa tgccagagct gttcctctgg gtacggttgc ttttccatat gggctccaag | 1260 |
| gagatcatct ctctttcatt gaagcaattt acaagaccaa aaaaaaaaaa aaaaaa | 1316 |

<210> SEQ ID NO 85
<211> LENGTH: 1116
<212> TYPE: DNA
<213> ORGANISM: Mus musculus

<400> SEQUENCE: 85

| | |
|---|---|
| ccattcaagg agctcaaatc tgtttagcat agtcttcttc acatgctcag aagttctcat | 60 |
| agagaagagt cttggtccag cattcactcc aacccataa ccattgccca tcaggaattc | 120 |
| atatatatga cagaggcaac agcattgtgt cgggcgtaaa tgggcaagat cttcagtccc | 180 |
| aggcaatggg caagtatgat atttgaagag aatggaagcc acttagacag tgtgatctag | 240 |
| cacaacaggt ctacagccag gtagaagaca atacctctga agagtctgag catgacatca | 300 |
| ctcaagaaga agagtaggag gaagccttct tcccaggccc tggggaatat tgttggctgc | 360 |
| agaatttctc acgggtggaa ggaaggtaat gagcctgtca cccattggaa ggccatcatt | 420 |
| ctaggtcaac tgccaacaaa cccttctctt tatttggtga agtatgacgg aattgacagt | 480 |
| gtctacggac aggagctcca cagcgatgag aggattttaa atcttaaggt cttgcctcac | 540 |
| aaagtagttt ttcctcaggt gagggatgtc cacctcgcag gcgccctggt ttgcagagag | 600 |
| gtacaacaca aatttgaggg gaaagatggc tctgaggaca actggagtgg gatggtgcta | 660 |
| gcccaggtgc cattttaca ggactatttt tacatttcct acaagaagga tccggtcctc | 720 |
| tacgtctatc agctcctgga tgactacaag gaaggtaacc tccacatcat tccagagacc | 780 |
| cctctggctg aggcgagatc aggtgatgac aatgacttct taataggttc ctgggtgcag | 840 |
| tacaccagag atgatggatc caaaaagttc ggaaaggttg tttacaaagt tctagccaat | 900 |
| cctactgtgt actttatcaa atttctcggt gacctccata tctatgtcta tactctggtg | 960 |
| tcaaatatca cttaaattga aaaaaaatca caaagtacag aaatgtaaac ttataggatt | 1020 |
| gaaaaaaaat gtttgttttc ctgtgttggg tacctatggg tctttgacaa cctcagtatc | 1080 |
| ttgtcaataa aatttgtttt gtctaaaaat taaaaa | 1116 |

<210> SEQ ID NO 86
<211> LENGTH: 1105
<212> TYPE: DNA
<213> ORGANISM: Mus musculus

<400> SEQUENCE: 86

| | |
|---|---|
| tttctcccat gttcctttt agggagttgc ctggaacaga caccaggggg acaggccacc | 60 |
| ggtgaggagg ctgggtccta agctgctcta agcccattcc tgcacagagg agagccagcc | 120 |
| atggcagagg aggtatggat gggcacctgg aggccccatc gccccgggg gcccatcatg | 180 |

```
gccctctaca gcagccctgg acccaagtac ctgattccac ccaccacggg ctttgtgaag      240
cacacaccca ccaaactccg agcaccggcc tacagcttcc gtggggctcc catgctcttg      300
gcggagaatt gctccccagg gccccgctac agtgtgaacc ccaagatcct gaagactggc      360
aaggaccttg gccctgccta ctccatcctg gggcgctacc ataccaagac cttgctgacc      420
cccggcccgg gtgattactt tccagagaaa tctaccaagt atgtgtttga ctcagcaccc      480
agccattcca tttctgcccg gactaagacc ttccgagtgg acagcactcc aggccctgct      540
gcatacatgc tgcctgtggt gatggggccc cacacggtgg gcaaggtctc ccagccctcc      600
ttctccatca agggccgcag caagttgggc agcttcagcg acgacctgca aagactcca       660 ggtcctgcgg cataccgtca gactgaggtt caagtgacca agttcaaggc tccacagtac      720
accatggctg cccgggtgga gcccccaggg gataaaaccc tgaagccagg accaggagcc      780
cacagccctg agaaggtgac cttgaacaag ccctgtgctc ctactgtcac cttttgcatc      840
aagcattctg actacatgac acccttggtt gtcgatgtgg aatagcctct gctctctgtg      900
actacgatcc tcccacagaa atgtgctggg ctggccatgg attggacaag tcaccaatgg      960
ggtccgctga cagcctggcc ctgcaccaca gagcacgcta gtttgacgg ttttgacaag     1020 ttattttttt ctatgctatc tcttgtttgt taatctggtt tcttgccatg tccaaattat     1080
taaataaacc acagatgcaa aaaaa                                           1105

<210> SEQ ID NO 87
<211> LENGTH: 951
<212> TYPE: DNA
<213> ORGANISM: Mus musculus

<400> SEQUENCE: 87
gaaatggtgg catctgtgtg gctaaccata catcgcgtat tgatgtgatc atctttgcca       60
gcgacggcta ctacgccatg gttggacagg ttcacggggg ccttatgggt gtgattcaga      120
gagcaatggt gaaagcctgc ccccatgtct ggtttgagcg ttctgaggtg aaagatcgcc      180
acctggtggc taagaggctg actgagcatg tccaggataa agcaagctg cccatcctca       240 tcttcccaga aggaacctgc atcaataaca catcagtgat gatgttcaag aagggaagct      300
ttgaaattgg agccactgtt taccctgtgg ctatcaagta tgaccctcag tttggtgacg      360
ccttctggaa cagcagcaag tatggcatgg tgacgtacct tctgaggatg atgaccagtt      420
gggccattgt ctgcagcgtt tggtacctgc ctcctatgac tcgagagaaa gatgaagatg      480
ctgtgcagtt tgctaacaga gtgaagtctg ccattgcccg gcaggaggat tggtagacct      540
gctgtgggac ggtggattga agagagaaaa ggtgaaggac acattcaagg aggagcagca      600
gaagctatat agcaagatga tagtcggaaa ccatgaggac cgcagccggt cctgagcctc      660
cgtcttgtgc tggctgaagc gccacctcta atcctgaag tgtgagccag ctgcagttgt        720
tgctgccaca gcctctaccg tcatccccgc cacccactgc tgcatccttc cggactctgg      780
ccctcaggct gttctggact ccaggactgg agctgcgtca gagctccgtg ggctgcctgc      840
tgtcctctaa ccagaatgct tctggctggg gctccctggg acaaaatgcc tcttgttctt      900
tatagtaagc ctctaagagg aatgccatta aagcagttct agctggtgaa a              951

<210> SEQ ID NO 88
<211> LENGTH: 488
<212> TYPE: DNA
<213> ORGANISM: Mus musculus

<400> SEQUENCE: 88
```

```
gatcccgggg tactctcagc tcaacagcag actctgaagc agattgtgat ctgtggagac      60
ccccaggcca aggacaccaa ggccctgctg caatgtgtcc actccatcta cgtccctaac     120
aaggtgctca ttctggctga tggagaccca tcgagcttcc tgtcccgtca gcttcccttc     180
ttgagcagcc ttcgaagagt agaagaccgg gccacagtct acatatttga gaaccaagcc     240
tgctccatgc ctatcacgga tccctgtgag ttacgaaagc tgctacacca atgactgccc     300
agaaccctat gagctgggcc agaaggcaga attttccaac tgaccagaga ctcaggcctt     360
gagaggctaa taccaaacct atagctactc ctgggtaccc tgcctccagg tgatcacagc     420
catccttgcg gctcccccat gggcacctac tcaccatgaa ataaacctaa cagtgtcccg     480
tggaaaaa                                                              488
```

<210> SEQ ID NO 89
<211> LENGTH: 849
<212> TYPE: DNA
<213> ORGANISM: Mus musculus

<400> SEQUENCE: 89

```
gggcattta tacgatagcg gagaaacaaa agatatccac ctggaaatgg agaacatggt      60
gaatccccga accactccca agctgactcg caacgagtct gtagctcgtt caagcaaact     120
gctggggtgg tgccaaaggc agacagaagg ctattcagga gtcaatgtga cagatctcac     180
tatgtcttgg aaaagtggcc tggccctgtg tgcgatcatc cacagatacc gcccccgatct    240 aatagacttt gattctttgg atgagcaaaa cgtggagaag aataatcagc tggcctttga     300
catcgctgag aaggaactgg tatctctccc atcatgacgg gcaaggagat ggcttcggtc     360
ggggagccag acaagctgtc catggtgatg tacctcacgc agttctacga gatgttcaag     420
gactcgctct cctccagcga cacccctcgac ctgaatgcag aggagaaagc cgtcctgata    480
gccagcacca atcccccat ctccttcctg agcaaactcg acagaccat ctctcggaag       540 cgttcgccca aggataaaaa agaaaaggac tcagatgggg ctggaaagag gagaaaaacc     600
agtcagtcag aggaggagga gcctccccgg agctacaaag agaaagacc gaccctggtg     660 agcacctga cggacagacg gatggatgct gccgttggga accagaacaa agtgaagtac      720
atggcgaccc agctgctggc caagtttgaa gagaacgcac tgctcagtc cactggtgtg      780 aggagacagg gctcataaag aaagagttcc gcagaacttg gggggcagcg acacgtgcta    840
ttctgcaa                                                              849
```

<210> SEQ ID NO 90
<211> LENGTH: 864
<212> TYPE: PRT
<213> ORGANISM: Mus musculus

<400> SEQUENCE: 90

```
Met Ala Asp Arg Val Asp Trp Leu Gln Ser Gln Ser Gly Val Cys Lys
  1               5                  10                  15

Val Gly Val Tyr Ser Pro Gly Asp Asn Gln His Gln Asp Trp Lys Met
             20                  25                  30

Asp Thr Ser Thr Asp Pro Val Arg Val Leu Ser Trp Leu Arg Lys Asp
         35                  40                  45

Leu Glu Lys Ser Thr Ala Gly Phe Gln Asp Ser Arg Phe Lys Pro Gly
     50                  55                  60

Glu Ser Ser Phe Val Glu Glu Val Ala Tyr Pro Val Asp Gln Arg Lys
 65                  70                  75                  80
```

-continued

```
Gly Phe Cys Val Asp Tyr Tyr Asn Thr Thr Asn Lys Gly Ser Pro Gly
                85                  90                  95

Arg Leu His Phe Glu Met Ser His Lys Glu Asn Pro Ser Gln Gly Leu
            100                 105                 110

Ile Ser His Val Gly Asn Gly Gly Ser Ile Asp Glu Val Ser Phe Tyr
        115                 120                 125

Ala Asn Arg Leu Thr Asn Leu Val Ile Ala Met Ala Arg Lys Glu Ile
    130                 135                 140

Asn Glu Lys Ile His Gly Ala Glu Asn Lys Cys Val His Gln Ser Leu
145                 150                 155                 160

Tyr Met Gly Asp Glu Pro Thr Pro His Lys Ser Leu Ser Thr Val Ala
                165                 170                 175

Ser Glu Leu Val Asn Glu Thr Val Thr Ala Cys Ser Lys Asn Ile Ser
            180                 185                 190

Ser Asp Lys Ala Pro Gly Ser Gly Asp Arg Ala Ser Gly Ser Ser Gln
        195                 200                 205

Ala Pro Gly Leu Arg Tyr Met Ser Thr Leu Lys Ile Lys Glu Ser Thr
    210                 215                 220

Lys Glu Gly Lys Cys Pro Asp Asp Lys Pro Gly Thr Lys Lys Ser Phe
225                 230                 235                 240

Phe Tyr Lys Glu Val Phe Glu Ser Arg Asn Ala Gly Asp Ala Lys Glu
                245                 250                 255

Gly Gly Arg Ser Leu Pro Gly Asp Gln Lys Leu Phe Arg Thr Ser Pro
            260                 265                 270

Asp Asn Arg Pro Asp Asp Phe Ser Asn Ser Ile Ser Gln Gly Ile Met
        275                 280                 285

Thr Tyr Ala Asn Ser Val Val Ser Asp Met Met Val Ser Ile Met Lys
    290                 295                 300

Thr Leu Lys Ile Gln Val Lys Asp Thr Thr Ile Ala Thr Ile Leu Leu
305                 310                 315                 320

Lys Lys Val Leu Met Lys His Ala Lys Glu Val Val Ser Asp Leu Ile
                325                 330                 335

Asp Ser Phe Met Lys Asn Leu His Gly Val Thr Gly Ser Leu Met Thr
            340                 345                 350

Asp Thr Asp Phe Val Ser Ala Val Lys Arg Ser Phe Phe Ser His Gly
        355                 360                 365

Ser Gln Lys Ala Thr Asp Ile Met Asp Ala Met Leu Gly Lys Leu Tyr
    370                 375                 380

Asn Val Met Phe Ala Lys Lys Phe Pro Glu Asn Ile Arg Arg Ala Arg
385                 390                 395                 400

Asp Lys Ser Glu Ser Tyr Ser Leu Ile Ser Thr Lys Ser Arg Ala Gly
                405                 410                 415

Asp Pro Lys Leu Ser Asn Leu Asn Phe Ala Met Lys Ser Glu Ser Lys
            420                 425                 430

Leu Lys Glu Asn Leu Phe Ser Thr Cys Lys Leu Glu Lys Glu Lys Thr
        435                 440                 445

Cys Ala Glu Thr Leu Gly Glu His Ile Ile Lys Glu Gly Leu His Met
    450                 455                 460

Trp His Lys Ser Gln Gln Lys Ser Pro Gly Leu Glu Arg Ala Ala Lys
465                 470                 475                 480

Leu Gly Asn Ala Pro Gln Glu Val Ser Phe Glu Cys Pro Asp Pro Cys
                485                 490                 495
```

```
Glu Ala Asn Pro Pro His Gln Pro Gln Pro Glu Asn Phe Ala Asn
            500                 505                 510

Phe Met Cys Asp Ser Asp Ser Trp Ala Lys Asp Leu Ile Val Ser Ala
        515                 520                 525

Leu Leu Leu Ile Gln Tyr His Leu Ala Gln Gly Gly Lys Met Asp Ala
        530                 535                 540

Gln Ser Phe Leu Glu Ala Ala Ser Thr Asn Phe Pro Thr Asn Lys
545                 550                 555                 560

Pro Pro Pro Pro Ser Pro Val Val Gln Asp Glu Cys Lys Leu Lys Ser
                565                 570                 575

Pro Pro His Lys Ile Cys Asp Gln Glu Gln Thr Glu Lys Lys Asp Leu
            580                 585                 590

Met Ser Val Ile Phe Asn Phe Ile Arg Asn Leu Leu Ser Glu Thr Ile
        595                 600                 605

Phe Lys Ser Ser Arg Asn Cys Glu Ser Asn Val His Glu Gln Asn Thr
        610                 615                 620

Gln Glu Glu Glu Ile His Pro Cys Glu Arg Pro Lys Thr Pro Cys Glu
625                 630                 635                 640

Arg Pro Ile Thr Pro Pro Ala Pro Lys Phe Cys Glu Asp Glu Ala
                645                 650                 655

Thr Gly Gly Ala Leu Ser Gly Leu Thr Lys Met Val Ala Asn Gln Leu
                660                 665                 670

Asp Asn Cys Met Asn Gly Gln Met Val Glu His Leu Met Asp Ser Val
            675                 680                 685

Met Lys Leu Cys Leu Ile Ile Ala Lys Ser Cys Asp Ser Pro Leu Ser
690                 695                 700

Glu Leu Gly Glu Glu Lys Cys Gly Asp Ala Ser Arg Pro Asn Ser Ala
705                 710                 715                 720

Phe Pro Asp Asn Leu Tyr Glu Cys Leu Pro Val Lys Gly Thr Gly Thr
                725                 730                 735

Ala Glu Ala Leu Leu Gln Asn Ala Tyr Leu Thr Ile His Asn Glu Leu
            740                 745                 750

Arg Gly Leu Ser Gly Gln Pro Pro Glu Gly Cys Glu Ile Pro Lys Val
        755                 760                 765

Ile Val Ser Asn His Asn Leu Ala Asp Thr Val Gln Asn Lys Gln Leu
    770                 775                 780

Gln Ala Val Leu Gln Trp Val Ala Ala Ser Glu Leu Asn Val Pro Ile
785                 790                 795                 800

Leu Tyr Phe Ala Gly Asp Asp Glu Gly Ile Gln Glu Lys Leu Leu Gln
                805                 810                 815

Leu Ser Ala Thr Ala Val Glu Lys Gly Arg Ser Val Gly Glu Val Leu
            820                 825                 830

Gln Ser Val Leu Arg Tyr Glu Lys Glu Arg Gln Leu Asp Glu Ala Val
        835                 840                 845

Gly Asn Val Thr Arg Leu Gln Leu Leu Asp Trp Leu Met Ala Asn Leu
    850                 855                 860
```

<210> SEQ ID NO 91
<211> LENGTH: 719
<212> TYPE: PRT
<213> ORGANISM: Mus musculus
<220> FEATURE:
<221> NAME/KEY: misc_feature
<222> LOCATION: (26)..(26)
<223> OTHER INFORMATION: Xaa can be any naturally occurring amino acid

<400> SEQUENCE: 91

```
Met Glu Gly Asp Ala Ser Asp Ser Gln Val Thr Ile Lys Asn Ile Glu
  1               5                  10                  15

Lys Glu Leu Ile Cys Pro Ala Cys Lys Xaa Leu Phe Thr His Pro Leu
                 20                  25                  30

Ile Leu Pro Cys Gln His Ser Val Cys His Lys Cys Val Lys Glu Leu
             35                  40                  45

Leu Leu Ser Leu Asp Asp Ser Phe Asn Asp Val Ala Ser Asp Ser Ser
         50                  55                  60

Asn Gln Ser Ser Pro Arg Leu Arg Leu Thr Ser Pro Ser Met Asp Lys
 65                  70                  75                  80

Ile Asp Lys Ile Asn Arg Pro Gly Trp Lys Arg Asn Ser Leu Thr Pro
                 85                  90                  95

Arg Pro Thr Thr Phe Pro Cys Pro Gly Cys Glu His Asp Val Asp Leu
            100                 105                 110

Gly Glu Arg Gly Val Ser Gly Leu Phe Arg Asn Phe Thr Leu Glu Thr
            115                 120                 125

Ile Val Glu Arg Tyr Arg Gln Ala Ala Arg Ala Thr Ala Ile Met
            130                 135                 140

Cys Asp Leu Cys Lys Pro Pro Gln Glu Ser Thr Lys Ser Cys Met
145                 150                 155                 160

Asp Cys Ser Ala Arg Gly Tyr Cys Asn Glu Cys Phe Lys Ile Tyr His
                165                 170                 175

Pro Trp Gly Thr Val Lys Ala Gln His Glu Tyr Val Gly Pro Thr Thr
                180                 185                 190

Asn Phe Arg Pro Lys Val Leu Met Cys Pro Glu His Glu Thr Glu Arg
            195                 200                 205

Ile Asn Met Tyr Cys Glu Leu Cys Arg Arg Pro Val Cys His Leu Cys
            210                 215                 220

Lys Leu Gly Gly Asn His Ser Asn His Arg Val Thr Thr Met Ser Ser
225                 230                 235                 240

Ala Tyr Lys Thr Leu Lys Glu Lys Leu Ser Lys Asp Ile Asp Phe Leu
                245                 250                 255

Ile Gly Lys Glu Ser Gln Val Lys Ser Gln Ile Ser Glu Leu Asn Leu
            260                 265                 270

Leu Met Lys Glu Thr Glu Cys Asn Val Glu Arg Ala Lys Glu Glu Ala
        275                 280                 285

Leu Ala His Phe Glu Lys Leu Phe Glu Ile Leu Glu Asp Arg Lys Ser
        290                 295                 300

Ser Val Leu Lys Ala Ile Asp Ala Ser Lys Lys Leu Arg Leu Asp Lys
305                 310                 315                 320

Phe His Thr Gln Met Glu Glu Tyr Gln Gly Leu Leu Glu Asn Asn Gly
                325                 330                 335

Leu Val Gly Tyr Ala Gln Glu Val Ala Glu Gly Asp Gly Ser Val Leu
                340                 345                 350

Leu Cys Ala Asp Gly Glu Gln Leu His Leu Arg Ile Gln Lys Ala Thr
            355                 360                 365

Glu Ser Leu Lys Ser Phe Arg Pro Ala Ala Gln Ala Ser Phe Glu Asp
        370                 375                 380

Tyr Val Val Asn Ile Ser Lys Gln Thr Glu Val Leu Gly Glu Leu Ser
385                 390                 395                 400

Phe Phe Ser Ser Gly Ile Asp Ile Pro Glu Ile Asn Glu Glu Gln Ser
                405                 410                 415
```

```
Lys Val Tyr Asn Asn Ala Leu Ile Asp Trp His His Pro Glu Lys Asp
                420                 425                 430

Lys Ala Asp Ser Tyr Val Leu Glu Tyr Arg Lys Ile Asn Arg Asp Glu
            435                 440                 445

Glu Met Ile Ser Trp Asn Glu Ile Glu Val His Gly Thr Ser Lys Val
        450                 455                 460

Val Ser Asn Leu Glu Ser Asn Ser Pro Tyr Ala Phe Arg Val Arg Ala
465                 470                 475                 480

Tyr Arg Gly Phe Tyr Leu Gln Ser Leu Gln Gln Arg Ile Asp Pro Ala
                485                 490                 495

Tyr Ser Ser Ser Ser Phe Ser Val Ser Cys Ser Met Arg Ser Val
            500                 505                 510

Ala Thr Thr Leu Ser Thr Ser Cys Trp Asp Leu Lys Arg Asp Arg Val
            515                 520                 525

Glu Ser Arg Ala Gly Phe Asn Val Leu Leu Ala Ala Glu Arg Ile Gln
        530                 535                 540

Val Gly His Tyr Thr Ser Leu Asp Tyr Ile Ile Gly Asp Val Gly Val
545                 550                 555                 560

Thr Lys Gly Lys His Phe Trp Ala Cys Arg Val Glu Pro Tyr Ser Tyr
                565                 570                 575

Leu Val Lys Val Gly Val Ala Ser Ser Asp Lys Leu Gln Glu Cys Val
            580                 585                 590

Arg Ser Pro Arg Asp Ala Ala Ser Pro Arg Tyr Glu Gln Asp Ser Gly
            595                 600                 605

His Asp Ser Gly Ser Glu Asp Ala Cys Phe Asp Ser Ser Gln Pro Phe
        610                 615                 620

Thr Leu Val Thr Ile Gly Met Lys Lys Phe Phe Ile Pro Lys Ser Pro
625                 630                 635                 640

Thr Ser Ser Asn Glu Pro Glu Asn Arg Val Leu Pro Met Pro Thr Ser
                645                 650                 655

Ile Gly Ile Phe Leu Asp Cys Asp Lys Gly Lys Val Ser Phe Tyr Asp
            660                 665                 670

Met Asp His Met Lys Cys Leu Tyr Glu Arg Gln Val Asp Cys Ser His
            675                 680                 685

Thr Met Tyr Pro Ala Phe Ala Leu Met Gly Ser Gly Ile Gln Leu
        690                 695                 700

Glu Glu Ala Ile Thr Ala Lys Tyr Leu Glu Tyr Glu Glu Asp Val
705                 710                 715

<210> SEQ ID NO 92
<211> LENGTH: 164
<212> TYPE: PRT
<213> ORGANISM: Mus musculus

<400> SEQUENCE: 92

Met Pro Ser Ser Arg Met Gly Leu Asn Pro Gln Leu Gly Arg Gln Ser
1               5                   10                  15

Pro Ile Pro Gln Asn Gly Leu Cys Phe His Pro Lys Asn Thr Ala Asn
            20                  25                  30

Thr His Thr Ser Asp Pro Glu Thr Ser Cys Val Asp Leu Gly Ser Pro
        35                  40                  45

Glu Asp Ala Glu Phe Gly Ser Glu Gly Lys Trp Glu Gly Thr Ser Ala
    50                  55                  60

Glu Gly Cys Leu Met Gly Thr Arg Val Glu Pro Leu Gly Lys Val Val
```

-continued

```
                65                  70                  75                  80
Gly Arg Thr Thr Leu Gly Pro Glu Leu Arg Ala Arg Leu Val Leu Ser
                    85                  90                  95

Pro Leu Pro Arg Ala Leu Val Ser Met Leu Val Leu Ser Ser Ala Trp
            100                 105                 110

Leu Ser Arg Gln Arg Gly Asp Gln Ala Ser Tyr Glu Ser Ala Leu Ser
        115                 120                 125

Leu Ser Gly Cys Lys Arg Pro Cys Gly Ser Ser Ala His Ala Ser Pro
    130                 135                 140

Trp Gln Cys Ala Leu Thr Glu Ala Pro Leu Pro Asn Trp Asn Lys Leu
145                 150                 155                 160

Glu Ala Glu Lys
```

<210> SEQ ID NO 93
<211> LENGTH: 100
<212> TYPE: PRT
<213> ORGANISM: Mus musculus
<220> FEATURE:
<221> NAME/KEY: misc_feature
<222> LOCATION: (79)..(79)
<223> OTHER INFORMATION: Xaa can be any naturally occurring amino acid

<400> SEQUENCE: 93

```
Asn Ser Thr Ser Arg Ser Pro Gly Ser Pro Ala Leu Cys Tyr Ile Pro
1               5                   10                  15

Cys Phe Gly Pro Asp Pro Ser Leu Asn Leu Ala Gln Thr Ser Pro Ser
            20                  25                  30

Phe Gly Ser Asn Val Pro Phe Leu Ser Pro Gly Phe Arg Phe Leu Pro
        35                  40                  45

Arg Asn Pro Ile Pro Pro Asp Val Ala Ser Thr Pro Thr Pro Lys Leu
    50                  55                  60

Trp Pro Leu Ala Lys Trp Pro Ser Gly Trp Glu Arg Glu Ala Xaa Ser
65                  70                  75                  80

Trp Glu Ser Cys Gly Arg Val Gly Leu Ala Cys Leu His Arg Val Arg
                85                  90                  95

Asn Leu Trp Arg
            100
```

<210> SEQ ID NO 94
<211> LENGTH: 187
<212> TYPE: PRT
<213> ORGANISM: Mus musculus

<400> SEQUENCE: 94

```
Met Asp Arg Ala Asp Thr Ile Tyr Asp Phe Lys Gly Ile Lys Gln Glu
1               5                   10                  15

Gly Leu Leu Ile Arg Lys Gly Met Thr Arg Glu Leu Lys Asn Glu Leu
            20                  25                  30

Arg Glu Val Arg Glu Gln Leu Thr Glu Lys Met Glu Glu Ile Lys Gln
        35                  40                  45

Ile Lys Asp Ile Met Asp Lys Asp Phe Asp Lys Leu Tyr Glu Phe Val
    50                  55                  60

Glu Ile Met Lys Glu Met Gln Gln Asp Met Asp Glu Lys Met Asp Val
65                  70                  75                  80

Leu Ile Asn Asn Gln Lys Asn Asn Lys Leu Pro Phe Gln Asn Gln Ala
                85                  90                  95

Lys Glu Gln Gln Lys Phe Trp Gln Leu Gly Lys Met Asp Lys Gly Ser
```

-continued

```
                100                 105                 110
Gln Ala Met Ile Thr Glu Glu Pro Asp Gly Ala Pro Leu Ala Cys Asp
            115                 120                 125

Lys Asn Val Val Pro Lys Pro Thr Arg Asn Pro Leu Glu Ser Leu
130                 135                 140

His Pro Cys Gln Ser Cys Cys Glu Thr Phe Thr Pro Cys Leu Gly Ala
145                 150                 155                 160

Phe Phe Thr Leu Val Val Trp Ser Cys Phe Leu Ile Tyr Leu Tyr Phe
                165                 170                 175

Asn Phe Ala Glu Val Glu His Val Leu Pro Thr
            180                 185
```

<210> SEQ ID NO 95
<211> LENGTH: 260
<212> TYPE: PRT
<213> ORGANISM: Mus musculus

<400> SEQUENCE: 95

```
Met Phe Leu Phe Ser Arg Lys Thr Lys Thr Pro Ile Ser Thr Tyr Ser
 1               5                  10                  15

Asp Ser Tyr Arg Ala Pro Thr Ser Ile Lys Glu Val Tyr Lys Asp Pro
                20                  25                  30

Pro Leu Trp Ala Trp Glu Ala Asn Lys Phe Val Thr Pro Gly Leu Thr
            35                  40                  45

Gln Thr Met His Arg His Val Asp Pro Glu Ala Leu Gln Lys Met Thr
        50                  55                  60

Lys Cys Ala Ala Gln Asp Tyr Thr Tyr Lys Ser Ser Ile Ser Gly His
65                  70                  75                  80

Pro Tyr Leu Pro Glu Lys Tyr Trp Leu Ser Pro Asp Glu Glu Asp Lys
                85                  90                  95

Cys Cys Pro Ser Tyr Leu Asp Asn Asp Arg Tyr Asn Thr Trp Lys Thr
            100                 105                 110

Ser Pro Cys Ser Asn Tyr Trp Asn Lys Tyr Thr Gly Cys Leu Pro Arg
        115                 120                 125

Leu Ser Lys Asp Thr Gly Met Glu Ser Val Arg Gly Met Pro Leu Glu
130                 135                 140

Tyr Pro Pro Lys Gln Glu Arg Leu Asn Ala Tyr Glu Arg Glu Val Val
145                 150                 155                 160

Val Asn Met Leu Asn Ser Leu Ser Arg Asn Arg Thr Leu Pro Gln Ile
                165                 170                 175

Val Pro Arg Cys Gly Cys Val Asp Pro Leu Pro Gly Arg Leu Pro Tyr
            180                 185                 190

Gln Gly Tyr Glu Ser Pro Cys Ser Gly Arg His Tyr Cys Leu Arg Gly
        195                 200                 205

Met Asp Tyr Cys Thr Thr Arg Glu Pro Ser Thr Glu Arg Arg Leu Arg
    210                 215                 220

Leu Cys Ala Arg Ser Ser Arg Leu Ser Val Ser Pro Phe Gly His Arg
225                 230                 235                 240

Pro Gly Met Gln Cys Ala Val Thr Thr Pro Pro Ile Ile Leu Pro
                245                 250                 255

Val Ser Gln Pro
            260
```

<210> SEQ ID NO 96
<211> LENGTH: 106

```
<212> TYPE: PRT
<213> ORGANISM: Mus musculus

<400> SEQUENCE: 96

Met Gly Cys Met Lys Ser Lys Glu Thr Phe Pro Phe Pro Thr Thr Leu
 1               5                  10                  15

Asp Ile Asp Lys Leu His Glu Ser Glu Ala Phe Ile Pro Asp Asp
             20                  25                  30

Ser Ser Gln Tyr Arg Thr Pro Ser Pro Gly Glu Gln Gln Val Gln
             35                  40                  45

Glu Val Lys Lys Leu Pro Glu Pro Gly Ala Val Ile Gly Ala Leu Ile
     50                  55                  60

Leu Glu Phe Ala Asp Arg Leu Ala Ser Glu Ile Val Glu Asp Ala Leu
 65                  70                  75                  80

Gln Gln Trp Ala Cys Glu Asn Ile Gln Tyr Tyr Asn Ile Pro Tyr Ile
                 85                  90                  95

Glu Ser Glu Gly Ser Asp Thr Thr Ile Asn
            100                 105

<210> SEQ ID NO 97
<211> LENGTH: 108
<212> TYPE: PRT
<213> ORGANISM: Mus musculus
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(97)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid
```

```
<400> SEQUENCE: 97

Val Xaa Xaa Leu Tyr His Leu Pro Ala Pro Ala Gly Ser Arg Ala Val
 1               5                  10                  15

Thr Cys Asp Pro Ala Pro Gly Pro Pro Thr His Leu Pro Ser Ile Cys
            20                  25                  30

Arg Ile Ser Lys Ile Phe Ser Ser Asp Pro Lys Ile Thr His Pro Gly
        35                  40                  45

Pro Pro Thr His Leu Pro Ser Thr Cys Arg Ile Ser Ser Cys Asp Pro
    50                  55                  60

Val Thr Pro Ala Pro Gly Pro Xaa Thr Xaa Leu Xaa Ser Thr Xaa Arg
 65                  70                  75                  80

Ile Xaa Ser Cys Asp Xaa Val Thr Pro Thr Leu Glu Pro Xaa Thr Xaa
            85                  90                  95

Xaa Thr Ser Thr Xaa Ser Ile Xaa Gly Ser Xaa Xaa
            100                 105

<210> SEQ ID NO 98
<211> LENGTH: 106
<212> TYPE: PRT
<213> ORGANISM: Mus musculus

<400> SEQUENCE: 98

Gly Asn Thr Leu Glu Gly Arg Val Lys Lys Asp Gln Ser Gln Pro Leu
 1               5                  10                  15

Lys Glu Leu Gly Arg Val Thr Thr Gly Asp Arg Glu Gln Arg Asp Gly
            20                  25                  30

His Asp Thr Ser Asp Pro Arg Arg Lys Arg Gly Ser Gly Pro Gly Ser
        35                  40                  45

Pro Thr Arg Ala Gln Ile His Pro Gln Lys Met Glu Gly Phe Val Ser
    50                  55                  60

Asp Leu Trp Lys Gly Cys Val His His Gly Ser Val Gly Val Leu Arg
 65                  70                  75                  80

Pro Pro His Cys Ser Pro Gly Val Cys Val Leu Pro Ile Leu His Gln
            85                  90                  95

Val Leu Gly Pro Pro Ala Cys Ser Pro Gly
            100                 105

<210> SEQ ID NO 99
<211> LENGTH: 145
<212> TYPE: PRT
<213> ORGANISM: Mus musculus

<400> SEQUENCE: 99

Ser Ser Arg Asp Tyr Met Asn Thr Ser Val Gln Glu Pro Pro Leu Asp
 1               5                  10                  15

Tyr Ser Phe Lys Ser Val Gln Met Val Gln Asp Leu Val Thr Glu Glu
            20                  25                  30

Pro Arg Thr Gly Leu Arg Pro Val Arg His Ser Lys Ser Gly Lys Leu
        35                  40                  45

Leu Thr Gln Ser Leu Trp Leu Asn Asn Val Leu Asn Asp Leu Lys
    50                  55                  60

Asp Phe Asn Gln Val Val Ser Gln Leu Leu Gln His Pro Glu Asn Leu
 65                  70                  75                  80

Ala Trp Ile Asp Leu Tyr Phe Asn Asp Leu Thr Thr Ile Asp Pro Val
            85                  90                  95
```

```
Leu Thr Thr Phe Phe Asn Leu Ser Val Leu Tyr Leu Asn Gly Asn Gly
                100                 105                 110

Ile His Arg Leu Gly Glu Val Asn Lys Val Ala Val Leu His Arg Phe
            115                 120                 125

Arg Arg Leu Ile Phe His Gly Asn Pro Ile Glu Glu Lys Gly Tyr
    130                 135                 140

Arg
145

<210> SEQ ID NO 100
<211> LENGTH: 50
<212> TYPE: PRT
<213> ORGANISM: Mus musculus

<400> SEQUENCE: 100

Met Ser Ser Val Tyr Gly Lys Arg Ile Asn Gln Pro Ile Glu Pro Leu
 1               5                  10                  15

Asn Arg Asp Tyr Gly His Val Ser His Val Lys Thr Asp Phe Tyr Arg
                20                  25                  30

Lys Asn Glu Ile Pro Ser Ile Lys Gly Pro Gly Phe Gly His Ile Asn
            35                  40                  45

Pro Ala
    50

<210> SEQ ID NO 101
<211> LENGTH: 149
<212> TYPE: PRT
<213> ORGANISM: Mus musculus

<400> SEQUENCE: 101

Met Asp Tyr Val His Leu Cys Pro Glu Asn Arg Arg Leu Pro Phe Pro
 1               5                  10                  15

Pro Arg Val Asn Ser Asp Ile Glu Val Glu Glu Ser Glu Ala Val Ser
                20                  25                  30

Val Val Gln His Trp Leu Asn Lys Thr Glu Glu Glu Ala Ser Arg Ser
            35                  40                  45

Ile Arg Glu Lys Met Ser Ile Asn Asp Ser Pro Thr His Gly His Asp
50                  55                  60

Ile His Val Thr Arg Asp Leu Val Lys His His Leu Ser Lys Ser Asp
65                  70                  75                  80

Met Leu Thr Asp Pro Ser Gln Glu Val Leu Glu Glu Arg Thr Arg Ile
                85                  90                  95

Gln Phe Ile Arg Trp Ser His Thr Arg Ile Phe Gln Val Pro Ser Glu
            100                 105                 110

Val Met Asp Asp Val Met Gln Glu Arg Ile Asp Gln Val Arg Arg Ser
        115                 120                 125

Val Ser His Leu Met Cys Asp Ser Tyr Asn Asp Pro Ser Phe Arg Thr
    130                 135                 140

Ser Cys Ser Glu Cys
145

<210> SEQ ID NO 102
<211> LENGTH: 435
<212> TYPE: PRT
<213> ORGANISM: Mus musculus

<400> SEQUENCE: 102

Met Glu Lys Pro Glu Ser Leu Ala Pro Val Ser Gly Leu Ser Ala Glu
```

-continued

```
  1               5              10              15
Ser Pro Gly Gly Val Ser Arg Ala Val Pro Gly Ser Ala Arg Gly Met
                20              25              30
Gln Thr Asp Thr Gly Leu Pro Pro Gly Val Ala Leu Leu Arg Gly Pro
                35              40              45
Gly Ser Leu Leu His Ser Gly Asn Pro Val Val Arg Ser Pro Gly Pro
                50              55              60
Ile Gln Pro Ser Glu Gly Ala Val Thr Leu Asn Ser Gly Pro Ala Pro
 65              70              75              80
Gln Leu Gln Glu Val Ala Ser Leu Gly Ser Ser Thr Ser Pro Gly Thr
                85              90              95
Gly Thr Gly Ala Thr Lys Ala Ser Thr Pro Gly Pro Glu Glu Ala Lys
               100             105             110
Val Tyr Ser Ser Glu Ser Ser Thr His Ser Gly Thr Ser Phe Thr Glu
               115             120             125
Arg Pro Arg Ser Ile Leu Lys Asn Ser Ser Ile Leu Ile Lys Lys
               130             135             140
Pro Pro Gly Ser Glu Lys Lys Ser Gln Arg Trp Asp Glu Met Asn Ile
145             150             155             160
Leu Ala Thr Tyr His Pro Ala Asp Lys Asp Tyr Gly Phe Met Lys Ala
               165             170             175
Asp Glu Pro Arg Thr Pro Tyr His Arg Leu Gln Asp Thr Asp Glu Asp
               180             185             190
Pro Ser Ala Glu Ser Ser Leu Lys Val Thr Pro Gln Ser Val Ala Glu
               195             200             205
Arg Phe Ala Thr Met Asp Asn Phe Leu Pro Lys Val Leu Gln Tyr Gly
               210             215             220
Asp Asn Lys Asn Ser Lys Asp Thr Asp Asn Phe Ala Lys Thr Tyr Ser
225             230             235             240
Ser Asp Phe Asp Lys His Arg Lys Ile His Tyr Ser Glu Gly Lys Phe
               245             250             255
Leu Lys Ser Pro Lys Asn Leu Pro Thr Glu Glu Glu Ser Ile Gly Ala
               260             265             270
Ser Ala Ser Ile Ser Ser Ser Asn Gln Ala Val Ala Thr Asp Leu Lys
               275             280             285
Pro Arg Pro Val Glu Lys Gly Trp Ala Gly Arg Leu Ala Thr Gly Val
               290             295             300
Lys Asn Asp Thr Val Leu Met Thr Asp Ser His Val Leu Ser Thr Asn
305             310             315             320
Asp Ser Ala Thr Tyr Arg Asn Gln Phe Pro Ser Ala Ser Asp Ser Ser
               325             330             335
Met Gly Gln Leu Ala Asn Leu Gln Arg Lys Glu Tyr Tyr Ser Lys Gly
               340             345             350
Arg Tyr Leu Arg Ser Gly Ser Arg Pro Glu Leu Gly Glu Asp Ile Glu
               355             360             365
Asp Glu Glu Gln Asp Ser Pro Ser Gly Leu Thr Trp Val Thr Glu Asn
               370             375             380
Pro Lys Gly Thr Pro Val Asn Gly Ser Gln Val Thr Pro Asn Cys Trp
385             390             395             400
Ala Lys Gly Pro Arg Cys Arg Ser Pro Gly Ser Ser Glu Lys Glu His
               405             410             415
Gly Ser Asn Gln Asn Pro Pro Ser Trp Asn Gly Arg Arg Glu Pro
               420             425             430
```

<210> SEQ ID NO 103
<211> LENGTH: 316
<212> TYPE: PRT
<213> ORGANISM: Mus musculus

<400> SEQUENCE: 103

```
Met Glu Ser Gly Asn Glu Arg Ile Ser Ser Gln Ser Gln Gly Thr Ile
  1               5                  10                  15
His Leu Ser Lys Glu Pro Thr Phe Leu Ile Gln Ala Thr Leu Pro
             20                  25                  30
Ser Asp Leu His Ser Thr Leu Leu Gln Glu Thr Gln Cys Gly Gly Leu
         35                  40                  45
Thr Lys Asn Ile Lys Ala Asn Thr Gln Lys Arg Arg Pro Gly Thr Val
     50                  55                  60
Ile Leu Ser Lys Arg Ser Ser Arg Ile Met Ser Glu Thr Gln Pro Arg
 65                  70                  75                  80
Pro Pro Val Ile Pro Ser Arg Arg Pro Gly Phe Arg Ile Cys Tyr Ile
                 85                  90                  95
Cys Gly Arg Glu Phe Gly Ser Gln Ser Leu Ala Ile His Glu Pro Gln
            100                 105                 110
Cys Leu Glu Lys Trp Arg Thr Glu Asn Ser Lys Leu Pro Lys His Leu
        115                 120                 125
Arg Arg Pro Glu Pro Pro Asn Arg Ser Pro Ser Val Ala Leu Thr Pro
    130                 135                 140
Thr Ala Phe Arg Gln Pro Met Arg Lys His Phe Arg Val Leu Arg Leu
145                 150                 155                 160
Ser Cys Cys Pro Val Lys Thr Ala Ala Ala Arg Ser Cys Gln Thr Val
                165                 170                 175
Ser Trp Phe Thr Arg Glu Ala Ala Ser Gln Arg Val Arg Thr Leu Asp
            180                 185                 190
His Gln Ala Trp Val Val Leu Met Phe Leu Leu Val Ser Arg Lys Leu
        195                 200                 205
Leu Ala Ala Ser Gln Pro Asp Gln Gly Leu Ser Ser Val Thr Phe Val
    210                 215                 220
Val Gly Asn Leu Ala Arg Cys Pro Phe Leu Ser Met Ser Pro Asn Ala
225                 230                 235                 240
Trp Lys Ser Gly Lys Leu Arg Met Thr Asn Ser Leu Glu Ser Cys Val
                245                 250                 255
Gly His Ser Pro Arg Ser Leu Asn Pro Phe Gln Leu Asp Ser Pro Ala
            260                 265                 270
Lys Arg Gly Arg Val Lys Pro His Leu Cys Leu Ala Gln Ile Val Ala
        275                 280                 285
Gly Leu Leu Leu Trp Thr Ala Tyr Leu Tyr Thr Arg Glu Val Val Asn
    290                 295                 300
Leu Asn Leu Val Asp Gln Lys Leu Gln Ile Arg Thr
305                 310                 315
```

<210> SEQ ID NO 104
<211> LENGTH: 255
<212> TYPE: PRT
<213> ORGANISM: Mus musculus

<400> SEQUENCE: 104

```
Met Ala Lys Gly Gly Lys Gly Pro Lys Gly Lys Ile Thr Leu Asn
 1               5                  10                  15

Val Ala Lys Asn Cys Ile Lys Ile Thr Phe Asp Gly Arg Lys Arg Leu
                 20                  25                  30

Asp Leu Ser Lys Met Gly Ile Thr Thr Phe Pro Lys Cys Ile Leu Arg
             35                  40                  45

Leu Ser Asp Ile Asp Glu Leu Asp Leu Ser Arg Asn Met Ile Arg Lys
         50                  55                  60

Ile Pro Asp Ser Ile Ala Lys Phe Gln Asn Leu Arg Trp Leu Asp Leu
 65                  70                  75                  80

His Ser Asn Tyr Ile Asp Lys Leu Pro Glu Ser Ile Gly Gln Met Thr
                 85                  90                  95

Ser Leu Leu Phe Leu Asn Val Ser Asn Asn Arg Leu Thr Thr Asn Gly
             100                 105                 110

Leu Pro Val Glu Leu Asn Gln Leu Lys Asn Ile Arg Thr Val Asn Leu
         115                 120                 125

Gly Leu Asn His Leu Asp Ser Val Pro Thr Thr Leu Gly Ala Leu Lys
130                 135                 140

Glu Leu His Glu Val Gly Leu His Asp Asn Leu Leu Thr Thr Ile Pro
145                 150                 155                 160

Ala Ser Ile Ala Lys Leu Pro Lys Leu Lys Leu Asn Ile Lys Arg
                 165                 170                 175

Asn Pro Phe Pro Asn Ala Asp Glu Ser Glu Met Phe Val Asp Ser Ile
                 180                 185                 190

Lys Arg Leu Glu Asn Leu Tyr Leu Val Glu Glu Lys Asp Met Cys Ser
         195                 200                 205

Ser Cys Leu Gln Arg Cys Gln Gln Ala Arg Asp Lys Leu Asn Lys Ile
         210                 215                 220

Lys Ser Met Ala Pro Ser Ala Pro Arg Lys Ala Leu Phe Ser Asn Leu
225                 230                 235                 240

Val Ser Pro Asn Ser Thr Ala Lys Asp Ala Gln Glu Glu Trp Arg
                 245                 250                 255

<210> SEQ ID NO 105
<211> LENGTH: 506
<212> TYPE: PRT
<213> ORGANISM: Mus musculus

<400> SEQUENCE: 105

Met Ala Leu Gly Thr Leu Phe Leu Ala Leu Ala Ala Gly Leu Ser Thr
 1               5                  10                  15

Ala Ser Pro Pro Asn Ile Leu Leu Ile Phe Ala Asp Asp Leu Gly Tyr
                 20                  25                  30

Gly Asp Leu Gly Ser Tyr Gly His Pro Ser Ser Thr Thr Pro Asn Leu
             35                  40                  45

Asp Gln Leu Ala Glu Gly Gly Leu Arg Phe Thr Asp Phe Tyr Val Pro
         50                  55                  60

Val Ser Leu Cys Thr Pro Ser Arg Ala Ala Leu Leu Thr Gly Arg Leu
 65                  70                  75                  80

Pro Val Arg Ser Ala Met Tyr Pro Gly Val Leu Gly Pro Ser Ser Gln
                 85                  90                  95

Gly Gly Leu Pro Leu Glu Glu Leu Thr Leu Ala Glu Val Leu Ala Ala
             100                 105                 110

Arg Gly Tyr Leu Thr Gly Met Ala Gly Lys Trp His Leu Gly Val Gly
```

-continued

```
               115                 120                 125
Pro Glu Gly Ala Phe Leu Pro Pro His Gln Gly Phe His Arg Phe Leu
            130                 135                 140
Gly Ile Pro Tyr Ser His Asp Gln Gly Pro Cys Gln Asn Leu Thr Cys
145                 150                 155                 160
Phe Pro Pro Asp Ile Pro Cys Lys Gly Gly Cys Asp Gln Gly Leu Val
                165                 170                 175
Pro Ile Pro Leu Leu Ala Asn Leu Thr Val Glu Ala Gln Pro Pro Trp
            180                 185                 190
Leu Pro Gly Leu Glu Ala Arg Tyr Val Ser Phe Ser Arg Asp Leu Met
                195                 200                 205
Ala Asp Ala Gln Arg Gln Gly Arg Pro Phe Phe Leu Tyr Tyr Ala Ser
            210                 215                 220
His His Thr His Tyr Pro Gln Phe Ser Gly Gln Ser Phe Thr Lys Arg
225                 230                 235                 240
Ser Gly Arg Gly Pro Phe Gly Asp Ser Leu Met Glu Leu Asp Gly Ala
                245                 250                 255
Val Gly Ala Leu Met Thr Thr Val Gly Asp Leu Gly Leu Leu Glu Glu
            260                 265                 270
Thr Leu Val Ile Phe Thr Ala Asp Asn Gly Pro Glu Leu Met Arg Met
                275                 280                 285
Ser Asn Gly Gly Cys Ser Gly Leu Leu Arg Cys Gly Lys Gly Thr Thr
            290                 295                 300
Phe Glu Gly Gly Val Arg Glu Pro Ala Leu Val Tyr Trp Pro Gly His
305                 310                 315                 320
Ile Thr Pro Gly Val Thr His Glu Leu Ala Ser Ser Leu Asp Leu Leu
                325                 330                 335
Pro Thr Leu Ala Ala Leu Thr Gly Ala Pro Leu Pro Asn Val Thr Leu
            340                 345                 350
Asp Gly Val Asp Ile Ser Pro Leu Leu Gly Thr Gly Lys Ser Pro
                355                 360                 365
Arg Lys Ser Val Phe Phe Tyr Pro Pro Tyr Pro Asp Glu Ile His Gly
            370                 375                 380
Val Phe Ala Val Arg Asn Gly Lys Tyr Lys Ala His Phe Phe Thr Gln
385                 390                 395                 400
Gly Ser Ala His Ser Asp Thr Thr Ser Asp Pro Ala Cys His Ala Ala
                405                 410                 415
Asn Arg Leu Thr Ala His Glu Pro Pro Leu Leu Tyr Asp Leu Ser Gln
            420                 425                 430
Asp Pro Gly Glu Asn Tyr Asn Val Leu Glu Ser Ile Glu Gly Val Ser
            435                 440                 445
Pro Glu Ala Leu Gln Ala Leu Lys His Ile Gln Leu Leu Lys Ala Gln
            450                 455                 460
Tyr Asp Ala Ala Met Thr Phe Gly Pro Ser Gln Ile Ala Lys Gly Glu
465                 470                 475                 480
Asp Pro Ala Leu Gln Ile Cys Cys Gln Pro Ser Cys Thr Pro His Pro
                485                 490                 495
Val Cys Cys His Cys Pro Gly Ser Gln Ser
                500                 505

<210> SEQ ID NO 106
<211> LENGTH: 310
<212> TYPE: PRT
<213> ORGANISM: Mus musculus
```

```
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid

<400> SEQUENCE: 106

Met Phe Leu Phe Ser Arg Lys Thr Lys Thr Pro Ile Ser Thr Tyr Ser
 1               5                  10                  15

Asp Ser Tyr Arg Ala Pro Thr Ser Ile Lys Glu Val Tyr Lys Asp Pro
             20                  25                  30

Pro Leu Trp Ala Trp Glu Ala Asn Lys Phe Val Thr Pro Gly Leu Thr
         35                  40                  45

Gln Thr Met His Arg His Val Asp Pro Glu Ala Leu Gln Lys Met Thr
     50                  55                  60

Lys Cys Ala Ala Gln Asp Tyr Thr Tyr Lys Ser Ser Ile Ser Gly His
 65                  70                  75                  80

Pro Tyr Leu Pro Glu Lys Tyr Trp Leu Ser Pro Asp Glu Glu Asp Lys
                 85                  90                  95

Cys Cys Pro Ser Tyr Leu Asp Asn Asp Arg Tyr Asn Thr Trp Lys Thr
            100                 105                 110

Ser Pro Cys Ser Asn Tyr Trp Asn Lys Tyr Thr Gly Cys Leu Pro Arg
        115                 120                 125

Leu Ser Lys Asp Thr Gly Met Glu Ser Val Arg Gly Met Pro Leu Glu
130                 135                 140

Tyr Pro Pro Lys Gln Glu Arg Leu Asn Ala Tyr Glu Arg Glu Val Val
145                 150                 155                 160

Val Asn Met Leu Asn Ser Leu Ser Arg Asn Arg Thr Leu Pro Gln Ile
                165                 170                 175

Val Pro Arg Cys Gly Cys Val Asp Pro Leu Pro Gly Arg Leu Pro Tyr
            180                 185                 190

Gln Gly Tyr Xaa Ser Xaa Cys Ser Gly Arg His Tyr Cys Leu Arg Gly
        195                 200                 205

Met Asp Tyr Cys Thr Thr Arg Glu Pro Ser Thr Glu Arg Arg Leu Leu
    210                 215                 220

Pro Leu Cys Ser Gln Gln Pro Thr Glu Cys Val Ala Leu Arg Ser Pro
225                 230                 235                 240

Ala Arg Asn Xaa Met Cys Cys Tyr Thr Pro Arg His His Phe Thr Arg
                245                 250                 255

Ile Pro Thr Leu Asp Gly Thr Gln Val Thr Ser Glu Asp Trp Trp Phe
            260                 265                 270

Gln Arg Asn Asn Tyr Val Val His Pro Glu Phe Val Ser Glu Thr Val
        275                 280                 285

Leu Ser Thr Phe Leu Val Ser Phe Ala Arg Pro Arg Glu Glu Val Leu
    290                 295                 300

Ile Thr Leu Thr Gln Lys
305                 310

<210> SEQ ID NO 107
<211> LENGTH: 81
<212> TYPE: PRT
```

<213> ORGANISM: Mus musculus

<400> SEQUENCE: 107

```
Ser Ser Gly Leu Thr Gly Leu Leu Arg Ile Arg Lys Ala Leu Gln Ser
1               5                   10                  15

Arg Ala Gln Val Thr Pro Asn Cys Trp Ala Lys Gly Pro Arg Cys Arg
            20                  25                  30

Ser Pro Gly Ser Ser Glu Lys Glu His Gly Ser Asn Gln Asn Pro Pro
        35                  40                  45

Ser Trp Asn Gly Arg Arg Glu Pro Gly Pro Arg Gln Gly Asp Glu
    50                  55                  60

Ser Leu Arg Leu Gln Trp Thr Gln Lys Lys Glu Arg Arg Pro Trp Lys
65              70                  75                  80

Met
```

<210> SEQ ID NO 108
<211> LENGTH: 168
<212> TYPE: PRT
<213> ORGANISM: Mus musculus

<400> SEQUENCE: 108

```
Met Ala Gln Met Ala Lys Lys Val His Trp Ser Ser Ala Ala Ala Gly
1               5                   10                  15

Ala Ala Ala Ala Ala Lys Ile Ser Lys Leu Glu Lys Thr Thr Lys Arg
            20                  25                  30

Phe Lys Leu Ile Lys Lys Arg Asn Pro Ser Ser Lys Leu Pro Lys Arg
        35                  40                  45

Ser Ser His Ser Leu Leu Cys Ser Leu Ser Arg Ser Cys Cys Cys Cys
    50                  55                  60

Arg Cys Arg Cys Cys Tyr Cys Arg Cys Cys Arg Cys Cys Cys Ser
65              70                  75                  80

Arg Ser Arg Arg Phe Arg Ser Arg Thr Thr Leu Lys Phe Phe Gln Ile
                85                  90                  95

Thr Glu Lys Gly Glu Gln Ser Leu Gln Arg Arg Ile Arg Arg Gln Leu
            100                 105                 110

Thr Arg Ser Gln Leu Glu Leu Ile Glu Pro Glu Pro Thr Met Ala Leu
        115                 120                 125

Glu Pro Ser Glu Ile Thr Val Ala Phe Phe Ser His Lys Asn Ala Asn
    130                 135                 140

Val Ser Asp Pro Glu Val Pro Pro Cys Leu Asp Ser Asp Pro Phe
145                 150                 155                 160

Pro Asn Gly Asp Leu Ala Ser Ser
                165
```

<210> SEQ ID NO 109
<211> LENGTH: 180
<212> TYPE: PRT
<213> ORGANISM: Mus musculus

<400> SEQUENCE: 109

```
Met Phe Thr Ser Glu Ile Gly Val Val Glu Glu Trp Leu Ser Glu Phe
1               5                   10                  15

Lys Thr Leu Pro Glu Thr Ser Leu Pro Asn Tyr Ala Thr Asn Leu Lys
            20                  25                  30

Asp Lys Ser Ser Leu Val Thr Ser Leu Tyr Lys Val Ile Gln Glu Pro
        35                  40                  45
```

```
Gln Ser Glu Leu Leu Glu Pro Val Cys His Gln Leu Phe Glu Phe Tyr
     50                  55                  60

Arg Ser Gly Glu Glu Gln Leu Leu Arg Phe Thr Leu Gln Phe Leu Pro
 65                  70                  75                  80

Glu Leu Met Trp Cys Tyr Leu Ala Val Ser Ala Ser Arg Asp Val His
                 85                  90                  95

Ser Ser Gly Cys Ile Glu Ala Leu Leu Leu Gly Val Tyr Asn Leu Glu
                100                 105                 110

Ile Val Asp Lys His Gly His Ser Lys Val Leu Ser Phe Thr Ile Pro
            115                 120                 125

Ser Leu Ser Lys Pro Ser Val Tyr His Glu Pro Ser Ser Ile Gly Ser
130                 135                 140

Met Ala Leu Thr Glu Ser Ala Leu Ser Gln His Gly Leu Ser Lys Val
145                 150                 155                 160

Val Tyr Ser Gly Pro His Pro Gln Arg Glu Met Leu Thr Ala Gln Asn
                165                 170                 175

Ser Leu Lys Tyr
            180

<210> SEQ ID NO 110
<211> LENGTH: 138
<212> TYPE: PRT
<213> ORGANISM: Mus musculus

<400> SEQUENCE: 110

Lys Lys Arg Leu Ala Ser Arg Lys Ser Leu Pro Arg Ile Pro Leu Ser
 1               5                  10                  15

Ser Ser Arg Leu Thr Gly Leu Ser Trp Gly Pro Cys Leu His Pro Gly
                 20                  25                  30

Arg Ser Ile Thr Lys Ser Asp Tyr Leu Pro Val Thr His Pro Gln Gly
             35                  40                  45

Ser Asp Phe Leu Pro Val Leu Ser Arg Gly Ser Asp Arg Asp Thr Gly
 50                  55                  60

Phe Ser Arg Val Asn Glu Arg Thr Leu Asn Pro Arg Val Pro Thr Pro
 65                  70                  75                  80

Ala Pro Gln Ser Ala Ser Met Ser His Arg Ser Tyr Gln Pro Pro Gln
                 85                  90                  95

Arg Met Gln Gln Thr Asn Val Ala Leu Leu Gly Arg Ser Leu Trp Gly
            100                 105                 110

Thr Arg Ser Pro Gln Gly Ser Leu Leu Thr Thr Pro Ala Met Phe Gly
            115                 120                 125

Val Pro Met Asn Arg Thr Glu Ile Ser Gly
130                 135

<210> SEQ ID NO 111
<211> LENGTH: 92
<212> TYPE: PRT
<213> ORGANISM: Mus musculus
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
```

```
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 111

Leu Thr Asn Lys Ser Cys His Ala Gln Gly Ser Glu Leu Gln Pro Pro
 1               5                  10                  15

Lys Xaa Tyr Gln Ile Ala Ser Cys Xaa Thr Pro Asp Glu Ser Leu Asn
             20                  25                  30

Leu Ser Val Ala Glu Thr Xaa Xaa Arg Arg Pro Xaa Cys Ala Ser Asp
         35                  40                  45

Thr Gln Ser Gln Pro Leu Arg Gly Pro Ser Arg Pro Ser Leu His Ser
     50                  55                  60

Arg Ser Thr Gly Thr Leu Ala Gly Pro Gly Arg Ser Xaa His Ser Ser
 65                  70                  75                  80

Val His Thr Phe Pro Thr Arg Thr Arg Val Arg Pro
             85                  90

<210> SEQ ID NO 112
<211> LENGTH: 795
<212> TYPE: PRT
<213> ORGANISM: Mus musculus

<400> SEQUENCE: 112

Met Phe Arg Ser Thr Arg Thr Thr Asp Gln Trp Arg Val Gly Glu Arg
 1               5                  10                  15

Leu Gln Cys Pro Ala Gly His Ala Arg Ala Leu Ala Arg Thr Ala
             20                  25                  30

Asp Gly Gly Ala Val Gly Pro Phe Lys Cys Val Phe Val Gly Glu Met
         35                  40                  45

Ala Ala Gln Val Gly Ala Val Arg Val Val Arg Ala Val Ala Ala Gln
     50                  55                  60

Glu Glu Pro Asp Lys Glu Gly Lys Glu Lys Pro His Val Gly Val Ser
 65                  70                  75                  80

Pro Arg Gly Val Lys Arg Gln Arg Gln Arg Ala Ser Ser Gly Gly Ser Gln
             85                  90                  95

Glu Lys Arg Gly Arg Pro Ser Gln Asp Pro Pro Leu Ala Pro Pro His
            100                 105                 110

Arg Arg Arg Arg Ser Arg Gln His Pro Gly Pro Leu Pro Pro Thr Asn
            115                 120                 125

Ala Ala Pro Thr Val Pro Gly Pro Val Glu Pro Leu Leu Leu Pro Pro
        130                 135                 140

Pro Pro Pro Pro Ser Leu Ala Pro Ala Gly Pro Thr Val Ala Ala Pro
145                 150                 155                 160

Leu Pro Ala Pro Gly Thr Ser Ala Leu Phe Thr Phe Ser Pro Leu Thr
                165                 170                 175

Val Ser Ala Ala Gly Pro Lys His Lys Gly His Lys Glu Arg His Lys
            180                 185                 190

His His His Arg Gly Ser Asp Gly Asp Pro Gly Ala Cys Val Pro
        195                 200                 205

Gly Asp Leu Lys His Lys Asp Lys Gln Glu Asn Gly Glu Arg Ser Gly
    210                 215                 220
```

-continued

```
Gly Val Pro Leu Ile Lys Ala Pro Lys Arg Glu Thr Ala Asp Glu Asn
225                 230                 235                 240

Gly Lys Thr Gln Arg Ala Asp Asp Phe Val Leu Lys Lys Ile Lys Lys
            245                 250                 255

Lys Lys Lys Lys Lys His Arg Glu Asp Met Arg Gly Arg Leu Lys
                260                 265                 270

Met Tyr Asn Lys Glu Val Gln Thr Val Cys Ala Gly Leu Thr Arg Ile
            275                 280                 285

Ser Lys Glu Ile Leu Thr Gln Gly Gln Leu Asn Ser Thr Ser Gly Val
    290                 295                 300

Asn Lys Glu Ser Phe Arg Tyr Leu Lys Asp Glu Gln Leu Cys Arg Leu
305                 310                 315                 320

Asn Leu Gly Met Gln Glu Tyr Arg Val Pro Gln Gly Val Gln Thr Pro
                325                 330                 335

Phe Thr Thr His Gln Glu His Ser Ile Arg Arg Asn Phe Leu Lys Thr
            340                 345                 350

Gly Thr Lys Phe Ser Asn Phe Ile His Glu Glu His Gln Ser Asn Gly
        355                 360                 365

Gly Ala Leu Val Leu His Ala Tyr Met Asp Glu Leu Ser Phe Leu Ser
    370                 375                 380

Pro Met Glu Met Glu Arg Phe Ser Glu Phe Leu Ala Leu Thr Phe
385                 390                 395                 400

Ser Glu Asn Glu Lys Asn Ala Ala Tyr Tyr Ala Leu Ala Ile Val His
                405                 410                 415

Gly Ala Ala Ala Tyr Leu Pro Asp Phe Leu Asp Tyr Phe Ala Phe Asn
                420                 425                 430

Phe Pro Asn Thr Pro Val Lys Met Glu Ile Leu Gly Lys Lys Asp Ile
            435                 440                 445

Glu Thr Thr Thr Ile Ser Asn Phe His Thr Gln Val Asn Arg Thr Tyr
    450                 455                 460

Cys Cys Gly Thr Tyr Arg Ala Gly Pro Met Arg Gln Ile Ser Leu Val
465                 470                 475                 480

Gly Ala Val Asp Glu Glu Val Gly Asp Tyr Phe Pro Glu Phe Leu Asp
                485                 490                 495

Met Leu Glu Glu Ser Pro Phe Leu Lys Met Thr Leu Pro Trp Gly Thr
            500                 505                 510

Leu Ser Ser Leu Gln Leu Gln Cys Arg Ser Gln Ser Asp Asp Gly Pro
    515                 520                 525

Ile Met Trp Val Arg Pro Gly Glu Gln Met Ile Pro Thr Ala Asp Met
    530                 535                 540

Pro Lys Ser Pro Phe Lys Arg Arg Ser Met Asn Glu Ile Lys Asn
545                 550                 555                 560

Leu Gln Tyr Leu Pro Arg Thr Ser Glu Pro Arg Glu Val Leu Phe Glu
            565                 570                 575

Asp Arg Thr Arg Ala His Ala Asp His Val Gly Gln Gly Phe Asp Trp
            580                 585                 590

Gln Ser Thr Ala Ala Val Gly Val Leu Lys Ala Val Gln Phe Gly Glu
        595                 600                 605

Trp Ser Asp Gln Pro Arg Ile Thr Lys Asp Val Ile Cys Phe His Ala
        610                 615                 620

Glu Asp Phe Thr Asp Val Val Gln Arg Leu Gln Leu Asp Leu His Glu
625                 630                 635                 640

Pro Pro Val Ser Gln Cys Val Gln Trp Val Asp Glu Ala Lys Leu Asn
```

-continued

```
                    645                 650                 655
Gln Met Arg Arg Glu Gly Ile Arg Tyr Ala Arg Ile Gln Leu Cys Asp
            660                 665                 670

Asn Asp Ile Tyr Phe Ile Pro Arg Asn Val Ile His Gln Phe Lys Thr
        675                 680                 685

Val Ser Ala Val Cys Ser Leu Ala Trp His Ile Arg Leu Lys Gln Tyr
    690                 695                 700

His Pro Val Val Glu Thr Ala Gln Asn Thr Glu Ser Asn Ser Asn Met
705                 710                 715                 720

Asp Cys Gly Leu Glu Val Asp Ser Gln Cys Val Arg Ile Lys Thr Glu
                725                 730                 735

Ser Glu Glu Arg Cys Thr Glu Met Gln Leu Leu Thr Thr Ala Ser Pro
            740                 745                 750

Ser Phe Pro Pro Pro Ser Glu Leu His Leu Gln Asp Leu Lys Thr Gln
        755                 760                 765

Pro Leu Pro Val Phe Lys Val Glu Ser Arg Leu Asp Ser Asp Gln Gln
    770                 775                 780

His Ser Leu Gln Ala His Pro Ser Thr Pro Val
785                 790                 795
```

<210> SEQ ID NO 113
<211> LENGTH: 99
<212> TYPE: PRT
<213> ORGANISM: Mus musculus

<400> SEQUENCE: 113

```
Met Tyr Gly Asp Phe Glu Glu Ala Phe Asp His Leu Gln Asn Arg Leu
  1               5                  10                  15

Ile Ala Thr Lys Asn Pro Glu Glu Ile Arg Gly Gly Gly Leu Leu Lys
                20                  25                  30

Tyr Ser Asn Leu Leu Val Arg Asp Phe Arg Pro Ala Asp Gln Glu Glu
            35                  40                  45

Ile Lys Thr Leu Glu Arg Tyr Met Cys Ser Arg Phe Phe Ile Asp Phe
        50                  55                  60

Pro Asp Ile Leu Glu Gln Gln Arg Lys Leu Glu Thr Tyr Leu Gln Asn
 65                  70                  75                  80

His Phe Ser Asp Glu Glu Arg Ser Lys Tyr Asp Tyr Leu Met Ile Leu
                85                  90                  95

Arg Arg Leu
```

<210> SEQ ID NO 114
<211> LENGTH: 151
<212> TYPE: PRT
<213> ORGANISM: Mus musculus

<400> SEQUENCE: 114

```
Met Glu Pro Glu Ser Ile Glu Ile Cys Pro Tyr Asn Pro His His Arg
  1               5                  10                  15

Ile Pro Leu Ser Arg Phe Gln Tyr His Leu Ala Ser Cys Arg Lys Lys
                20                  25                  30

Asn Pro Lys Lys Ala Lys Lys Met Ala Ser Cys Lys Tyr Asn Ala Cys
            35                  40                  45

His Val Val Pro Ile Arg Lys Leu Ala Glu His Glu Ala Thr Cys Val
        50                  55                  60

Asn Arg Ser Ser Val Glu Glu Glu Asp Thr Leu Gly Pro Leu Gln Val
 65                  70                  75                  80
```

```
Ser Leu Pro Gln Pro Gln Asn Gln Asp Thr Leu Gln Val Arg Trp Leu
                 85                  90                  95

Ser Asn Pro Asp Ile Trp Asn Val Asp Gly Ala Asn Cys His Pro Met
            100                 105                 110

Phe Val Leu Lys Ser Phe Val Pro Gln Lys Leu Val Cys Glu Ser Asp
        115                 120                 125

Ile Gln Glu Ser Arg Gly Gly Asp Gln Cys Pro Glu Asp Pro Gln Thr
    130                 135                 140

Arg Thr Arg Lys Ala Asn Phe
145                 150

<210> SEQ ID NO 115
<211> LENGTH: 177
<212> TYPE: PRT
<213> ORGANISM: Mus musculus
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid

<400> SEQUENCE: 115

Asn Thr Arg Ala Ile Ser Xaa Leu Xaa Xaa Ala His Ser Arg Ser Arg
1               5                   10                  15

Leu Glu Ser Gly Tyr His Gln His Ser Pro Glu Thr Tyr Ile Pro Tyr
            20                  25                  30

Phe Lys Asn His Asn Val Thr Thr Ile Ile Arg Leu Asn Lys Arg Met
        35                  40                  45

Tyr Asp Ala Lys Arg Phe Thr Asp Ala Gly Phe Asp His His Asp Leu
    50                  55                  60

Phe Phe Pro Asp Gly Ser Thr Pro Ala Glu Ser Ile Val Gln Glu Phe
65                  70                  75                  80

Leu Asp Ile Cys Glu Asn Val Lys Gly Ala Ile Ala Val His Cys Lys
                85                  90                  95

Ala Gly Leu Gly Arg Thr Gly Thr Leu Ile Gly Cys Tyr Leu Met Lys
            100                 105                 110

His Tyr Arg Met Thr Ala Ala Glu Ser Ile Ala Trp Leu Arg Ile Cys
        115                 120                 125

Arg Pro Gly Ser Val Ile Gly Pro Gln Gln Phe Leu Val Met Lys
    130                 135                 140

Gln Ser Ser Leu Trp Leu Glu Gly Asp Tyr Phe Arg Gln Lys Leu Xaa
145                 150                 155                 160

Gly Gln Glu Met Ala Pro Ser Glu Lys Pro Ser Pro Thr Pro Phe Gly
                165                 170                 175

Cys

<210> SEQ ID NO 116
<211> LENGTH: 143
<212> TYPE: PRT
<213> ORGANISM: Mus musculus

<400> SEQUENCE: 116
```

```
Met Ala Lys Pro Leu Trp Leu Ser Leu Ile Leu Phe Ile Ile Pro Val
  1               5                  10                  15

Ala Leu Ala Val Gly Val Asp Gln Ser Lys Asn Glu Val Lys Ala Gln
             20                  25                  30

Asn Tyr Phe Gly Ser Ile Asn Ile Ser Asn Ala Asn Val Lys Gln Cys
         35                  40                  45

Val Trp Phe Ala Met Lys Glu Tyr Asn Lys Glu Ser Glu Asp Lys Tyr
 50                  55                  60

Val Phe Leu Val Asp Lys Ile Leu His Ala Lys Leu Gln Ile Thr Asp
 65                  70                  75                  80

Arg Met Glu Tyr Gln Ile Asp Val Gln Ile Ser Arg Ser Asn Cys Lys
                 85                  90                  95

Lys Pro Leu Asn Asn Thr Glu Asn Cys Ile Pro Gln Lys Lys Pro Glu
             100                 105                 110

Leu Glu Lys Lys Met Ser Cys Ser Phe Leu Val Gly Ala Leu Pro Trp
         115                 120                 125

Asn Gly Glu Phe Asn Leu Leu Ser Lys Glu Cys Lys Asp Val Ala
130                 135                 140

<210> SEQ ID NO 117
<211> LENGTH: 119
<212> TYPE: PRT
<213> ORGANISM: Mus musculus
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid

<400> SEQUENCE: 117

Met Thr Arg Val Pro Arg Thr Glu Ser Cys Ser Ser Tyr Ala Ser Ser
  1               5                  10                  15

Arg Arg Pro Ser Ser Gly Thr Glu Leu Thr Ser Ser Asp Ile Ser Leu
             20                  25                  30

Met Arg Glu Met Asp Ile Lys Asp Phe Cys Thr His Glu Val Glu Pro
         35                  40                  45

Met Ala Met Glu Cys Asp His Val Gln Ile Thr Ala Cys Arg Gly Thr
 50                  55                  60

Gln His Cys Ser Ala Gly Arg Val Arg Arg Asp Gly Asn Ala Leu
 65                  70                  75                  80

Tyr His Met Cys Ser Arg Gly Cys Xaa Leu Ser Val Tyr Leu Leu Tyr
                 85                  90                  95

Lys Thr Ser Thr Thr Cys Phe Asn Ala Ala Glu Lys Thr Glu Xaa
             100                 105                 110

Phe Trp Ala Met Trp Arg Arg
         115

<210> SEQ ID NO 118
<211> LENGTH: 206
<212> TYPE: PRT
<213> ORGANISM: Mus musculus

<400> SEQUENCE: 118

Arg Ala Val Leu Glu Gln Leu Asp Ser Ser Lys Ala Ser Trp Ala Trp
  1               5                  10                  15

Leu Gln Arg Arg Gly Leu Ile Pro Ala Val Gln Gly Arg Gln Thr Gly
```

-continued

```
                20                  25                  30
Leu Lys Cys His Pro Leu Cys Ser Asn Ser Pro Ile Cys Ile Ala
             35                  40                  45
Arg Leu Ala Ile Glu Arg Glu Arg His Gly Arg Asp Ser Gly Glu Ile
 50                  55                  60
Arg Arg Leu Leu Asn Ser Leu Asp Cys Lys Gln Asp Glu Tyr Thr Arg
 65                  70                  75                  80
Ser Met Ile Leu His Asn Ile Thr Arg Cys Val Tyr Leu Leu Glu Ala
                 85                  90                  95
Glu Ala Ser Ser Cys Thr Met Asp Asp Ile Asp Leu Val Ala Asp Met
            100                 105                 110
Leu Asp Glu Lys Asp Asn Ser Val Lys Ile Gln Ala Leu Asn Ala Leu
            115                 120                 125
Lys Ala Phe Ser Gly Ile Arg Lys Phe Arg Leu Lys Ile Gln Glu His
            130                 135                 140
Cys Ile Lys Val Leu Glu Leu Ile Ser Thr Ile Trp Asp Leu Glu Leu
145                 150                 155                 160
His Val Ala Gly Leu Arg Leu Leu Asn Asn Leu Pro Leu Pro Asp Tyr
                165                 170                 175
Val His Pro Gln Leu Arg Arg Val Met Pro Ala Leu Met Glu Ile Ile
            180                 185                 190
Gln Ser Asp Cys Ile Leu Ala Gln Tyr Lys Leu Ser Ala Ser
            195                 200                 205
```

<210> SEQ ID NO 119
<211> LENGTH: 137
<212> TYPE: PRT
<213> ORGANISM: Mus musculus

<400> SEQUENCE: 119

```
Met Leu Tyr Pro Glu Tyr His Lys Val Gln Gln Met Met Arg Asp Gln
 1               5                  10                  15
Ser Ile Leu Ser Pro Ser Pro Tyr Glu Gly Tyr Arg Ser Leu Pro Glu
                20                  25                  30
His Gln Pro Leu Leu Phe Lys Glu Asp His Gln Ala Val Phe Gln Asp
            35                  40                  45
Pro Gln Gly Gly Gln Gln Leu Phe Gly Val Ser Met Val Leu Val Leu
 50                  55                  60
Ile Gly Ser His Pro Asp Leu Ser Tyr Leu Pro Arg Ala Gly Ala Asp
 65                  70                  75                  80
Leu Val Ile Asp Pro Asp Gln Pro Leu Ser Pro Lys Arg Asn Pro Ile
                 85                  90                  95
Asp Val Asp Pro Phe Thr His Glu Ser Thr His Gln Glu Gly Leu Tyr
            100                 105                 110
Ala Leu Gly Pro Leu Ala Gly Asp Asn Phe Val Arg Phe Val Gln Gly
            115                 120                 125
Gly Ala Trp Leu Leu Pro Ala Pro Cys
            130                 135
```

<210> SEQ ID NO 120
<211> LENGTH: 130
<212> TYPE: PRT
<213> ORGANISM: Mus musculus

<400> SEQUENCE: 120

Met Glu Thr Leu Pro Pro Pro Lys Gln Glu Thr Lys Lys Gly His Asn

-continued

```
                1               5                  10                  15
Gly Ser Lys Arg Ala Gln Pro Pro Ile Thr Gly Lys Val Ser His Leu
                    20                  25                  30

Gly Cys Leu Thr Ile Asn Tyr Asp Ala Ile Glu Gln Pro Leu Leu Leu
                    35                  40                  45

Leu Gln Gly Ile Cys Ser Asn Leu Gly Leu Glu Leu Gly Val Asn Phe
                    50                  55                  60

His Leu Ala Ile Asn Cys Ala Gly His Glu Leu Met Asp Tyr Ser Lys
 65                 70                  75                  80

Gly Lys Tyr Glu Val Met Val Gly Thr His Lys Ser Ala Leu Lys Met
                    85                  90                  95

Val Glu Leu Tyr Val Asp Leu Ile Asn Lys Tyr Pro Ser Ile Ile Ala
                    100                 105                 110

Leu Ile Asp Pro Phe Arg Lys Glu Ala Pro Leu Pro Gly Val Ser Leu
                    115                 120                 125

Asn Ser
    130

<210> SEQ ID NO 121
<211> LENGTH: 113
<212> TYPE: PRT
<213> ORGANISM: Mus musculus

<400> SEQUENCE: 121

Met Ser Asp Leu Val Glu Ile Thr His Leu Ile Asn Gly Lys Lys Leu
 1               5                  10                  15

Leu Ala Val Phe Gly Ser Thr Asp Ser Glu Ser Ser Asp Asp Ser Leu
                    20                  25                  30

Val Asp Leu Ala Val Gly Phe Gly Ala Arg Phe Ile Lys Leu Gly Gly
                    35                  40                  45

Leu Ser Arg Gly Glu Arg Met Thr Lys Tyr Asn Arg Leu Leu Ala Ile
                    50                  55                  60

Glu Glu Glu Leu Ile Gln Arg Gly Val Trp Gly Phe Ser Glu Glu His
 65                 70                  75                  80

Asn Phe Ser Phe Phe Gln Glu Asp Ala Thr Ala Thr Met Ala Glu Glu
                    85                  90                  95

Leu Leu Gly Ser Trp Thr Pro Ser Ser His Arg Gly Asp Arg Gly Ile
                    100                 105                 110

Gly

<210> SEQ ID NO 122
<211> LENGTH: 699
<212> TYPE: PRT
<213> ORGANISM: Mus musculus

<400> SEQUENCE: 122

Met Glu Val His Glu Leu Phe Arg Tyr Phe Arg Met Pro Glu Leu Ile
 1               5                  10                  15

Asp Ile Arg Gln Tyr Val Arg Thr Leu Pro Thr Asn Thr Leu Met Gly
                    20                  25                  30

Phe Gly Ala Phe Ala Ala Leu Thr Thr Phe Trp Tyr Ala Thr Arg Pro
                    35                  40                  45

Lys Ala Leu Lys Pro Pro Cys Asp Leu Ser Met Gln Ser Val Glu Ile
                    50                  55                  60

Ala Gly Thr Thr Asp Gly Ile Arg Arg Ser Ala Val Leu Glu Asp Asp
 65                 70                  75                  80
```

-continued

```
Lys Leu Leu Val Tyr Tyr Asp Asp Val Arg Thr Met Tyr Asp Gly
                 85                  90                  95
Phe Gln Arg Gly Ile Gln Val Ser Asn Asn Gly Pro Cys Leu Gly Ser
            100                 105                 110
Arg Lys Pro Asn Gln Pro Tyr Glu Trp Ile Ser Tyr Lys Glu Val Ala
        115                 120                 125
Glu Leu Ala Glu Cys Ile Gly Ser Gly Leu Ile Gln Lys Gly Phe Lys
    130                 135                 140
Pro Cys Ser Glu Gln Phe Ile Gly Leu Phe Ser Gln Asn Arg Pro Glu
145                 150                 155                 160
Trp Val Ile Val Glu Gln Gly Cys Phe Ser Tyr Ser Met Val Val
                165                 170                 175
Pro Leu Tyr Asp Thr Leu Gly Ala Asp Ala Ile Thr Tyr Ile Val Asn
            180                 185                 190
Lys Ala Glu Leu Ser Val Ile Phe Ala Asp Lys Pro Glu Lys Ala Lys
        195                 200                 205
Leu Leu Leu Glu Gly Val Glu Asn Lys Leu Thr Pro Cys Leu Lys Ile
    210                 215                 220
Ile Val Ile Met Asp Ser Tyr Gly Ser Asp Leu Val Glu Arg Gly Lys
225                 230                 235                 240
Lys Cys Gly Val Glu Ile Ile Ser Leu Lys Ala Leu Glu Asp Leu Gly
                245                 250                 255
Arg Val Asn Arg Val Lys Pro Lys Pro Pro Glu Pro Glu Asp Leu Ala
            260                 265                 270
Ile Ile Cys Phe Thr Ser Gly Thr Thr Gly Asn Pro Lys Gly Ala Met
        275                 280                 285
Ile Thr His Gln Asn Ile Ile Asn Asp Cys Ser Gly Phe Ile Lys Ala
    290                 295                 300
Thr Glu Ser Ala Phe Ile Ala Ser Thr Asp Asp Val Leu Ile Ser Phe
305                 310                 315                 320
Leu Pro Leu Ala His Met Phe Glu Thr Val Val Glu Cys Val Met Leu
                325                 330                 335
Cys His Gly Ala Lys Ile Gly Phe Phe Gln Gly Asp Ile Arg Leu Leu
            340                 345                 350
Met Asp Asp Leu Lys Val Leu Gln Pro Thr Ile Phe Pro Val Val Pro
        355                 360                 365
Arg Leu Leu Asn Arg Met Phe Asp Arg Ile Phe Gly Gln Ala Asn Thr
    370                 375                 380
Ser Leu Lys Arg Trp Leu Leu Asp Phe Ala Ser Lys Arg Lys Glu Ala
385                 390                 395                 400
Asp Val Arg Ser Gly Ile Val Arg Asn Asn Ser Leu Trp Asp Lys Leu
                405                 410                 415
Ile Phe His Lys Ile Gln Ser Ser Leu Gly Gly Lys Val Arg Leu Met
            420                 425                 430
Ile Thr Gly Ala Ala Pro Val Ser Ala Thr Val Leu Thr Phe Leu Arg
        435                 440                 445
Thr Ala Leu Gly Cys Gln Phe Tyr Glu Gly Tyr Gly Gln Thr Glu Cys
    450                 455                 460
Thr Ala Gly Cys Cys Leu Ser Leu Pro Gly Asp Trp Thr Ala Gly His
465                 470                 475                 480
Val Gly Ala Pro Met Pro Cys Asn Tyr Val Lys Leu Val Asp Val Glu
                485                 490                 495
```

-continued

```
Glu Met Asn Tyr Leu Ala Ser Lys Gly Glu Gly Val Cys Val Lys
            500                 505                 510
Gly Ala Asn Val Phe Lys Gly Tyr Leu Lys Asp Pro Ala Arg Thr Ala
        515                 520                 525
Glu Ala Leu Asp Lys Asp Gly Trp Leu His Thr Gly Asp Ile Gly Lys
    530                 535                 540
Trp Leu Pro Asn Gly Thr Leu Lys Ile Ile Asp Arg Lys Lys His Ile
545                 550                 555                 560
Phe Lys Leu Ala Gln Gly Glu Tyr Ile Ala Pro Glu Lys Ile Glu Asn
                565                 570                 575
Ile Tyr Leu Arg Ser Glu Ala Val Ala Gln Val Phe Val His Gly Glu
            580                 585                 590
Ser Leu Gln Ala Phe Leu Ile Ala Val Val Pro Asp Val Glu Ser
        595                 600                 605
Leu Pro Ser Trp Ala Gln Lys Arg Gly Leu Gln Gly Ser Phe Glu Glu
    610                 615                 620
Leu Cys Arg Asn Lys Asp Ile Asn Lys Ala Ile Leu Asp Asp Leu Leu
625                 630                 635                 640
Lys Leu Gly Lys Glu Ala Gly Leu Lys Pro Phe Glu Gln Val Lys Gly
                645                 650                 655
Ile Ala Val His Pro Glu Leu Phe Ser Ile Asp Asn Gly Leu Leu Thr
            660                 665                 670
Pro Thr Leu Lys Ala Lys Arg Pro Glu Leu Arg Asn Tyr Phe Arg Ser
        675                 680                 685
Gln Ile Asp Glu Leu Tyr Ala Thr Ile Lys Ile
    690                 695

<210> SEQ ID NO 123
<211> LENGTH: 627
<212> TYPE: PRT
<213> ORGANISM: Mus musculus

<400> SEQUENCE: 123

Met Glu Gly Leu Ala Gly Tyr Val Tyr Lys Ala Ala Ser Glu Gly Lys
  1               5                  10                  15
Val Leu Thr Leu Ala Ala Leu Leu Asn Arg Ser Glu Ser Asp Ile
            20                  25                  30
Arg Tyr Leu Leu Gly Tyr Val Ser Gln Gln Gly Gly Gln Arg Ser Thr
        35                  40                  45
Pro Leu Ile Ile Ala Ala Arg Asn Gly His Ala Lys Val Val Arg Leu
    50                  55                  60
Leu Leu Glu His Tyr Arg Val Gln Thr Gln Thr Gly Thr Val Arg
65                  70                  75                  80
Phe Asp Gly Tyr Val Ile Asp Gly Ala Thr Ala Leu Trp Cys Ala Ala
                85                  90                  95
Gly Ala Gly His Phe Glu Val Val Lys Leu Leu Val Ser His Gly Ala
            100                 105                 110
Asn Val Asn His Thr Thr Val Thr Asn Ser Thr Pro Leu Arg Ala Ala
        115                 120                 125
Cys Phe Asp Gly Arg Leu Asp Ile Val Lys Tyr Leu Val Glu Asn Asn
    130                 135                 140
Ala Asn Ile Ser Ile Ala Asn Lys Tyr Asp Asn Thr Cys Leu Met Ile
145                 150                 155                 160
Ala Ala Tyr Lys Gly His Thr Asp Val Val Arg Tyr Leu Leu Glu Gln
                165                 170                 175
```

-continued

Arg Ala Asp Pro Asn Ala Lys Ala His Cys Gly Ala Thr Ala Leu His
            180                 185                 190

Phe Ala Ala Glu Ala Gly His Ile Asp Ile Val Lys Glu Leu Ile Lys
            195                 200                 205

Trp Arg Ala Ala Ile Val Val Asn Gly His Gly Met Thr Pro Leu Lys
        210                 215                 220

Val Ala Ala Glu Ser Cys Lys Ala Asp Val Val Glu Leu Leu Leu Ser
225                 230                 235                 240

His Ala Asp Cys Asp Arg Arg Ser Arg Ile Glu Ala Leu Glu Leu Leu
                    245                 250                 255

Gly Ala Ser Phe Ala Asn Asp Arg Glu Asn Tyr Asp Ile Met Lys Thr
                260                 265                 270

Tyr His Tyr Leu Tyr Leu Ala Met Leu Glu Arg Phe Gln Asp Gly Asp
            275                 280                 285

Asn Ile Leu Glu Lys Glu Val Leu Pro Pro Ile His Ala Tyr Gly Asn
        290                 295                 300

Arg Thr Glu Cys Arg Asn Pro Gln Glu Leu Glu Ala Ile Arg Gln Asp
305                 310                 315                 320

Arg Asp Ala Leu His Met Glu Gly Leu Ile Val Arg Glu Arg Ile Leu
                    325                 330                 335

Gly Ala Asp Asn Ile Asp Val Ser His Pro Ile Ile Tyr Arg Gly Ala
                340                 345                 350

Val Tyr Ala Asp Asn Met Glu Phe Glu Gln Cys Ile Lys Leu Trp Leu
            355                 360                 365

His Ala Leu His Leu Arg Gln Lys Gly Asn Arg Asn Thr His Lys Asp
        370                 375                 380

Leu Leu Arg Phe Ala Gln Val Phe Ser Gln Met Ile His Leu Asn Glu
385                 390                 395                 400

Ala Val Lys Ala Pro Asp Ile Glu Cys Val Leu Arg Cys Ser Val Leu
                    405                 410                 415

Glu Ile Glu Gln Ser Met Asn Arg Val Lys Asn Ile Ser Asp Ala Asp
                420                 425                 430

Val His Ser Ala Met Asp Asn Tyr Glu Cys Asn Leu Tyr Thr Phe Leu
            435                 440                 445

Tyr Leu Val Cys Ile Ser Thr Lys Thr Gln Cys Ser Glu Glu Asp Gln
        450                 455                 460

Cys Arg Ile Asn Lys Gln Ile Tyr Asn Leu Ile His Leu Asp Pro Arg
465                 470                 475                 480

Thr Arg Glu Gly Phe Ser Leu Leu His Leu Ala Val Asn Ser Asn Thr
                    485                 490                 495

Pro Val Asp Asp Phe His Thr Asn Asp Val Cys Ser Phe Pro Asn Ala
                500                 505                 510

Leu Val Thr Lys Leu Leu Leu Asp Cys Gly Ala Glu Val Asn Ala Val
            515                 520                 525

Asp Asn Glu Gly Asn Ser Ala Leu His Ile Ile Val Gln Tyr Asn Arg
        530                 535                 540

Pro Ile Ser Asp Phe Leu Thr Leu His Ser Ile Ile Ile Ser Leu Val
545                 550                 555                 560

Glu Ala Gly Ala His Thr Asp Met Thr Asn Lys Gln Asn Lys Thr Pro
                    565                 570                 575

Leu Asp Lys Ser Thr Thr Gly Val Ser Glu Ile Leu Leu Lys Thr Gln
                580                 585                 590

```
Met Lys Met Ser Leu Lys Cys Leu Ala Ala Arg Ala Val Arg Ala Asn
        595                 600                 605
Asp Ile Asn Tyr Gln Asp Gln Ile Pro Arg Thr Leu Glu Glu Phe Val
        610                 615                 620
Gly Phe His
625

<210> SEQ ID NO 124
<211> LENGTH: 849
<212> TYPE: PRT
<213> ORGANISM: Mus musculus

<400> SEQUENCE: 124

Met Ile Ala Tyr Cys Gly Thr Thr Met Ser Asp Asp Ile Asp Trp
 1               5                  10                  15
Leu His Ser Arg Arg Gly Val Cys Lys Val Asp Leu Tyr Ser Pro Lys
                20                  25                  30
Gly Gln Gln Asp Gln Asp Arg Lys Val Ile Cys Phe Val Asp Val Ser
            35                  40                  45
Thr Leu Asn Val Glu Asp Lys Asp Ser Lys Gly Ala Ala Gly Ser Arg
        50                  55                  60
Ser Glu Gly Glu Leu Asn Leu Glu Thr Leu Glu Glu Lys Glu Ile Ile
 65                  70                  75                  80
Val Ile Lys Asp Thr Glu Lys Gln Asp Gln Ser Lys Thr Glu Gly Ser
                85                  90                  95
Val Cys Leu Phe Lys Gln Ala Pro Ser Asp Pro Ile Ser Val Leu Asn
            100                 105                 110
Trp Leu Leu Asn Asp Leu Gln Lys Tyr Ala Leu Gly Phe Gln His Ala
        115                 120                 125
Leu Ser Pro Ser Ala Ser Ser Cys Lys His Lys Val Gly Asp Leu Glu
    130                 135                 140
Gly Asp Tyr Ser Lys Ile Pro Ser Glu Asn Cys Tyr Ser Val Tyr Ala
145                 150                 155                 160
Asp Gln Val Asn Phe Asp Tyr Leu Asn Lys Gly Pro Gln Asn Leu Arg
                165                 170                 175
Leu Glu Met Ala Ala Ser Lys Asn Thr Asn Asn Gln Ser Pro Ser
            180                 185                 190
Asn Pro Ala Thr Lys Ser Pro Ser Asn Gln Arg Ser Val Ala Thr Pro
        195                 200                 205
Glu Gly Glu Cys Ser Met Asp Asp Leu Ser Phe Tyr Val Asn Arg Leu
    210                 215                 220
Ser Ser Leu Val Ile Gln Met Ala Arg Lys Glu Ile Lys Asp Lys Leu
225                 230                 235                 240
Glu Gly Gly Ser Lys Cys Leu His His Ser Met Tyr Thr Ser Gly Asp
                245                 250                 255
Lys Gly Lys Thr Ser Pro Arg Ser Ala Val Ser Lys Ile Ala Ser Glu
            260                 265                 270
Met Ala His Glu Ala Val Glu Leu Thr Ser Ser Glu Met Arg Gly Asn
        275                 280                 285
Gly Glu Asp Cys Arg Asp Gly Arg Lys Thr Phe Leu Tyr Ser Glu Met
    290                 295                 300
Cys Asn Lys Asn Lys Cys Gly Glu Lys Gln Gln Met Cys Pro Lys Asp
305                 310                 315                 320
Ser Lys Glu Phe Ala Asp Ser Ile Ser Lys Gly Leu Met Val Tyr Ala
                325                 330                 335
```

-continued

```
Asn Gln Val Ala Ser Asp Met Met Val Ser Val Met Lys Thr Leu Lys
                340                 345                 350

Val His Ser Cys Gly Lys Pro Ile Pro Ala Cys Val Val Leu Lys Arg
                355                 360                 365

Val Leu Leu Lys His Thr Lys Glu Ile Val Ser Asp Leu Ile Asp Ser
                370                 375                 380

Cys Met Lys Asn Leu His Asn Ile Thr Gly Val Leu Met Thr Asp Ser
385                 390                 395                 400

Asp Phe Val Ser Ala Val Lys Arg Asn Leu Phe Asn His Gly Lys Gln
                405                 410                 415

Asn Ala Ala Asp Ile Met Glu Ala Met Leu Lys Arg Leu Val Ser Ala
                420                 425                 430

Leu Leu Gly Glu Lys Lys Glu Thr Lys Ser Gln Ser Leu Ala Tyr Ala
                435                 440                 445

Thr Leu Lys Ala Gly Thr Asn Asp Pro Lys Cys Lys Asn Gln Ser Leu
                450                 455                 460

Glu Phe Ser Ala Met Lys Ala Glu Met Lys Gly Lys Asp Lys Cys Lys
465                 470                 475                 480

Ser Lys Ala Asp Pro Cys Cys Lys Ser Leu Thr Ser Ala Glu Arg Val
                485                 490                 495

Ser Glu His Ile Leu Lys Glu Ser Leu Thr Met Trp Asn Asn Gln Lys
                500                 505                 510

Gln Gly Asn Gln Gly Lys Val Thr Asn Lys Val Cys Cys Thr Ser Lys
                515                 520                 525

Asp Glu Lys Arg Glu Lys Ile Ser Pro Ser Thr Asp Ser Leu Ala Lys
                530                 535                 540

Asp Leu Ile Val Ser Ala Leu Met Leu Ile Gln Tyr His Leu Thr Gln
545                 550                 555                 560

Gln Ala Lys Gly Lys Asp Pro Cys Glu Glu Cys Pro Gly Ser Ser
                565                 570                 575

Met Gly Tyr Met Ser Gln Ser Ala Gln Tyr Glu Lys Cys Gly Gly Gly
                580                 585                 590

Gln Ser Ser Lys Ser Leu Ser Met Lys His Phe Glu Thr Arg Gly Ala
                595                 600                 605

Pro Gly Pro Ser Thr Cys Met Lys Glu Asn Gln Leu Glu Ser Gln Lys
                610                 615                 620

Met Asp Met Ser Asn Met Val Leu Ser Leu Ile Gln Lys Leu Leu Ser
625                 630                 635                 640

Glu Ser Pro Phe Ser Cys Asp Glu Leu Thr Glu Ser Asp Asn Lys Arg
                645                 650                 655

Cys Cys Asp Pro Arg Ser Ser Lys Ala Ala Pro Met Ala Lys Arg Pro
                660                 665                 670

Glu Glu Gln Cys Gln Asp Asn Ala Glu Leu Asp Phe Ile Ser Gly Met
                675                 680                 685

Lys Gln Met Asn Arg Gln Phe Ile Asp Gln Leu Val Glu Ser Val Met
                690                 695                 700

Lys Leu Cys Leu Ile Met Ala Lys Tyr Ser Asn Asn Gly Ala Ala Leu
705                 710                 715                 720

Ala Glu Leu Glu Glu Gln Ala Ala Leu Val Gly Ser Gly Ser Arg Cys
                725                 730                 735

Gly Arg Asp Ala Met Met Ser Gln Asn Tyr Ser Glu Thr Pro Gly Pro
                740                 745                 750
```

Glu Val Ile Val Asn Asn Gln Cys Ser Thr Thr Asn Leu Gln Lys Gln
            755                 760                 765

Leu Gln Ala Val Leu Gln Trp Ile Ala Ala Ser Gln Phe Asn Val Pro
        770                 775                 780

Met Leu Tyr Phe Met Gly Asp Asp Gly Gln Leu Glu Lys Leu Pro
785                 790                 795                 800

Glu Val Ser Ala Lys Ala Ala Glu Lys Gly Tyr Ser Val Gly Asp Leu
                805                 810                 815

Leu Gln Glu Val Met Lys Phe Ala Lys Glu Arg Gln Leu Asp Glu Ala
            820                 825                 830

Val Gly Asn Met Ala Arg Lys Gln Leu Leu Asp Trp Leu Leu Ala Asn
        835                 840                 845

Leu

<210> SEQ ID NO 125
<211> LENGTH: 184
<212> TYPE: PRT
<213> ORGANISM: Mus musculus
<220> FEATURE:
<221> NAME/KEY: misc_feature
<222> LOCATION: (52)..(52)
<223> OTHER INFORMATION: Xaa can be any naturally occurring amino acid

<400> SEQUENCE: 125

Met Ser Thr Cys Pro Leu Pro Thr Cys Tyr Glu Ser Lys Asp Leu Thr
1               5                   10                  15

Ser Leu Tyr Asp Val Gln Ser Phe Pro Lys Ile Thr Asp Thr Lys Lys
            20                  25                  30

Thr Asp Asp Leu Tyr Trp Arg Gln Leu Glu Met Lys Pro Leu Pro Ile
        35                  40                  45

Ser Cys Ser Xaa Ser Asn His Tyr Ile Asp Tyr Glu Pro Leu Lys Ser
    50                  55                  60

Ala Tyr Arg Asp Pro Tyr Ala Met Cys Pro Asn Pro Val Arg Leu Ser
65                  70                  75                  80

Lys Ser Asn Ile Leu Gln Asn Lys Thr Asp Thr Ala Asp Phe Thr Phe
            85                  90                  95

Asp Asn Phe Leu Ser Lys Pro Glu Phe Leu Gly Met Asn Met Glu Ser
        100                 105                 110

Asn Glu Glu Thr Arg Pro Leu Leu Asp Trp Ile Pro Arg Ala Gly Val
    115                 120                 125

Pro Lys His His Ser Asn Leu Arg Asn Leu Arg Asn Thr Phe Ser Lys
130                 135                 140

Ser Met Ala Gln Lys Arg Leu His Asn Ser Ile Gln Glu Gln Lys
145                 150                 155                 160

Asp Leu Arg Asp Lys Leu Gln Cys Gly Met Arg His Gln Phe Phe Gly
            165                 170                 175

Tyr Asn Gly His His Phe Tyr Asn
            180

<210> SEQ ID NO 126
<211> LENGTH: 203
<212> TYPE: PRT
<213> ORGANISM: Mus musculus

<400> SEQUENCE: 126

Met Glu Leu Asp Gln Asp Lys Lys Lys Glu Thr Pro Glu Glu Thr Glu
1               5                   10                  15

```
Asn Val Asn Glu Val Gln Leu Glu Lys Gln Asn Gln Asp Glu Glu Thr
             20                  25                  30

Glu Ala Glu Ala Glu Ala Asp Lys Ala Ile Leu Glu Arg Ser Asp
         35                  40                  45

Ser Val Lys Thr Glu Cys Pro Pro Gln Ala Glu Lys Gln Asn Gln Asp
 50                  55                  60

Glu Glu Thr Glu Ala Glu Ala Glu Glu Ala Asp Lys Ala Ile Leu Glu
 65                  70                  75                  80

Arg Ser Asp Ser Val Lys Thr Glu Cys Pro Pro Gln Ala Glu Lys Gln
             85                  90                  95

Ile Gln Glu Glu Lys Cys Glu Thr Gln Glu Ala Asp Arg Ser Glu Gly
            100                 105                 110

Thr Glu Leu Gly Lys Leu His Ser Gln Leu Asp Gln Leu Pro Asp Asn
            115                 120                 125

Val Met Leu Ala Gly Val Lys Ile Gln Ala Trp Trp Arg Gly Thr Leu
        130                 135                 140

Val Arg Arg Thr Leu Leu Leu Ala Ala Leu Asn Ala Trp Thr Ile Gln
145                 150                 155                 160

Cys Trp Trp Arg Glu Ala Lys Ala Arg Leu Gln Gly Arg Lys Leu His
                165                 170                 175

Glu Val Met Arg Tyr Arg Leu Arg Asn Leu Asn Leu Lys Ser Ile Ser
            180                 185                 190

Lys Arg Lys Gln Pro Asn Gln Ser Ser Phe Leu
            195                 200

<210> SEQ ID NO 127
<211> LENGTH: 727
<212> TYPE: PRT
<213> ORGANISM: Mus musculus

<400> SEQUENCE: 127

Met Ala Phe Gln Lys Ala Val Lys Gly Thr Ile Leu Val Gly Gly Gly
 1               5                  10                  15

Ala Leu Ala Thr Val Leu Gly Leu Ser Gln Phe Ala His Tyr Arg Arg
             20                  25                  30

Lys Gln Val Ser Leu Ala Tyr Val Glu Ala Ala Gly Tyr Leu Thr Glu
         35                  40                  45

Pro Val Asn Arg Glu Pro Pro Ser Arg Glu Ala Gln Leu Met Thr Leu
 50                  55                  60

Lys Asn Thr Pro Glu Phe Asp Ile Leu Val Ile Gly Gly Gly Ala Thr
 65                  70                  75                  80

Gly Cys Gly Cys Ala Leu Asp Ala Val Thr Arg Gly Leu Lys Thr Ala
             85                  90                  95

Leu Val Glu Arg Asp Asp Phe Ser Ser Gly Thr Ser Ser Arg Ser Thr
            100                 105                 110

Lys Leu Ile His Gly Gly Val Arg Tyr Leu Gln Lys Ala Ile Met Asn
            115                 120                 125

Leu Asp Val Glu Gln Tyr Arg Met Val Lys Glu Ala Leu His Glu Arg
        130                 135                 140

Ala Asn Leu Leu Glu Ile Ala Pro His Leu Ser Ala Pro Val Pro Ile
145                 150                 155                 160

Met Leu Pro Leu Tyr Lys Trp Trp Gln Leu Pro Tyr Tyr Trp Val Gly
                165                 170                 175

Ile Lys Met Tyr Asp Leu Val Ala Gly Ser Gln Cys Leu Lys Ser Ser
            180                 185                 190
```

-continued

```
Tyr Val Leu Ser Lys Ser Arg Ala Leu Glu His Phe Pro Met Leu Gln
            195                 200                 205

Lys Asp Lys Leu Val Gly Ala Ile Val Tyr Asp Gly Gln His Asn
    210                 215                 220

Asp Ala Arg Met Asn Leu Ala Ile Ala Leu Thr Ala Ala Arg Tyr Gly
225                 230                 235                 240

Ala Ala Thr Ala Asn Tyr Met Glu Val Val Ser Leu Leu Lys Lys Thr
                245                 250                 255

Asp Pro Glu Thr Gly Lys Glu Arg Val Ser Gly Ala Arg Cys Lys Asp
            260                 265                 270

Val Leu Thr Gly Gln Glu Phe Asp Val Arg Ala Lys Cys Val Ile Asn
        275                 280                 285

Ala Ser Gly Pro Phe Thr Asp Ser Val Arg Lys Met Asp Asp Lys Asn
    290                 295                 300

Val Val Pro Ile Cys Gln Pro Ser Ala Gly Val His Ile Val Met Pro
305                 310                 315                 320

Gly Tyr Tyr Ser Pro Glu Asn Met Gly Leu Leu Asp Pro Ala Thr Ser
                325                 330                 335

Asp Gly Arg Val Ile Phe Phe Leu Pro Trp Glu Lys Met Thr Ile Ala
            340                 345                 350

Gly Thr Thr Asp Thr Pro Thr Asp Val Thr His His Pro Ile Pro Ser
        355                 360                 365

Glu Glu Asp Ile Asn Phe Ile Leu Asn Glu Val Arg Asn Tyr Leu Ser
    370                 375                 380

Ser Asp Val Glu Val Arg Arg Gly Asp Val Leu Ala Ala Trp Ser Gly
385                 390                 395                 400

Ile Arg Pro Leu Val Thr Asp Pro Lys Ser Ala Asp Thr Gln Ser Ile
                405                 410                 415

Ser Arg Asn His Val Val Asp Ile Ser Asp Ser Gly Leu Ile Thr Ile
            420                 425                 430

Ala Gly Gly Lys Trp Thr Thr Tyr Arg Ser Met Ala Glu Asp Thr Val
        435                 440                 445

Asp Ala Ala Val Lys Phe His Asn Leu Asn Ala Gly Pro Ser Arg Thr
    450                 455                 460

Val Gly Leu Phe Leu Gln Gly Gly Lys Asp Trp Ser Pro Thr Leu Tyr
465                 470                 475                 480

Ile Arg Leu Val Gln Asp Tyr Gly Leu Glu Ser Glu Val Ala Gln His
                485                 490                 495

Leu Ala Lys Thr Tyr Gly Asp Lys Ala Phe Glu Val Ala Lys Met Ala
            500                 505                 510

Ser Val Thr Gly Lys Arg Trp Pro Val Val Gly Val Arg Leu Val Ser
        515                 520                 525

Glu Phe Pro Tyr Ile Glu Ala Glu Val Lys Tyr Gly Ile Lys Glu Tyr
    530                 535                 540

Ala Cys Thr Ala Val Asp Met Ile Ser Arg Arg Thr Arg Leu Ala Phe
545                 550                 555                 560

Leu Asn Val Gln Ala Ala Glu Glu Ala Leu Pro Arg Ile Val Glu Leu
                565                 570                 575

Met Gly Arg Glu Leu Asp Trp Ser Glu Leu Arg Lys Gln Glu Glu Leu
            580                 585                 590

Gly Thr Ala Thr Arg Phe Leu Tyr Tyr Glu Met Gly Tyr Lys Ser Arg
        595                 600                 605
```

```
Thr Glu Gln Leu Thr Asp Ser Thr Glu Ile Ser Leu Leu Pro Ser Asp
            610                 615                 620

Ile Asp Arg Tyr Lys Lys Arg Phe His Lys Phe Asp Glu Asp Glu Lys
625                 630                 635                 640

Gly Phe Ile Thr Ile Val Asp Val Gln Arg Val Leu Glu Ser Ile Asn
                645                 650                 655

Val Gln Met Asp Glu Asn Thr Leu His Glu Ile Leu Cys Glu Val Asp
            660                 665                 670

Leu Asn Lys Asn Gly Gln Val Glu Leu His Glu Phe Leu Gln Leu Met
        675                 680                 685

Ser Ala Val Gln Lys Gly Arg Val Ser Gly Ser Arg Leu Ala Ile Leu
    690                 695                 700

Met Lys Thr Ala Glu Glu Asn Leu Asp Arg Arg Val Pro Ile Pro Val
705                 710                 715                 720

Asp Arg Ser Cys Gly Gly Leu
                725

<210> SEQ ID NO 128
<211> LENGTH: 668
<212> TYPE: PRT
<213> ORGANISM: Mus musculus

<400> SEQUENCE: 128

Met Asp Lys Tyr Asp Asp Leu Gly Leu Glu Ala Ser Lys Phe Ile Glu
1               5                   10                  15

Asp Leu Asn Met Tyr Glu Ala Ser Lys Asp Gly Leu Phe Arg Val Asp
            20                  25                  30

Lys Gly Ala Gly Asn Asn Pro Glu Phe Glu Glu Thr Arg Arg Val Phe
        35                  40                  45

Ala Thr Lys Met Ala Lys Ile His Leu Gln Gln Gln Gln Gln Gln Gln
    50                  55                  60

Leu Leu Gln Glu Glu Ala Leu Pro Arg Ala Gly Arg Ser Pro Val Asn
65                  70                  75                  80

Gly Gly Asn Arg Gln Gly Ala Ser Gly Lys Leu Ala Ala Asp Gly Ala
                85                  90                  95

Ala Lys Pro Pro Leu Ala Val Pro Thr Val Ala Pro Gly Leu Ala Thr
            100                 105                 110

Thr Thr Ala Ala Ala Gln Pro Ser Tyr Pro Ser Gln Glu Gln Arg Ile
        115                 120                 125

Arg Pro Ser Ala His Gly Ala Arg Pro Gly Ser Gln Asn Cys Gly Ser
    130                 135                 140

Arg Glu Gly Pro Val Ser Ser Gln Arg Pro Ala Leu His Gly Leu Ser
145                 150                 155                 160

Pro Ser Cys Glu Asp Pro Ser Cys Leu Thr His Gly Asp Tyr Tyr Asp
                165                 170                 175

Asn Phe Ser Leu Ala Ser Pro Gln Trp Gly Asp Lys Pro Glu Gly Cys
            180                 185                 190

Pro Ser Val Ser Leu Gly Val Gly Ser Gly Trp Pro Gly Cys Pro Gly
        195                 200                 205

Asn Asp Ser Thr Leu Pro Lys Ser Cys Gly Asp His His Pro Tyr Gln
    210                 215                 220

Pro Gln Leu Ser Thr Val Cys Ser Gly Arg Ser Phe Glu Ser Gly Ile
225                 230                 235                 240

Ser Gly Gln Asp Gly Gly Ile Gly Gly His Ser Ser Glu Lys Pro Thr
                245                 250                 255
```

```
Gly Leu Trp Ser Thr Ala Ser Ser Gln Arg Val Asn Leu Gly Phe Ser
            260                 265                 270

Ser Met Gly Leu Glu Asn Gly Thr Ser Ala Gln Pro Lys Gly Thr Thr
        275                 280                 285

Val Ser Ala Pro Met Val Pro Ser Ser Ala Ser Gln Gly Ala Cys Pro
        290                 295                 300

Lys Arg Asp Ser Gly Leu Gly Tyr Glu Ala Ser Gly Arg Val Phe Lys
305                 310                 315                 320

Pro Leu Val Asp Thr Gln Pro Trp Leu Gln Asp Gly Pro Lys Ser Tyr
                325                 330                 335

Leu Ser Val Ser Ala Pro Leu Ser Ser Thr Ala Gly Lys Asp Ser Thr
            340                 345                 350

Gln Pro Gly Met Thr Thr Gly Leu Asp Pro Lys Phe Gly Cys Val Glu
        355                 360                 365

Ser Gly Thr Ser Pro Lys Pro Ser Pro Thr Ser Asn Val His Pro Val
        370                 375                 380

Met Ser Thr Pro Ser Glu Leu Ser Cys Lys Glu Ser Ser Pro Ser Trp
385                 390                 395                 400

Ser Thr Asp Ser Ser Leu Glu Pro Val Leu Pro Gly Ser Pro Thr Pro
                405                 410                 415

Ser Arg Val Arg Leu Pro Cys Gln Thr Leu Ala Pro Gly Pro Glu Leu
            420                 425                 430

Gly Pro Ser Thr Ala Glu Leu Lys Leu Glu Ala Leu Thr Gln Arg Leu
        435                 440                 445

Glu Arg Glu Met Asp Ala His Pro Lys Ala Asp Tyr Phe Gly Ser Cys
450                 455                 460

Val Lys Cys Ser Lys Gly Val Phe Gly Ala Gly Gln Ala Cys Gln Ala
465                 470                 475                 480

Met Gly Asp Leu Tyr His Asn Ala Cys Phe Thr Cys Ala Ala Cys Ser
                485                 490                 495

Arg Lys Leu Arg Gly Lys Ala Phe Tyr Phe Val Asn Gly Lys Val Phe
            500                 505                 510

Cys Glu Glu Asp Phe Leu Tyr Ser Gly Phe Gln Gln Ser Ala Asp Arg
        515                 520                 525

Cys Phe Leu Cys Gly His Leu Ile Met Asp Met Ile Leu Gln Ala Leu
        530                 535                 540

Gly Lys Ser Tyr His Pro Gly Cys Phe Arg Cys Val Ile Cys Asn Glu
545                 550                 555                 560

Cys Leu Asp Gly Val Pro Phe Thr Val Asp Ser Glu Asn Lys Ile Tyr
                565                 570                 575

Cys Val Arg Asp Tyr His Lys Val Leu Ala Pro Lys Cys Ala Ala Cys
            580                 585                 590

Gly Leu Pro Ile Leu Pro Pro Glu Gly Ser Asp Glu Thr Ile Arg Val
        595                 600                 605

Val Ser Met Asp Arg Asp Tyr His Val Glu Cys Tyr His Cys Glu Asp
        610                 615                 620

Cys Gly Leu Glu Leu Asn Asp Glu Asp Gly His Arg Cys Tyr Pro Leu
625                 630                 635                 640

Glu Asp His Leu Phe Cys His Ser Cys His Val Lys Arg Leu Glu Lys
                645                 650                 655

Gly Pro Ser Pro Ala Pro Leu His Gln His His Phe
            660                 665
```

<210> SEQ ID NO 129
<211> LENGTH: 198
<212> TYPE: PRT
<213> ORGANISM: Mus musculus

<400> SEQUENCE: 129

Met Leu Pro Cys Cys Tyr Lys Ser Ile Thr Tyr Lys Glu Gln Glu Asp
1               5                   10                  15

Leu Thr Leu Arg Pro His Cys Cys Leu Pro Cys Ser Cys Leu Pro Cys
            20                  25                  30

Ser Cys Leu Gln Cys Ser Glu Ser Leu Gly Gly Leu Gln Val Gly Arg
        35                  40                  45

Ser Thr Ala Gln Glu Lys Asp His Ser Gln Leu Lys Glu Leu Tyr Ser
    50                  55                  60

Ala Gly Asn Leu Thr Val Leu Ser Thr Asp Pro Leu Leu His Gln Asp
65                  70                  75                  80

Pro Val Gln Leu Asp Phe His Phe Arg Leu Thr Pro His Ser Ser Ala
                85                  90                  95

His Trp His Gly Leu Leu Cys Asp His Arg Leu Phe Leu Asp Ile Pro
            100                 105                 110

Tyr Gln Ala Leu Asp Gln Gly Asn Arg Glu Ser Leu Thr Ala Thr Leu
        115                 120                 125

Glu Tyr Val Glu Glu Lys Thr Asn Val Asp Ser Val Phe Val Asn Phe
    130                 135                 140

Gln Ile Asp Arg Lys Asp Arg Gly Ala Leu Leu Arg Ala Phe Ser Tyr
145                 150                 155                 160

Met Gly Phe Glu Val Val Arg Pro Asp His Pro Ala Leu Pro Pro Trp
                165                 170                 175

Asp Asn Val Ile Phe Met Val Tyr Pro Leu Glu Arg Asp Leu Gly His
            180                 185                 190

Pro Gly Ser Glu Pro Pro
        195

<210> SEQ ID NO 130
<211> LENGTH: 291
<212> TYPE: PRT
<213> ORGANISM: Mus musculus

<400> SEQUENCE: 130

Met Glu Lys Pro Ala Ala Ser Thr Pro Gln Gly Ser Arg Pro Ala
1               5                   10                  15

Leu Gly Arg Glu Ser Val Gln Val Pro Asp Asp Gln Asp Phe Arg Ser
            20                  25                  30

Phe Arg Ser Glu Cys Glu Ala Glu Val Gly Trp Asn Leu Thr Tyr Ser
        35                  40                  45

Lys Ala Gly Val Ser Val Trp Val Gln Ala Val Glu Met Asp Arg Thr
    50                  55                  60

Leu His Lys Ile Lys Cys Arg Met Glu Cys Cys Asp Val Pro Ala Glu
65                  70                  75                  80

Thr Leu Tyr Asp Val Leu His Asp Ile Glu Tyr Arg Lys Lys Trp Asp
                85                  90                  95

Ser Asn Val Ile Glu Thr Phe Asp Ile Ala Arg Leu Thr Val Asn Ala
            100                 105                 110

Asp Val Gly Tyr Tyr Ser Trp Arg Cys Pro Lys Pro Leu Lys Asn Arg
        115                 120                 125

```
Asp Val Ile Thr Leu Arg Ser Trp Leu Pro Met Gly Ala Asp Tyr Ile
            130                 135                 140

Ile Met Asn Tyr Ser Val Lys His Pro Lys Tyr Pro Pro Arg Lys Asp
145                 150                 155                 160

Leu Val Arg Ala Val Ser Ile Gln Thr Gly Tyr Leu Ile Gln Ser Thr
                165                 170                 175

Gly Pro Lys Ser Cys Val Ile Thr Tyr Leu Ala Gln Val Asp Pro Lys
                180                 185                 190

Gly Ser Leu Pro Lys Trp Val Val Asn Lys Ser Ser Gln Phe Leu Ala
            195                 200                 205

Pro Lys Ala Met Lys Lys Met Tyr Lys Ala Cys Ile Lys Tyr Pro Glu
        210                 215                 220

Trp Lys Gln Lys His Gln Pro His Phe Lys Pro Trp Leu His Pro Glu
225                 230                 235                 240

Gln Ser Pro Leu Pro Ser Leu Ala Leu Ser Glu Leu Ser Val Gln His
                245                 250                 255

Ala Asp Ser Leu Glu Asn Ile Asp Glu Ser Ala Val Thr Glu Ser Arg
                260                 265                 270

Glu Glu Arg Ala Gly Gly Ala Gly Gly Glu Gly Ser Asp Asp Asp Thr
            275                 280                 285

Ser Leu Thr
    290

<210> SEQ ID NO 131
<211> LENGTH: 417
<212> TYPE: PRT
<213> ORGANISM: Mus musculus

<400> SEQUENCE: 131

Met Ala Leu Ser Ala Lys Leu Thr Leu Asp Lys Val Asp Leu Lys Gly
1               5                   10                  15

Lys Arg Val Ile Met Arg Val Asp Phe Asn Val Pro Met Lys Asn Asn
                20                  25                  30

Gln Ile Thr Asn Asn Gln Arg Ile Lys Ala Ala Ile Pro Ser Ile Lys
            35                  40                  45

His Cys Leu Asp Asn Gly Ala Lys Ser Val Val Leu Met Ser His Leu
        50                  55                  60

Gly Arg Pro Asp Gly Ile Pro Met Pro Asp Lys Tyr Ser Leu Glu Pro
65                  70                  75                  80

Val Ala Asp Glu Leu Lys Ser Leu Leu Asn Lys Asp Val Ile Phe Leu
                85                  90                  95

Lys Asp Cys Val Gly Pro Glu Val Glu Gln Ala Cys Ala Asn Pro Asp
                100                 105                 110

Asn Gly Ser Ile Ile Leu Leu Glu Asn Leu Arg Phe His Val Glu Glu
            115                 120                 125

Glu Gly Lys Gly Lys Asp Ser Ser Gly Lys Lys Ile Ser Ala Asp Pro
        130                 135                 140

Ala Lys Val Glu Ala Phe Gln Ala Ser Leu Ser Lys Leu Gly Asp Val
145                 150                 155                 160

Tyr Val Asn Asp Ala Phe Gly Thr Ala His Arg Ala His Ser Ser Met
                165                 170                 175

Val Gly Val Asn Leu Pro Gln Lys Ala Ser Gly Phe Leu Met Lys Lys
            180                 185                 190

Glu Leu Asp Tyr Phe Ser Lys Ala Leu Glu Lys Pro Glu Arg Pro Phe
        195                 200                 205
```

```
Leu Ala Ile Leu Gly Gly Ala Lys Val Lys Asp Lys Ile Gln Leu Ile
    210                 215                 220

Lys Asn Met Leu Asp Lys Val Asn Phe Met Ile Ile Gly Gly Gly Met
225                 230                 235                 240

Ala Tyr Thr Phe Leu Lys Glu Leu Lys Asn Met Gln Ile Gly Ala Ser
                245                 250                 255

Leu Phe Asp Glu Glu Gly Ala Thr Ile Val Lys Glu Ile Met Glu Lys
            260                 265                 270

Ala Glu Lys Asn Gly Val Lys Ile Val Phe Pro Val Asp Phe Val Thr
        275                 280                 285

Gly Asp Lys Phe Asp Glu Asn Ala Lys Val Gly Gln Ala Thr Ile Glu
    290                 295                 300

Ser Gly Ile Pro Ser Gly Trp Met Gly Leu Asp Cys Gly Pro Glu Ser
305                 310                 315                 320

Ile Lys Ile Asn Ala Gln Ile Val Ala Gln Ala Lys Leu Ile Val Trp
                325                 330                 335

Asn Gly Pro Ile Gly Val Phe Glu Trp Asp Ala Phe Ala Lys Gly Thr
            340                 345                 350

Lys Ala Leu Met Asp Glu Val Val Lys Ala Thr Ser Asn Gly Cys Val
        355                 360                 365

Thr Ile Ile Gly Gly Gly Asp Thr Ala Thr Cys Cys Ala Lys Trp Gly
    370                 375                 380

Thr Glu Asp Lys Val Ser His Val Ser Thr Gly Gly Gly Ala Ser Leu
385                 390                 395                 400

Glu Leu Leu Glu Gly Lys Ile Leu Pro Gly Val Glu Ala Leu Ser Asn
                405                 410                 415

Met

<210> SEQ ID NO 132
<211> LENGTH: 136
<212> TYPE: PRT
<213> ORGANISM: Mus musculus
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 132

Met Thr Ser Gln Ile Gln Asp Leu Leu Ala Thr Asp Gln Asp Leu Leu
1               5                   10                  15

Leu Ile Gln Lys Ala Thr Met Met Arg Lys Val Arg Thr Lys Ser Xaa
                20                  25                  30

Lys Lys Leu Arg Tyr Xaa Arg Leu Gln Asn Asp Gly Met Thr Val Trp
            35                  40                  45

His Gly Ser Gln Pro Glu Ser Met Pro Lys Pro Thr Phe Ser Ile Ser
        50                  55                  60

Asp Val Glu Arg Ile Arg Lys Gly Gln Asp Ser Glu Leu Leu Arg Tyr
65                  70                  75                  80

Leu Val Glu Glu Phe Pro Leu Glu Gln Gly Phe Thr Val Val Phe Gln
                85                  90                  95

Val Arg Arg Pro Asn Leu Asp Leu Val Ala Asn Ser Val Glu Glu Ala
            100                 105                 110
```

```
Gln Ile Trp Met Arg Gly Leu Gln Leu Leu Val Asp Leu Val Ala Ser
    115                 120                 125

Met Asp His Gln Glu Gln Met Asp
    130                 135

<210> SEQ ID NO 133
<211> LENGTH: 51
<212> TYPE: PRT
<213> ORGANISM: Mus musculus

<400> SEQUENCE: 133

Met Ala Arg Tyr Arg Cys Cys Arg Ser Lys Ser Arg Ser Arg Cys Arg
1               5                   10                  15

Arg Arg Arg Arg Cys Arg Arg Arg Arg Arg Cys Cys Arg Arg
            20                  25                  30

Arg Arg Arg Arg Cys Cys Arg Arg Arg Ser Tyr Thr Ile Arg Cys
        35                  40                  45

Lys Lys Tyr
    50

<210> SEQ ID NO 134
<211> LENGTH: 102
<212> TYPE: PRT
<213> ORGANISM: Mus musculus

<400> SEQUENCE: 134

Met Val Arg Tyr Arg Val Arg Ser Leu Ser Glu Arg Ser His Glu Val
1               5                   10                  15

Tyr Arg Gln Gln Leu His Gly Gln Glu Gln Gly His His Gly Gln Glu
            20                  25                  30

Glu Gln Gly Leu Ser Arg Met His Val Glu Val Tyr Glu Arg Thr His
        35                  40                  45

Gly Gln Ser Gln Tyr Arg Arg His Cys Ser Arg Arg Arg Leu His
    50                  55                  60

Arg Ile His Arg Arg Gln His Arg Ser Cys Arg Arg Arg Lys Arg Arg
65                  70                  75                  80

Ser Cys Arg His Arg Arg Arg His Arg Arg Gly Cys Arg Thr Arg Lys
                85                  90                  95

Arg Thr Cys Arg Arg His
            100

<210> SEQ ID NO 135
<211> LENGTH: 520
<212> TYPE: PRT
<213> ORGANISM: Mus musculus

<400> SEQUENCE: 135

Met Ala Ala Leu Arg Leu Leu Ala Trp Ala Leu Pro Arg Gly Val Ser
1               5                   10                  15

Ala Leu Arg Pro Pro Ala Leu Pro His Arg Leu Ile Arg Arg Tyr
            20                  25                  30

Val Ser Asp Arg Ser Gly Ser Val His Phe Tyr Thr Asp Pro Val Lys
        35                  40                  45

Ala Val Glu Gly Val Lys Asp Gly Ser Thr Val Met Leu Gly Gly Phe
    50                  55                  60

Gly Leu Cys Gly Ile Pro Glu Asn Leu Ile Gly Ala Leu Lys Thr Lys
65                  70                  75                  80

Gly Val Lys Asp Leu Lys Ile Val Ser Ser Asn Val Gly Val Asp Asp
```

-continued

```
                    85                  90                  95
Phe Gly Leu Gly Ile Leu Leu Ala Ser Lys Gln Val Arg Arg Val Val
                100                 105                 110
Cys Ser Tyr Leu Gly Glu Asn Ala Leu Cys Glu Lys Leu Tyr Leu Ala
            115                 120                 125
Gly Glu Leu Glu Leu Glu Met Thr Pro Gln Gly Thr Leu Ala Glu Arg
        130                 135                 140
Ile Arg Ala Gly Gly Thr Gly Val Pro Ala Phe Tyr Thr Pro Thr Gly
145                 150                 155                 160
Tyr Gly Thr Leu Val Gln Glu Gly Gly Ser Pro Ile Arg Tyr Ala Pro
                165                 170                 175
Asp Gly His Leu Ile Thr Leu Ser Glu Pro Arg Glu Val Arg Glu Phe
            180                 185                 190
Gln Gly Arg Phe Tyr Leu Leu Glu His Ala Ile Arg Ala Asp Phe Ala
        195                 200                 205
Leu Ile Lys Gly Trp Lys Ala Asp Arg Ser Gly Asn Val Ile Phe Arg
210                 215                 220
Gly Ser Ala Arg Asn Phe Asn Val Pro Met Cys Lys Ala Ala Asp Ile
225                 230                 235                 240
Ser Val Val Glu Val Glu Ile Val Asp Val Gly Thr Phe Ala Pro
                245                 250                 255
Glu Asp Ile His Val Pro Asn Ile Tyr Val Asp Arg Val Ile Lys Gly
            260                 265                 270
Pro Lys Phe Glu Lys Arg Ile Glu Arg Leu Thr Thr Arg Asp Ser Lys
        275                 280                 285
Pro Ala Pro Gly Ser Lys Asp Asn Asp Pro Ser Arg Thr Arg Ile Ile
        290                 295                 300
Lys Arg Ala Ala Leu Glu Phe Gln Asp Gly Met Tyr Ala Asn Leu Gly
305                 310                 315                 320
Ile Gly Ile Pro Val Leu Ala Ser Asn Tyr Ile Ser Pro Lys Met Thr
                325                 330                 335
Val Tyr Leu His Ser Glu Asn Gly Ile Leu Gly Leu Gly Pro Phe Pro
            340                 345                 350
Leu Lys Asn Glu Val Asp Ala Asp Val Ile Asn Ala Gly Lys Gln Thr
        355                 360                 365
Val Thr Val Val Pro Gly Gly Cys Phe Phe Ala Ser Asp Asp Ser Phe
        370                 375                 380
Ala Met Ile Arg Gly Gly His Leu Gln Leu Thr Met Leu Gly Ala Met
385                 390                 395                 400
Gln Val Ser Gln Tyr Gly Asp Leu Ala Asn Trp Met Val Pro Gly Lys
                405                 410                 415
Lys Val Lys Gly Met Gly Gly Ala Met Asp Leu Val Ser Ser Lys Lys
            420                 425                 430
Thr Arg Val Val Val Thr Met Glu His Cys Thr Lys Thr Lys Gln Pro
        435                 440                 445
Lys Ile Leu Lys Lys Cys Thr Met Pro Leu Thr Gly Lys Arg Cys Val
        450                 455                 460
Asp Leu Ile Ile Thr Glu Lys Ala Val Phe Glu Val Asn His Ser Lys
465                 470                 475                 480
Gly Leu Thr Leu Val Glu Leu Trp Glu Gly Ser Ser Val Asp Asp Ile
                485                 490                 495
Lys Ala Thr Thr Ala Cys Ser Phe Ala Val Ser Pro Asn Leu Lys Pro
            500                 505                 510
```

```
Met Gln Gln Ile Lys Leu Asp Ala
        515                 520

<210> SEQ ID NO 136
<211> LENGTH: 520
<212> TYPE: PRT
<213> ORGANISM: Mus musculus

<400> SEQUENCE: 136

Met Ala Ala Leu Arg Leu Leu Ala Trp Ala Leu Pro Arg Gly Val Ser
  1               5                  10                  15

Ala Leu Arg Pro Arg Pro Ala Leu Pro His Arg Leu Ile Arg Arg Tyr
                 20                  25                  30

Val Ser Asp Arg Ser Gly Ser Val His Phe Tyr Thr Asp Pro Val Lys
             35                  40                  45

Ala Val Glu Gly Val Lys Asp Gly Ser Thr Val Met Leu Gly Gly Phe
         50                  55                  60

Gly Leu Cys Gly Ile Pro Glu Asn Leu Ile Gly Ala Leu Lys Thr Lys
 65                  70                  75                  80

Gly Val Lys Asp Leu Lys Ile Val Ser Ser Asn Val Gly Val Asp Asp
                 85                  90                  95

Phe Gly Leu Gly Ile Leu Leu Ala Ser Lys Gln Val Arg Arg Val Val
                100                 105                 110

Cys Ser Tyr Leu Gly Glu Asn Ala Leu Cys Glu Lys Leu Tyr Leu Ala
                115                 120                 125

Gly Glu Leu Glu Leu Glu Met Thr Pro Gln Gly Thr Leu Ala Glu Arg
            130                 135                 140

Ile Arg Ala Cys Gly Thr Gly Val Pro Ala Phe Tyr Thr Pro Thr Gly
145                 150                 155                 160

Tyr Gly Thr Leu Val Gln Glu Gly Gly Ser Pro Ile Arg Tyr Ala Pro
                165                 170                 175

Asp Gly His Leu Ile Thr Leu Ser Glu Pro Arg Glu Val Arg Glu Phe
                180                 185                 190

Gln Gly Arg Phe Tyr Leu Leu Glu His Ala Ile Arg Ala Asp Phe Ala
            195                 200                 205

Leu Ile Lys Gly Trp Lys Ala Asp Arg Ser Gly Asn Val Ile Phe Arg
210                 215                 220

Gly Ser Ala Arg Asn Phe Asn Val Pro Met Cys Lys Ala Ala Asp Ile
225                 230                 235                 240

Ser Val Val Glu Val Glu Glu Ile Val Asp Val Gly Thr Phe Ala Pro
                245                 250                 255

Glu Asp Ile His Ile Pro Asn Ile Tyr Val Asp Arg Val Ile Lys Gly
                260                 265                 270

Pro Lys Phe Glu Lys Arg Ile Glu Arg Leu Thr Thr Arg Asp Ser Lys
            275                 280                 285

Pro Ala Pro Gly Ser Lys Asp Asn Asp Pro Ser Arg Thr Arg Ile Ile
        290                 295                 300

Lys Arg Ala Ala Leu Glu Phe Gln Asp Gly Met Tyr Ala Asn Leu Gly
305                 310                 315                 320

Ile Gly Ile Pro Val Leu Ala Ser Asn Tyr Ile Ser Pro Lys Met Thr
                325                 330                 335

Val Tyr Leu His Ser Glu Asn Gly Ile Leu Gly Leu Gly Pro Phe Pro
                340                 345                 350

Leu Lys Asn Glu Val Asp Ala Asp Val Ile Asn Ala Gly Lys Gln Thr
```

```
                355                 360                 365
Val Thr Val Val Pro Gly Gly Cys Phe Phe Ala Ser Asp Asp Ser Phe
    370                 375                 380

Ala Met Ile Arg Gly Gly His Leu Gln Leu Thr Met Leu Gly Ala Met
385                 390                 395                 400

Gln Val Ser Gln Tyr Gly Asp Leu Ala Asn Trp Met Val Pro Gly Lys
                405                 410                 415

Lys Val Lys Gly Met Gly Gly Ala Met Asp Leu Val Ser Ser Lys Lys
            420                 425                 430

Thr Arg Val Val Val Thr Met Glu His Cys Thr Lys Thr Lys Gln Pro
            435                 440                 445

Lys Ile Leu Lys Lys Cys Thr Met Pro Leu Thr Gly Lys Arg Cys Val
        450                 455                 460

Asp Leu Ile Ile Thr Glu Lys Ala Val Phe Glu Val Asn His Ser Lys
465                 470                 475                 480

Gly Leu Thr Leu Val Glu Leu Trp Glu Gly Ser Ser Val Asp Asp Ile
                485                 490                 495

Lys Ala Thr Thr Ala Cys Ser Phe Ala Val Ser Pro Asn Leu Lys Pro
            500                 505                 510

Met Gln Gln Ile Lys Leu Asp Ala
        515                 520

<210> SEQ ID NO 137
<211> LENGTH: 143
<212> TYPE: PRT
<213> ORGANISM: Mus musculus

<400> SEQUENCE: 137

Met Ser Asp Pro Ser Lys Thr Asn Gln Cys Pro Pro Cys Cys Pro
1               5                   10                  15

Pro Lys Pro Cys Cys Pro Pro Lys Pro Cys Cys Pro Gln Lys Pro Pro
            20                  25                  30

Cys Cys Pro Lys Ser Pro Cys Cys Pro Pro Lys Ser Pro Cys Cys Pro
        35                  40                  45

Pro Lys Pro Cys Pro Cys Pro Pro Cys Pro Cys Pro Ala
    50                  55                  60

Thr Cys Pro Cys Pro Leu Lys Pro Pro Cys Cys Pro Gln Lys Cys Ser
65                  70                  75                  80

Cys Cys Pro Lys Lys Cys Thr Cys Cys Pro Gln Pro Pro Cys Cys
            85                  90                  95

Ala Gln Pro Thr Cys Cys Ser Ser Glu Asn Lys Thr Glu Ser Asp Ser
                100                 105                 110

Asp Thr Ser Gly Gln Thr Leu Glu Lys Gly Ser Gln Ser Pro Gln Ser
            115                 120                 125

Pro Pro Gly Ala Gln Gly Asn Trp Asn Gln Lys Lys Ser Asn Lys
        130                 135                 140

<210> SEQ ID NO 138
<211> LENGTH: 579
<212> TYPE: PRT
<213> ORGANISM: Mus musculus

<400> SEQUENCE: 138

Met Ile Thr Trp Ser Phe Ile Asp Leu Trp Arg Thr Ser His Ser Thr
1               5                   10                  15

Leu Phe Gln Met Thr Leu Ala Thr Val Leu Met Ala Pro Val Leu Gly
```

-continued

```
                 20                  25                  30
Asp Cys Gly Pro Pro Leu Leu Pro Phe Ala Ser Pro Thr Asn Gln
             35                  40                  45
Leu Tyr Glu Ser Thr Thr Phe Pro Ser Gly Thr Val Leu Lys Tyr Thr
 50                  55                  60
Cys His His Gly Phe Lys Arg Val Asn Ser Ser His Leu Ser Cys Asp
 65                  70                  75                  80
Glu Asn Gly Ser Trp Val Tyr Ser Thr Phe Cys Ala Arg Lys Arg Cys
                 85                  90                  95
Lys Asn Pro Gly Glu Leu Val Asn Gly Lys Val Glu Ile Pro Ser Asp
             100                 105                 110
Leu Leu Val Gly Ser Ile Ile Glu Phe Ser Cys Ser Lys Gly Tyr Leu
             115                 120                 125
Leu Ile Gly Ser Ala Thr Ser Arg Cys Glu Val Gln Gly Lys Gly Val
             130                 135                 140
Asp Trp Ser Asp Ser Leu Pro Glu Cys Val Ile Ala Thr Cys Glu Pro
145                 150                 155                 160
Pro Pro Pro Ile Ser Asn Gly Lys His Ser Gly Arg Asp Asp Leu
             165                 170                 175
Tyr Thr Phe Gly Ser Val Val Ile Tyr Asn Cys Asp Pro Thr Phe Thr
             180                 185                 190
Leu Leu Gly Asn Ala Ser Ile Val Cys Thr Val Asn Arg Thr Val
             195                 200                 205
Gly Val Trp Arg Pro His Pro Pro Ala Cys Gln Lys Ile Val Cys His
             210                 215                 220
Arg Pro Gln Ile Pro Lys Gly Tyr Leu Ala Pro Gly Phe Arg Gln Phe
225                 230                 235                 240
Tyr Ala Tyr Arg Asp Ala Leu Glu Ile Arg Cys Lys Lys Gly Phe Ile
                 245                 250                 255
Leu Arg Gly Ser Ser Val Ile His Cys Glu Ala Asn Gly Glu Trp Phe
             260                 265                 270
Pro Ser Ile Pro Thr Cys Glu Pro Asn Gly Cys Thr Asn Ile Pro Asp
             275                 280                 285
Ile Ser Tyr Ala Ser Trp Glu Gly Tyr Lys Phe Pro Leu Arg Asn Phe
             290                 295                 300
Glu Val Phe Glu Ile Gly Ala Lys Leu Lys Tyr Gln Cys Lys Pro Gly
305                 310                 315                 320
Tyr Arg Ala Ser Leu Asn Asp Pro Gln Thr Val Thr Cys Gln Glu Asn
                 325                 330                 335
Leu Thr Trp Ser Ser Thr Asn Gly Cys Glu Arg Ile Cys Cys Pro Thr
             340                 345                 350
Pro Asp Met Glu Lys Ile Lys Ile Val Ser Glu Arg Arg Asp Phe Thr
             355                 360                 365
Gly Thr Cys Ile Tyr Ala Tyr Gly Asp Tyr Val Phe Tyr Ile Cys Asn
             370                 375                 380
Glu Gly Ser Tyr Pro Met Ser Thr Asp Gly Arg Ser Ser Cys Gln Ala
385                 390                 395                 400
Asp Gly Lys Trp Asp Pro Ala Ile Pro Ser Cys Gln Ala Asp Ser Gly
                 405                 410                 415
Leu Gln Asn Arg Leu Ala Leu Phe Thr Phe Pro Asn Ile Ser Glu Thr
             420                 425                 430
Asn Val Thr Asn Lys Thr Tyr Leu Phe Gly His Glu Glu Asn Ser Thr
             435                 440                 445
```

```
Glu His Ala Met Lys Gly Val Cys Leu Lys Pro Met Val Ile Asn Gly
    450                 455                 460

Asn Leu Ser Val Glu Arg Val Ile Tyr Ala Glu Leu Glu Asn Ile Thr
465                 470                 475                 480

Ile Gln Cys Asp Pro Gly Tyr Thr Ile Val Gly Ser Pro Asn Ile Ile
                485                 490                 495

Cys Ser Asn Arg Thr Trp Tyr Pro Glu Val Pro Ser Cys Gln Met Glu
                500                 505                 510

Val Leu Glu Asp Cys Arg Ile Val Ser Arg Gly Ala Gln Leu Leu His
                515                 520                 525

Cys Leu Ser Ser Pro Glu Asp Val His Arg Ala Leu Lys Val Tyr Lys
    530                 535                 540

Leu Phe Leu Glu Ile Glu Arg Leu Glu His Gln Lys Glu Lys Trp Ile
545                 550                 555                 560

Gln Leu His Arg Lys Pro Gln Ser Met Lys Ile Asn Arg Ser Phe Arg
                565                 570                 575

Leu Cys Asn

<210> SEQ ID NO 139
<211> LENGTH: 326
<212> TYPE: PRT
<213> ORGANISM: Mus musculus

<400> SEQUENCE: 139

Met Ala Arg Phe Ala Trp Thr Arg Val Ala Pro Val Ala Leu Val Thr
1               5                   10                  15

Phe Trp Leu Val Leu Ser Leu Ser Pro Thr Asp Ala Gln Val Asn Leu
                20                  25                  30

Ser Ser Val Asp Phe Leu Asp Leu Pro Ala Leu Leu Gly Val Pro Val
                35                  40                  45

Asp Pro Lys Arg Ala Arg Gly Tyr Leu Leu Val Ala Arg Pro Ala Asp
    50                  55                  60

Ala Cys His Ala Ile Glu Gly Pro Gly Pro Asp Asn His Ser Leu Asp
65                  70                  75                  80

Pro Leu Val Leu Val Arg Pro Leu Gly Cys Ser Trp Glu Gln Thr Gly
                85                  90                  95

Arg Arg Ala Gln Arg Ala Gly Ala Thr Ala Ala Ser Val Gly Pro Glu
                100                 105                 110

Ala Pro Gly Gln Leu Arg Glu Phe Glu Asp Leu Glu Val Thr Val Arg
            115                 120                 125

Cys Asp Gln Pro Ala Arg Val Leu Leu Pro His Ala Glu Pro Cys Pro
    130                 135                 140

Asp Pro Glu Cys His Pro Val Val Ala Ser Trp Ala Leu Ala Arg
145                 150                 155                 160

Ala Leu Ala Leu Ala Ser Thr Leu Phe Val Leu Arg Gln Leu Trp
                165                 170                 175

Pro Trp Val Arg Gly Leu Gly Ser Arg Gly Thr Ala Val Lys Thr Gln
                180                 185                 190

Thr Cys Gln Lys Ala Gln Val Arg Thr Phe Thr Arg Leu Ser Asp Leu
            195                 200                 205

Cys Ala Ile Cys Leu Asp Asp Tyr Glu Glu Gly Glu Arg Leu Lys Ile
    210                 215                 220

Leu Pro Cys Ala His Ala Tyr His Cys Arg Cys Ile Asp Pro Trp Phe
225                 230                 235                 240
```

-continued

Ser Arg Ala Gly Ala Ser Cys Pro Leu Cys Lys Gln Ser Val Ala Ser
                245                 250                 255

Thr His Asp Gly Ser Thr Asp Gly Ser Val Gly Gly Glu Pro Pro
            260                 265                 270

Leu Pro Gly His Arg Pro Pro Ile Trp Ala Ile Gln Ala Arg Leu Arg
                275                 280                 285

Ser Arg Arg Leu Glu Leu Leu Ala Arg Thr Val Pro Cys Arg Arg Cys
            290                 295                 300

Ser Ser Thr Thr Ser Leu Gly Val Ala Glu Asn Val Ala Gln Ser Glu
305                 310                 315                 320

Ala Thr Ser Glu Leu Ser
                325

<210> SEQ ID NO 140
<211> LENGTH: 278
<212> TYPE: PRT
<213> ORGANISM: Mus musculus

<400> SEQUENCE: 140

Met Glu Pro Asp Leu Asn Glu Glu Ser Glu Arg Ile Arg Thr Ser
 1               5                  10                  15

Arg Asn Arg Arg Ser Leu Glu His Arg Arg Asn Ser Leu Leu Pro Phe
            20                  25                  30

Gln Trp Lys Ala Thr Asn Asn Ser Arg Trp Met Ala Gln Val Val Ala
        35                  40                  45

Ser Glu Phe Ser Leu Val Ala Phe Leu Leu Leu Val Met Val Phe
    50                  55                  60

Ser Lys Lys Trp Leu Tyr Pro Ser Lys Ser Arg Phe His Gln Arg Tyr
65                  70                  75                  80

Pro Gln Asn Val Thr Lys Arg Val Tyr Thr Ser Ile His Ser Met Ser
                85                  90                  95

Thr Gly Leu Leu Tyr Ile Cys Val Ser Lys Ser Cys Pro Ser Ser Asp
            100                 105                 110

Asn Gly Glu Asp Asn Phe Lys Met Trp Thr Ile His Pro Val Phe Gly
        115                 120                 125

Val Ala Lys Ile Ser Phe Thr Leu Ala Ile Gly Leu Gly Phe Val Leu
    130                 135                 140

Thr Thr Trp Leu His Leu Pro Tyr Leu Pro Cys Leu Gln Arg Met Pro
145                 150                 155                 160

Phe Phe Gly Leu Ile Gly Ile Ile Leu Ser Phe Cys Glu Val Thr Leu
                165                 170                 175

Ile Phe Leu Thr Leu Leu Leu Phe Pro Val Asn Leu Trp Ile Tyr Glu
            180                 185                 190

Leu Arg Lys Asn Ile Ser Val Pro Ile Gly Trp Ser Tyr Phe Ile Gly
        195                 200                 205

Trp Leu Val Leu Ile Leu Tyr Phe Thr Cys Gly Ile Leu Cys Tyr Leu
    210                 215                 220

Asn His Lys Asn Tyr Trp Ser Leu Ile Met Ser Ser Thr Thr Ile Asn
225                 230                 235                 240

Thr Ala Cys Ser Ser Leu Gly Pro Glu Ser Leu Val Ser Pro Ser Gln
                245                 250                 255

Thr Pro Ala Ala Arg Arg Thr Ala Arg Ser Leu Leu Arg Met Thr Lys
            260                 265                 270

Ser Ile Ser Pro Asp Lys

275

<210> SEQ ID NO 141
<211> LENGTH: 373
<212> TYPE: PRT
<213> ORGANISM: Mus musculus

<400> SEQUENCE: 141

```
Met Asp Leu Pro Arg Arg Trp Leu Phe Arg Met Leu Leu Val Ala
 1               5                  10                  15

Thr Ser Ser Gly Ile Leu Leu Met Leu Tyr Ser Ser Ala Gly Gln Gln
                20                  25                  30

Ser Pro Glu Thr Gln Val Pro Ala Arg Asn Met Ala Tyr Pro Arg Ala
            35                  40                  45

Phe Phe Asp Pro Lys Pro Pro Asn Ser Glu Asn Arg Lys Ser Arg Leu
        50                  55                  60

Cys Gln His Ser Leu Ser Leu Ala Ile Gln Lys Asp Arg Arg Phe Arg
 65                  70                  75                  80

Ser Leu Phe Asp Leu Ser Thr Pro Val Leu Leu Trp Glu Gly Leu Phe
                85                  90                  95

Thr Gln Glu Leu Trp Asn Asn Leu Ser Gln His Lys Val Pro Tyr Gly
            100                 105                 110

Trp Gln Gly Leu Ser His Glu Val Ile Ala Ser Thr Leu Arg Leu Leu
        115                 120                 125

Lys Ser Pro Glu Ser Gly Glu Leu Phe Gly Ala Pro Arg Lys Leu Pro
130                 135                 140

Leu Ser Cys Ile Arg Cys Ala Val Val Gly Asn Gly Gly Ile Leu Asn
145                 150                 155                 160

Gly Ser Arg Gln Gly Gln Lys Ile Asp Ala His Asp Tyr Val Phe Arg
                165                 170                 175

Leu Asn Gly Ala Ile Thr Glu Ala Phe Glu Arg Asp Val Gly Thr Lys
            180                 185                 190

Thr Ser Phe Tyr Gly Phe Thr Val Asn Thr Met Lys Asn Ser Leu Ile
        195                 200                 205

Ser Tyr Ala Lys Leu Gly Phe Thr Ser Val Pro Gln Gly Gln Asn Leu
    210                 215                 220

Arg Tyr Ile Phe Ile Pro Ser Ser Ile Arg Asp Tyr Leu Met Leu Arg
225                 230                 235                 240

Ser Ala Ile Leu Gly Val Pro Val Pro Glu Gly Pro Asp Lys Gly Asp
                245                 250                 255

Arg Pro His Thr Tyr Phe Gly Pro Glu Thr Ser Ala Ser Lys Phe Lys
            260                 265                 270

Leu Leu His Pro Asp Phe Ile Ser Tyr Leu Thr Glu Arg Phe Leu Lys
        275                 280                 285

Ser Lys Leu Ile Asn Thr Arg Phe Gly Asp Met Tyr Met Pro Ser Thr
    290                 295                 300

Gly Ala Leu Met Leu Leu Thr Ala Leu His Thr Cys Asp Gln Val Ser
305                 310                 315                 320

Ala Tyr Gly Phe Ile Thr Asn Asn Tyr Gln Lys Tyr Ser Asp His Tyr
                325                 330                 335

Phe Glu Arg Glu Lys Lys Pro Leu Ile Phe Tyr Ala Asn His Asp Leu
            340                 345                 350

Ser Leu Glu Ala Ser Leu Trp Arg Asp Leu His Asn Ala Gly Ile Leu
        355                 360                 365
```

Trp Leu Tyr Gln Arg
        370

<210> SEQ ID NO 142
<211> LENGTH: 485
<212> TYPE: PRT
<213> ORGANISM: Mus musculus

<400> SEQUENCE: 142

Met Ala Glu Leu Arg Pro Ser Val Ala Pro Gly Pro Ala Ala Pro Pro
 1               5                  10                  15

Ala Ser Gly Pro Ser Ala Pro Pro Ala Phe Ala Ser Leu Phe Pro Pro
                20                  25                  30

Gly Leu His Ala Ile Tyr Gly Glu Cys Arg Arg Leu Tyr Pro Asp Gln
            35                  40                  45

Pro Asn Pro Leu Gln Val Thr Ala Ile Val Lys Tyr Trp Leu Gly Gly
        50                  55                  60

Pro Asp Pro Leu Asp Tyr Val Ser Met Tyr Arg Asn Met Gly Cys Pro
65                  70                  75                  80

Ser Ala Asn Ile Pro Glu His Trp His Tyr Ile Ser Phe Gly Leu Ser
                85                  90                  95

Asp Leu Tyr Gly Asp Asn Arg Val His Glu Phe Thr Gly Thr Asp Gly
            100                 105                 110

Pro Ser Gly Phe Gly Phe Glu Leu Thr Phe Arg Leu Lys Arg Glu Thr
        115                 120                 125

Gly Glu Ser Ala Pro Pro Thr Trp Pro Ala Glu Leu Met Gln Gly Leu
    130                 135                 140

Ala Arg Tyr Val Phe Gln Ser Glu Asn Thr Phe Cys Ser Gly Asp His
145                 150                 155                 160

Val Ser Trp His Ser Pro Leu Asp Asn Ser Glu Ser Arg Ile Gln His
                165                 170                 175

Met Leu Leu Thr Glu Asp Pro Gln Met Gln Pro Val Arg Thr Pro Phe
            180                 185                 190

Gly Val Val Thr Phe Leu Gln Ile Val Gly Val Cys Thr Glu Glu Leu
        195                 200                 205

His Ser Ala Gln Gln Trp Asn Gly Gln Gly Ile Gln Glu Leu Leu Arg
    210                 215                 220

Thr Val Pro Ile Ala Gly Gly Pro Trp Leu Ile Thr Asp Met Arg Arg
225                 230                 235                 240

Gly Glu Thr Ile Phe Glu Ile Asp Pro His Leu Gln Gln Glu Arg Val
                245                 250                 255

Asp Lys Gly Ile Glu Thr Asp Gly Ser Asn Leu Ser Gly Val Ser Ala
            260                 265                 270

Lys Cys Ala Trp Asp Asp Leu Ser Arg Pro Pro Glu Asp Glu Glu Asp
        275                 280                 285

Ser Arg Ser Ile Cys Leu Gly Thr Gln Pro Arg Arg Leu Ser Gly Lys
    290                 295                 300

Asp Thr Glu Gln Ile Arg Glu Thr Leu Arg Arg Gly Leu Glu Ile Asn
305                 310                 315                 320

Ser Lys Pro Val Leu Pro Pro Ile Asn Ser Gln Arg Gln Asn Gly Leu
                325                 330                 335

Thr His Asp Arg Ala Pro Ser Arg Lys Asp Ser Leu Gly Ser Asp Ser
            340                 345                 350

Ser Thr Ala Ile Ile Pro His Glu Leu Ile Arg Thr Arg Gln Leu Glu
        355                 360                 365

```
Ser Val His Leu Lys Phe Asn Gln Glu Ser Gly Ala Leu Ile Pro Leu
    370                 375                 380

Cys Leu Arg Gly Arg Leu Leu His Gly Arg His Phe Thr Tyr Lys Ser
385                 390                 395                 400

Ile Thr Gly Asp Met Ala Ile Thr Phe Val Ser Thr Gly Val Glu Gly
                405                 410                 415

Ala Phe Ala Thr Glu Glu His Pro Tyr Ala Ala His Gly Pro Trp Leu
            420                 425                 430

Gln Ile Leu Leu Thr Glu Glu Phe Val Glu Lys Met Leu Glu Asp Leu
        435                 440                 445

Glu Asp Leu Thr Ser Pro Glu Phe Lys Leu Pro Lys Glu Tyr Ser
    450                 455                 460

Trp Pro Glu Lys Lys Leu Lys Val Ser Ile Leu Pro Asp Val Val Phe
465                 470                 475                 480

Asp Ser Pro Leu His
                485

<210> SEQ ID NO 143
<211> LENGTH: 418
<212> TYPE: PRT
<213> ORGANISM: Mus musculus

<400> SEQUENCE: 143

Met Ala Thr Lys Asn Ser Pro Ser Pro Lys Pro Met Gly Thr Ala Gln
1               5                   10                  15

Gly Asp Pro Gly Glu Ala Gly Thr Leu Pro Ala Pro Glu Ala Ala Gly
            20                  25                  30

Ile Arg Asp Thr Gly Ser Thr Gln Leu Lys Thr Lys Pro Lys Lys Ile
        35                  40                  45

Arg Lys Ile Lys Ala Leu Val Ile Asp Leu Gly Ser Gln Tyr Cys Lys
    50                  55                  60

Cys Gly Tyr Ala Gly Glu Pro Arg Pro Thr Tyr Phe Ile Ser Ser Thr
65                  70                  75                  80

Val Gly Lys Arg Ser Ala Glu Met Ala Ala Asp Ala Gly Asp Asn Phe
                85                  90                  95

Lys Glu Thr Tyr Val Gly His Glu Leu Leu Asn Met Glu Ala Ser Leu
            100                 105                 110

Lys Leu Val Asn Pro Leu Lys His Gly Val Val Asp Trp Asp Cys
        115                 120                 125

Ile Gln Asn Ile Trp Glu Tyr Ile Phe His Thr Ala Met Lys Ile Met
    130                 135                 140

Pro Glu Glu His Ala Val Leu Val Ser Asp Pro Pro Leu Ser Pro Thr
145                 150                 155                 160

Ser Asn Arg Glu Lys Tyr Ala Glu Leu Leu Phe Glu Thr Phe Gly Ile
                165                 170                 175

Pro Ala Met His Val Thr Ser Gln Ala Leu Leu Ser Ile Tyr Ser Tyr
            180                 185                 190

Gly Lys Thr Ser Gly Leu Val Val Glu Ser Gly His Gly Val Ser His
        195                 200                 205

Val Val Pro Ile Ser Glu Gly Asp Leu Leu Pro Gly Leu Pro Ser Arg
    210                 215                 220

Val Asp Tyr Ala Gly Cys Asp Leu Thr Asn Tyr Leu Met Gln Leu Leu
225                 230                 235                 240

Asn Glu Ala Gly His Lys Phe Ser Asp Asp His Leu His Ile Ile Glu
```

```
                    245                 250                 255
His Ile Lys Lys Lys Cys Cys Tyr Ala Ala Leu Leu Pro Glu Glu
                260                 265                 270

Met Ser Leu Gly Leu Asp Glu Leu His Val Asp Tyr Glu Leu Pro Asp
            275                 280                 285

Gly Lys Ile Ile Thr Ile Gly Gln Glu Arg Phe Arg Cys Ser Glu Met
        290                 295                 300

Leu Phe Lys Pro Ser Leu Val Gly Cys Thr Gln Pro Gly Leu Pro Glu
305                 310                 315                 320

Leu Thr Ala Thr Cys Leu Ala Arg Cys Gln Gly Thr Gly Phe Lys Glu
                325                 330                 335

Glu Met Ala Ala Asn Val Leu Leu Cys Gly Gly Cys Thr Met Leu Asp
            340                 345                 350

Gly Phe Pro Glu Arg Phe Gln Arg Glu Leu Ser Leu Leu Cys Pro Gly
        355                 360                 365

Asp Ser Pro Thr Val Ala Ala Pro Glu Arg Lys Thr Ser Val Trp
370                 375                 380

Thr Gly Gly Ser Ile Leu Ala Ser Leu Gln Ala Phe Gln Gln Leu Trp
385                 390                 395                 400

Val Ser Lys Glu Glu Phe Glu Glu Arg Gly Cys Ala Ala Ile Tyr Ser
                405                 410                 415

Lys Cys

<210> SEQ ID NO 144
<211> LENGTH: 440
<212> TYPE: PRT
<213> ORGANISM: Mus musculus

<400> SEQUENCE: 144

Met Ser Leu Asp Gly Val Trp Ala Pro Gln Thr Ala Asn Ile Gly Asp
 1               5                  10                  15

Gly Pro Ala Lys Lys Ala Ser Asp Gln Ala Ser Met Gln Thr Gln Val
            20                  25                  30

Leu Gln Thr Ala Ser Leu Lys Asp Gly Pro Ala Lys Arg Ala Val Trp
        35                  40                  45

Val Arg Arg Asp Asn Ala Glu Thr Glu Asp Pro Val Lys Ser Thr Met
    50                  55                  60

Ser Lys Asp Arg Pro Arg Leu Glu Val Thr Lys Ala Val Val Asp
65                  70                  75                  80

Leu Gly Thr Gly Phe Cys Lys Cys Gly Phe Ala Gly Leu Pro Lys Pro
                85                  90                  95

Thr His Lys Ile Ser Thr Thr Val Gly Lys Pro Tyr Met Glu Thr Ala
            100                 105                 110

Lys Thr Gly Asp Asn Arg Lys Glu Thr Phe Val Gly His Glu Leu Phe
        115                 120                 125

Asn Pro Asp Ile His Leu Lys Leu Val Asn Pro Leu Arg His Gly Ile
    130                 135                 140

Ile Val Asp Trp Asp Thr Val Gln Asp Ile Trp Glu Tyr Leu Phe Arg
145                 150                 155                 160

Gln Glu Met Lys Ile Ala Pro Glu Glu His Ala Val Leu Val Ser Asp
                165                 170                 175

Pro Pro Leu Ser Pro His Thr Asn Arg Glu Lys Tyr Ala Glu Met Leu
            180                 185                 190

Phe Glu Thr Phe Asn Thr Pro Ala Met His Ile Ala Tyr Gln Ser Arg
```

```
                195                 200                 205
Leu Ser Met Tyr Ser Tyr Gly Arg Thr Ser Gly Leu Val Val Glu Val
        210                 215                 220
Gly His Gly Val Ser Tyr Val Val Pro Ile Tyr Glu Gly Tyr Pro Leu
225                 230                 235                 240
Pro Ser Ile Thr Gly Arg Leu Asp Tyr Ala Gly Ser Asp Leu Thr Thr
                245                 250                 255
Tyr Leu Met Asn Leu Met Asn Asn Ser Gly Lys His Phe Ser Glu Asp
                260                 265                 270
His Leu Gly Ile Val Glu Asp Ile Lys Thr Arg Cys Cys Phe Val Ala
                275                 280                 285
Leu Asp Pro Ile Glu Glu Lys Lys Ile Pro Ala Pro Glu His Glu Ile
        290                 295                 300
His Tyr Thr Leu Pro Asp Gly Lys Glu Ile Arg Leu Gly Gln Glu Arg
305                 310                 315                 320
Phe Leu Cys Ser Glu Met Phe Ser Lys Pro Ser Leu Ile Lys Ser Met
                325                 330                 335
Gln Leu Gly Leu His Thr Gln Thr Val Ser Cys Leu Asn Lys Cys Asp
        340                 345                 350
Ile Ala Leu Lys Arg Asp Leu Met Gly Asn Ile Leu Leu Cys Gly Gly
                355                 360                 365
Ser Thr Met Leu Arg Gly Phe Pro Asn Arg Leu Gln Lys Glu Leu Ser
        370                 375                 380
Ser Met Cys Pro Asn Asp Thr Pro Gln Val Asn Val Leu Pro Glu Arg
385                 390                 395                 400
Asp Thr Ala Val Trp Thr Gly Gly Ser Ile Leu Ala Ser Leu Gln Gly
                405                 410                 415
Phe Gln Pro Leu Trp Val His Arg Leu Glu Tyr Glu Glu His Gly Pro
                420                 425                 430
Phe Phe Leu Tyr Arg Arg Cys Phe
        435                 440

<210> SEQ ID NO 145
<211> LENGTH: 438
<212> TYPE: PRT
<213> ORGANISM: Mus musculus

<400> SEQUENCE: 145

Met Leu Glu Asp Leu Ser Gln Gly Lys Gly Ser Asn His Glu Lys Arg
1               5                   10                  15
Lys Met Glu Ser Thr Ala Gln Ile Thr Glu Glu Asp Ser Lys Leu Asp
                20                  25                  30
Glu Val Val Gly Leu Gln Lys Gln Ile Cys Asp Leu Gly Thr Glu Leu
        35                  40                  45
Thr Arg Gln Ser Ser Leu Trp Cys Val Ala His Lys Asp Leu Gln Ser
        50                  55                  60
Gln Ile Asp Ala Leu Ile Lys Glu Asn Gln Glu Ile Arg Ala Glu Leu
65                  70                  75                  80
Lys Thr Leu Lys Lys Gln Asp Ala Glu Ala Thr Lys Ala Cys Ile Gly
                85                  90                  95
Ser Pro Thr Pro Ala Arg Ala Ser Asn Thr Leu Pro Val Tyr Ile Lys
                100                 105                 110
Ile Glu Gly Ile Asp Ser Glu Arg Thr Thr Ser Trp Asp Glu Arg Asp
        115                 120                 125
```

```
Glu Leu Ser Gly Ser Pro Pro Asn Arg Ser Thr Met Ala Thr Gly Arg
    130                 135                 140

Thr Asp Ser Gln Asp Glu Arg Leu Ser Phe Thr Ser Val Asp Glu Lys
145                 150                 155                 160

Val Ile His Met Ser Ser Lys Phe Leu Gln Arg Ser Phe Gly Arg Met
                165                 170                 175

Ser Pro Glu Pro Leu Ser Asp Ser Thr Phe Leu Asp Lys Glu Ser Leu
            180                 185                 190

Ala Asp Ile Trp Ser Ser Asn Pro Glu Thr Ser Asp Ser Glu Leu Leu
        195                 200                 205

Leu His Ala Gln Ala Ser Arg Val Ile Pro Cys Phe Ser Pro Asn Ala
    210                 215                 220

Leu Trp Val Gln Asn Ile Pro Thr Lys Ser Arg Ala Pro Lys Glu Ile
225                 230                 235                 240

Gln Gln Thr Ser Asp Thr Thr Lys Thr Asp Glu Thr Lys Glu Lys Arg
                245                 250                 255

His Pro Asn Gly Lys Val Glu Arg Met Leu Ser Asp Gly Arg Thr Ile
            260                 265                 270

Ile Thr Phe Pro Asn Gly Thr Arg Lys Glu Ile Ser Ala Asp Lys Lys
        275                 280                 285

Thr Thr Leu Ile Arg Phe Phe Asn Gly Asp Met Lys Lys Ile Lys Ser
    290                 295                 300

Asp Gln Lys Val Ile Tyr Tyr Ala Asp Ala Gln Thr Met His Thr
305                 310                 315                 320

Thr Tyr Pro Asp Gly Val Glu Val Val Gln Phe Pro Asn Lys Trp Thr
                325                 330                 335

Glu Lys Phe Tyr Pro Asp Gly Ser Lys Glu Thr Val Phe Pro Asp Gly
            340                 345                 350

Thr Val Lys Gln Leu Lys Asp Gly Cys Glu Glu Thr Val Phe Pro Asp
        355                 360                 365

Gly Thr Phe Val Thr Val Lys Arg Asn Gly Asp Lys Thr Ile Met Phe
    370                 375                 380

Ser Asn Gly Glu Lys Glu Ile His Thr Ala Arg Phe Lys Arg Lys Glu
385                 390                 395                 400

Phe Pro Asp Gly Thr Ile Lys Thr Val Tyr Cys Asn Gly Cys Gln Glu
                405                 410                 415

Thr Lys Tyr Ala Ser Gly Arg Val Arg Val Asp Glu Lys Gly Thr
            420                 425                 430

Val Ile Leu Asp Trp Lys
        435

<210> SEQ ID NO 146
<211> LENGTH: 430
<212> TYPE: PRT
<213> ORGANISM: Mus musculus

<400> SEQUENCE: 146

Met Ala Thr Leu Ser Phe Lys Pro Ser Glu Arg Tyr Arg Leu Ser Asp
  1               5                  10                  15

Trp Arg Thr Asn Ser Tyr Leu Leu Ser Thr Asn Ala Glu Arg Gln Gln
                20                  25                  30

Asp Ala Ser His Gln Ile Arg Gln Glu Ala Arg Ile Leu Arg Asn Glu
            35                  40                  45

Thr Asn Asn Gln Ile Val Trp Asp Glu His Asp Asn Arg Thr Arg Leu
    50                  55                  60
```

```
Ala Glu Arg Ile Asp Thr Val Asn Arg Trp Lys Glu Thr Leu Asp Lys
 65                  70                  75                  80

Cys Leu Thr Asp Leu Asp Ala Glu Ile Asp Ser Leu Ala Gln Ala Lys
                 85                  90                  95

Glu Ser Ala Glu Gln Asn Leu Gln Ala Lys Asn Leu Pro Leu Asp Val
            100                 105                 110

Ala Ile Glu Cys Leu Thr Leu Arg Glu Ser Arg Arg Asp Ile Asp Val
        115                 120                 125

Val Arg Asp Pro Val Glu Glu Leu Leu Lys Glu Val Glu Val Ile
130                 135                 140

Glu Ala Thr Lys Lys Val Leu Gln Glu Lys Ile Ser Gln Ala Phe Gln
145                 150                 155                 160

His Leu Cys Leu Leu Gln Glu Ile Arg Gln Gln Leu Asn Ser Asp His
                165                 170                 175

Arg Asp Lys Met Glu Thr Leu Glu Ile Asp Arg Gly Cys Leu Ser Leu
            180                 185                 190

Asn Leu Thr Ser Pro Asn Ile Ser Leu Lys Val Asn Pro Thr Arg Ile
        195                 200                 205

Pro Lys Asp Ser Thr Thr Leu Gln Gln Trp Asp Glu Phe Thr Arg Phe
210                 215                 220

Asn Lys Asn Arg Ala Glu Ala Glu Met Lys Ala Ser Ile Glu Leu Arg
225                 230                 235                 240

Glu Ala Ile Ala Leu Ala Ile Ala Gln Thr Asn Asn Glu Leu Asp Ala
                245                 250                 255

Gln Arg Val Ala Thr Glu Phe Thr Phe Arg Lys Arg Leu Arg Glu Met
            260                 265                 270

Glu Ser Phe Tyr Ser Glu Leu Lys Trp Gln Glu Lys Asn Thr Leu Glu
        275                 280                 285

Glu Ile Ala Glu Leu Gln Gly Asp Ile Arg Arg Leu Glu Glu Asp Leu
290                 295                 300

Arg Arg Lys Met Met Asn Leu Lys Leu Ala His Thr Arg Leu Glu Ser
305                 310                 315                 320

Arg Thr Tyr Arg Ser Asn Val Glu Leu Cys Arg Asp Gln Thr Gln Tyr
                325                 330                 335

Gly Leu Ile Asp Glu Val His Gln Leu Glu Ala Thr Ile Asn Thr Met
            340                 345                 350

Lys Gln Lys Leu Ala Gln Thr Gln Asn Ala Leu Asp Ala Leu Phe Lys
        355                 360                 365

His Leu Ala Arg Ile Gln Ala Asp Ile Ala Cys Lys Thr Asn Thr Leu
370                 375                 380

Leu Leu Asp Thr Lys Cys Met Asp Thr Arg Arg Lys Leu Thr Val Pro
385                 390                 395                 400

Ala Glu Lys Phe Val Pro Gln Val Asp Thr Phe Thr Arg Thr Thr Asn
                405                 410                 415

Arg Thr Leu Ser Pro Leu Lys Ile Cys Gln Leu Glu Leu Thr
            420                 425                 430

<210> SEQ ID NO 147
<211> LENGTH: 367
<212> TYPE: PRT
<213> ORGANISM: Mus musculus

<400> SEQUENCE: 147

Met Trp Gly Ser Arg Ala Gln Gln Ser Gly Pro Asp Arg Gly Gly Ala
```

```
             1               5              10              15

Cys Leu Leu Ala Ala Phe Leu Leu Cys Phe Ser Leu Leu His Ala Gln
                         20                  25                  30

Asp Tyr Thr Pro Ser Gln Thr Pro Pro Thr Ser Asn Thr Ser Leu
                     35                  40                  45

Lys Pro Arg Gly Arg Val Gln Lys Glu Leu Cys Gly Lys Thr Lys Phe
                 50                  55                  60

Gln Gly Lys Ile Tyr Gly Gly Gln Ile Ala Lys Ala Glu Arg Trp Pro
     65                  70                  75                  80

Trp Gln Ala Ser Leu Ile Phe Arg Gly Arg His Ile Cys Gly Ala Val
                         85                  90                  95

Leu Ile Asp Lys Thr Trp Leu Leu Ser Ala Ala His Cys Phe Gln Arg
                     100                 105                 110

Ser Leu Thr Pro Ser Asp Tyr Arg Ile Leu Leu Gly Tyr Asn Gln Leu
                 115                 120                 125

Ser Asn Pro Ser Asn Tyr Ser Arg Gln Met Thr Val Asn Lys Val Ile
                 130                 135                 140

Leu His Glu Asp Tyr Ser Lys Leu Ser Arg Leu Glu Lys Asn Ile Val
    145                 150                 155                 160

Leu Ile Gln Leu His His Pro Val Ile Tyr Ser Thr His Ile Phe Pro
                         165                 170                 175

Ala Cys Val Pro Asp Gly Thr Thr Lys Val Ser Pro Asn Asn Leu Cys
                     180                 185                 190

Trp Ile Ser Gly Trp Gly Met Leu Ser Ala Asp Lys Phe Leu Gln Ala
                 195                 200                 205

Pro Phe Pro Leu Leu Asp Ala Glu Val Ser Leu Ile Asp Glu Glu Glu
                 210                 215                 220

Cys Thr Thr Phe Phe Gln Thr Pro Glu Val Ser Ile Thr Glu Tyr Asp
    225                 230                 235                 240

Val Ile Lys Asp Asp Val Leu Cys Ala Gly Asp Leu Thr Asn Gln Lys
                         245                 250                 255

Ser Ser Cys Arg Gly Asp Ser Gly Gly Pro Leu Val Cys Phe Leu Asn
                     260                 265                 270

Ser Phe Trp Tyr Val Val Gly Leu Ala Asn Trp Asn Gly Ala Cys Leu
                 275                 280                 285

Glu Pro Ile His Ser Pro Asn Ile Phe Thr Lys Val Ser Tyr Phe Ser
                 290                 295                 300

Asp Trp Ile Lys Gln Lys Lys Ala Asn Thr Pro Ala Ala Asp Val Ser
    305                 310                 315                 320

Ser Ala Pro Leu Glu Glu Met Ala Ser Ser Leu Arg Gly Trp Gly Asn
                         325                 330                 335

Tyr Ser Ala Gly Ile Thr Leu Lys Pro Arg Ile Ser Thr Thr Leu Leu
                     340                 345                 350

Ser Ser Gln Ala Leu Leu Leu Gln Ser Ile Trp Leu Arg Ile Leu
                 355                 360                 365

<210> SEQ ID NO 148
<211> LENGTH: 117
<212> TYPE: PRT
<213> ORGANISM: Mus musculus

<400> SEQUENCE: 148

Met Asp Thr Lys Met Gln Ser Leu Pro Thr Thr His Pro His Pro His
     1               5                  10                  15
```

```
Ser Ser Ser Arg Pro Gln Ser His Thr Ser Asn Gln Cys Asn Gln Cys
            20                  25                  30

Thr Cys Ser His His Cys Arg Ser Cys Ser Gln Ala Gly His Ala Gly
        35                  40                  45

Ser Ser Ser Pro Ser Pro Gly Pro Pro Met Lys His Pro Lys Pro
    50                  55                  60

Ser Val His Ser Arg His Ser Pro Ala Arg Pro Ser His Arg Gly Ser
65                  70                  75                  80

Cys Pro Lys Asn Arg Lys Thr Phe Glu Gly Lys Val Ser Lys Arg Lys
                85                  90                  95

Ala Val Arg Arg Arg Lys Arg Thr His Arg Ala Lys Arg Thr Ser
            100                 105                 110

Gly Arg Arg Tyr Lys
        115

<210> SEQ ID NO 149
<211> LENGTH: 347
<212> TYPE: PRT
<213> ORGANISM: Mus musculus

<400> SEQUENCE: 149

Met Tyr Gly His His Gly Asn Arg Ile Ala Pro Gly Leu Val Lys Met
1               5                   10                  15

Ala Gly Arg Ser Val Arg Val Pro Arg Arg Gly Ser Ala Gly Thr Gln
            20                  25                  30

Ser Arg Gly Gln Leu Ala Ala Gly Arg Asp Leu Leu Ala Arg Glu Gln
        35                  40                  45

Glu Tyr Lys Arg Leu Asn Glu Glu Leu Glu Ala Lys Thr Ala Asp Leu
    50                  55                  60

Val Arg Gln Ala Glu Glu Val Ile Arg Glu Gln Gln Glu Val Arg Ala
65                  70                  75                  80

Arg Pro Phe Ser Ala Leu Thr Thr Ser Cys Lys Glu Gly Gly Ser
                85                  90                  95

Ser Ser Arg Asp Leu Leu Ser Ser Glu Gly Thr His Pro Trp Thr Glu
            100                 105                 110

Thr Lys Pro Lys Thr Lys Asn Thr Gly Pro Val Asn Lys Ile Gln Asn
        115                 120                 125

Arg Leu His Ser Ala Asp Lys Glu Arg Lys Thr Asn Ser Ser Ala Lys
    130                 135                 140

Leu Lys Tyr Pro Asp Ala Gln Thr Ala Asn Asp Val Ala Ile Pro Asp
145                 150                 155                 160

Asp Phe Ser Asp Phe Ser Leu Ala Lys Thr Ile Ser Arg Ile Glu Gly
                165                 170                 175

Gln Leu Asp Glu Asp Gly Leu Pro Glu Cys Ala Glu Asp Ser Phe
            180                 185                 190

Cys Gly Val Ser Lys Asp Ile Gly Thr Glu Ala Gln Ile Arg Phe Leu
        195                 200                 205

Lys Ala Lys Leu His Val Met Gln Glu Glu Leu Asp Ser Val Val Cys
    210                 215                 220

Glu Cys Ser Lys Lys Glu Asp Lys Ile Gln Asp Leu Lys Ser Lys Val
225                 230                 235                 240

Lys Asn Leu Glu Glu Asp Cys Val Arg Gln Arg Thr Val Thr Ser
                245                 250                 255

Gln Gln Ser Gln Ile Glu Lys Tyr Lys Asn Leu Phe Glu Glu Ala Asn
            260                 265                 270
```

```
Lys Lys Cys Asp Glu Leu Gln Gln Gln Leu Ser Ser Val Glu Arg Glu
            275                 280                 285

Leu Glu Ser Lys Arg Arg Leu Gln Lys Gln Ala Ala Ser Ser Gln Ser
        290                 295                 300

Ala Thr Glu Val Arg Leu Asn Arg Ala Leu Glu Glu Ala Glu Lys Tyr
305                 310                 315                 320

Lys Val Glu Leu Ser Lys Leu Arg Gln Thr Asn Lys Asp Asn Gln Tyr
                325                 330                 335

Leu Asn Asn Asp Leu Glu Arg Arg Ala Ser Asn
            340                 345

<210> SEQ ID NO 150
<211> LENGTH: 526
<212> TYPE: PRT
<213> ORGANISM: Mus musculus

<400> SEQUENCE: 150

Met Ala Ser Val Val Lys Thr Ile Trp Gln Ser Lys Glu Ile His
 1               5                  10                  15

Glu Ala Gly Asp Pro Pro Ala Gly Val Glu Ser Arg Ala Gln Leu Val
                20                  25                  30

Pro Glu Ala Pro Gly Gly Val Thr Ser Pro Ala Lys Gly Ile Thr Lys
            35                  40                  45

Lys Lys Lys Ala Val Ser Phe His Gly Val Glu Pro Arg Met Ser His
        50                  55                  60

Glu Pro Met His Trp Cys Leu Asn Leu Lys Arg Ser Ser Ala Cys Thr
65                  70                  75                  80

Asn Val Ser Leu Leu Asn Leu Ala Ala Val Glu Pro Asp Ser Ser Gly
                85                  90                  95

Thr Asp Ser Thr Thr Glu Asp Ser Gly Pro Leu Ala Leu Pro Gly Thr
            100                 105                 110

Pro Ala Ser Pro Thr Thr Pro Trp Ala Pro Glu Asp Pro Asp Ile Thr
        115                 120                 125

Glu Leu Leu Ser Gly Val Asn Ser Gly Leu Val Arg Ala Lys Asp Ser
130                 135                 140

Ile Thr Ser Leu Lys Glu Lys Thr Thr Arg Val Asn Gln His Val Gln
145                 150                 155                 160

Thr Leu Gln Ser Glu Cys Ser Val Leu Ser Glu Asn Leu Glu Arg Arg
                165                 170                 175

Arg Gln Glu Ala Glu Leu Glu Gly Tyr Cys Ser Gln Leu Lys Gly
            180                 185                 190

Pro Arg Pro Asp Val Leu Thr Gln Glu Asn Cys Arg Lys Val Thr Arg
        195                 200                 205

Ser Val Glu Asp Ala Glu Ile Lys Thr Asn Val Leu Lys Gln Asn Ser
210                 215                 220

Ala Leu Leu Glu Glu Lys Leu Arg Tyr Leu Gln Gln Leu Gln Asp
225                 230                 235                 240

Glu Thr Pro Arg Arg Gln Glu Ala Glu Leu Glu Leu Glu Gln Lys
                245                 250                 255

Leu Glu Ala Gly Leu Ser Arg His Gly Leu Ser Pro Ala Thr Pro Ile
            260                 265                 270

Gln Gly Cys Ser Gly Pro Pro Gly Ser Pro Glu Glu Pro Arg Gln
        275                 280                 285

Arg Gly Leu Ser Phe Ser Gly Trp Gly Met Ala Val Arg Thr Gly Glu
```

```
                290                 295                 300
Gly Pro Ser Leu Ser Glu Gln Glu Leu Gln Lys Val Ser Thr Gly Leu
305                 310                 315                 320
Glu Glu Leu Arg Arg Glu Val Ser Ser Leu Ala Ala Arg Trp His Gln
                325                 330                 335
Glu Glu Gly Ala Val Gln Glu Pro Leu Arg Leu Leu Gly Gly Leu Gly
                340                 345                 350
Gly Arg Leu Asp Gly Phe Leu Gly Gln Trp Glu Arg Ala Gln Arg Glu
                355                 360                 365
Gln Ala Gln Ser Ala Arg Gly Leu Gln Glu Leu Arg Ala Arg Ala Asp
                370                 375                 380
Glu Leu Cys Thr Met Val Glu Arg Ser Ala Val Ser Val Ala Ser Leu
385                 390                 395                 400
Arg Ser Glu Leu Glu Ala Leu Gly Pro Val Lys Pro Ile Leu Glu Glu
                405                 410                 415
Leu Gly Arg Gln Leu Gln Asn Ser Arg Arg Gly Ala Asp His Val Leu
                420                 425                 430
Asn Leu Asp Arg Ser Ala Gln Gly Pro Cys Ala Arg Cys Ala Ser Gln
                435                 440                 445
Gly Gln Gln Leu Ser Thr Glu Ser Leu Gln Gln Leu Leu Glu Arg Ala
                450                 455                 460
Leu Thr Pro Leu Val Asp Glu Val Lys Gln Lys Gly Leu Ala Pro Ala
465                 470                 475                 480
Ser Pro Ser Cys Gln Arg Leu His Lys Lys Ile Leu Glu Leu Glu Arg
                485                 490                 495
Gln Ala Leu Ala Lys His Val Arg Ala Glu Ala Leu Ser Ser Thr Phe
                500                 505                 510
Gly Trp Pro Lys Thr Arg Pro Phe Gly Pro Arg Thr Tyr Cys
                515                 520                 525

<210> SEQ ID NO 151
<211> LENGTH: 357
<212> TYPE: PRT
<213> ORGANISM: Mus musculus

<400> SEQUENCE: 151

Met Asp Asp Ala Ala Val Leu Arg Lys Lys Gly Tyr Ile Val Gly Ile
  1               5                  10                  15
Asn Leu Gly Lys Gly Ser Tyr Ala Lys Val Lys Ser Ala Tyr Ser Glu
                 20                  25                  30
Arg Leu Lys Phe Asn Val Ala Val Lys Ile Ile Asp Arg Lys Lys Thr
             35                      40                  45
Pro Thr Asp Phe Val Glu Arg Phe Leu Pro Arg Glu Met Asp Ile Leu
     50                  55                  60
Ala Thr Val Asn His Arg Ser Ile Ile Lys Thr Tyr Glu Ile Phe Glu
 65                  70                  75                  80
Thr Ser Asp Gly Arg Ile Tyr Ile Val Met Glu Leu Gly Val Gln Gly
                 85                  90                  95
Asp Leu Leu Thr Phe Ile Lys Cys Arg Gly Ala Leu His Glu Asp Val
                100                 105                 110
Gly Gly Lys Met Phe Arg Gln Val Ser Ser Ala Val Lys Tyr Cys His
                115                 120                 125
Asp Leu Asp Val Val His Arg Asp Leu Lys Cys Glu Asn Leu Leu Leu
            130                 135                 140
```

```
Asp Lys Asp Phe Asn Ile Lys Leu Ser Asp Phe Gly Phe Ser Lys Gly
145                 150                 155                 160

Cys Leu Arg Asp Gly Ser Gly Arg Ile Val Leu Ser Lys Thr Phe Cys
            165                 170                 175

Gly Ser Ala Ala Tyr Ala Ala Pro Glu Val Arg Gln Gly Ile Pro Tyr
        180                 185                 190

Gln Pro Lys Val Tyr Asp Ile Trp Ser Leu Gly Val Ile Leu Tyr Ile
        195                 200                 205

Met Val Cys Gly Ser Met Pro Tyr Asp Asp Ser Asp Ile Lys Lys Leu
    210                 215                 220

Arg Ile Gln Lys Glu His Arg Val Asp Phe Pro Arg Ser Lys Asn Leu
225                 230                 235                 240

Thr Gly Glu Cys Lys Asp Leu Ile Tyr Arg Ile Leu Gln Pro Asp Val
                245                 250                 255

Asn Arg Arg Leu His Ile Asp Glu Ile Leu Ser His Ser Trp Leu Gln
            260                 265                 270

Pro Pro Lys Pro Lys Ala Met Ser Ser Ala Ser Phe Lys Arg Glu Gly
        275                 280                 285

Glu Gly Lys Tyr Arg Ala Asp Cys Lys Leu Asp Thr Arg Pro Gly Ser
        290                 295                 300

Arg Pro Glu His Arg Pro Asp His Lys Leu Ala Thr Lys Pro Gln Gln
305                 310                 315                 320

Arg Met Leu Val Thr Pro Glu Asn Glu Asp Arg Met Glu Asp Arg Leu
                325                 330                 335

Ala Glu Thr Ser Arg Ala Lys Asp His His Ile Ser Gly Ala Glu Val
            340                 345                 350

Glu Lys Ala Ser Thr
        355

<210> SEQ ID NO 152
<211> LENGTH: 693
<212> TYPE: PRT
<213> ORGANISM: Mus musculus

<400> SEQUENCE: 152

Asn Ser Glu Pro Met Ser Arg Leu Tyr Ser Lys Leu Tyr Lys Glu Ala
1               5                   10                  15

Glu Lys Ile Lys Lys Trp Lys Val Ser Ile Glu Ser Glu Leu Lys Gln
            20                  25                  30

Lys Glu Asn Lys Leu Gln Glu Asn Arg Lys Ile Ile Glu Ala Gln Arg
        35                  40                  45

Lys Ala Ile Gln Glu Leu Gln Phe Glu Asn Glu Lys Val Ser Leu Lys
    50                  55                  60

Leu Glu Glu Glu Ile Gln Glu Asn Lys Asp Leu Ile Lys Glu Asn Asn
65                  70                  75                  80

Ala Thr Ile His Trp Cys Asn Leu Leu Lys Glu Thr Cys Ala Arg Ser
                85                  90                  95

Ala Glu Lys Thr Asn Lys Tyr Glu Tyr Glu Arg Glu Glu Thr Arg Gln
            100                 105                 110

Val Tyr Val Asp Leu Asn Ser Asn Ile Glu Lys Met Ile Leu Ala Phe
        115                 120                 125

Glu Glu Leu Arg Val Gln Ala Glu Asn Ala Arg Leu Glu Met His Phe
    130                 135                 140

Lys Leu Lys Glu Asp His Glu Lys Ile Gln His Leu Glu Glu Glu Tyr
145                 150                 155                 160
```

```
Gln Lys Glu Val Asn Asn Lys Glu Asn Gln Val Ser Glu Leu Leu Ile
                165                 170                 175

Gln Ser Ala Glu Lys Glu Asn Lys Met Lys Asp Leu Thr Phe Leu Leu
        180                 185                 190

Glu Glu Ser Arg Asp Lys Ala Asn Gln Leu Glu Glu Lys Thr Lys Leu
    195                 200                 205

Gln Asp Glu Asn Leu Lys Glu Leu Ser Glu Lys Asp His Leu Thr
210                 215                 220

Ser Glu Leu Glu Asp Ile Lys Met Ser Met Gln Arg Ser Met Ser Thr
225                 230                 235                 240

Gln Lys Ala Leu Glu Glu Asp Leu Gln Ile Ala Thr Lys Thr Ile Ser
                245                 250                 255

Gln Leu Thr Glu Val Lys Glu Ala Gln Met Glu Glu Leu Asn Lys Ala
        260                 265                 270

Lys Thr Thr His Ser Phe Val Val Thr Glu Leu Lys Ala Thr Thr Cys
    275                 280                 285

Thr Leu Glu Glu Leu Leu Arg Thr Glu Gln Gln Arg Leu Glu Lys Asn
290                 295                 300

Glu Asp Gln Leu Lys Leu Ile Thr Val Glu Leu Gln Lys Lys Ser Asn
305                 310                 315                 320

Glu Leu Glu Glu Met Thr Lys Phe Lys Asn Asn Lys Glu Val Glu Leu
                325                 330                 335

Glu Glu Leu Lys Asn Ile Leu Ala Glu Asp Gln Lys Leu Leu Asp Glu
        340                 345                 350

Lys Lys Gln Val Glu Lys Leu Ala Glu Glu Leu Gln Glu Lys Glu Gln
    355                 360                 365

Glu Leu Thr Phe Leu Leu Glu Thr Arg Glu Lys Glu Val His Asp Leu
370                 375                 380

Gln Glu Gln Val Thr Val Thr Lys Thr Ser Glu Gln His Tyr Leu Lys
385                 390                 395                 400

Gln Val Glu Glu Met Lys Thr Glu Leu Glu Lys Glu Lys Leu Lys Asn
                405                 410                 415

Thr Glu Leu Thr Ala Ser Cys Asp Met Leu Leu Leu Glu Asn Lys Lys
        420                 425                 430

Phe Val Gln Glu Ala Ser Asp Met Ala Leu Glu Leu Lys Lys His Gln
    435                 440                 445

Glu Asp Ile Ile Asn Cys Lys Lys Gln Glu Glu Arg Leu Leu Lys Gln
450                 455                 460

Ile Glu Asn Leu Glu Glu Lys Glu Met His Leu Arg Asp Glu Leu Glu
465                 470                 475                 480

Ser Val Arg Lys Glu Phe Ile Gln Gln Gly Asp Glu Val Lys Cys Lys
                485                 490                 495

Leu Asp Lys Ser Glu Glu Asn Ala Arg Ser Ile Glu Cys Glu Val Leu
        500                 505                 510

Lys Lys Glu Lys Gln Met Lys Ile Leu Glu Ser Lys Cys Asn Asn Leu
    515                 520                 525

Lys Lys Gln Val Glu Asn Lys Ser Lys Asn Ile Glu Glu Leu His Gln
530                 535                 540

Glu Asn Lys Thr Leu Lys Lys Lys Ser Ser Ala Glu Ile Lys Gln Leu
545                 550                 555                 560

Asn Ala Tyr Glu Ile Lys Val Ser Lys Leu Glu Leu Glu Leu Glu Ser
                565                 570                 575
```

```
Thr Lys Gln Arg Phe Glu Glu Met Thr Asn Asn Tyr Gln Lys Glu Ile
            580                 585                 590

Glu Asn Lys Lys Ile Ser Glu Gly Lys Leu Leu Gly Glu Val Glu Lys
        595                 600                 605

Ala Lys Ala Thr Val Asp Glu Ala Val Lys Leu Gln Lys Glu Ile Asp
    610                 615                 620

Leu Arg Cys Gln His Lys Ile Ala Glu Met Val Ala Leu Met Glu Lys
625                 630                 635                 640

His Lys His Gln Tyr Asp Lys Ile Val Glu Glu Arg Asp Ser Glu Leu
                645                 650                 655

Gly Leu Tyr Lys Asn Arg Glu Gln Glu Gln Ser Ser Ala Lys Ile Ala
            660                 665                 670

Leu Glu Thr Glu Leu Ser Asn Ile Arg Asn Glu Leu Val Ser Leu Lys
        675                 680                 685

Lys Gln Leu Glu Ile
    690

<210> SEQ ID NO 153
<211> LENGTH: 284
<212> TYPE: PRT
<213> ORGANISM: Mus musculus

<400> SEQUENCE: 153

Met Ser Asp Leu Gly Ser Glu Glu Leu Glu Glu Gly Glu Asn Asp
  1               5                  10                  15

Leu Gly Glu Tyr Glu Gly Glu Arg Asn Glu Val Gly Glu Arg His Gly
            20                  25                  30

His Gly Lys Ala Arg Leu Ser Asn Gly Asp Thr Tyr Glu Gly Ser Tyr
        35                  40                  45

Glu Phe Gly Lys Arg His Gly Gln Gly Thr Tyr Lys Phe Lys Asn Gly
    50                  55                  60

Ala Arg Tyr Thr Gly Asp Tyr Val Lys Asn Lys His Gly Gln Gly
 65                 70                  75                  80

Thr Phe Ile Tyr Pro Asp Gly Ser Arg Tyr Glu Gly Glu Trp Ala Asp
             85                  90                  95

Asp Gln Arg His Gly Gln Gly Val Tyr Tyr Val Asn Asn Asp Thr
                100                 105                 110

Tyr Thr Gly Glu Trp Phe Asn His Gln Arg His Gly Gln Gly Thr Tyr
            115                 120                 125

Leu Tyr Ala Glu Thr Gly Ser Lys Tyr Val Gly Thr Trp Val His Gly
130                 135                 140

Gln Gln Glu Gly Ala Ala Glu Leu Ile His Leu Asn His Arg Tyr Gln
145                 150                 155                 160

Gly Lys Phe Met Asn Lys Asn Pro Val Gly Pro Gly Lys Tyr Val Phe
                165                 170                 175

Asp Ile Gly Cys Glu Gln His Gly Glu Tyr Arg Leu Thr Asp Thr Glu
            180                 185                 190

Arg Gly Glu Glu Glu Glu Glu Glu Thr Leu Val Asn Ile Val Pro
        195                 200                 205

Lys Trp Lys Ala Leu Asn Ile Thr Glu Leu Ala Leu Trp Thr Pro Thr
    210                 215                 220

Leu Ser Glu Glu Gln Pro Pro Glu Gly Gln Gly Gln Glu Glu Pro
225                 230                 235                 240

Gln Gly Leu Thr Gly Val Gly Asp Pro Ser Glu Asp Ile Gln Ala Glu
                245                 250                 255
```

-continued

```
Gly Phe Glu Gly Glu Leu Glu Pro Arg Gly Ala Asp Glu Asp Val Asp
            260                 265                 270

Thr Phe Arg Gln Glu Ser Gln Glu Asn Ser Thr Thr
        275                 280

<210> SEQ ID NO 154
<211> LENGTH: 438
<212> TYPE: PRT
<213> ORGANISM: Mus musculus

<400> SEQUENCE: 154

Met Ser Arg Arg Asp Val Val Leu Thr Asn Val Thr Val Val Gln Leu
  1               5                  10                  15

Arg Arg Asp Arg Cys Pro Cys Pro Cys Pro Cys Pro Cys Pro Cys Pro
                 20                  25                  30

Val Ile Arg Pro Pro Pro Lys Val Glu Asp Pro Pro Thr Val
             35                  40                  45

Glu Glu Gln Pro Pro Pro Pro Pro Pro Pro Pro Pro Pro
 50                  55                  60

Pro Pro Pro Pro Pro Pro Gln Ile Glu Pro Asp Lys Phe Glu Glu
 65                  70                  75                  80

Ala Pro Pro Pro Pro Pro Pro Pro Pro Pro Pro Pro
             85                  90                  95

Pro Pro Leu Gln Lys Pro Ala Arg Glu Leu Thr Val Gly Ile Asn Gly
            100                 105                 110

Phe Gly Arg Ile Gly Arg Leu Val Leu Arg Val Cys Met Glu Lys Gly
            115                 120                 125

Ile Arg Val Val Ala Val Asn Asp Pro Phe Ile Asp Pro Glu Tyr Met
        130                 135                 140

Val Tyr Met Phe Lys Tyr Asp Ser Thr His Gly Arg Tyr Lys Gly Asn
145                 150                 155                 160

Val Glu His Lys Asn Gly Gln Leu Val Val Asp Asn Leu Glu Ile Asn
                165                 170                 175

Thr Tyr Gln Cys Lys Asp Pro Lys Glu Ile Pro Trp Ser Ser Ile Gly
            180                 185                 190

Asn Pro Tyr Val Val Glu Cys Thr Gly Val Tyr Leu Ser Ile Glu Ala
        195                 200                 205

Ala Ser Ala His Ile Ser Ser Gly Ala Arg Arg Val Val Thr Ala
    210                 215                 220

Pro Ser Pro Asp Ala Pro Met Phe Val Met Gly Val Asn Glu Lys Asp
225                 230                 235                 240

Tyr Asn Pro Gly Ser Met Thr Ile Val Ser Asn Ala Ser Cys Thr Thr
                245                 250                 255

Asn Cys Leu Ala Pro Leu Ala Lys Val Ile His Glu Asn Phe Gly Ile
            260                 265                 270

Val Glu Gly Leu Met Thr Thr Val His Ser Tyr Thr Ala Thr Gln Lys
        275                 280                 285

Thr Val Asp Gly Pro Ser Lys Lys Asp Trp Arg Gly Gly Arg Gly Ala
    290                 295                 300

His Gln Asn Ile Ile Pro Ser Ser Thr Gly Ala Ala Lys Ala Val Gly
305                 310                 315                 320

Lys Val Ile Pro Glu Leu Lys Gly Lys Leu Thr Gly Met Ala Phe Arg
                325                 330                 335

Val Pro Thr Pro Asn Val Ser Val Val Asp Leu Thr Cys Arg Leu Ala
```

```
              340                 345                 350
Lys Pro Ala Ser Tyr Ser Ala Ile Thr Glu Ala Val Lys Ala Ala Ala
                355                 360                 365

Lys Gly Pro Leu Ala Gly Ile Leu Ala Tyr Thr Glu Asp Gln Val Val
        370                 375                 380

Ser Thr Asp Phe Asn Gly Asn Pro His Ser Ser Ile Phe Asp Ala Lys
385                 390                 395                 400

Ala Gly Ile Ala Leu Asn Asp Asn Phe Val Lys Leu Val Ala Trp Tyr
                405                 410                 415

Asp Asn Glu Tyr Gly Tyr Ser Arg Val Val Asp Leu Leu Arg Tyr
            420                 425                 430

Met Phe Ser Arg Glu Lys
        435

<210> SEQ ID NO 155
<211> LENGTH: 284
<212> TYPE: PRT
<213> ORGANISM: Mus musculus

<400> SEQUENCE: 155

Met Ser Asp Leu Gly Ser Glu Glu Leu Glu Glu Gly Glu Asn Asp
  1               5                  10                  15

Leu Gly Glu Tyr Glu Gly Glu Arg Asn Glu Val Gly Glu Arg His Gly
                20                  25                  30

His Gly Lys Ala Arg Leu Ser Asn Gly Asp Thr Tyr Glu Gly Ser Tyr
            35                  40                  45

Glu Phe Gly Lys Arg His Gly Gln Gly Thr Tyr Lys Phe Lys Asn Gly
    50                  55                  60

Ala Arg Tyr Thr Gly Asp Tyr Val Lys Asn Lys His Gly Gln Gly
 65                  70                  75                  80

Thr Phe Ile Tyr Pro Asp Gly Ser Arg Tyr Glu Gly Glu Trp Ala Asp
                85                  90                  95

Asp Gln Arg His Gly Gln Gly Val Tyr Tyr Val Asn Asn Asp Thr
            100                 105                 110

Tyr Thr Gly Glu Trp Phe Asn His Gln Arg His Gly Gln Gly Thr Tyr
        115                 120                 125

Leu Tyr Ala Glu Thr Gly Ser Lys Tyr Val Gly Thr Trp Val His Gly
    130                 135                 140

Gln Gln Glu Gly Ala Ala Glu Leu Ile His Leu Asn His Arg Tyr Gln
145                 150                 155                 160

Gly Lys Phe Met Asn Lys Asn Pro Val Gly Pro Gly Lys Tyr Val Phe
                165                 170                 175

Asp Ile Gly Cys Glu Gln His Gly Glu Tyr Arg Leu Thr Asp Thr Glu
            180                 185                 190

Arg Gly Glu Glu Glu Glu Glu Glu Thr Leu Val Asn Ile Val Pro
        195                 200                 205

Lys Trp Lys Ala Leu Asn Ile Thr Glu Leu Ala Leu Trp Thr Pro Thr
    210                 215                 220

Leu Ser Glu Glu Gln Pro Pro Glu Gly Gln Gly Gln Glu Glu Pro
225                 230                 235                 240

Gln Gly Leu Thr Gly Val Gly Asp Pro Ser Glu Asp Ile Gln Ala Glu
                245                 250                 255

Gly Phe Glu Gly Glu Leu Glu Pro Arg Gly Ala Asp Glu Asp Val Asp
            260                 265                 270
```

```
Thr Phe Arg Gln Glu Ser Gln Glu Asn Ser Thr Thr
        275                 280
```

<210> SEQ ID NO 156
<211> LENGTH: 268
<212> TYPE: PRT
<213> ORGANISM: Mus musculus
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (97)..(99)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid

<400> SEQUENCE: 156

```
Gly Ser Pro Asp Pro Asp Pro Thr Thr Pro Asp Tyr Leu Thr Ser Leu
  1               5                  10                  15

Leu Ala Phe Xaa Asp Phe Gln Val Thr Gly Ser Xaa His Cys Pro Tyr
             20                  25                  30

Ser Thr Ala Gln Xaa Ala Val Gly Lys Asp Asn Phe Thr Leu Ile Pro
         35                  40                  45

Glu Gly Val Asn Gly Ile Glu Glu Arg Met Thr Val Val Trp Asp Lys
 50                  55                  60

Ala Val Ala Thr Gly Lys Met Asp Glu Asn Gln Phe Val Ala Val Thr
 65                  70                  75                  80

Ser Thr Asn Ala Ala Lys Ile Phe Asn Leu Tyr Pro Arg Xaa Gly Arg
                 85                  90                  95

Xaa Xaa Xaa Gly Ser Asp Ala Asp Val Val Leu Trp Asp Pro Asp Lys
            100                 105                 110

Met Lys Thr Ile Thr Ala Lys Ser His Xaa Ser Thr Val Glu Tyr Asn
            115                 120                 125

Ile Phe Glu Gly Met Glu Cys His Gly Ser Pro Leu Val Val Ile Ser
            130                 135                 140

Gln Gly Lys Ile Val Phe Glu Asp Gly Asn Ile Ser Val Ser Xaa Gly
145                 150                 155                 160

Met Gly Arg Phe Ile Pro Arg Lys Pro Phe Pro Glu His Leu Tyr Gln
                165                 170                 175

Arg Val Arg Ile Arg Ser Lys Val Phe Gly Leu His Ser Val Ser Arg
            180                 185                 190

Gly Met Tyr Asp Gly Pro Val Tyr Glu Val Pro Ala Thr Pro Lys His
            195                 200                 205

Ala Ala Pro Ala Pro Ser Ala Lys Ser Ser Pro Ser Lys His Gln Pro
```

```
                210                 215                 220
Pro Pro Ile Arg Asn Leu His Gln Ser Asn Phe Ser Leu Ser Gly Ala
225                 230                 235                 240

Gln Ile Asp Asp Asn Asn Pro Arg Arg Thr Gly His Arg Ile Val Ala
                245                 250                 255

Pro Pro Gly Gly Arg Ser Asn Ile Thr Ser Leu Gly
            260                 265

<210> SEQ ID NO 157
<211> LENGTH: 308
<212> TYPE: PRT
<213> ORGANISM: Mus musculus

<400> SEQUENCE: 157

Met Phe Glu Thr Pro Lys Ser Lys Pro Val Thr Val Ala Lys Thr Gln
  1               5                  10                  15

Gly Ile Arg Gly Val Lys Phe Val Asp Phe Thr Ser Thr Gln Gln Gly
                 20                  25                  30

Cys Gln Glu Met Ala Pro Met Asp Leu Asn Leu Lys Ser Arg Gln Asp
             35                  40                  45

Asp Gln Ile Thr Val Lys Ser Leu Glu Trp Lys Gly Gly Ile Phe Asp
         50                  55                  60

Gln Gln Lys Lys Gln Leu Glu Ser Glu Asn Thr Leu Pro Met Glu Ser
 65                  70                  75                  80

Asp Gln Glu Pro Lys Pro Ala Asp Met Thr Pro Ile Glu Ile Gln Ser
                 85                  90                  95

Lys Leu Gln Phe Lys Asp Thr Ala Ser Phe Glu Leu Ala Pro Glu Pro
            100                 105                 110

Val Val Gln Ser Val Lys Ala Lys Glu Phe Gln Asn Glu Leu Gln Val
        115                 120                 125

Pro Ser Met Lys Pro Cys Gln Leu Ile Pro Val Ser Gln Met His Gln
130                 135                 140

Glu Lys Ala Val Glu Ser Thr Leu Asp Pro Gln Leu Gln Gly Val Glu
145                 150                 155                 160

Thr Val Ala Leu Ile Thr Glu Pro Gln Ile Glu Ser Thr Lys Ser Ile
                165                 170                 175

Gln Trp Ile Pro Ile Ser Glu Phe Gln Ser Glu Lys Gly Ile Gly Ser
            180                 185                 190

Asn Ser Lys Ser Gln Ser Gln Glu Ala Arg Pro Thr Glu Leu Lys Pro
        195                 200                 205

Pro Val Leu Trp Arg Gly Val Arg Ser Pro Glu Leu Thr Ala Arg Ser
    210                 215                 220

Lys Ile Gln Gly Glu Lys Ser Val Ala Phe His Leu Glu Pro Gln Leu
225                 230                 235                 240

Arg Ala Gln Glu Pro Lys Thr Phe Asn Leu Thr Ser Glu Pro Gln Pro
                245                 250                 255

Gln Ala Ile Thr Thr Glu Glu Leu Asn Lys Glu Leu Gly Thr Glu Ser
            260                 265                 270

Val Arg Ser Val Gln Trp Leu Ser Gln Gln Glu Phe Pro Ser Val Lys
        275                 280                 285

Phe Leu Arg Ser Lys Ser Trp Ser Pro Phe Gln Gly Ala Pro Glu Phe
    290                 295                 300

Gln Phe Ala Leu
305
```

-continued

<210> SEQ ID NO 158
<211> LENGTH: 1579
<212> TYPE: PRT
<213> ORGANISM: Mus musculus

<400> SEQUENCE: 158

| | | | | | | | | | | | | | | |
|---|---|---|---|---|---|---|---|---|---|---|---|---|---|---|
| Met | Ala | Ala | Ser | Ser | Thr | Val | Val | Glu | Asp | Ile | Thr | Lys | Asp | Glu | Gln |
| 1 | | | | 5 | | | | | 10 | | | | | 15 | |
| Glu | Glu | Thr | Pro | Glu | Ile | Ile | Glu | Gln | Ile | Pro | Ala | Ser | Glu | Ser | Asn |
| | | | 20 | | | | | 25 | | | | | 30 | | |
| Val | Glu | Glu | Met | Ala | Gln | Ala | Ala | Glu | Ser | Gln | Ala | Asn | Asp | Val | Gly |
| | | 35 | | | | | 40 | | | | | 45 | | | |
| Phe | Lys | Lys | Val | Phe | Lys | Phe | Val | Gly | Phe | Lys | Phe | Thr | Val | Lys | Lys |
| | 50 | | | | | 55 | | | | | 60 | | | | |
| Asp | Lys | Asn | Glu | Lys | Ser | Asp | Thr | Val | Gln | Leu | Leu | Thr | Val | Lys | Lys |
| 65 | | | | | 70 | | | | | 75 | | | | | 80 |
| Asp | Glu | Gly | Glu | Gly | Ala | Glu | Ala | Ser | Val | Gly | Ala | Gly | Asp | His | Gln |
| | | | | 85 | | | | | 90 | | | | | 95 | |
| Glu | Pro | Gly | Val | Glu | Thr | Val | Gly | Glu | Ser | Ala | Ser | Lys | Glu | Ser | Glu |
| | | | 100 | | | | | 105 | | | | | 110 | | |
| Leu | Lys | Gln | Ser | Thr | Glu | Lys | Gln | Glu | Gly | Thr | Leu | Lys | Gln | Ala | Gln |
| | | 115 | | | | | 120 | | | | | 125 | | | |
| Ser | Ser | Thr | Glu | Ile | Pro | Leu | Gln | Ala | Glu | Ser | Gly | Gln | Gly | Thr | Glu |
| | 130 | | | | | 135 | | | | | 140 | | | | |
| Glu | Glu | Ala | Ala | Lys | Asp | Gly | Glu | Glu | Asn | Arg | Glu | Lys | Glu | Pro | Thr |
| 145 | | | | | 150 | | | | | 155 | | | | | 160 |
| Lys | Pro | Leu | Glu | Ser | Pro | Thr | Ser | Pro | Val | Ser | Asn | Glu | Thr | Thr | Ser |
| | | | | 165 | | | | | 170 | | | | | 175 | |
| Ser | Phe | Lys | Lys | Phe | Phe | Thr | His | Gly | Trp | Ala | Gly | Trp | Arg | Lys | Lys |
| | | | 180 | | | | | 185 | | | | | 190 | | |
| Thr | Ser | Phe | Lys | Lys | Pro | Lys | Glu | Asp | Asp | Leu | Glu | Thr | Ser | Glu | Lys |
| | | 195 | | | | | 200 | | | | | 205 | | | |
| Arg | Lys | Glu | Gln | Glu | Ala | Glu | Lys | Val | Asp | Glu | Glu | Gly | Glu | Lys | |
| | 210 | | | | | 215 | | | | | 220 | | | | |
| Thr | Glu | Pro | Ala | Pro | Ala | Glu | Glu | Gln | Glu | Pro | Ala | Glu | Gly | Thr | Asp |
| 225 | | | | | 230 | | | | | 235 | | | | | 240 |
| Gln | Ala | Arg | Leu | Ser | Ala | Asp | Tyr | Glu | Lys | Val | Glu | Leu | Pro | Leu | Glu |
| | | | | 245 | | | | | 250 | | | | | 255 | |
| Asp | Gln | Val | Gly | Asp | Leu | Glu | Ala | Leu | Ser | Glu | Lys | Cys | Ala | Pro | Leu |
| | | | 260 | | | | | 265 | | | | | 270 | | |
| Ala | Thr | Glu | Val | Phe | Asp | Glu | Lys | Thr | Glu | Ala | His | Gln | Glu | Val | Val |
| | | 275 | | | | | 280 | | | | | 285 | | | |
| Ala | Glu | Val | His | Val | Ser | Thr | Val | Glu | Lys | Met | Thr | Lys | Gly | Gln | Gly |
| | 290 | | | | | 295 | | | | | 300 | | | | |
| Gly | Ala | Glu | Val | Glu | Gly | Asp | Val | Val | Glu | Gly | Ser | Gly | Glu | Ser | |
| 305 | | | | | 310 | | | | | 315 | | | | | 320 |
| Leu | Pro | Pro | Glu | Lys | Leu | Ala | Glu | Thr | Gln | Glu | Val | Pro | Gln | Glu | Ala |
| | | | | 325 | | | | | 330 | | | | | 335 | |
| Glu | Pro | Val | Glu | Glu | Leu | Met | Lys | Thr | Lys | Glu | Val | Cys | Val | Ser | Gly |
| | | | 340 | | | | | 345 | | | | | 350 | | |
| Gly | Asp | His | Thr | Gln | Leu | Thr | Asp | Leu | Ser | Pro | Glu | Glu | Lys | Met | Leu |
| | | 355 | | | | | 360 | | | | | 365 | | | |
| Pro | Lys | His | Pro | Glu | Gly | Ile | Val | Ser | Glu | Val | Glu | Met | Leu | Ser | Ser |
| | 370 | | | | | 375 | | | | | 380 | | | | |

```
Gln Glu Arg Ile Lys Val Gln Gly Ser Pro Leu Lys Lys Leu Phe Ser
385                 390                 395                 400

Ser Ser Gly Leu Lys Lys Leu Ser Gly Lys Gln Lys Gly Lys Arg
            405                 410                 415

Gly Gly Gly Gly Gly Asp Glu Pro Gly Glu Tyr Gln His Ile Gln
                420                 425                 430

Thr Glu Ser Pro Glu Ser Ala Asp Glu Gln Lys Gly Glu Ser Ser Ala
        435                 440                 445

Ser Ser Pro Glu Glu Pro Glu Glu Ile Ala Cys Leu Glu Lys Gly Pro
465     450                 455                 460

Ser Glu Ala Pro Gln Glu Ala Glu Ala Glu Glu Gly Ala Thr Ser Asp
465             470                 475                 480

Gly Glu Lys Lys Arg Glu Gly Ile Thr Pro Trp Ala Ser Phe Lys Lys
                485                 490                 495

Met Val Thr Pro Lys Lys Arg Val Arg Arg Pro Ser Glu Ser Asp Lys
            500                 505                 510

Glu Glu Glu Leu Asp Lys Val Lys Ser Ala Thr Leu Ser Ser Thr Glu
        515                 520                 525

Ser Thr Ala Ser Gly Met Gln Asp Glu Val Arg Ala Val Gly Glu Glu
530                 535                 540

Gln Arg Ser Glu Glu Pro Lys Arg Arg Val Asp Thr Ser Val Ser Trp
545                 550                 555                 560

Glu Ala Leu Ile Cys Val Gly Ser Ser Lys Lys Arg Ala Arg Lys Ala
                565                 570                 575

Ser Ser Ser Asp Asp Glu Gly Gly Pro Arg Thr Leu Gly Gly Asp Gly
            580                 585                 590

His Arg Ala Glu Glu Ala Ser Lys Asp Lys Glu Ala Asp Ala Leu Pro
                595                 600                 605

Ala Ser Thr Gln Glu Gln Asp Gln Ala His Gly Ser Ser Ser Pro Glu
610                 615                 620

Pro Ala Gly Ser Pro Ser Glu Gly Glu Gly Val Ser Thr Trp Glu Ser
625                 630                 635                 640

Phe Lys Arg Leu Val Thr Pro Arg Lys Lys Ser Lys Ser Lys Leu Glu
                645                 650                 655

Glu Arg Ala Glu Asp Ser Gly Ala Glu Gln Leu Ala Ser Glu Ile Glu
                660                 665                 670

Pro Ser Arg Glu Glu Ser Trp Val Ser Ile Lys Lys Phe Ile Pro Gly
            675                 680                 685

Arg Arg Lys Lys Arg Ala Asp Gly Lys Gln Glu Gln Ala Ala Val Glu
690                 695                 700

Asp Ser Gly Pro Gly Glu Ile Asn Glu Asp Asp Pro Asp Val Pro Ala
705                 710                 715                 720

Val Val Pro Leu Ser Glu Tyr Asp Ala Val Glu Arg Glu Lys Leu Glu
                725                 730                 735

Ala Gln Arg Ala Gln Glu Asn Val Glu Leu Pro Gln Leu Lys Gly Ala
                740                 745                 750

Val Tyr Val Ser Glu Glu Leu Ser Lys Thr Leu Val His Thr Val Ser
            755                 760                 765

Val Ala Val Ile Asp Gly Thr Arg Ala Val Thr Ser Ala Glu Glu Arg
            770                 775                 780

Ser Pro Ser Trp Ile Ser Ala Ser Met Thr Glu Pro Leu Glu His Ala
785                 790                 795                 800
```

-continued

```
Glu Gly Val Ala Thr Pro Pro Val Gly Glu Val Thr Glu Lys Asp Ile
                805                 810                 815
Thr Ala Glu Ala Thr Pro Ala Leu Ala Gln Thr Leu Pro Gly Gly Lys
            820                 825                 830
Asp Ala His Asp Asp Ile Val Thr Ser Glu Val Asp Phe Thr Ser Glu
        835                 840                 845
Ala Val Thr Ala Ala Glu Thr Thr Glu Ala Leu Arg Ala Glu Glu Leu
    850                 855                 860
Thr Glu Ala Ser Gly Ala Glu Glu Thr Thr Asp Met Val Ser Ala Val
865                 870                 875                 880
Ser Gln Leu Ser Asp Ser Pro Asp Thr Thr Glu Ala Thr Pro Val
                885                 890                 895
Gln Glu Val Glu Gly Gly Met Leu Asp Thr Glu Gln Glu Arg Gln
                900                 905                 910
Thr Gln Ala Val Leu Gln Ala Val Ala Asp Lys Val Lys Glu Asp Ser
            915                 920                 925
Gln Val Pro Ala Thr Gln Thr Leu Gln Arg Ala Gly Pro Lys Ala Leu
        930                 935                 940
Glu Lys Val Glu Val Glu Glu Asp Ser Glu Val Leu Ala Thr Glu
945                 950                 955                 960
Lys Glu Lys Asp Val Val Pro Glu Gly Pro Val Gln Glu Ala Glu Thr
                965                 970                 975
Glu His Leu Ala Gln Gly Ser Glu Thr Val Gln Ala Thr Pro Glu Ser
            980                 985                 990
Leu Glu Val Pro Glu Val Thr Glu Asp Val Asp Arg Ala Thr Thr Cys
        995                 1000                1005
Gln Val Ile Lys His Gln Gln Leu Met Glu Gln Ala Val Ala Pro Glu
    1010                1015                1020
Ser Ser Glu Thr Leu Thr Asp Ser Glu Thr Asn Gly Ser Thr Pro Leu
1025                1030                1035                1040
Ala Asp Ser Asp Thr Pro Asn Gly Thr Gln Gln Asp Glu Thr Val Asp
                1045                1050                1055
Ser Gln Asp Ser Asn Ala Ile Ala Ala Val Lys Gln Ser Gln Val Thr
            1060                1065                1070
Glu Glu Glu Ala Ala Ala Gln Thr Glu Gly Pro Ser Thr Pro Ser
        1075                1080                1085
Ser Phe Pro Ala Gln Glu Glu His Arg Glu Lys Pro Gly Arg Asp Val
    1090                1095                1100
Leu Glu Pro Thr Gln Ala Leu Ala Ala Gly Ala Val Pro Ile Leu Ala
1105                1110                1115                1120
Lys Ala Glu Val Gly Gln Glu Gly Glu Ala Gly Gln Phe Asp Gly Glu
                1125                1130                1135
Lys Val Lys Asp Gly Gln Cys Val Lys Glu Leu Glu Val Pro Val His
            1140                1145                1150
Thr Gly Pro Asn Ser Gln Lys Thr Ala Asp Leu Thr Arg Asp Ser Glu
        1155                1160                1165
Val Met Glu Val Ala Arg Cys Gln Glu Thr Glu Ser Asn Glu Glu Gln
    1170                1175                1180
Ser Ile Ser Pro Glu Lys Arg Glu Met Gly Thr Asp Val Glu Lys Glu
1185                1190                1195                1200
Glu Thr Glu Thr Lys Thr Glu Gln Ala Ser Glu Glu His Glu Gln Glu
                1205                1210                1215
Thr Ala Ala Pro Glu His Glu Gly Thr His Pro Lys Pro Val Leu Thr
```

-continued

```
                1220                1225                1230
Ala Asp Met Pro His Ser Glu Arg Gly Lys Ala Leu Gly Ser Leu Glu
            1235                1240                1245

Gly Ser Pro Ser Leu Pro Asp Gln Asp Lys Ala Asp Cys Ile Glu Val
    1250                1255                1260

Gln Val Gln Ser Ser Asp Thr Pro Val Thr Gln Thr Glu Ala Val
1265                1270                1275                1280

Lys Lys Val Glu Glu Thr Val Ala Thr Ser Glu Met Asp Glu Ser Leu
                1285                1290                1295

Glu Cys Ala Gly Ala Gln Ser Leu Pro Ala Glu Lys Leu Ser Glu Thr
            1300                1305                1310

Gly Gly Tyr Gly Thr Leu Gln His Gly Glu Asp Thr Val Pro Gln Gly
        1315                1320                1325

Pro Glu Ser Gln Ala Glu Ser Ile Pro Ile Ile Val Thr Pro Ala Pro
    1330                1335                1340

Glu Ser Ile Leu His Ser Asp Leu Gln Arg Gly Val Ser Ala Ser Gln
1345                1350                1355                1360

Lys Gln Arg Ser Asp Glu Asp Asn Lys Pro Asp Ala Gly Pro Asp Ala
                1365                1370                1375

Ala Gly Lys Glu Ser Ala Ala Arg Glu Lys Ile Leu Arg Ala Glu Pro
            1380                1385                1390

Glu Ile Leu Glu Leu Glu Ser Lys Ser Asn Lys Ile Val Gln Ser Val
        1395                1400                1405

Ile Gln Thr Ala Val Asp Gln Phe Ala Arg Thr Glu Thr Ala Pro Glu
    1410                1415                1420

Thr His Ala Ser Asp Leu Gln Asn Gln Val Pro Val Met Gln Ala Asp
1425                1430                1435                1440

Ser Gln Gly Ala Gln Gln Met Leu Asp Lys Asp Glu Ser Asp Leu Gln
                1445                1450                1455

Val Ser Pro Gln Asp Gly Thr Leu Ser Ala Val Ala Gln Glu Gly Leu
            1460                1465                1470

Ala Val Ser Asp Ser Ser Glu Gly Met Ser Lys Ala Ser Glu Met Ile
        1475                1480                1485

Thr Thr Leu Ala Val Glu Ser Ala Ser Val Lys Glu Ser Val Glu Lys
    1490                1495                1500

Leu Pro Leu Gln Cys Lys Asp Glu Lys Glu His Ala Ala Asp Gly Pro
1505                1510                1515                1520

Gln His Gln Ser Leu Ala Lys Ala Glu Ala Asp Ala Ser Gly Asn Leu
                1525                1530                1535

Thr Lys Glu Ser Pro Asp Thr Asn Gly Pro Lys Leu Thr Glu Glu Gly
            1540                1545                1550

Asp Ala Leu Lys Glu Glu Met Asn Lys Ala Gln Thr Glu Glu Asp Asp
        1555                1560                1565

Leu Gln Glu Pro Lys Gly Asp Leu Thr Glu Ser
    1570                1575

<210> SEQ ID NO 159
<211> LENGTH: 304
<212> TYPE: PRT
<213> ORGANISM: Mus musculus

<400> SEQUENCE: 159

Met Glu Phe Gln Lys Gly Ser Ser Asp Gln Arg Thr Phe Ile Ser Ala
  1               5                  10                  15
```

```
Ile Leu Asn Met Leu Ser Leu Gly Leu Ser Thr Ala Ser Leu Leu Ser
            20                  25                  30

Ser Glu Trp Phe Val Gly Thr Gln Lys Val Pro Lys Pro Leu Cys Gly
        35                  40                  45

Gln Ser Leu Ala Ala Lys Cys Phe Asp Met Pro Met Ser Leu Asp Gly
    50                  55                  60

Gly Ile Ala Asn Thr Ser Ala Gln Glu Val Val Gln Tyr Thr Trp Glu
65                  70                  75                  80

Thr Gly Asp Asp Arg Phe Ser Phe Leu Ala Phe Arg Ser Gly Met Trp
                85                  90                  95

Leu Ser Cys Glu Glu Thr Met Glu Glu Pro Gly Glu Lys Cys Arg Arg
            100                 105                 110

Phe Ile Glu Leu Thr Pro Pro Ala Gln Arg Gly Glu Lys Gly Leu Leu
        115                 120                 125

Glu Phe Ala Thr Leu Gln Gly Ser Cys His Pro Thr Leu Arg Phe Gly
    130                 135                 140

Gly Glu Trp Leu Met Glu Lys Ala Ser Leu Leu His Leu Pro Trp Gly
145                 150                 155                 160

Pro Val Ala Lys Val Phe Trp Leu Ser Leu Gly Ala Gln Thr Ala Tyr
                165                 170                 175

Ile Gly Leu Gln Leu Ile Ser Phe Leu Leu Leu Thr Asp Leu Leu
            180                 185                 190

Leu Thr Thr Asn Pro Gly Cys Gly Leu Lys Leu Ser Ala Phe Ala Ala
        195                 200                 205

Val Ser Leu Val Leu Ser Gly Leu Gly Met Val Ala His Met Leu
    210                 215                 220

Tyr Ser Gln Val Phe Gln Ala Thr Ala Asn Leu Gly Pro Glu Leu Glu
225                 230                 235                 240

Thr Thr Leu Leu Glu Leu Arg Leu Gly Leu Leu His Ser Val Gly Phe
                245                 250                 255

Leu His Leu Leu His Gly Val Thr Val Thr Thr Phe Asn Met Tyr Thr
            260                 265                 270

Arg Met Val Leu Glu Phe Lys Cys Arg His Ser Lys Ser Phe Asn Thr
        275                 280                 285

Asn Pro Ser Cys Leu Ala His Thr Thr Ala Val Ser Phe Leu Leu Arg
    290                 295                 300

<210> SEQ ID NO 160
<211> LENGTH: 754
<212> TYPE: PRT
<213> ORGANISM: Mus musculus

<400> SEQUENCE: 160

Met Ala Gln Ala His Pro Arg Ser Gly Thr Arg Leu Phe Arg Thr Tyr
1               5                   10                  15

Ala Ala Arg Gly Val Arg Gly Ser Gln Arg Gln Pro Gly Gly Leu Ala
            20                  25                  30

Glu Gln Trp Phe Gln Pro Pro Asn Leu Lys Arg Ala Phe Ser Ser Ser
        35                  40                  45

Leu Ser Asp Ser Asn Glu Ser Pro Ala Val Ala Ser Asp Asp Pro Asp
    50                  55                  60

Asp Pro Asp Phe Pro Gly Ser Leu Val Gly Gln Arg Arg Arg Arg Pro
65                  70                  75                  80

Arg Gly Ser Gly Ser Arg Asn Gln Arg Thr Leu Thr Asn Thr Pro Arg
                85                  90                  95
```

```
Val Gln Arg Leu Arg Pro Arg Leu Pro Gln Lys Cys Ser Thr Pro Cys
            100                 105                 110
Ser Arg Leu Arg Pro Pro Phe Pro Asn Cys Ser Pro Gly Cys Leu
        115                 120                 125
Gly Ser Asp His Ser Val Cys Ile Gln Ser Arg Asp Ser Asn Glu Leu
            130                 135                 140
Gly Thr Ser Ala Ser Leu Phe Ser Ser Pro Ala Ser Pro Gly Ala Pro
145                 150                 155                 160
Asp Pro Leu Tyr Ala Asp Ser Ala Val Pro Gly Ser Phe His Leu Pro
                165                 170                 175
Ala Ala Ser Leu Ser Glu Pro Ser Val Pro Cys Pro Gln Val Ala Ala
            180                 185                 190
Thr Gly Asp Arg Tyr Thr Gly Arg Ala Leu Arg Ala Glu Ala Ser Phe
            195                 200                 205
Arg Ser Ser Leu Phe Ser Leu Val Asn Ser Gly Ala Thr Glu Glu Asn
210                 215                 220
Lys Phe Gly Thr Asp Gly Glu Asn Val Lys Glu Ser Cys Cys Glu Arg
225                 230                 235                 240
Arg Gln Gln Met Gly Asn Arg Leu Thr Asp Pro Asp Leu Thr Ser Pro
                245                 250                 255
Gly Lys Arg Lys Ala Ala Cys Lys Lys Val Val Ser Gln Gly Val Asp
            260                 265                 270
Gln Arg Asp Tyr Glu Glu Ser Ser Ala Cys Lys Asp Leu Arg Val Pro
            275                 280                 285
Gly Glu Ile Ser Arg Pro Lys Arg Thr Gly Pro Leu Arg Lys Arg Lys
            290                 295                 300
Gln Gln Glu Ala Thr Gly Thr Pro Pro Arg His Tyr His Gln Ser Lys
305                 310                 315                 320
Lys Lys Arg Lys Ala Ser Val Ser Leu Trp Asn Leu Asn Thr Ser Gln
                325                 330                 335
Arg Asp Ser Trp Thr Lys Thr Arg Ala Ser Phe Gly Phe His Lys Lys
            340                 345                 350
Lys Ile Ile Thr Ser Val Ile Glu Val Cys Ser Ser Val Ala Ser Ser
            355                 360                 365
Ser Ser Arg Ser Leu Leu Ser Glu Cys Ser Thr Pro Pro Ile Lys Asn
        370                 375                 380
Arg Ala His Leu Thr Val Ser Ser Arg Cys Ser Ser Val Tyr Leu Leu
385                 390                 395                 400
Ser Pro Leu Lys Thr Leu His Val Thr Asp Gln Arg Pro Ser Tyr Ala
                405                 410                 415
Glu Lys Val Tyr Gly Glu Cys Asn Gln Glu Gly Pro Ile Pro Phe Ser
            420                 425                 430
Asp Cys Leu Ser Thr Glu Lys Leu Glu Arg Cys Glu Lys Ile Gly Glu
        435                 440                 445
Gly Val Phe Gly Glu Val Phe Gln Ile Ile Asn Asp Gln Ala Pro Val
        450                 455                 460
Ala Leu Lys Ile Ile Ala Ile Glu Gly Leu Asp Leu Val Asn Gly Ser
465                 470                 475                 480
His Gln Lys Thr Phe Glu Glu Ile Leu Pro Glu Ile Ile Ile Ser Lys
                485                 490                 495
Glu Leu Ser Leu Leu Ser Ser Glu Ala Tyr Asn Arg Thr Glu Gly Phe
            500                 505                 510
```

-continued

```
Ile Gly Leu Asn Ser Val His Cys Val Gln Gly Leu Tyr Pro Pro Leu
            515                 520                 525

Leu Leu Lys Ala Trp Asp His Tyr Asn Thr Thr Lys Arg Ser Ala Asn
        530                 535                 540

Asp Arg Pro Asp Phe Phe Gln Glu Asp Gln Leu Phe Ile Ile Leu Glu
545                 550                 555                 560

Phe Glu Phe Gly Gly Val Asp Leu Glu Arg Met Lys Thr Lys Leu Ser
                565                 570                 575

Ser Val Ala Thr Ala Lys Ser Ile Leu His Gln Ile Thr Ala Ser Leu
            580                 585                 590

Ala Val Ala Glu Ala Ser Leu His Phe Glu His Arg Asp Leu His Trp
        595                 600                 605

Gly Asn Val Leu Leu Lys Lys Thr Asn Leu Lys Glu Leu Arg Tyr Thr
    610                 615                 620

Leu Asn Gly Lys Thr Ser Thr Ile Pro Thr His Gly Leu Gln Val Asn
625                 630                 635                 640

Ile Ile Asp Tyr Thr Leu Ser Arg Leu Glu Arg Asp Gly Ile Val Val
                645                 650                 655

Phe Cys Asp Ile Ser Ala Glu Glu Asp Leu Phe Thr Gly Glu Gly Asp
            660                 665                 670

Tyr Gln Phe Glu Ile Tyr Arg Leu Met Arg Lys Glu Asn Lys Asn Cys
        675                 680                 685

Trp Gly Glu Tyr His Pro Tyr Asn Asn Val Leu Trp Leu His Tyr Leu
    690                 695                 700

Thr Asp Lys Ile Leu Asn Lys Met Lys Phe Lys Thr Lys Cys Gln Ser
705                 710                 715                 720

Ala Ala Met Lys Gln Ile Arg Lys Asn Leu Gln His Phe His Arg Thr
                725                 730                 735

Val Leu Ser Phe Ser Ser Ala Thr Asp Leu Leu Cys Gln His Ser Leu
            740                 745                 750

Phe Arg

<210> SEQ ID NO 161
<211> LENGTH: 299
<212> TYPE: PRT
<213> ORGANISM: Mus musculus

<400> SEQUENCE: 161

Met Ser Leu Ser Val Leu Ser Arg Lys Glu Lys Glu Lys Val Ile His
1               5                   10                  15

Arg Leu Leu Val Gln Ala Pro Pro Gly Glu Phe Val Asn Ala Phe Asp
            20                  25                  30

Asp Leu Cys Leu Leu Ile Arg Asp Glu Lys Leu Met His His Gln Gly
        35                  40                  45

Glu Cys Ala Gly His Gln His Cys Gln Lys Tyr Cys Val Pro Leu Cys
    50                  55                  60

Ile Asp Gly Asn Pro Val Leu Leu Ser His His Asn Val Met Gly Asp
65                  70                  75                  80

Phe Arg Phe Phe Asp Tyr Gln Ser Lys Leu Ser Phe Arg Phe Asp Leu
                85                  90                  95

Leu Gln Asn Gln Leu Arg Asp Ile Gln Ser His Gly Ile Ile Arg Asn
            100                 105                 110

Glu Thr Glu Tyr Leu Arg Ser Val Val Met Cys Ala Leu Lys Leu Tyr
        115                 120                 125
```

```
Val Asn Asp His Tyr Pro Asn Gly Asn Cys Asn Val Leu Arg Lys Thr
    130                 135                 140

Val Lys Ser Lys Glu Phe Leu Ile Ala Cys Ile Glu Asp His Ser Tyr
145                 150                 155                 160

Asp Asn Gly Glu Cys Trp Asn Gly Leu Trp Lys Ser Lys Trp Ile Phe
                165                 170                 175

Gln Val Asn Pro Phe Leu Thr Gln Val Thr Gly Arg Ile Phe Val Gln
            180                 185                 190

Ala His Phe Phe Arg Cys Val Asn Leu His Ile Glu Val Ser Lys Asp
        195                 200                 205

Leu Lys Glu Ser Leu Glu Val Val Asn Gln Ala Gln Leu Ala Leu Ser
    210                 215                 220

Phe Ala Arg Leu Val Glu Glu Gln Glu Asn Lys Phe Gln Ala Ala Val
225                 230                 235                 240

Ile Glu Glu Leu Gln Glu Leu Ser Asn Glu Ala Leu Arg Lys Ile Leu
                245                 250                 255

Arg Arg Asp Leu Pro Val Thr Arg Thr Leu Ile Asp Trp Gln Arg Ile
            260                 265                 270

Leu Ser Asp Leu Asn Leu Val Met Tyr Pro Lys Leu Gly Tyr Val Ile
    275                 280                 285

Tyr Ser Arg Ser Val Leu Cys Asn Trp Ile Ile
    290                 295
```

<210> SEQ ID NO 162
<211> LENGTH: 170
<212> TYPE: PRT
<213> ORGANISM: Mus musculus

<400> SEQUENCE: 162

```
Met Ala Gln Met Val Ala Gly Asp Gln Asp Ala Gly Thr Leu Trp Val
  1               5                  10                  15

Pro Ser Gln Ser Glu Ser Gln Thr Glu Ser Asp Ile Ser Thr Gln Ser
                 20                  25                  30

Leu Arg Lys Pro Thr Met Ser Tyr Val Ile Leu Lys Thr Leu Ala Asp
             35                  40                  45

Lys Arg Val His Asn Cys Val Ser Leu Ala Thr Leu Lys Lys Ala Val
         50                  55                  60

Ser Ile Thr Gly Tyr Asn Met Thr His Asn Thr Trp Arg Phe Lys Arg
 65                  70                  75                  80

Val Leu Gln Asn Leu Leu Asp Lys Gly Met Ile Met His Val Thr Cys
                 85                  90                  95

Cys Lys Gly Ala Ser Gly Ser Leu Cys Leu Cys Lys Glu Arg Ala Leu
            100                 105                 110

Lys Ser Asn His Arg Ala Lys Arg Cys Gln Asp Arg Gln Lys Ser Gln
        115                 120                 125

Lys Pro Gln Lys Pro Gly Gln Arg Glu Ser Glu Pro Cys Gln Leu Leu
    130                 135                 140

Leu Ser Ser Lys Lys Asn Asp Gln Leu Phe Lys Gly Val Arg Arg
145                 150                 155                 160

Val Ala Lys Gly Asn Arg His Cys His Tyr
                165                 170
```

<210> SEQ ID NO 163
<211> LENGTH: 398
<212> TYPE: PRT
<213> ORGANISM: Mus musculus

<400> SEQUENCE: 163

```
Met Ala Glu Ala Val Gln Pro Ser Gly Glu Ser Gln Gly Ala Glu Leu
 1               5                   10                  15

Thr Ile Gln Ile Gln Gln Pro Ala Glu Arg Ala Leu Arg Thr Pro Ala
            20                  25                  30

Lys Arg Gly Thr Gln Ser Val Leu Arg Val Ser Gln Leu Leu Leu Arg
        35                  40                  45

Ala Ile Ala Gly His Gln His Leu Thr Leu Asp Ala Leu Lys Lys Glu
    50                  55                  60

Leu Gly Asn Ala Gly Tyr Glu Val Arg Arg Glu Ile Ser Ser His His
65                  70                  75                  80

Glu Gly Lys Ser Thr Arg Leu Glu Lys Gly Thr Leu Leu Arg Val Ser
                85                  90                  95

Gly Ser Asp Ala Ala Gly Tyr Phe Arg Val Trp Lys Ile Ser Lys Pro
            100                 105                 110

Arg Glu Lys Ala Gly Gln Ser Arg Leu Thr Leu Gly Ser His Ser Ser
        115                 120                 125

Gly Lys Thr Val Leu Lys Ser Pro Arg Pro Leu Arg Pro Arg Ser Arg
    130                 135                 140

Arg Lys Ala Ala Lys Ala Arg Glu Val Trp Arg Arg Lys Ala Arg
145                 150                 155                 160

Ala Leu Lys Ala Arg Ser Arg Arg Val Arg Thr Arg Ser Thr Ser Gly
                165                 170                 175

Ala Arg Ser Arg Thr Arg Ser Arg Ala Ser Ser Arg Ala Thr Ser Arg
            180                 185                 190

Ala Thr Ser Arg Ala Arg Ser Arg Ala Arg Ser Arg Ala Gln Ser Ser
        195                 200                 205

Ala Arg Ser Ser Ala Arg Ser Ser Ala Lys Ser Ser Ala Lys Ser Ser
    210                 215                 220

Thr Arg Ser Ser Ala Lys Ser Trp Ala Arg Ser Lys Ala Arg Ser Arg
225                 230                 235                 240

Ala Arg Ser Arg Ala Lys Asp Leu Val Arg Ser Lys Ala Arg Glu Gln
                245                 250                 255

Ala Gln Ala Arg Glu Gln Ala His Ala Arg Ala Arg Glu Gln Ala His
            260                 265                 270

Ala Arg Ala Arg Thr Gln Asp Trp Val Arg Ala Lys Ala Gln Glu Phe
        275                 280                 285

Val Ser Ala Lys Glu Gln Gln Tyr Val Arg Ala Lys Glu Gln Glu Arg
    290                 295                 300

Ala Lys Ala Arg Glu Gln Val Arg Ile Gly Ala Arg Asp Glu Ala Arg
305                 310                 315                 320

Ile Lys Ala Lys Asp Tyr Asn Arg Val Arg Pro Thr Lys Glu Asp Thr
                325                 330                 335

Ser Pro Arg Pro Ala Glu Glu Lys Ser Ser Asn Ser Lys Leu Arg Glu
            340                 345                 350

Glu Lys Gly Gln Glu Pro Glu Arg Pro Val Lys Gln Thr Ile Gln Lys
        355                 360                 365

Pro Ala Leu Asp Asn Ala Pro Ser Ile Gln Gly Lys Ala Cys Thr Lys
    370                 375                 380

Ser Phe Thr Lys Ser Gly Gln Pro Gly Asp Thr Glu Ser Pro
385                 390                 395
```

```
<210> SEQ ID NO 164
<211> LENGTH: 227
<212> TYPE: PRT
<213> ORGANISM: Mus musculus

<400> SEQUENCE: 164

Met Thr Ser Leu Lys Lys Ser Arg Arg Lys Pro Ser Ser Gln Ala
 1               5                  10                  15

Leu Gly Asn Ile Val Gly Cys Arg Ile Ser His Gly Trp Lys Glu Gly
             20                  25                  30

Asn Glu Pro Val Thr His Trp Lys Ala Ile Ile Leu Gly Gln Leu Pro
         35                  40                  45

Thr Asn Pro Ser Leu Tyr Leu Val Lys Tyr Asp Gly Ile Asp Ser Val
     50                  55                  60

Tyr Gly Gln Glu Leu His Ser Asp Glu Arg Ile Leu Asn Leu Lys Val
 65                  70                  75                  80

Leu Pro His Lys Val Val Phe Pro Gln Val Arg Asp Val His Leu Ala
                 85                  90                  95

Gly Ala Leu Val Cys Arg Glu Val Gln His Lys Phe Glu Gly Lys Asp
            100                 105                 110

Gly Ser Glu Asp Asn Trp Ser Gly Met Val Leu Ala Gln Val Pro Phe
        115                 120                 125

Leu Gln Asp Tyr Phe Tyr Ile Ser Tyr Lys Lys Asp Pro Val Leu Tyr
    130                 135                 140

Val Tyr Gln Leu Leu Asp Asp Tyr Lys Glu Gly Asn Leu His Ile Ile
145                 150                 155                 160

Pro Glu Thr Pro Leu Ala Glu Ala Arg Ser Gly Asp Asp Asn Asp Phe
                165                 170                 175

Leu Ile Gly Ser Trp Val Gln Tyr Thr Arg Asp Asp Gly Ser Lys Lys
            180                 185                 190

Phe Gly Lys Val Val Tyr Lys Val Leu Ala Asn Pro Thr Val Tyr Phe
        195                 200                 205

Ile Lys Phe Leu Gly Asp Leu His Ile Tyr Val Tyr Thr Leu Val Ser
    210                 215                 220

Asn Ile Thr
225

<210> SEQ ID NO 165
<211> LENGTH: 254
<212> TYPE: PRT
<213> ORGANISM: Mus musculus

<400> SEQUENCE: 165

Met Ala Glu Glu Val Trp Met Gly Thr Trp Arg Pro His Arg Pro Arg
 1               5                  10                  15

Gly Pro Ile Met Ala Leu Tyr Ser Ser Pro Gly Pro Lys Tyr Leu Ile
             20                  25                  30

Pro Pro Thr Thr Gly Phe Val Lys His Thr Pro Thr Lys Leu Arg Ala
         35                  40                  45

Pro Ala Tyr Ser Phe Arg Gly Ala Pro Met Leu Leu Ala Glu Asn Cys
     50                  55                  60

Ser Pro Gly Pro Arg Tyr Ser Val Asn Pro Lys Ile Leu Lys Thr Gly
 65                  70                  75                  80

Lys Asp Leu Gly Pro Ala Tyr Ser Ile Leu Gly Arg Tyr His Thr Lys
                 85                  90                  95

Thr Leu Leu Thr Pro Gly Pro Gly Asp Tyr Phe Pro Glu Lys Ser Thr
```

```
                100                 105                 110
Lys Tyr Val Phe Asp Ser Ala Pro Ser His Ser Ile Ser Ala Arg Thr
            115                 120                 125

Lys Thr Phe Arg Val Asp Ser Thr Pro Gly Pro Ala Ala Tyr Met Leu
        130                 135                 140

Pro Val Val Met Gly Pro His Thr Val Gly Lys Val Ser Gln Pro Ser
145                 150                 155                 160

Phe Ser Ile Lys Gly Arg Ser Lys Leu Gly Ser Phe Ser Asp Asp Leu
                165                 170                 175

His Lys Thr Pro Gly Pro Ala Ala Tyr Arg Gln Thr Glu Val Gln Val
            180                 185                 190

Thr Lys Phe Lys Ala Pro Gln Tyr Thr Met Ala Ala Arg Val Glu Pro
        195                 200                 205

Pro Gly Asp Lys Thr Leu Lys Pro Gly Pro Gly Ala His Ser Pro Glu
210                 215                 220

Lys Val Thr Leu Asn Lys Pro Cys Ala Pro Thr Val Thr Phe Cys Ile
225                 230                 235                 240

Lys His Ser Asp Tyr Met Thr Pro Leu Val Val Asp Val Glu
                245                 250

<210> SEQ ID NO 166
<211> LENGTH: 152
<212> TYPE: PRT
<213> ORGANISM: Mus musculus

<400> SEQUENCE: 166

Met Val Gly Gln Val His Gly Gly Leu Met Gly Val Ile Gln Arg Ala
1               5                   10                  15

Met Val Lys Ala Cys Pro His Val Trp Phe Glu Arg Ser Glu Val Lys
            20                  25                  30

Asp Arg His Leu Val Ala Lys Arg Leu Thr Glu His Val Gln Asp Lys
        35                  40                  45

Ser Lys Leu Pro Ile Leu Ile Phe Pro Glu Gly Thr Cys Ile Asn Asn
    50                  55                  60

Thr Ser Val Met Met Phe Lys Lys Gly Ser Phe Glu Ile Gly Ala Thr
65                  70                  75                  80

Val Tyr Pro Val Ala Ile Lys Tyr Asp Pro Gln Phe Gly Asp Ala Phe
                85                  90                  95

Trp Asn Ser Ser Lys Tyr Gly Met Val Thr Tyr Leu Leu Arg Met Met
            100                 105                 110

Thr Ser Trp Ala Ile Val Cys Ser Val Trp Tyr Leu Pro Pro Met Thr
        115                 120                 125

Arg Glu Lys Asp Glu Asp Ala Val Gln Phe Ala Asn Arg Val Lys Ser
    130                 135                 140

Ala Ile Ala Arg Gln Glu Asp Trp
145                 150

<210> SEQ ID NO 167
<211> LENGTH: 97
<212> TYPE: PRT
<213> ORGANISM: Mus musculus

<400> SEQUENCE: 167

Asp Pro Gly Val Leu Ser Ala Gln Gln Thr Leu Lys Gln Ile Val
1               5                   10                  15

Ile Cys Gly Asp Pro Gln Ala Lys Asp Thr Lys Ala Leu Leu Gln Cys
```

-continued

```
                    20                  25                  30
Val His Ser Ile Tyr Val Pro Asn Lys Val Leu Ile Leu Ala Asp Gly
         35                  40                  45

Asp Pro Ser Ser Phe Leu Ser Arg Gln Leu Pro Phe Leu Ser Ser Leu
     50                  55                  60

Arg Arg Val Glu Asp Arg Ala Thr Val Tyr Ile Phe Glu Asn Gln Ala
 65                  70                  75                  80

Cys Ser Met Pro Ile Thr Asp Pro Cys Glu Leu Arg Lys Leu Leu His
                 85                  90                  95

Gln

<210> SEQ ID NO 168
<211> LENGTH: 1757
<212> TYPE: DNA
<213> ORGANISM: Homo sapiens
<220> FEATURE:
<221> NAME/KEY: CDS
<222> LOCATION: (17)..(1570)
<223> OTHER INFORMATION: Scot-t
<300> PUBLICATION INFORMATION:
<301> AUTHORS: Tanaka, H. et al.
<302> TITLE: Cloning and characterization of a human orthologue of
      testis-specific succinyl CoA: 3-oxo acid CoA transferase (Scot-t)
      cDNA
<303> JOURNAL: Mol. Hum. Reprod.
<304> VOLUME: 8
<305> ISSUE: 1
<306> PAGES: 16-23
<307> DATE: 2002
<308> DATABASE ACCESSION NUMBER: GenBank/AB050193
<309> DATABASE ENTRY DATE: 2002-03-15
<313> RELEVANT RESIDUES: (1)..(1757)

<400> SEQUENCE: 168
ccgacccggg ccgact atg gcg gcg ctg cgg ctc ctg gcg tca gtg ctc ggg        52
                  Met Ala Ala Leu Arg Leu Leu Ala Ser Val Leu Gly
                   1               5                  10 cgc ggg gtc ccc gcc ggc ggc tca ggg ctc gcg ctg tcc cag ggc tgc        100
Arg Gly Val Pro Ala Gly Gly Ser Gly Leu Ala Leu Ser Gln Gly Cys
             15                  20                  25 gcc cgc tgc ttt gcc acc agt ccc cgg ctc cgt gcc aag ttc tac gcg        148
Ala Arg Cys Phe Ala Thr Ser Pro Arg Leu Arg Ala Lys Phe Tyr Ala
         30                  35                  40 gac ccg gtg gag atg gtg aag gac atc tct gac ggg gcg acc gtc atg        196
Asp Pro Val Glu Met Val Lys Asp Ile Ser Asp Gly Ala Thr Val Met
 45                  50                  55                  60 atc ggg ggc ttc ggg ctc tgc ggg atc ccc gag aac ctg atc gcc gcg        244
Ile Gly Gly Phe Gly Leu Cys Gly Ile Pro Glu Asn Leu Ile Ala Ala
                 65                  70                  75 ctg ctc agg acc cgc gtg aaa gac ctg cag gtg gtc agc agc aac gtg        292
Leu Leu Arg Thr Arg Val Lys Asp Leu Gln Val Val Ser Ser Asn Val
             80                  85                  90 ggc gtg gag gac ttc ggc ctg ggc ctc ctg gcc gcc agg cag gtc        340
Gly Val Glu Asp Phe Gly Leu Gly Leu Leu Leu Ala Ala Arg Gln Val
         95                 100                 105 cgt cgc atc gtc tgt tcc tac gtg ggc gag aac acc ctg tgc gag agc        388
Arg Arg Ile Val Cys Ser Tyr Val Gly Glu Asn Thr Leu Cys Glu Ser
    110                 115                 120 cag tac ctg gca gga gag ctg gag ctg gag ctc acg ccc cag ggc acc        436
Gln Tyr Leu Ala Gly Glu Leu Glu Leu Glu Leu Thr Pro Gln Gly Thr
125                 130                 135                 140 ctg gcc gag cgc atc cgc gcg ggg ggc gcc ggg gtg ccc gcc ttc tac        484
Leu Ala Glu Arg Ile Arg Ala Gly Gly Ala Gly Val Pro Ala Phe Tyr
```

-continued

|  |  |  |  |  |  |  |  |  |  |  |  |  |  |  |  |
|---|---|---|---|---|---|---|---|---|---|---|---|---|---|---|---|
|  |  | 145 |  |  |  | 150 |  |  |  | 155 |  |  |  |  |  |
| acc | ccc | acg | ggc | tac | ggg | acc | ctg | gtc | cag | gaa | ggg | ggc | gcc | ccc | atc | 532 |
| Thr | Pro | Thr | Gly | Tyr | Gly | Thr | Leu | Val | Gln | Glu | Gly | Gly | Ala | Pro | Ile |
|  |  | 160 |  |  |  | 165 |  |  |  | 170 |  |  |  |  |  |
| cgc | tac | acc | ccg | gac | ggc | cac | ctg | gcg | ctc | atg | agc | cag | ccc | cga | gag | 580 |
| Arg | Tyr | Thr | Pro | Asp | Gly | His | Leu | Ala | Leu | Met | Ser | Gln | Pro | Arg | Glu |
|  | 175 |  |  |  |  | 180 |  |  |  | 185 |  |  |  |  |  |
| gtg | agg | gag | ttc | aac | ggc | gac | cac | ttc | ctt | ttg | gag | cgc | gcc | atc | cgg | 628 |
| Val | Arg | Glu | Phe | Asn | Gly | Asp | His | Phe | Leu | Leu | Glu | Arg | Ala | Ile | Arg |
|  | 190 |  |  |  | 195 |  |  |  |  | 200 |  |  |  |  |  |
| gca | gac | ttc | gcc | ctg | gtg | aaa | ggg | tgg | aag | gcc | gac | cgg | gca | gga | aac | 676 |
| Ala | Asp | Phe | Ala | Leu | Val | Lys | Gly | Trp | Lys | Ala | Asp | Arg | Ala | Gly | Asn |
| 205 |  |  |  |  | 210 |  |  |  |  | 215 |  |  |  |  | 220 |
| gtg | gtc | ttc | agg | aga | agc | gcc | cgc | aat | ttc | aac | gtg | ccc | atg | tgc | aaa | 724 |
| Val | Val | Phe | Arg | Arg | Ser | Ala | Arg | Asn | Phe | Asn | Val | Pro | Met | Cys | Lys |
|  |  |  |  | 225 |  |  |  |  | 230 |  |  |  |  | 235 |  |
| gct | gca | gac | gtc | acg | gcg | gtg | gag | gtg | gaa | gag | atc | gtg | gag | gtg | ggg | 772 |
| Ala | Ala | Asp | Val | Thr | Ala | Val | Glu | Val | Glu | Glu | Ile | Val | Glu | Val | Gly |
|  |  |  |  | 240 |  |  |  |  | 245 |  |  |  |  | 250 |  |
| gct | ttc | ccc | cca | gaa | gac | atc | cac | gtt | cct | aac | att | tat | gta | gat | cgc | 820 |
| Ala | Phe | Pro | Pro | Glu | Asp | Ile | His | Val | Pro | Asn | Ile | Tyr | Val | Asp | Arg |
|  |  |  | 255 |  |  |  |  | 260 |  |  |  |  | 265 |  |  |
| gtg | ata | aag | ggg | cag | aaa | tac | gag | aaa | cga | att | gag | cgc | tta | acg | atc | 868 |
| Val | Ile | Lys | Gly | Gln | Lys | Tyr | Glu | Lys | Arg | Ile | Glu | Arg | Leu | Thr | Ile |
|  | 270 |  |  |  |  | 275 |  |  |  |  | 280 |  |  |  |  |  |
| ctg | aaa | gag | gaa | gat | gga | gac | gct | gga | aag | gaa | gag | gac | gcc | agg | acg | 916 |
| Leu | Lys | Glu | Glu | Asp | Gly | Asp | Ala | Gly | Lys | Glu | Glu | Asp | Ala | Arg | Thr |
| 285 |  |  |  |  | 290 |  |  |  |  | 295 |  |  |  |  | 300 |
| cgc | atc | atc | aga | cgc | gca | gct | ctg | gaa | ttt | gag | gac | ggc | atg | tac | gcc | 964 |
| Arg | Ile | Ile | Arg | Arg | Ala | Ala | Leu | Glu | Phe | Glu | Asp | Gly | Met | Tyr | Ala |
|  |  |  |  | 305 |  |  |  |  | 310 |  |  |  |  | 315 |  |
| aat | ctg | ggc | ata | ggc | atc | ccc | ctg | ctg | gcc | agc | aac | ttc | atc | agt | ccc | 1012 |
| Asn | Leu | Gly | Ile | Gly | Ile | Pro | Leu | Leu | Ala | Ser | Asn | Phe | Ile | Ser | Pro |
|  |  |  | 320 |  |  |  |  | 325 |  |  |  |  | 330 |  |  |
| agc | atg | act | gtc | cat | ctt | cac | agt | gag | aac | ggg | atc | ctg | ggc | ctg | ggc | 1060 |
| Ser | Met | Thr | Val | His | Leu | His | Ser | Glu | Asn | Gly | Ile | Leu | Gly | Leu | Gly |
|  |  | 335 |  |  |  |  | 340 |  |  |  |  | 345 |  |  |  |
| ccg | ttt | ccc | acg | gaa | gat | gag | gtg | gat | gcc | gac | ctc | atc | aat | gca | ggc | 1108 |
| Pro | Phe | Pro | Thr | Glu | Asp | Glu | Val | Asp | Ala | Asp | Leu | Ile | Asn | Ala | Gly |
| 350 |  |  |  |  | 355 |  |  |  |  | 360 |  |  |  |  |  |
| aag | cag | acg | gtc | acg | gtg | ctt | ccc | ggg | ggc | tgc | ttc | ttc | gcc | agc | gac | 1156 |
| Lys | Gln | Thr | Val | Thr | Val | Leu | Pro | Gly | Gly | Cys | Phe | Phe | Ala | Ser | Asp |
| 365 |  |  |  | 370 |  |  |  |  | 375 |  |  |  |  | 380 |  |
| gac | tcc | ttc | gcc | atg | atc | cga | ggg | gga | cac | atc | caa | cta | acc | atg | ctt | 1204 |
| Asp | Ser | Phe | Ala | Met | Ile | Arg | Gly | Gly | His | Ile | Gln | Leu | Thr | Met | Leu |
|  |  |  |  | 385 |  |  |  |  | 390 |  |  |  |  | 395 |  |
| gga | gcc | atg | cag | gtt | tcc | aaa | tac | ggc | gac | ctg | gcg | aac | tgg | atg | atc | 1252 |
| Gly | Ala | Met | Gln | Val | Ser | Lys | Tyr | Gly | Asp | Leu | Ala | Asn | Trp | Met | Ile |
|  |  |  | 400 |  |  |  |  | 405 |  |  |  |  | 410 |  |  |
| cct | ggc | aag | aag | gtg | aaa | ggc | atg | ggc | ggt | gcc | atg | gac | ttg | gtg | tcc | 1300 |
| Pro | Gly | Lys | Lys | Val | Lys | Gly | Met | Gly | Gly | Ala | Met | Asp | Leu | Val | Ser |
|  |  | 415 |  |  |  |  | 420 |  |  |  |  | 425 |  |  |  |
| agt | cag | aag | acc | aga | gtg | gtg | gtc | acc | atg | cag | cac | tgc | aca | aag | gac | 1348 |
| Ser | Gln | Lys | Thr | Arg | Val | Val | Val | Thr | Met | Gln | His | Cys | Thr | Lys | Asp |
|  | 430 |  |  |  |  | 435 |  |  |  |  | 440 |  |  |  |  |
| aac | acc | ccc | aag | atc | atg | gag | aaa | tgc | acc | atg | ccg | ctg | acc | ggg | aag | 1396 |
| Asn | Thr | Pro | Lys | Ile | Met | Glu | Lys | Cys | Thr | Met | Pro | Leu | Thr | Gly | Lys |
| 445 |  |  |  |  | 450 |  |  |  |  | 455 |  |  |  |  | 460 |
| cgg | tgc | gtg | gac | cgc | atc | atc | acc | gag | aag | gcc | gtg | ttt | gac | gtg | cac | 1444 |

```
Arg Cys Val Asp Arg Ile Ile Thr Glu Lys Ala Val Phe Asp Val His
                465                 470                 475 agg aag aaa gag ctg acg ctg agg gag ctc tgg gag ggc ctg acg gtg        1492
Arg Lys Lys Glu Leu Thr Leu Arg Glu Leu Trp Glu Gly Leu Thr Val
            480                 485                 490 gac gac atc aaa aag agc acg ggg tgt gcc ttt gct gtg tcc ccg aac        1540
Asp Asp Ile Lys Lys Ser Thr Gly Cys Ala Phe Ala Val Ser Pro Asn
        495                 500                 505 ctc agg ccc atg cag cag gtg gca ccc tga cgggacctgg atctgggcgg          1590
Leu Arg Pro Met Gln Gln Val Ala Pro
    510                 515 ggtggtgcgc tcctcagggc gggtgccacc gggttcccca ggggaataca tgtccccagc      1650
tctgggaggg gtttgctact ggcctcctac tttcctccct aggtggacag tgctcctcta      1710
gagagctgcg actttaatta aaacaacag gaaaacagaa aaaaaa                      1757

<210> SEQ ID NO 169
<211> LENGTH: 517
<212> TYPE: PRT
<213> ORGANISM: Homo sapiens

<400> SEQUENCE: 169

Met Ala Ala Leu Arg Leu Leu Ala Ser Val Leu Gly Arg Gly Val Pro
1               5                   10                  15

Ala Gly Gly Ser Gly Leu Ala Leu Ser Gln Gly Cys Ala Arg Cys Phe
            20                  25                  30

Ala Thr Ser Pro Arg Leu Arg Ala Lys Phe Tyr Ala Asp Pro Val Glu
        35                  40                  45

Met Val Lys Asp Ile Ser Asp Gly Ala Thr Val Met Ile Gly Gly Phe
    50                  55                  60

Gly Leu Cys Gly Ile Pro Glu Asn Leu Ile Ala Ala Leu Leu Arg Thr
65                  70                  75                  80

Arg Val Lys Asp Leu Gln Val Val Ser Ser Asn Val Gly Val Glu Asp
                85                  90                  95

Phe Gly Leu Gly Leu Leu Leu Ala Ala Arg Gln Val Arg Arg Ile Val
            100                 105                 110

Cys Ser Tyr Val Gly Glu Asn Thr Leu Cys Glu Ser Gln Tyr Leu Ala
        115                 120                 125

Gly Glu Leu Glu Leu Glu Leu Thr Pro Gln Gly Thr Leu Ala Glu Arg
    130                 135                 140

Ile Arg Ala Gly Gly Ala Gly Val Pro Ala Phe Tyr Thr Pro Thr Gly
145                 150                 155                 160

Tyr Gly Thr Leu Val Gln Glu Gly Gly Ala Pro Ile Arg Tyr Thr Pro
                165                 170                 175

Asp Gly His Leu Ala Leu Met Ser Gln Pro Arg Glu Val Arg Glu Phe
            180                 185                 190

Asn Gly Asp His Phe Leu Leu Glu Arg Ala Ile Arg Ala Asp Phe Ala
        195                 200                 205

Leu Val Lys Gly Trp Lys Ala Asp Arg Ala Gly Asn Val Val Phe Arg
    210                 215                 220

Arg Ser Ala Arg Asn Phe Asn Val Pro Met Cys Lys Ala Ala Asp Val
225                 230                 235                 240

Thr Ala Val Glu Val Glu Glu Ile Val Glu Val Gly Ala Phe Pro Pro
                245                 250                 255

Glu Asp Ile His Val Pro Asn Ile Tyr Val Asp Arg Val Ile Lys Gly
            260                 265                 270
```

```
Gln Lys Tyr Glu Lys Arg Ile Glu Arg Leu Thr Ile Leu Lys Glu Glu
        275                 280                 285

Asp Gly Asp Ala Gly Lys Glu Glu Asp Ala Arg Thr Arg Ile Ile Arg
    290                 295                 300

Arg Ala Ala Leu Glu Phe Glu Asp Gly Met Tyr Ala Asn Leu Gly Ile
305                 310                 315                 320

Gly Ile Pro Leu Leu Ala Ser Asn Phe Ile Ser Pro Ser Met Thr Val
                325                 330                 335

His Leu His Ser Glu Asn Gly Ile Leu Gly Leu Gly Pro Phe Pro Thr
            340                 345                 350

Glu Asp Glu Val Asp Ala Asp Leu Ile Asn Ala Gly Lys Gln Thr Val
        355                 360                 365

Thr Val Leu Pro Gly Gly Cys Phe Phe Ala Ser Asp Asp Ser Phe Ala
    370                 375                 380

Met Ile Arg Gly Gly His Ile Gln Leu Thr Met Leu Gly Ala Met Gln
385                 390                 395                 400

Val Ser Lys Tyr Gly Asp Leu Ala Asn Trp Met Ile Pro Gly Lys Lys
                405                 410                 415

Val Lys Gly Met Gly Gly Ala Met Asp Leu Val Ser Ser Gln Lys Thr
            420                 425                 430

Arg Val Val Val Thr Met Gln His Cys Thr Lys Asp Asn Thr Pro Lys
        435                 440                 445

Ile Met Glu Lys Cys Thr Met Pro Leu Thr Gly Lys Arg Cys Val Asp
    450                 455                 460

Arg Ile Ile Thr Glu Lys Ala Val Phe Asp Val His Arg Lys Lys Glu
465                 470                 475                 480

Leu Thr Leu Arg Glu Leu Trp Glu Gly Leu Thr Val Asp Asp Ile Lys
                485                 490                 495

Lys Ser Thr Gly Cys Ala Phe Ala Val Ser Pro Asn Leu Arg Pro Met
            500                 505                 510

Gln Gln Val Ala Pro
        515

<210> SEQ ID NO 170
<211> LENGTH: 558
<212> TYPE: DNA
<213> ORGANISM: Homo sapiens
<220> FEATURE:
<221> NAME/KEY: CDS
<222> LOCATION: (135)..(248)
<223> OTHER INFORMATION: protamine-1
<220> FEATURE:
<221> NAME/KEY: CDS
<222> LOCATION: (340)..(381)
<223> OTHER INFORMATION: protamine-1
<300> PUBLICATION INFORMATION:
<301> AUTHORS: Domenjoud, L. et al.
<302> TITLE: Genomic sequences of human protamines whose genes, PRM1
       and PRM2, are clustered
<303> JOURNAL: Genomics
<304> VOLUME: 8
<305> ISSUE: 1
<306> PAGES: 127-133
<307> DATE: 1990
<308> DATABASE ACCESSION NUMBER: GenBank/M60331
<309> DATABASE ENTRY DATE: 1995-03-07
<313> RELEVANT RESIDUES: (1)..(558)

<400> SEQUENCE: 170 cccctggca tctataacag gccgcagagc tggccctga ctcacagccc acagagttcc    60
```

```
acctgctcac aggttggctg gctcagccaa ggtggtgccc tgctctgagc attcagccaa      120
gcccatcctg cacc atg gcc agg tac aga tgc tgt cgc agc cag agc cgg       170
             Met Ala Arg Tyr Arg Cys Cys Arg Ser Gln Ser Arg
              1               5                  10 agc aga tat tac cgc cag aga caa aga agt cgc aga cga agg agg cgg       218
Ser Arg Tyr Tyr Arg Gln Arg Gln Arg Ser Arg Arg Arg Arg Arg
             15                  20                  25 agc tgc cag aca cgg agg aga gcc atg agt aagtgggccc agctgagggt         268
Ser Cys Gln Thr Arg Arg Arg Ala Met Ser
         30                  35 gggctggggc tgaggctggg agctctcagg gcccagcctt cctctcacca cttttcttgg     328
tctcaccagg g tgc tgc cgc ccc agg tac aga ccg aga tgt aga aga cac      378
             Cys Cys Arg Pro Arg Tyr Arg Pro Arg Cys Arg Arg His
              40                  45                  50 taa ttgcacaaaa tagcacatcc accaaactcc tgcctgagaa tgttaccaga            431
cttcaagatc ctcttgccac atcttgaaaa tgccaccatc caataaaaat caggagcctg    491
ctaaggaaca atgccgcctg tcaataaatg ttgaaaagtc atcccactct tctctccttg    551
ttcttga                                                              558

<210> SEQ ID NO 171
<211> LENGTH: 38
<212> TYPE: PRT
<213> ORGANISM: Homo sapiens

<400> SEQUENCE: 171

Met Ala Arg Tyr Arg Cys Cys Arg Ser Gln Ser Arg Ser Arg Tyr Tyr
 1               5                  10                  15

Arg Gln Arg Gln Arg Ser Arg Arg Arg Arg Arg Ser Cys Gln Thr
             20                  25                  30

Arg Arg Arg Ala Met Ser
         35

<210> SEQ ID NO 172
<211> LENGTH: 13
<212> TYPE: PRT
<213> ORGANISM: Homo sapiens

<400> SEQUENCE: 172

Cys Cys Arg Pro Arg Tyr Arg Pro Arg Cys Arg Arg His
 1               5                  10

<210> SEQ ID NO 173
<211> LENGTH: 826
<212> TYPE: DNA
<213> ORGANISM: Homo sapiens
<220> FEATURE:
<221> NAME/KEY: CDS
<222> LOCATION: (101)..(373)
<223> OTHER INFORMATION: protamine-2
<220> FEATURE:
<221> NAME/KEY: CDS
<222> LOCATION: (537)..(572)
<223> OTHER INFORMATION: protamine-2

<400> SEQUENCE: 173
aacagtaaca ccaagggcag gtgggcaggc ctccgccctc ctcccctact ccagggccca     60
ctgcagcctc agcccaggag ccaccagatc tcccaacacc atg gtc cga tac cgc      115
                                             Met Val Arg Tyr Arg
                                              1               5 gtg agg agc ctg agc gaa cgc tcg cac gag gtg tac agg cag cag ttg      163
```

-continued

```
Val Arg Ser Leu Ser Glu Arg Ser His Glu Val Tyr Arg Gln Gln Leu
            10                  15                  20 cat ggg caa gag caa gga cac cac ggc caa gag gag caa ggg ctg agc       211
His Gly Gln Glu Gln Gly His His Gly Gln Glu Glu Gln Gly Leu Ser
        25                  30                  35 ccg gag cac gtc gag gtc tac gag agg acc cat ggc cag tct cac tat       259
Pro Glu His Val Glu Val Tyr Glu Arg Thr His Gly Gln Ser His Tyr
    40                  45                  50 agg cgc aga cac tgc tct cga agg agg ctg cac cgg atc cac agg cgg       307
Arg Arg Arg His Cys Ser Arg Arg Arg Leu His Arg Ile His Arg Arg
55                  60                  65 cag cat cgc tcc tgc aga agg cgc aaa aga cgc tcc tgc agg cac cgg       355
Gln His Arg Ser Cys Arg Arg Arg Lys Arg Arg Ser Cys Arg His Arg
70                  75                  80                  85 agg agg cat cgc aga ggt ctgcctgcgc cccgccttg ccctgcatgt               403
Arg Arg His Arg Arg Gly
                90 ccctgaccac cccaggcaca ggagggaggc ggggacccac cccacctgac aaaagctcca     463 gccccctaaa ccccgtcccc acccagagtt ccctaggtga ccccctcaac cagaactttc     523 tttcccaaaa ggc tgc aga acc agg aag aga aca tgc aga agg cac taa        572
            Cys Arg Thr Arg Lys Arg Thr Cys Arg Arg His
                        95                  100 gcttcctggg cccctcaccc ccagctggaa attaagaaaa agtcgcccga acaccaagt      632 gaggccatag caattcccct acatcaaatg ctcaagcccc cagctggaag ttaagagaaa     692
gtcacctgcc caagaaacac cgagtgaggc catagcaact cccctacatc aaatgctcaa     752
gccctgagtt gccgccgaga agcccacaag atctgagtga aattgagcaa agtcacctgc     812
ccaataaagc ttga                                                      826

<210> SEQ ID NO 174
<211> LENGTH: 91
<212> TYPE: PRT
<213> ORGANISM: Homo sapiens

<400> SEQUENCE: 174

Met Val Arg Tyr Arg Val Arg Ser Leu Ser Glu Arg Ser His Glu Val
1               5                   10                  15

Tyr Arg Gln Gln Leu His Gly Gln Glu Gln Gly His His Gly Gln Glu
            20                  25                  30

Glu Gln Gly Leu Ser Pro Glu His Val Glu Val Tyr Glu Arg Thr His
        35                  40                  45

Gly Gln Ser His Tyr Arg Arg Arg His Cys Ser Arg Arg Arg Leu His
    50                  55                  60

Arg Ile His Arg Arg Gln His Arg Ser Cys Arg Arg Arg Lys Arg Arg
65                  70                  75                  80

Ser Cys Arg His Arg Arg Arg His Arg Arg Gly
                85                  90

<210> SEQ ID NO 175
<211> LENGTH: 11
<212> TYPE: PRT
<213> ORGANISM: Homo sapiens

<400> SEQUENCE: 175

Cys Arg Thr Arg Lys Arg Thr Cys Arg Arg His
1               5                   10
```

```
<210> SEQ ID NO 176
<211> LENGTH: 25
<212> TYPE: DNA
<213> ORGANISM: Artificial
<220> FEATURE:
<223> OTHER INFORMATION: Description of artificial sequence: Synthetic
      oligonucleotide

<400> SEQUENCE: 176
tgctctgtga cgcgcggccc gaggc                                              25

<210> SEQ ID NO 177
<211> LENGTH: 26
<212> TYPE: DNA
<213> ORGANISM: Artificial
<220> FEATURE:
<223> OTHER INFORMATION: Description of artificial sequence: Synthetic
      oligonucleotide

<400> SEQUENCE: 177
cctccacgat ctcttccacc tccacc                                             26

<210> SEQ ID NO 178
<211> LENGTH: 25
<212> TYPE: DNA
<213> ORGANISM: Artificial
<220> FEATURE:
<223> OTHER INFORMATION: Description of artificial sequence: Synthetic
      oligonucleotide

<400> SEQUENCE: 178
tccattcctc accactgcac acctg                                              25

<210> SEQ ID NO 179
<211> LENGTH: 24
<212> TYPE: DNA
<213> ORGANISM: Artificial
<220> FEATURE:
<223> OTHER INFORMATION: Description of artificial sequence: Synthetic
      oligonucleotide

<400> SEQUENCE: 179
cccctggcat ctataacagg ccgc                                               24

<210> SEQ ID NO 180
<211> LENGTH: 24
<212> TYPE: DNA
<213> ORGANISM: Artificial
<220> FEATURE:
<223> OTHER INFORMATION: Description of artificial sequence: Synthetic
      oligonucleotide

<400> SEQUENCE: 180
tcaagaacaa ggagagaaga gtgg                                               24

<210> SEQ ID NO 181
<211> LENGTH: 24
<212> TYPE: DNA
<213> ORGANISM: Artificial
<220> FEATURE:
<223> OTHER INFORMATION: Description of artificial sequence: Synthetic
      oligonucleotide

<400> SEQUENCE: 181
ctccagggcc cactgcagcc tcag                                               24

<210> SEQ ID NO 182
```

```
<211> LENGTH: 24
<212> TYPE: DNA
<213> ORGANISM: Artificial
<220> FEATURE:
<223> OTHER INFORMATION: Description of artificial sequence: Synthetic
      oligonucleotide

<400> SEQUENCE: 182
gaattgctat ggcctcactt ggtg                                              24

<210> SEQ ID NO 183
<211> LENGTH: 24
<212> TYPE: DNA
<213> ORGANISM: Artificial
<220> FEATURE:
<223> OTHER INFORMATION: Description of artificial sequence: Synthetic
      oligonucleotide

<400> SEQUENCE: 183
cggtggaggt ggaagagatc gtgg                                              24
```